US008859543B2

(12) United States Patent
Bartolomé-Nebreda et al.

(10) Patent No.: US 8,859,543 B2
(45) Date of Patent: Oct. 14, 2014

(54) IMIDAZO[1,2-A]PYRAZINE DERIVATIVES AND THEIR USE FOR THE PREVENTION OR TREATMENT OF NEUROLOGICAL, PSYCHIATRIC AND METABOLIC DISORDERS AND DISEASES

(75) Inventors: José Manuel Bartolomé-Nebreda, Toledo (ES); Susana Conde-Ceide, Toledo (ES); Gregor James MacDonald, Zoersel (BE); Joaquin Pastor-Fernández, Toledo (ES); Michiel Luc Maria Van Gool, Madrid (ES); María Luz Martín-Martín, Salamanca (ES); Greta Constantia Peter Vanhoof, Zoersel (BE)

(73) Assignee: Janssen Pharmaceutica NV, Beerse (BE)

( * ) Notice: Subject to any disclaimer, the term of this patent is extended or adjusted under 35 U.S.C. 154(b) by 211 days.

(21) Appl. No.: 13/583,514

(22) PCT Filed: Mar. 8, 2011

(86) PCT No.: PCT/EP2011/053445
§ 371 (c)(1), (2), (4) Date: Sep. 7, 2012

(87) PCT Pub. No.: WO2011/110545
PCT Pub. Date: Sep. 15, 2011

(65) Prior Publication Data

US 2012/0329792 A1 Dec. 27, 2012

(30) Foreign Application Priority Data

Mar. 9, 2010 (EP) .................................... 10155981

(51) Int. Cl.
*C07D 487/04* (2006.01)
*A61K 31/5377* (2006.01)

(52) U.S. Cl.
CPC .......... *C07D 487/04* (2013.01); *A61K 31/5377* (2013.01)
USPC ....................................... 514/233.2; 544/117

(58) Field of Classification Search
CPC .......................... C07D 487/04; A61K 31/5377
USPC ....................................... 514/233.2; 544/117
See application file for complete search history.

(56) References Cited

U.S. PATENT DOCUMENTS

| | | | |
|---|---|---|---|
| 4,242,513 | A | 12/1980 | Hoover et al. |
| 4,713,381 | A | 12/1987 | Ao et al. |
| 5,137,876 | A | 8/1992 | MacCoss et al. |
| 5,317,019 | A | 5/1994 | Bender et al. |
| 5,360,796 | A | 11/1994 | Hansen, Jr. et al. |
| 5,486,525 | A | 1/1996 | Summers, Jr. et al. |
| 5,498,774 | A | 3/1996 | Mitsudera et al. |
| 6,054,587 | A | 4/2000 | Reddy et al. |
| 6,245,769 | B1 | 6/2001 | Arvanitis et al. |
| 6,248,755 | B1 | 6/2001 | Chapman et al. |
| 6,352,990 | B1 | 3/2002 | McCarthy |
| 6,403,588 | B1 | 6/2002 | Hayakawa et al. |
| 6,589,947 | B1 | 7/2003 | Hamanaka et al. |
| 6,777,395 | B2 | 8/2004 | Bhat et al. |
| 6,806,268 | B2 | 10/2004 | Gall |
| 6,844,341 | B2 | 1/2005 | Thomas |
| 6,855,719 | B1 | 2/2005 | Thomas et al. |
| 6,900,217 | B2 | 5/2005 | Chen |
| 6,936,617 | B2 | 8/2005 | Hutchison et al. |
| 6,992,080 | B2 | 1/2006 | Dwyer et al. |
| 6,992,188 | B1 | 1/2006 | Chen |
| 7,074,801 | B1 | 7/2006 | Yoshida et al. |
| 7,078,405 | B2 | 7/2006 | Hibi et al. |
| 7,078,410 | B2 | 7/2006 | Berg et al. |
| 7,105,533 | B2 | 9/2006 | Campbell et al. |
| 7,132,426 | B2 | 11/2006 | Jones et al. |
| 7,148,353 | B2 | 12/2006 | Fang et al. |
| 7,186,714 | B2 | 3/2007 | Gudmundsson et al. |
| 7,186,740 | B2 | 3/2007 | Paruch et al. |
| 7,186,832 | B2 | 3/2007 | Sun et al. |
| 7,189,723 | B2 | 3/2007 | Mitchell et al. |
| 7,196,095 | B2 | 3/2007 | Biftu et al. |
| 7,244,740 | B2 | 7/2007 | Gudmundsson et al. |
| 7,259,164 | B2 | 8/2007 | Mitchell et al. |
| 7,306,631 | B2 | 12/2007 | Glenn, Jr. et al. |

(Continued)

FOREIGN PATENT DOCUMENTS

| | | | |
|---|---|---|---|
| CA | 2398956 | A1 | 8/2001 |
| CA | 2668738 | A1 | 7/2008 |

(Continued)

OTHER PUBLICATIONS

Belanger, et al. "Discovery of imidazo[1,2-a]pyrazine-based Aurora kinase inhibitors", Bioorganic & Medicinal Chemistry Letters (2010), 20(17), 5170-5174.

Belanger, et al. "Discovery of orally bioavailable imidazo[1,2-a]pyrazine-based Aurora kinase inhibitors", Bioorganic & Medicinal Chemistry Letters (2010), 20(22), 6739-6743.

Bouloc, et al. "Structure-based design of imidazo[1,2-a]pyrazine derivatives as selective inhibitors of Aurora-A kinase in cells", Bioorganic & Medicinal Chemistry Letters (2010), 20(20), 5988-5993.

(Continued)

*Primary Examiner* — Rebecca Anderson
(74) *Attorney, Agent, or Firm* — Hal B. Woodrow

(57) ABSTRACT

The present invention relates to novel imidazo[1,2-a]pyrazine derivatives which are inhibitors of the phosphodiesterase 10 enzyme (PDE10) and which are useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

10 Claims, No Drawings

(56) References Cited

U.S. PATENT DOCUMENTS

| | | | |
|---|---|---|---|
| 7,312,341 | B2 | 12/2007 | DeSimone et al. |
| 7,320,995 | B2 | 1/2008 | Bonjouklian et al. |
| 7,348,359 | B2 | 3/2008 | Gardinier et al. |
| 7,393,848 | B2 | 7/2008 | Currie et al. |
| 7,405,295 | B2 | 7/2008 | Currie et al. |
| 7,417,041 | B2 | 8/2008 | Blumberg et al. |
| 7,491,716 | B2 | 2/2009 | Engler |
| 7,504,404 | B2 | 3/2009 | McArthur et al. |
| 7,511,040 | B2 | 3/2009 | Belanger et al. |
| 7,557,103 | B2 | 7/2009 | Collins et al. |
| 7,563,797 | B2 | 7/2009 | Araldi et al. |
| 7,572,807 | B2 | 8/2009 | Li et al. |
| 7,576,085 | B2 | 8/2009 | Guzi et al. |
| 7,622,584 | B2 | 11/2009 | Kim et al. |
| 7,666,880 | B2 | 2/2010 | Lee et al. |
| 7,674,801 | B2 | 3/2010 | Basarab et al. |
| 2001/0041673 | A1 | 11/2001 | Fossa |
| 2002/0049208 | A1 | 4/2002 | Bakthavatchalam et al. |
| 2003/0027820 | A1 | 2/2003 | Gall |
| 2004/0014957 | A1 | 1/2004 | Eldrup et al. |
| 2004/0058938 | A1 | 3/2004 | Cullmann et al. |
| 2005/0031588 | A1 | 2/2005 | Sommadossi et al. |
| 2005/0079176 | A1 | 4/2005 | Pierson, III et al. |
| 2005/0079387 | A1 | 4/2005 | Lee et al. |
| 2005/0165232 | A1 | 7/2005 | Beresis et al. |
| 2005/0234029 | A1 | 10/2005 | Dodic et al. |
| 2005/0245520 | A1 | 11/2005 | Dodic et al. |
| 2005/0288295 | A1 | 12/2005 | Currie et al. |
| 2006/0094699 | A1 | 5/2006 | Kampen et al. |
| 2006/0100235 | A1 | 5/2006 | Andersen et al. |
| 2006/0135517 | A1 | 6/2006 | Lee et al. |
| 2006/0154105 | A1 | 7/2006 | Yamamoto et al. |
| 2006/0178367 | A1 | 8/2006 | Currie et al. |
| 2006/0258722 | A1 | 11/2006 | Yasuma et al. |
| 2007/0004736 | A1 | 1/2007 | Kubo et al. |
| 2007/0049591 | A1 | 3/2007 | Pinkerton et al. |
| 2007/0078136 | A1 | 4/2007 | Vaccaro et al. |
| 2007/0099925 | A1 | 5/2007 | Calderwood et al. |
| 2007/0105864 | A1 | 5/2007 | Guzi et al. |
| 2007/0117804 | A1 | 5/2007 | Zhao et al. |
| 2007/0149535 | A1 | 6/2007 | Berset et al. |
| 2007/0185063 | A1 | 8/2007 | Storer et al. |
| 2007/0197507 | A1 | 8/2007 | Morgan et al. |
| 2007/0219205 | A1 | 9/2007 | Brenchley et al. |
| 2008/0021217 | A1 | 1/2008 | Borchardt et al. |
| 2008/0045536 | A1 | 2/2008 | Vaccaro et al. |
| 2008/0070894 | A1 | 3/2008 | Kawamura et al. |
| 2008/0102028 | A1 | 5/2008 | Morel |
| 2008/0103136 | A1 | 5/2008 | Sato et al. |
| 2008/0113978 | A1 | 5/2008 | Barbosa et al. |
| 2008/0161341 | A1 | 7/2008 | Calderwood et al. |
| 2008/0167314 | A1 | 7/2008 | Uchikawa et al. |
| 2008/0207634 | A1 | 8/2008 | Gudmundsson |
| 2008/0221092 | A1 | 9/2008 | Bluhm et al. |
| 2008/0242862 | A1 | 10/2008 | Calderwood et al. |
| 2008/0255358 | A1 | 10/2008 | Bamford et al. |
| 2008/0300242 | A1 | 12/2008 | Kuntz et al. |
| 2008/0305081 | A1 | 12/2008 | Hashihayata et al. |
| 2008/0318975 | A1 | 12/2008 | Wagner et al. |
| 2009/0005374 | A1 | 1/2009 | Melvin, Jr. et al. |
| 2009/0023737 | A1 | 1/2009 | Xu et al. |
| 2009/0054409 | A1 | 2/2009 | Andrews et al. |
| 2009/0124625 | A1 | 5/2009 | Bessis et al. |
| 2009/0143376 | A1 | 6/2009 | Milburn et al. |
| 2009/0153035 | A1 | 6/2009 | Shin et al. |
| 2009/0156604 | A1 | 6/2009 | Holder et al. |
| 2009/0175852 | A1 | 7/2009 | Ciavarri et al. |
| 2009/0176778 | A1 | 7/2009 | Schmitz et al. |
| 2009/0203732 | A1 | 8/2009 | Dhanak et al. |
| 2009/0209573 | A1 | 8/2009 | Wu et al. |
| 2009/0215818 | A1 | 8/2009 | Adams et al. |
| 2009/0270436 | A1 | 10/2009 | Iino et al. |
| 2009/0317361 | A1 | 12/2009 | Cho et al. |
| 2009/0325953 | A1 | 12/2009 | Sahoo et al. |
| 2010/0029633 | A1 | 2/2010 | Allen et al. |
| 2010/0029638 | A1 | 2/2010 | Melvin, Jr. et al. |
| 2010/0063068 | A1 | 3/2010 | Pracitto et al. |

FOREIGN PATENT DOCUMENTS

| | | | |
|---|---|---|---|
| CL | 3212-2007 | | 6/2008 |
| EP | 0728759 | | 8/1996 |
| EP | 1 293 213 | A1 | 3/2003 |
| IT | 1374954 | B1 | 5/2010 |
| JP | 6247969 | A | 9/1994 |
| JP | 2001-006877 | | 1/2001 |
| JP | 2001-057292 | A | 2/2001 |
| JP | 2003-313126 | A | 11/2003 |
| JP | 2004-002826 | A | 1/2004 |
| JP | 2005-343889 | A | 12/2005 |
| WO | WO 90/15534 | A1 | 12/1990 |
| WO | WO 91/19497 | A1 | 12/1991 |
| WO | WO 92/10190 | A1 | 6/1992 |
| WO | WO 92/10498 | A1 | 6/1992 |
| WO | WO 96/34866 | A1 | 11/1996 |
| WO | WO 02/34748 | A1 | 5/2002 |
| WO | WO 02/066478 | A1 | 8/2002 |
| WO | WO 2004/017950 | A2 | 3/2004 |
| WO | WO 2004/026877 | A1 | 4/2004 |
| WO | WO 2004/035579 | A1 | 4/2004 |
| WO | WO 2004/075846 | | 9/2004 |
| WO | WO 2004/087710 | | 10/2004 |
| WO | WO 2004/089416 | A2 | 10/2004 |
| WO | WO 2004/103991 | A1 | 12/2004 |
| WO | WO 2005/014599 | A1 | 2/2005 |
| WO | WO 2005/020885 | A2 | 3/2005 |
| WO | WO 2005/047290 | A2 | 5/2005 |
| WO | WO 2006/044509 | A2 | 4/2006 |
| WO | WO 2006/102194 | | 9/2006 |
| WO | WO 2007/003386 | A1 | 1/2007 |
| WO | WO 2007/013673 | A1 | 2/2007 |
| WO | WO 2007/048779 | | 5/2007 |
| WO | WO 2007/087548 | A2 | 8/2007 |
| WO | WO 2007/145921 | A1 | 12/2007 |
| WO | WO 2008/003511 | A1 | 1/2008 |
| WO | WO 2008/030579 | A2 | 3/2008 |
| WO | WO 2008/030795 | A2 | 3/2008 |
| WO | WO 2008/057402 | A2 | 5/2008 |
| WO | WO 2008/079460 | A2 | 7/2008 |
| WO | WO 2008/081910 | A1 | 7/2008 |
| WO | WO 2008/121687 | A2 | 10/2008 |
| WO | WO 2008/124153 | A1 | 10/2008 |
| WO | WO 2008/133192 | A1 | 11/2008 |
| WO | WO 2008/134553 | A1 | 11/2008 |
| WO | WO 2008/138834 | A1 | 11/2008 |
| WO | WO 2008/141079 | A1 | 11/2008 |
| WO | WO 2008/156614 | A2 | 12/2008 |
| WO | WO 2009/005675 | A1 | 1/2009 |
| WO | WO 2009/016286 | A2 | 2/2009 |
| WO | WO 2009/016560 | A2 | 2/2009 |
| WO | WO 2009/017701 | A2 | 2/2009 |
| WO | WO 2009/021990 | A1 | 2/2009 |
| WO | WO 2009/023253 | A2 | 2/2009 |
| WO | WO 2009/024585 | A2 | 2/2009 |
| WO | WO 2009/037394 | A2 | 3/2009 |
| WO | WO 2009/060197 | A1 | 5/2009 |
| WO | WO 2009/061856 | A1 | 5/2009 |
| WO | WO 2009/077334 | | 6/2009 |
| WO | WO 2009/081857 | A1 | 7/2009 |
| WO | WO 2009/086123 | A1 | 7/2009 |
| WO | WO 2009/086130 | A1 | 7/2009 |
| WO | WO 2009/097233 | A1 | 8/2009 |
| WO | WO 2009/108546 | A1 | 9/2009 |
| WO | WO 2009/112679 | A1 | 9/2009 |
| WO | WO 2009/117157 | A1 | 9/2009 |
| WO | WO 2009/124653 | A2 | 10/2009 |
| WO | WO 2009/126691 | A1 | 10/2009 |
| WO | WO 2009/143156 | A2 | 11/2009 |
| WO | WO 2009/146358 | | 12/2009 |
| WO | WO 2009/152072 | A1 | 12/2009 |
| WO | WO 2010/002985 | A1 | 1/2010 |
| WO | WO 2010/009155 | A2 | 1/2010 |
| WO | WO 2010/011837 | A1 | 1/2010 |

(56) References Cited

FOREIGN PATENT DOCUMENTS

| | | |
|---|---|---|
| WO | WO 2010/016005 A1 | 2/2010 |
| WO | WO 2010/018327 A1 | 2/2010 |
| WO | WO 2010/033906 A2 | 3/2010 |
| WO | WO 2010/036407 A2 | 4/2010 |
| WO | WO 2010/047279 A1 | 4/2010 |
| WO | WO 2010/048149 A2 | 4/2010 |
| WO | WO 2010/059836 A1 | 5/2010 |
| WO | WO 2010/059838 A2 | 5/2010 |
| WO | WO 2010/069684 A1 | 6/2010 |
| WO | WO 2010/084425 A1 | 7/2010 |
| WO | WO 2010/084690 A1 | 7/2010 |
| WO | WO 2010/088368 A2 | 8/2010 |
| WO | WO 2010/088518 A2 | 8/2010 |
| WO | WO 2010/098458 A1 | 9/2010 |
| WO | WO 2010/108074 A2 | 9/2010 |
| WO | WO 2010/110277 A1 | 9/2010 |
| WO | WO 2010/119264 A1 | 10/2010 |
| WO | WO 2011/013729 A1 | 2/2011 |
| WO | WO 2011/021520 A1 | 2/2011 |
| WO | WO 2011/059099 A1 | 5/2011 |
| WO | WO 2011/089400 A1 | 7/2011 |
| WO | WO 2011/110545 A1 | 9/2011 |

OTHER PUBLICATIONS

Blokland et al., Expert Opin. Ther. Patents (2012) 22(4), pp. 349-354.

Carverley, M.J. Tetrahedron, 1987, 43(20), 4609-19.

Charych et al., The Journal of Neuroscience, Jul. 7, 2010 • 30(27):9027-9037.

Ennanceur, Behav Brain Res 1988, 31, 47-59.

Gaudry et al., Organic Syntheses, 1976, 55, 24-27.

Gehlert, et al. "3-(4-Chloro-2-morpholin-4-yl-thiazol-5-yl)-8-(1-ethylpropy1)-2,6-dimethyl-imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.

Gennaro et al. Remington's Pharmaceutical Sciences (18$^{th}$ ed., Mack Publishing Company, 1990, see especially Part 8: Pharmaceutical preparations and their Manufacture), pp. 1435-1712 (split/uploaded into 4 separate files due to size).

Gudmundsson, et al. "Imidazo[1,2-a]pyridines with potent activity against herpesviruses", Bioorganic & Medicinal Chemistry Letters (2007), 17(10), 2735-2739.

Gudmundsson, et al. "Synthesis of Novel Imidazo[1,2-a]pyridines with Potent Activity against Herpesviruses", Organic Letters (2003), 5(8), 1369-1372 CODEN: ORLEF7; ISSN: 1523-7060.

Hebb et al., Current Opinion in Pharmacology 2007, 7:86-92.

Il'icheva, et al. "Theoretical Study of the Structure of Adenosine Deaminase Complexes with Adenosine Analogues: I. Aza-, Deaza-, and Isomeric Azadeazaanalogues of Adenosine", Russian Journal of Bioorganic Chemistry (2005), 31(5), 439-452.

Kehler et al., Expert Opin. Ther. Patents (2007) 17(2), pp. 147-158.

Kehler et al. Expert Opin. Ther. Patents (2009) 19(12), pp. 1715-1725.

Kerekes, et al. "Aurora Kinase Inhibitors Based on the Imidazo[1,2-a]pyrazine Core: Fluorine and Deuterium Incorporation Improve Oral Absorption and Exposure" Journal of Medicinal Chemistry (2011), 54(1), 201-210.

Kobe, et al. "Use of distance geometry approach for the in vitro antiviral activity evaluation of N-bridgehead C-nucleosides", European Journal of Medicinal Chemistry (1992), 27(3), 259-66.

Kolar, et al. "Transformations of the pyrido[1,2-a]pyrazine ring system into imidazo[1,2-a]pyridines, imidazo[1,2-a]pyrimidines and 2-oxa-6a,10c-diazaaceanthrylenes", Journal of Heterocyclic Chemistry (1996), 33(3), 639-642.

Lhassani, et al. "Synthesis and antiviral activity of imidazo[1,2-a]pyridines", European Journal of Medicinal Chemistry (1999), 34(3), 271-274.

MacCoss, et al. "Synthesis and biological evaluation of nucleosides containing 8-aminoimidazo[1,2-a]pyrazine as an isosteric replacement for adenine", Journal of Heterocyclic Chemistry (1993), 30(5), 1213-20.

Meng, et al. "Bioisosteric approach to the discovery of imidazo[1,2-a]pyrazines as potent Aurora kinase inhibitors" Bioorganic & Medicinal Chemistry Letters (2011), 21(1), 592-598.

Pan, et al. "Synthesis of novel isoxazolinyl substituted imidazo[1,2-a]pyridine C-nucleoside analogs", Tetrahedron Letters (1998), 39(45), 8191-8194.

Schmidt et al., The Journal of Pharmacology and Experimental Therapeutics, vol. 325, No. 2, pp. 681-690, 2008.

Siuciak, Judith A., CNS Drugs 2008; 22 (12): 983-993.

van den Heuvel, M. et al.; J. Org. Chem., 2004, 250.

Wang, et al. "Synthesis of novel isoxazolinyl substituted imidazo[1,2-a]pyridine C-nucleoside analogs", Hecheng Huaxue (2001), 9(5), 386-389.

Wang, X. et al. Tetrahedron Lett., 2000, 4335-4338.

Yu, Tao et al. "Discovery of a Potent, Injectable Inhibitor of Aurora Kinases Based on the Imidazo-[1,2-a]-Pyrazine Core", ACS Medicinal Chemistry Letters (2010), 1(5), 214-218.

Zarubin, et al. "Theoretical study of adenosine and its isosteric analogs. A possible mechanism of their binding in an active site of mammalian adenosine deaminase", Vestnik Samarskogo Gosudarstvennogo Universiteta, Estestvennonauchnaya Seriya (2003), (Spec.), 152-173.

Bioorganic & Medicinal Chemistry, Letters, vol. 17, No. 2, pp. 486-490, 2007.

International Search Report for PCT/EP2011/053445 dated Aug. 18, 2011.

International Search Report for PCT/EP2010/066264 dated Dec. 8, 2010.

IMIDAZO[1,2-A]PYRAZINE DERIVATIVES AND THEIR USE FOR THE PREVENTION OR TREATMENT OF NEUROLOGICAL, PSYCHIATRIC AND METABOLIC DISORDERS AND DISEASES

CROSS REFERENCE TO RELATED APPLICATIONS

This application is the national stage of PCT Application No. PCT/EP2011/053445, filed Mar. 8, 2011, the entire disclosure of which is hereby incorporated in its entirety, which claims priority from European Patent Application No. 10155981.3, filed Mar. 9, 2010.

FIELD OF THE INVENTION

The present invention relates to novel imidazo[1,2-a]pyrazine derivatives which are inhibitors of the phosphodiesterase 10 enzyme (PDE10) and which are useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

Scheme A

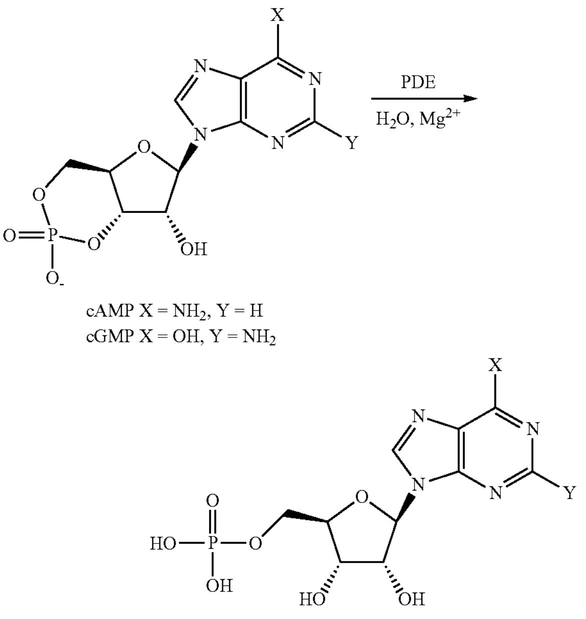

cAMP X = $NH_2$, Y = H
cGMP X = OH, Y = $NH_2$

5'-AMP/GMP

On the basis of substrate specificity, the PDE families can be divided into three groups: i) the cAMP-specific PDEs, which include PDE4, 7 and 8; ii) the cGMP-selective enzymes PDE5, 6, and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may play different physiological functions. Compounds that inhibit selectively PDE families or isozymes may display particular therapeutic activity, fewer side effects, or both.

The discovery of phosphodiesterase 10A (PDE10A) was reported in 1999. Of all the 11 known PDE families, PDE10 has the most restricted distribution with high expression only in the brain and testes.

In the brain, PDE10A mRNA and protein are highly expressed in a majority of striatal Medium Spiny Neurons (MSNs). This unique distribution of PDE10A in the brain, together with its increased pharmacological characterization, indicates a potential use of PDE10A inhibitors for treating neurological and psychiatric disorders like schizophrenia.

In the basal ganglia, MSNs constitute the major site for reception and integration of cortical glutamatergic and midbrain dopaminergic input, and form key output pathways that help discriminate and act on relevant and irrelevant cognitive and motor patterns.

MSNs are GABAergic projection neurons evenly distributed between two distinct pathways. Striatonigral MSNs (in the direct pathway) express the $D_1$ dopamine receptor and neuropeptides dynorphin and substance P; striatopallidal MSNs (in the indirect pathway) express the $D_2$ dopamine receptors and neuropeptide enkephalin. $D_1$ dopamine receptors are positively coupled to cAMP production, while $D_2$ dopamine receptors are negatively coupled to cAMP production. These pathways affect the concentration of extracellular dopamine and modulate motor and behavioural responses.

PDE10 Inhibitors and Schizophrenia

Due to the predominant localisation of PDE10 in MSNs, the majority of research on PDE10 inhibitors has been focused on preclinical models of psychosis.

On the basis of studies performed on knockout mice, the effects of PDE10 inhibition on striatal gene expression have been compared to the effects induced by a $D_1$ agonist and a $D_2$ antagonist.

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affection, poverty of speech and the inability to experience pleasure. In addition, schizophrenic patients suffer from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered, which proposes that hyperactivity of dopamine transmission is responsible for the positive symptoms observed in schizophrenic patients.

The efficacy of currently marketed antipsychotics correlates with their ability to block $D_2$ dopamine receptors. Acute and chronic administration of antipsychotics such as haloperidol has characteristic effects on striatal gene expression. Inhibition of PDE10A has also been observed to produce alterations in striatal gene expression similar to those exerted by haloperidol.

Atypical antipsychotics, such as clozapine, olanzapine, risperidone and paliperidone display a more beneficial profile of extrapyramidal side effects (EPS) and tardive dyskinesia associated with acute and long-term $D_2$ receptor blockade. However there is still a need to develop novel antipsychotics with an extended therapeutic profile and less side effects, e.g. by using approaches beyond dopamine $D_2$ receptor blockade.

PDE10 inhibitors may possess a pharmacological profile similar to that of the atypical antipsychotics, but lacking the non-target related side effects that are often observed with the currently available antipsychotics. Although EPS-like side effects are observed at relatively low doses, they are relatively mild.

Since PDE10 inhibitors can be used to raise levels of cAMP and/or cGMP within cells that express the PDE10 enzyme, for example neurons that comprise the basal ganglia, PDE10 inhibitors may be useful in treating schizophrenia and additionally, a variety of conditions as described herein such as Parkinson's disease, Huntington's disease, addiction, and depression. PDE10 inhibitors may be also useful in other conditions such as obesity, non-insulin dependent diabetes, bipolar disorder, obsessive compulsive disorder and pain.

The efficacy of PDE10A inhibition in models of cognition and against negative symptoms of schizophrenia has also been suggested by recent in vivo studies in which this mechanism has been associated with increased sociality in the Social Approach/Social Avoidance assay, reversed effect of chronic MK-801 treatment in a forced swim test, enhancement of social odor recognition in mice and improved novel object recognition in rats.

BACKGROUND ART

WO 2009/146358 discloses substituted 2-phenyl and 2-pyridinyl-imidazo[1,2-c]pyrazine-8-carboxamide derivatives as sirtuin-modulating compounds.

Bioorg. Med. Chem. Lett. 17 (2007) 486-490 discloses [8-(4-methylpiperazin-1-yl)imidazo[1,2-a]pyrazin-2-yl][4-(pyridin-2-yl)-1,4-diazepan-1-yl]methanone; [8-(4-methylpiperazin-1-yl)imidazo[1,2-a]pyrazin-2-yl] (3-phenylpiperidin-1-yl)methanone; [8-(4-methylpiperazin-1-yl)imidazo[1,2-a]pyrazin-2-yl][4-(6-methylpyridin-2-yl)-1,4-diazepan-1-yl]methanone; 8-(4-methylpiperazin-1-yl)-N-(2-phenylpropyl)imidazo[1,2-c]pyrazine-2-carboxamide as mGluR1 antagonists ($K_i$ between 407-1204 nM).

DESCRIPTION OF THE INVENTION

We have now found novel compounds that are PDE10 inhibitors. As already indicated above, compounds having this type of action are likely to be useful in the treatment of neurological, psychiatric (and metabolic) disorders. In particular, the present compounds are likely to be useful in antipsychotic therapy, providing extended therapeutic profile, low EPS liability and less off-target effects than observed with the current antipsychotics. The present compounds are centrally active, potent compounds which display efficacy in preclinical behavior challenge models in which known clinical useful antipsychotics display similar positive responses, such as in the reversal of apomorphine-induced stereotypy and phencyclidine (PCP)-induced hyperlocomotion in rodents. Additionally, representative compounds reverse the hypolocomotion effects exerted by SCH23390, a D1 receptor antagonist, and the behavioural effects exerted by depletion of monoamines in rodents, such as the sedation observed after administration of reserpine and the sedation and catalepsy induced by Ro-4-1248. Thus, the present compounds may act as dopamine modulating agents, inhibiting states of dopaminergic ($D_2$) hyperactivity and reversing states of dopaminergic ($D_1$) hypoactivity.

The present invention relates to compounds having PDE10 inhibitory activity, said compounds having the Formula (I)

(I)

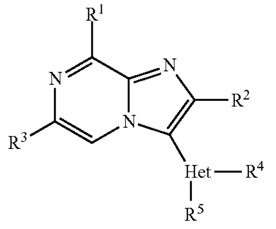

and the stereoisomeric forms thereof, wherein $R^1$ is selected from the group consisting of a radical of formula (a-1), (a-2) and (a-3);

(a-1)

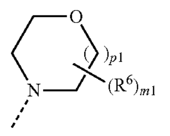

(a-2)

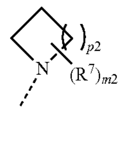

-continued (a-3)

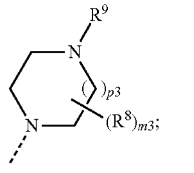

wherein each $R^6$, $R^7$, and $R^8$ independently is selected from the group consisting of fluoro; $C_{1-4}$alkyl; $C_{1-4}$alkyloxy; and $C_{1-4}$alkyl substituted with 1, 2 or 3 fluoro atoms;

$R^9$ is hydrogen or $C_{1-4}$alkyl;

each $m_1$, $m_2$, and $m_3$ is independently selected from 0, 1, 2, 3 and 4;

$p_2$ is selected from 1, 2, 3 and 4;

each $p_1$ and $p_3$ is independently selected from 1 and 2;

or $R^1$ is selected from the group consisting of unsubstituted pyridinyl; pyridinyl substituted with 1 or 2 substituents selected from the group consisting of halogen, $C_{1-4}$alkyl, trifluoromethyl and $C_{1-4}$alkyloxy; and unsubstituted tetrahydropyranyl;

$R^2$ is selected from the group consisting of hydrogen; $C_{1-4}$alkyl; trifluoromethyl; $C_{3-8}$ cycloalkyl; $C_{1-4}$alkyloxy; and cyano;

$R^3$ is selected from the group consisting of hydrogen; $C_{1-4}$alkyl; $C_{3-8}$cycloalkyl; and $C_{1-4}$alkyl substituted with 1, 2 or 3 fluoro atoms;

Het is a 5- or 6-membered heterocyclic ring, selected from the group consisting of pyridinyl; pyrimidinyl; pyridazinyl; pyrazinyl; pyrrolyl; oxazolyl; thiazolyl; imidazolyl; pyrazolyl; isothiazolyl; isoxazolyl; oxadiazolyl and triazolyl;

$R^4$ is selected from the group consisting of hydrogen; $C_{1-4}$alkyl; $C_{1-4}$alkyl substituted with 1, 2 or 3 fluoro atoms; (difluorocyclopropyl)methyl; (cyclopropyl)difluoromethyl; hydroxy$C_{1-4}$alkyl; $C_{3-8}$cycloalkyl; ($C_{3-8}$cycloalkyl)-$C_{1-4}$ alkyl; $C_{1-4}$alkyloxy$C_{1-6}$alkyl; $C_{1-4}$alkyloxy; $C_{1-4}$alkyloxy substituted with 1, 2 or 3 fluoro atoms; ($C_{3-8}$cycloalkyl)$C_{1-4}$ alkyloxy; ($C_{1-4}$alkyloxy$C_{1-4}$alkyl)oxy; ($C_{1-4}$alkyl)-carbonyl; ($C_{1-4}$alkyl)carbonyl$C_{1-4}$alkyl; ($C_{3-8}$cycloalkyl)carbonyl; ($C_{3-8}$cycloalkyl)-carbonyl$C_{1-4}$alkyl; unsubstituted phenyl; phenyl substituted with 1 or 2 substituents selected from the group consisting of halogen, $C_{1-4}$alkyl, trifluoromethyl, trifluoromethoxy, cyano and $C_{1-4}$alkyloxy; unsubstituted benzyl; benzyl substituted with 1 or 2 substituents selected from the group consisting of halogen, $C_{1-4}$alkyl, trifluoromethyl, trifluoromethoxy, cyano and $C_{1-4}$alkyloxy; unsubstituted tetrahydrofuranyl; tetrahydrofuranylmethyl; unsubstituted tetrahydropyranyl; tetrahydropyranylmethyl; pyridinylmethyl; quinolinylmethyl; $(NR^{10}R^{11})C_{1-4}$alkyl; and $NR^{10}R^{11}$;

$R^5$ is hydrogen or fluoro;

$R^{10}$ and $R^{11}$ are independently selected from hydrogen and $C_{1-4}$alkyl, or taken together with the ring nitrogen atom may form a radical of Formula (b-1), (b-2) or (b-3)

(b-1)

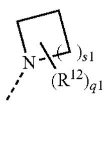

-continued (b-2)

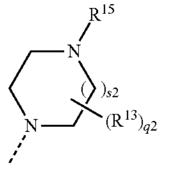

(b-3)

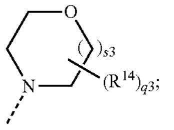

wherein each $R^{12}$, $R^{13}$ and $R^{14}$ independently is $C_{1-4}$alkyl or $C_{1-4}$alkyloxy;

$R^{15}$ is hydrogen or $C_{1-4}$alkyl;

each $q_1$, $q_2$ and $q_3$ is independently selected from 0, 1, 2, 3 and 4;

$s_1$ is selected from 1, 2, 3 and 4;

each $s_2$ and $s_3$ is independently selected from 1 and 2;

and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of neurological, psychiatric or metabolic disorders and diseases.

Additionally, the invention relates to the use of a compound of Formula (I) in combination with an additional pharmaceutical agent for use in the treatment or prevention of neurological, psychiatric or metabolic disorders and diseases.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a product comprising a compound of Formula (I) and an additional pharmaceutical agent, as a combined preparation for simultaneous, separate or sequential use in the treatment or prevention of neurological, psychiatric or metabolic disorders and diseases.

DETAILED DESCRIPTION OF THE INVENTION

The chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However it should be clear that the other non-depicted tautomeric form is also included within the scope of the present invention.

DEFINITIONS

The term "halogen" or "halo" as used herein alone or as part of another group refers to fluoro, chloro, bromo or iodo, with fluoro or chloro being preferred.

The term "$C_{1-4}$alkyl" or"$C_{1-6}$alkyl" as employed herein alone or as part of another group, unless otherwise stated, refers to a saturated straight or branched hydrocarbon radical, having unless otherwise stated, from 1 to 4 or 1 to 6 carbon atoms, which is attached to the rest of the molecule by a single bond, such as methyl, ethyl, propyl, butyl, 1-pentyl, 1-methylethyl, 1,1-dimethylethyl, 2-methylpropyl, and 3-methylbutyl.

The term "$C_{3-8}$cycloalkyl" as employed herein alone or as part of another group unless otherwise stated, is generic to cyclopropyl, cyclobutyl, cyclopentyl, cyclohexyl, cycloheptyl and cyclooctyl.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or reversal of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "treatment" is intended to refer to all processes, wherein there may be a slowing, interrupting, arresting or stopping of the progression of a disease, but does not necessarily indicate a total elimination of all symptoms.

Unless otherwise stated, heterocyclic substituents in $R^1$, Het, and $R^4$, such as for example, pyridinyl, tetrahydropyranyl, may be attached to the remainder of the molecule of formula (I) through any available ring carbon atom. Thus, for example, when Het is pyridinyl, it may be pyridin-2-yl, pyridin-3-yl or pyridin-4-yl, unless otherwise specified. When Het is pyridine and $R^4$ is different to hydrogen, then $R^4$ is placed in Het preferably in meta- or para-position relative to the position of attachment of Het to the imidazo[1,2-a]pyrazine core.

Substituents covered by the term Het may be attached to the remainder of the molecule of formula (I) through any available ring carbon or heteroatom as appropriate, if not otherwise specified. Het as used herein, is preferably a 5- or 6-aromatic membered heterocyclic ring preferably bound to the imidazo[1,2-a]pyrazine ring system through an available carbon atom of the ring.

The invention includes all possible stereoisomers of the compound of Formula (I) of the present invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereoisomers (or diastereomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereoisomers, racemates E, Z, cis, trans isomers and mixtures thereof of the compound. The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomeric form is indicated, this means that said form is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Whenever used hereinbefore or hereinafter, the term "compound of formula (I)" is meant to also include the addition salts, the solvates and the stereochemically isomeric forms thereof.

The terms "stereoisomeric forms" or "stereochemically isomeric forms" as employed hereinbefore or hereinafter are used interchangeably.

Preferred features of the compounds of this invention are now set forth.

The present invention relates in particular to a compound according to Formula (I) or a stereochemically isomeric form thereof, wherein $R^1$ is selected from the group consisting of a radical of formula (a-1), a radical of formula (a-2); a radical of formula (a-3); unsubstituted pyridinyl; pyridinyl substituted with halogen, $C_{1-4}$alkyl, trifluoromethyl or $C_{1-4}$alkyloxy; and unsubstituted tetrahydropyranyl;

wherein each $R^6$, $R^7$ and $R^8$ independently is selected from the group consisting of $C_{1-4}$alkyl; and $C_{1-4}$alkyloxy;

$R^9$ is selected from hydrogen and $C_{1-4}$alkyl;

each $m_1$, $m_2$ and $m_3$ is selected from 0, 1 and 2;

$p_2$ is selected from 2 and 3;

each $p_1$ and $p_3$ is 1;

$R^2$ is selected from the group consisting of hydrogen; methyl; ethyl; prop-2-yl; trifluoromethyl; cyano; methoxy and cyclopropyl;

$R^3$ is selected from the group consisting of hydrogen; methyl; trifluoromethyl; 3,3,3-trifluoropropyl; and cyclopropyl; and Het is selected from the group consisting of pyridinyl; pyrimidinyl; 1H-pyrrolyl; oxazolyl; thiazolyl; 1H-imidazolyl; and 1H-pyrazolyl;

$R^4$ is selected from the group consisting of hydrogen; $C_{1-4}$alkyl; $C_{1-4}$alkyl substituted with 1, 2 or 3 fluoro atoms; (difluorocyclopropyl)methyl; (cyclopropyl)difluoromethyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; $C_{1-4}$alkyloxy substituted with 1, 2 or 3 fluoro atoms; ($C_{3-8}$cycloalkyl)$C_{1-4}$alkyloxy; ($C_{1-4}$alkyloxy$C_{1-4}$alkyl)oxy; ($C_{1-4}$alkyl)-carbonyl$C_{1-4}$alkyl; ($C_{3-8}$cycloalkyl)carbonyl$C_{1-4}$alkyl; unsubstituted phenyl; phenyl substituted with halogen, $C_{1-4}$alkyl, trifluoromethyl, trifluoromethoxy, cyano or $C_{1-4}$alkyloxy; unsubstituted benzyl; benzyl substituted with halogen, $C_{1-4}$alkyl, trifluoromethyl, trifluoromethoxy, cyano or $C_{1-4}$alkyloxy; unsubstituted tetrahydrofuranyl; tetrahydrofuranylmethyl; unsubstituted tetrahydropyranyl; tetrahydropyranylmethyl; pyridinylmethyl; quinolinylmethyl; ($NR^{10}R^{11}$) $C_{1-4}$alkyl; and $NR^{10}R^{11}$;

wherein $R^{10}$ and $R^{11}$ are independently selected from hydrogen and $C_{1-4}$alkyl, or taken together with the ring nitrogen atom may form a radical of Formula (b-1), (b-2) or (b-3); wherein each $R^{12}$, $R^{13}$ and $R^{14}$ is independently selected from $C_{1-4}$alkyl and $C_{1-4}$alkyloxy;

$R^{15}$ is selected from hydrogen and $C_{1-4}$alkyl;

each $q_1$, $q_2$ and $q_3$ is selected from 0, 1 and 2;

$s_1$ is selected from 2 and 3;

each $s_2$ and $s_3$ is 1;

and $R^5$ is as previously defined;

or a pharmaceutically acceptable salt or a solvate thereof.

In a more preferred embodiment, the invention relates to a compound according to formula (I) or a stereochemically isomeric form thereof, wherein $R^1$ is selected from the group consisting of a radical of formula (a-1); a radical of formula (a-2); unsubstituted pyridin-3-yl; and unsubstituted pyridin-4-yl;

wherein each $m_1$, $m_2$ and $m_3$ is 0; $p_2$ is selected from 2 and 3; and each of $p_1$ and $p_3$ is 1;

$R^4$ is selected from the group consisting of hydrogen; $C_{1-4}$alkyl; fluoroethyl; fluoropropyl; difluoroethyl; trifluoromethyl; trifluoroethyl; (difluorocyclopropyl)methyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; trifluoromethyloxy; trifluoroethyloxy; ($C_{3-8}$cycloalkyl)$C_{1-4}$alkyloxy; ($C_{1-4}$alkyloxy$C_{1-4}$alkyl)oxy; ($C_{1-4}$alkyl)carbonyl$C_{1-4}$alkyl; ($C_{3-8}$cycloalkyl)carbonyl$C_{1-4}$alkyl; unsubstituted phenyl; phenyl substituted with halogen; unsubstituted benzyl; benzyl substituted with halogen; unsubstituted tetrahydrofuranyl; unsubstituted tetrahydropyranyl; tetrahydrofuranylmethyl; tetrahydropyranylmethyl; pyridinylmethyl; quinolinylmethyl; ($NR^{10}R^{11}$)$C_{1-4}$alkyl; and $NR^{10}R^{11}$;

wherein $R^{10}$ and $R^{11}$ are independently hydrogen or $C_{1-4}$alkyl, or taken together with the nitrogen can be a radical of formula (b-1), (b-2) or (b-3), wherein $R^{12}$ is $C_{1-4}$alkyloxy;

$s_1$ is 2;

$q_1$ is selected from 0 and 1;

each $q_2$ and $q_3$ is 0;

each $s_2$ and $s_3$ is 1; and $R^{15}$ is hydrogen;

and $R^2$, $R^3$, Het and $R^5$ are as previously defined;

or a pharmaceutically acceptable salt or a solvate thereof.

In another preferred embodiment, the invention relates to a compound of formula (I) or a stereoisomeric form thereof, wherein $R^1$ is selected from the group consisting of unsubstituted morpholin-4-yl; unsubstituted pyridin-3-yl; unsubstituted pyridin-4-yl and unsubstituted pyrrolidin-1-yl;

$R^2$ is selected from the group consisting of hydrogen; methyl; ethyl; prop-2-yl; trifluoromethyl; cyano; methoxy and cyclopropyl;

$R^3$ is selected from the group consisting of hydrogen; methyl; trifluoromethyl; 3,3,3-trifluoropropyl; and cyclopropyl; and Het is selected from the group consisting of pyridin-2-yl; pyridin-3-yl; pyridin-4-yl; pyrimidin-5-yl; 1H-pyrrol-3-yl; 1,3-oxazol-4-yl; 1,3-thiazol-5-yl; 1H-imidazol-5-yl; and 1H-pyrazol-5-yl;

$R^4$ is selected from the group consisting of hydrogen; methyl; ethyl; prop-2-yl; 2-methylpropyl; 2-fluoroethyl; 3-fluoropropyl; 2,2-difluoroethyl; 2,2,2-trifluoroethyl; 2,2-difluorocyclopropylmethyl; 2-hydroxyethyl; cyclopropyl; cyclopropylmethyl; methyloxy; 1-methylethyloxy; ethyloxymethyl; 2-methyloxyethyl; 2-ethyloxyethyl; 3-methyloxypropyl; 1-methoxy-1-methylethyl; 1-ethoxy-1-methylethyl; 2-methoxy-2-methylpropyl; 2-(1-methylethoxy)ethyl; 3-methoxypropyl; 2-methoxypropyl; 1-methoxyprop-2-yl; 1-methoxybut-2-yl; 2-methoxy-3-methylbutyl; 3-methoxy-3-methylbutyl; 3-methoxybutyl; 2,2,2-trifluoroethyloxy; cyclopropylmethyloxy; (2-methyloxyethyl)oxy; 2-methoxy-2-methylpropyloxy; 2-oxopropyl; 3-oxobutyl; 2-cyclopropyl-2-oxoethyl; 4-fluorophenyl; 2-chlorobenzyl; 4-chlorobenzyl; tetrahydrofuran-3-yl; tetrahydro-2H-pyran-4-yl; tetrahydrofuran-2-ylmethyl; tetrahydro-2H-pyran-2-ylmethyl; tetrahydro-2H-pyran-4-ylmethyl; pyridin-2-ylmethyl; pyridin-3-ylmethyl; pyridin-4-ylmethyl; quinolin-2-ylmethyl; (1-methylethyl)amino; pyrrolidin-1-yl; piperazin-1-yl; morpholin-4-yl; 3-methoxy-pyrrolidin-1-yl; 2-pyrrolidin-1-ylethyl; and 2-morpholin-4-ylethyl;

$R^5$ is hydrogen or fluoro;

or a pharmaceutically acceptable salt or a solvate thereof.

In another preferred embodiment, the invention relates to a compound of formula (I) or a stereoisomeric form thereof, wherein $R^1$ is selected from unsubstituted morpholin-4-yl or unsubstituted pyridin-4-yl;

$R^2$ is methyl;

$R^3$ is hydrogen;

Het is selected from the group consisting of pyridin-3-yl; pyrimidin-5-yl; 1H-pyrrol-3-yl; 1,3-thiazol-5-yl; and 1H-pyrazol-4-yl;

$R^4$ is selected from the group consisting of 2-methylpropyl; cyclopropyl; ethyloxymethyl; 2-methyloxyethyl; 1-methoxy-1-methylethyl; (2-methyloxyethyl)oxy; tetrahydro-2H-pyran-4-yl; and piperazin-1-yl;

$R^5$ is hydrogen;

or a pharmaceutically acceptable salt or a solvate thereof.

In a particular embodiment, the invention relates to a compound according to formula (I) or a stereoisomerically isomeric form thereof, wherein $R^1$ is selected from the group consisting of 4-morpholinyl and unsubstituted pyridin-4-yl;

$R^2$ is selected from the group consisting of $C_{1-4}$alkyl; trifluoromethyl; $C_{3-8}$cycloalkyl; and $C_{1-4}$alkyloxy;

$R^3$ is hydrogen;

Het is selected from the group consisting of pyridinyl and pyrimidinyl;

$R^4$ is selected from the group consisting of $C_{1-4}$alkyl; $C_{3-8}$cycloalkyl; $C_{1-4}$alkyloxy$C_{1-6}$alkyl; ($C_{3-8}$cycloalkyl)$C_{1-4}$alkyloxy; ($C_{1-4}$alkyloxy$C_{1-4}$alkyl)oxy; unsubstituted tetrahydropyranyl; 4-morpholinyl; and 1-piperazinyl;

$R^5$ is hydrogen;

and the pharmaceutically acceptable salts and the solvates thereof.

In a particular embodiment, the invention relates to a compound according to formula (I) or a stereoisomerically isomeric form thereof, wherein $R^1$ is selected from the group consisting of morpholin-4-yl; and unsubstituted pyridin-4-yl;

$R^2$ is selected from the group consisting of $C_{1-4}$alkyl; $C_{3-8}$cycloalkyl; and cyano;

$R^3$ is hydrogen;

Het is selected from the group consisting of pyrrolyl; oxazolyl; thiazolyl; and pyrazolyl;

$R^4$ is selected from the group consisting of $C_{1-4}$alkyl; $C_{1-4}$alkyl substituted with 1, 2 or 3 fluoro atoms; (difluorocyclopropyl)methyl; $C_{1-4}$alkyloxy$C_{1-6}$alkyl; ($C_{1-4}$alkyl)carbonyl$C_{1-4}$alkyl; unsubstituted tetrahydrofuranyl; tetrahydrofuranylmethyl; tetrahydropyranylmethyl; and pyridinylmethyl;

$R^5$ is hydrogen;

and the pharmaceutically acceptable salts and the solvates thereof.

In an additional embodiment, the invention relates to compounds according to formula (I), having the formula (I-a) or (I-b)

(I-a)

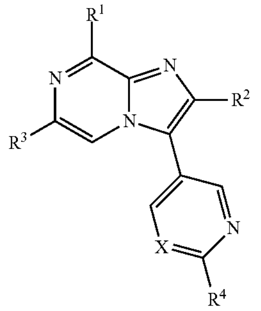

(I-b)

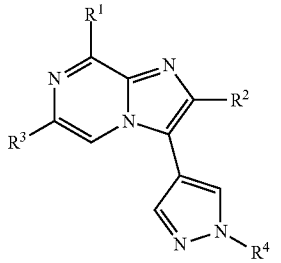

wherein $R^1$, $R^2$, $R^3$ and $R^4$ are as previously defined and X is $CR^5$ or N.

In a further particular embodiment, the invention relates to compounds according to formula (I-a), wherein $R^1$ is selected from 4-morpholinyl and unsubstituted pyridin-4-yl;

$R^2$ is selected from the group consisting of methyl; ethyl; trifluoromethyl; methoxy and cyclopropyl;

$R^3$ is hydrogen;

$R^4$ is selected from the group consisting of $C_{1-4}$alkyl; $C_{3-8}$cycloalkyl; $C_{1-4}$alkyloxy$C_{1-6}$alkyl; ($C_{3-8}$cycloalkyl)$C_{1-4}$ alkyloxy; ($C_{1-4}$alkyloxy$C_{1-4}$alkyl)oxy; unsubstituted tetrahydropyranyl; and 4-morpholinyl;

X is $CR^5$ or N;

$R^5$ is hydrogen;

and the pharmaceutically acceptable salts and the solvates thereof.

In a further particular embodiment, the invention relates to compounds according to formula (I-b), wherein $R^1$ is selected from the group consisting of morpholin-4-yl; and unsubstituted pyridin-4-yl;

$R^2$ is selected from the group consisting of methyl; ethyl; cyano; and cyclopropyl;

$R^3$ is hydrogen;

$R^4$ is selected from the group consisting of $C_{1-4}$alkyl; $C_{1-4}$alkyl substituted with 1, 2 or 3 fluoro atoms; (difluorocyclopropyl)methyl; $C_{1-4}$alkyloxy$C_{1-6}$alkyl; ($C_{1-4}$alkyl)carbonyl$C_{1-4}$alkyl; unsubstituted tetrahydrofuranyl; tetrahydrofuranylmethyl; tetrahydropyranylmethyl; and pyridinylmethyl;

In a further embodiment, the invention relates to compounds according to any of the other embodiments, wherein $R^1$ is selected from morpholin-4-yl and pyridin-4-yl.

In a further embodiment, the invention relates to compounds according to any of the other embodiments, wherein $R^1$ is morpholin-4-yl.

In a further embodiment, the invention relates to compounds according to any of the other embodiments, wherein $R^2$ is selected from the group consisting of $C_{1-4}$alkyl; trifluoromethyl; $C_{3-8}$cycloalkyl; $C_{1-4}$alkyloxy; and cyano.

In a further embodiment, the invention relates to compounds according to any of the other embodiments, wherein $R^2$ is $C_{1-4}$alkyl.

In a further embodiment, the invention relates to compounds according to any of the other embodiments, wherein $R^2$ is $C_{1-4}$alkyl and $R^3$ is hydrogen In a further embodiment, the invention relates to compounds according to any of the other embodiments, wherein $R^2$ is methyl and $R^3$ is hydrogen In a further embodiment, the invention relates to compounds according to any of the other embodiments, wherein Het is a 5- or 6-membered heterocyclic ring, selected from the group consisting of pyridinyl; pyrimidinyl; pyrrolyl; oxazolyl; thiazolyl; and pyrazolyl;

In a further embodiment, the invention relates to compounds according to any of the other embodiments, wherein Het is a 5- or 6-membered heterocyclic ring, selected from the group consisting of pyridinyl; pyrimidinyl; oxazolyl; and thiazolyl.

In a further embodiment, the invention relates to compounds according to any of the other embodiments, wherein Het is selected from the group consisting of pyridinyl; pyrimidinyl; and thiazolyl.

In a further embodiment, the invention relates to compounds according to any of the other embodiments, wherein Het is selected from the group consisting of pyridin-3-yl; pyrimidin-5-yl; and 1,3-thiazol-5-yl.

In a further embodiment, the invention relates to compounds according to any of the other embodiments, wherein Het is selected from the group consisting of pyridin-3-yl; and pyrimidin-5-yl.

In a further embodiment, the invention relates to compounds according to any of the other embodiments, wherein Het is pyridin-3-yl.

In a further embodiment, the invention relates to compounds according to any of the other embodiments, wherein Het is 1,3-thiazol-5-yl.

In a further embodiment, the invention relates to compounds according to any of the other embodiments, wherein $R^4$ is selected from the group consisting of $C_{1-4}$alkyl; $C_{3-8}$cycloalkyl; $C_{1-4}$alkyloxy$C_{1-6}$alkyl; ($C_{1-4}$alkyloxy$C_{1-4}$alkyl)oxy; unsubstituted tetrahydropyranyl; 4-morpholinyl; and piperazin-1-yl.

In a further embodiment, the invention relates to compounds according to any of the other embodiments, wherein $R^4$ is selected from the group consisting of 2-methylpropyl; cyclopropyl; ethyloxymethyl; 2-methyloxyethyl; 1-methoxy-1-methylethyl; (2-methyloxyethyl)oxy; tetrahydro-2H-pyran-4-yl; morpholin-4-yl; and piperazin-1-yl.

In a further embodiment, the invention relates to compounds according to any of the other embodiments, wherein $R^4$ is selected from the group consisting of $C_{1-4}$alkyl; $C_{3-8}$cycloalkyl; $C_{1-4}$alkyloxy$C_{1-6}$alkyl; ($C_{1-4}$alkyloxy$C_{1-4}$alkyl)oxy; unsubstituted tetrahydropyranyl; and morpholin-4-yl.

In a further embodiment, the invention relates to compounds according to any of the other embodiments, wherein $R^4$ is selected from the group consisting of 2-methylpropyl; cyclopropyl; ethyloxymethyl; 2-methyloxyethyl; 1-methoxy-1-methylethyl; (2-methyloxyethyl)oxy; tetrahydro-2H-pyran-4-yl; and morpholin-4-yl.

In a further embodiment, the invention relates to compounds according to any of the other embodiments, wherein $R^4$ is selected from the group consisting of 2-methyloxyethyl; and tetrahydro-2H-pyran-4-yl.

In a further embodiment, the invention relates to compounds according to any of the other embodiments, wherein $R^4$ is selected from the group consisting of $C_{1-4}$alkyl; and $C_{1-4}$alkyloxy$C_{1-6}$alkyl.

In a further embodiment, the invention relates to compounds according to any of the other embodiments, wherein $R^4$ is selected from the group consisting of 2-methylpropyl; and 2-methyloxyethyl.

In a further embodiment, the invention relates to compounds according to any of the other embodiments, wherein $R^5$ is hydrogen.

In a further embodiment, the invention relates to compounds according to formula (I-a) wherein X is CH.

In a further embodiment, the invention relates to compounds according to formula (I-a) wherein X is N.

All possible combinations of the above-indicated interesting embodiments are considered to be embraced within the scope of this invention.

Particularly preferred compounds may be selected from the group of:

3-[1-(cyclopropylmethyl)-1H-pyrazol-4-yl]-8-(4-morpholinyl)-imidazo[1,2-a]pyrazine;
3-[1-(2-methoxyethyl)-1H-pyrazol-4-yl]-2-methyl-8-(4-morpholinyl)-imidazo[1,2-a]pyrazine;
3-[1-(cyclopropylmethyl)-1H-pyrazol-4-yl]-2-methyl-8-(4-morpholinyl)-imidazo[1,2-a]pyrazine;
2-methyl-3-(2-methyl-4-pyridinyl)-8-(4-morpholinyl)-imidazo[1,2-a]pyrazine;
3-[1-(2-methoxyethyl)-1H-pyrazol-4-yl]-8-(4-morpholinyl)-imidazo[1,2-a]pyrazine;
3-[1-[(1S)-2-methoxy-1-methylethyl]-1H-pyrazol-4-yl]-2-methyl-8-(4-morpholinyl)-imidazo[1,2-a]pyrazine;
3-[1-(2-methoxyethyl)-1H-pyrazol-4-yl]-2-methyl-8-(4-pyridinyl)-imidazo[1,2-a]pyrazine;
2-methyl-8-(4-morpholinyl)-3-[1-(3-pyridinylmethyl)-1H-pyrazol-4-yl]-imidazo[1,2-a]pyrazine;
2-methyl-8-(4-morpholinyl)-3-(1H-pyrrol-3-yl)-imidazo[1,2-a]pyrazine;
2-methyl-3-[1-(2-methylpropyl)-1H-pyrazol-4-yl]-8-(4-morpholinyl)-imidazo[1,2-a]pyrazine;
3-[1-(2-methoxyethyl)-1H-pyrrol-3-yl]-2-methyl-8-(4-morpholinyl)-imidazo[1,2-a]pyrazine;
2-methyl-8-(4-morpholinyl)-3-[1-(2-pyridinylmethyl)-1H-pyrazol-4-yl]-imidazo[1,2-a]pyrazine;
2-ethyl-3-[1-(2-methoxyethyl)-1H-pyrazol-4-yl]-8-(4-morpholinyl)-imidazo[1,2-a]pyrazine;
3-[1-[(2-chlorophenyl)methyl]-1H-pyrazol-4-yl]-2-methyl-8-(4-morpholinyl)-imidazo[1,2-a]pyrazine;
2-methyl-8-(4-morpholinyl)-3-[1-(4-pyridinylmethyl)-1H-pyrazol-4-yl]-imidazo[1,2-a]pyrazine;
3-[1-(2-methoxyethyl)-1H-pyrazol-4-yl]-8-(4-morpholinyl)-2-(trifluoromethyl)-imidazo[1,2-a]pyrazine;
3-[1-[(2S)-2-methoxypropyl]-1H-pyrazol-4-yl]-2-methyl-8-(4-morpholinyl)-imidazo[1,2-a]pyrazine;
3-[1-(2-methoxyethyl)-1H-pyrazol-4-yl]-2-methyl-8-(1-pyrrolidinyl)-imidazo[1,2-a]pyrazine;
3-[1-(2-methoxyethyl)-1H-pyrazol-4-yl]-8-(4-morpholinyl)-imidazo[1,2-a]pyrazine-2-carbonitrile;
2-cyclopropyl-3-[1-(2-methoxyethyl)-1H-pyrazol-4-yl]-8-(4-morpholinyl)-imidazo[1,2-a]pyrazine;
2-[[4-[2-methyl-8-(4-morpholinyl)imidazo[1,2-a]pyrazin-3-yl]-1H-pyrazol-1-yl]methyl]-quino line;
3-[1-(2-ethoxyethyl)-1H-pyrazol-4-yl]-2-methyl-8-(4-pyridinyl)-imidazo[1,2-a]pyrazine;
3-[1-[(2S)-2-methoxypropyl]-1H-pyrazol-4-yl]-2-methyl-8-(4-pyridinyl)-imidazo[1,2-a]pyrazine;
3-[1-(3-methoxypropyl)-1H-pyrazol-4-yl]-2-methyl-8-(4-pyridinyl)-imidazo[1,2-a]pyrazine;
2-methyl-3-[1-(1-methylethyl)-1H-pyrazol-4-yl]-8-(4-morpholinyl)-imidazo[1,2-a]pyrazine;
3-[1-(3-methoxypropyl)-1H-pyrazol-4-yl]-2-methyl-8-(4-morpholinyl)-imidazo[1,2-a]pyrazine;
3-[1-(2-ethoxyethyl)-1H-pyrazol-4-yl]-2-methyl-8-(4-morpholinyl)-imidazo[1,2-a]pyrazine;
2-methyl-8-(4-morpholinyl)-3-[1-(tetrahydro-3-furanyl)-1H-pyrazol-4-yl]-imidazo[1,2-a]pyrazine;
3-[1-(2,2-difluoro ethyl)-1H-pyrazol-4-yl]-2-methyl-8-(4-morpholinyl)-imidazo[1,2-a]pyrazine;
3-[1-[(2,2-difluorocyclopropyl)methyl]-1H-pyrazol-4-yl]-2-methyl-8-(4-morpholinyl)-imidazo[1,2-a]pyrazine;
3-[1-[(1R)-2-methoxy-1-methylethyl]-1H-pyrazol-4-yl]-2-methyl-8-(4-pyridinyl)-imidazo[1,2-a]pyrazine;
3-[1-[(1R)-2-methoxy-1-methylethyl]-1H-pyrazol-4-yl]-2-methyl-8-(4-morpholinyl)-imidazo[1,2-a]pyrazine;
1-[4-[2-methyl-8-(4-morpholinyl)imidazo[1,2-a]pyrazin-3-yl]-1H-pyrazol-1-yl]-2-propanone;
3-[1-[(4-chlorophenyl)methyl]-1H-pyrazol-4-yl]-2-methyl-8-(4-morpholinyl)-imidazo[1,2-a]pyrazine;
3-(1-ethyl-1H-pyrazol-4-yl)-2-methyl-8-(4-morpholinyl)-imidazo[1,2-a]pyrazine;
3-[1-[(1S)-2-methoxy-1-methylethyl]-1H-pyrazol-4-yl]-2-methyl-8-(4-pyridinyl)-imidazo[1,2-a]pyrazine;
4-[4-[2-methyl-8-(4-morpholinyl)imidazo[1,2-a]pyrazin-3-yl]-1H-pyrazol-1-yl]-2-butanone;
2-methyl-3-[1-[2-(4-morpholinyl)ethyl]-1H-pyrazol-4-yl]-8-(4-pyridinyl)-imidazo[1,2-a]pyrazine;
2-methyl-8-(4-morpholinyl)-3-[1-[(tetrahydro-2H-pyran-2-yl)methyl]-1H-pyrazol-4-yl]-imidazo[1,2-a]pyrazine;
3-[1-(2-methoxy-2-methylpropyl)-1H-pyrazol-4-yl]-2-methyl-8-(4-morpholinyl)-imidazo[1,2-a]pyrazine;
2-methyl-3-[1-[2-(1-methylethoxy)ethyl]-1H-pyrazol-4-yl]-8-(4-morpholinyl)-imidazo[1,2-a]pyrazine;
2-methyl-8-(4-morpholinyl)-3-[1-[[tetrahydro-2H-pyran-2-yl]methyl]-1H-pyrazol-4-yl]-imidazo[1,2-a]pyrazine;
2-methyl-8-(4-pyridinyl)-3-[1-[[tetrahydro-2H-pyran-2-yl]methyl]-1H-pyrazol-4-yl]-imidazo[1,2-a]pyrazine;
3-[1-[[2,2-difluorocyclopropyl]methyl]-1H-pyrazol-4-yl]-2-methyl-8-(4-morpholinyl)-imidazo[1,2-a]pyrazine;
3-[1-[1-(methoxymethyl)propyl]-1H-pyrazol-4-yl]-2-methyl-8-(4-morpholinyl)-imidazo[1,2-a]pyrazine;
2-methyl-8-(4-morpholinyl)-3-[1-[tetrahydro-3-furanyl]-1H-pyrazol-4-yl]-imidazo[1,2-a]pyrazine;
2-methyl-8-(4-morpholinyl)-3-[1-[[tetrahydro-2-furanyl]methyl]-1H-pyrazol-4-yl]-imidazo[1,2-a]pyrazine;
3-[1-[3-methoxybutyl]-1H-pyrazol-4-yl]-2-methyl-8-(4-morpholinyl)-imidazo[1,2-a]pyrazine;
3-[1-(2-fluoro ethyl)-1H-pyrazol-4-yl]-2-methyl-8-(4-morpholinyl)-imidazo[1,2-a]pyrazine;
3-[1-(3-fluoropropyl)-1H-pyrazol-4-yl]-2-methyl-8-(4-morpholinyl)-imidazo[1,2-a]pyrazine;
2-methyl-8-(4-morpholinyl)-3-[1-[2-(4-morpholinyl)ethyl]-1H-pyrazol-4-yl]-imidazo[1,2-a]pyrazine;
2-methyl-8-(4-morpholinyl)-3-[1-(2,2,2-trifluoroethyl)-1H-pyrazol-4-yl]-imidazo[1,2-a]pyrazine;
2-methyl-8-(4-morpholinyl)-3-[1-[(tetrahydro-2H-pyran-4-yl)methyl]-1H-pyrazol-4-yl]-imidazo[1,2-a]pyrazine;
3-[1-(2-methoxyethyl)-1H-pyrazol-4-yl]-2-methyl-8-(3-pyridinyl)-imidazo[1,2-a]pyrazine;
3-[1-[2-methoxy-3-methylbutyl]-1H-pyrazol-4-yl]-2-methyl-8-(4-morpholinyl)-imidazo[1,2-a]pyrazine;
2-methyl-3-[1-(2-methylpropyl)-1H-pyrazol-4-yl]-8-(4-pyridinyl)-imidazo[1,2-a]pyrazine;

1-cyclopropyl-2-[4-[2-methyl-8-(4-morpholinyl)imidazo[1,2-a]pyrazin-3-yl]-1H-pyrazol-1-yl]-ethanone;

2-cyclopropyl-3-[1-(2-methoxyethyl)-1H-pyrazol-4-yl]-8-(4-pyridinyl)-imidazo[1,2-a]pyrazine;

2-methyl-8-(4-pyridinyl)-3-[1-(2,2,2-trifluoroethyl)-1H-pyrazol-4-yl]-imidazo[1,2-a]pyrazine;

3-[1-(2-methoxy-2-methylpropyl)-1H-pyrazol-4-yl]-2-methyl-8-(4-pyridinyl)-imidazo[1,2-a]pyrazine;

3-[6-(2-methoxyethyl)-3-pyridinyl]-2-methyl-8-(4-morpholinyl)-imidazo[1,2-a]pyrazine;

4-[2-methyl-8-(4-pyridinyl)imidazo[1,2-a]pyrazin-3-yl]-1H-pyrazole-1-ethanol;

2-methyl-3-[2-(2-methylpropyl)-5-thiazolyl]-8-(4-morpholinyl)-imidazo[1,2-a]pyrazine;

2-methoxy-3-[1-(2-methoxyethyl)-1H-pyrazol-4-yl]-8-(4-morpholinyl)-imidazo[1,2-a]pyrazine;

2-methyl-3-[2-(2-methylpropyl)-4-oxazolyl]-8-(4-morpholinyl)-imidazo[1,2-a]pyrazine;

2-methyl-3-[6-(4-morpholinyl)-3-pyridinyl]-8-(4-pyridinyl)-imidazo[1,2-a]pyrazine;

2-methoxy-3-[1-(2-methoxyethyl)-1H-pyrazol-4-yl]-8-(1-pyrrolidinyl)-imidazo[1,2-a]pyrazine;

3-[6-(2-methoxyethyl)-3-pyridinyl]-2-methyl-8-(4-pyridinyl)-imidazo[1,2-a]pyrazine;

2-methyl-3-[6-(1-methylethoxy)-3-pyridinyl]-8-(4-morpholinyl)-imidazo[1,2-a]pyrazine;

2-methyl-8-(4-morpholinyl)-3-[6-(4-morpholinyl)-3-pyridinyl]-imidazo[1,2-a]pyrazine;

2-methyl-3-[2-(1-methylethoxy)-4-pyridinyl]-8-(4-morpholinyl)-imidazo[1,2-a]pyrazine;

2-cyclopropyl-3-[1-(2-methoxy-2-methylpropyl)-1H-pyrazol-4-yl]-8-(4-pyridinyl)-imidazo[1,2-a]pyrazine;

2-methyl-8-(4-morpholinyl)-3-[6-(2,2,2-trifluoroethoxy)-3-pyridinyl]-imidazo[1,2-a]pyrazine;

3-[1-(2-methoxyethyl)-1H-pyrazol-4-yl]-2-methyl-8-(4-morpholinyl)-6-(3,3,3-trifluoropropyl)-imidazo[1,2-a]pyrazine, 3-[6-(2-methoxy-2-methylpropoxy)-3-pyridinyl]-2-methyl-8-(4-morpholinyl)-imidazo[1,2-a]pyrazine;

3-[6-(cyclopropylmethoxy)-3-pyridinyl]-2-methyl-8-(4-morpholinyl)-imidazo[1,2-a]pyrazine;

3-[6-(2-methoxyethoxy)-3-pyridinyl]-2-methyl-8-(4-morpholinyl)-imidazo[1,2-a]pyrazine;

3-[6-(2-methoxy-2-methylpropoxy)-3-pyridinyl]-2-methyl-8-(4-pyridinyl)-imidazo[1,2-a]pyrazine;

2-methyl-3-[6-(1-methylethyl)-3-pyridinyl]-8-(4-morpholinyl)-imidazo[1,2-a]pyrazine;

2-cyclopropyl-3-[1-(2-methoxy-2-methylpropyl)-1H-pyrazol-4-yl]-8-(4-morpholinyl)-imidazo[1,2-a]pyrazine;

2-cyclopropyl-8-(4-morpholinyl)-3-[1-(2,2,2-trifluoroethyl)-1H-pyrazol-4-yl]-imidazo[1,2-a]pyrazine;

2-cyclopropyl-8-(4-pyridinyl)-3-[1-(2,2,2-trifluoroethyl)-1H-pyrazol-4-yl]-imidazo[1,2-a]pyrazine;

3-[6-(2-methoxyethoxy)-3-pyridinyl]-2-methyl-8-(4-pyridinyl)-imidazo[1,2-a]pyrazine;

2-methyl-8-(4-pyridinyl)-3-[6-(2,2,2-trifluoroethoxy)-3-pyridinyl]-imidazo[1,2-a]pyrazine;

6-cyclopropyl-3-[1-(2-methoxyethyl)-1H-pyrazol-4-yl]-2-methyl-8-(4-morpholinyl)-imidazo[1,2-a]pyrazine;

2-methyl-3-[2-(1-methylethyl)-1H-imidazol-5-yl]-8-(4-morpholinyl)-imidazo[1,2-a]pyrazine;

3-[6-(4-fluorophenyl)-3-pyridinyl]-2-methyl-8-(4-morpholinyl)-imidazo[1,2-a]pyrazine;

2-methyl-8-(4-morpholinyl)-3-[2-(1-pyrrolidinyl)-4-pyridinyl]-imidazo[1,2-a]pyrazine;

3-[6-(2-methoxyethyl)-3-pyridinyl]-2-methyl-8-(4-morpholinyl)-6-(trifluoromethyl)-imidazo[1,2-a]pyrazine;

2-cyclopropyl-3-[6-(2-methoxyethyl)-3-pyridinyl]-8-(4-morpholinyl)-imidazo[1,2-a]pyrazine;

3-[6-(2-methoxyethyl)-3-pyridinyl]-2,6-dimethyl-8-(4-morpholinyl)-imidazo[1,2-a]pyrazine;

3-[6-(2-methoxyethyl)-3-pyridinyl]-8-(4-morpholinyl)-2-(trifluoromethyl)-imidazo[1,2-a]pyrazine;

N-(1-methylethyl)-4-[2-methyl-8-(4-morpholinyl)imidazo[1,2-a]pyrazin-3-yl]-2-pyridinamine;

3-[2-(2-methoxyethyl)-4-pyridinyl]-2-methyl-8-(4-morpholinyl)-imidazo[1,2-a]pyrazine;

3-[6-(2-methoxyethyl)-3-pyridinyl]-2-(1-methylethyl)-8-(4-morpholinyl)-imidazo[1,2-a]pyrazine;

2-methyl-8-(4-morpholinyl)-3-[6-(1-pyrrolidinyl)-3-pyridinyl]-imidazo[1,2-a]pyrazine;

2-methoxy-3-[6-(2-methoxyethyl)-3-pyridinyl]-8-(4-morpholinyl)-imidazo[1,2-a]pyrazine;

3-[6-(2-methoxy-2-methylpropyl)-3-pyridinyl]-2-methyl-8-(4-morpholinyl)-imidazo[1,2-a]pyrazine;

2-methyl-3-(6-methyl-3-pyridinyl)-8-(4-morpholinyl)-imidazo[1,2-a]pyrazine;

2-methyl-3-[6-[2-(1-methylethoxy)ethyl]-3-pyridinyl]-8-(4-morpholinyl)-imidazo[1,2-a]pyrazine;

3-(6-cyclopropyl-3-pyridinyl)-2-methyl-8-(4-morpholinyl)-imidazo[1,2-a]pyrazine;

3-[5-(2-methoxyethyl)-2-pyridinyl]-2-methyl-8-(4-morpholinyl)-imidazo[1,2-a]pyrazine;

3-[6-[(3S)-3-methoxy-1-pyrrolidinyl]-3-pyridinyl]-2-methyl-8-(4-morpholinyl)-imidazo[1,2-a]pyrazine;

N-(1-methylethyl)-5-[2-methyl-8-(4-morpholinyl)imidazo[1,2-a]pyrazin-3-yl]-2-pyridinamine;

2-methyl-8-(4-morpholinyl)-3-[6-(1-piperazinyl)-3-pyridinyl]-imidazo[1,2-a]pyrazine;

2-methyl-8-(4-morpholinyl)-3-[6-(tetrahydro-2H-pyran-4-yl)-3-pyridinyl]-imidazo[1,2-a]pyrazine;

3-[6-(2-ethoxyethyl)-3-pyridinyl]-2-methyl-8-(4-morpholinyl)-imidazo[1,2-a]pyrazine;

3-[6-(1-methoxy-1-methylethyl)-3-pyridinyl]-2-methyl-8-(4-morpholinyl)-imidazo[1,2-a]pyrazine;

2-methyl-3-[2-(2-methylpropyl)-4-pyridinyl]-8-(4-morpholinyl)-imidazo[1,2-a]pyrazine;

3-[6-(1-ethoxy-1-methylethyl)-3-pyridinyl]-2-methyl-8-(4-morpholinyl)-imidazo[1,2-a]pyrazine;

2-methyl-3-[6-(2-methylpropyl)-3-pyridinyl]-8-(4-morpholinyl)-imidazo[1,2-a]pyrazine;

3-[6-(ethoxymethyl)-3-pyridinyl]-2-methyl-8-(4-morpholinyl)-imidazo[1,2-a]pyrazine;

2-methyl-8-(4-morpholinyl)-3-[6-[2-(1-pyrrolidinyl)ethyl]-3-pyridinyl]-imidazo[1,2-a]pyrazine;

5-[2-methyl-8-(4-morpholinyl)imidazo[1,2-a]pyrazin-3-yl]-2-pyridineethanol;

2-methyl-8-(4-morpholinyl)-3-[2-(4-morpholinyl)-4-pyridinyl]-imidazo[1,2-a]pyrazine;

3-[6-(3-methoxypropyl)-3-pyridinyl]-2-methyl-8-(4-morpholinyl)-imidazo[1,2-a]pyrazine;

3-[6-(3-methoxy-3-methylbutyl)-3-pyridinyl]-2-methyl-8-(4-morpholinyl)-imidazo[1,2-a]pyrazine;

2-cyclopropyl-3-[6-(2-methoxyethoxy)-3-pyridinyl]-8-(4-morpholinyl)-imidazo[1,2-a]pyrazine;

2-cyclopropyl-3-[6-(2-methoxy-2-methylpropoxy)-3-pyridinyl]-8-(4-morpholinyl)-imidazo[1,2-a]pyrazine;

2-methyl-8-(4-morpholinyl)-3-[2-(4-morpholinyl)-5-pyrimidinyl]-imidazo[1,2-a]pyrazine;

3-[6-(2-methoxyethyl)-3-pyridinyl]-2-methyl-8-(1-pyrrolidinyl)-imidazo[1,2-a]pyrazine;

3-[6-(2-methoxyethyl)-3-pyridinyl]-2-methyl-8-(3-pyridinyl)-imidazo[1,2-a]pyrazine;

2-cyclopropyl-8-(4-morpholinyl)-3-[6-(4-morpholinyl)-3-pyridinyl]-imidazo[1,2-a]pyrazine;

3-(2-methoxy-5-pyrimidinyl)-2-methyl-8-(4-morpholinyl)-imidazo[1,2-a]pyrazine;

3-(6-ethyl-3-pyridinyl)-2-methyl-8-(4-morpholinyl)-imidazo[1,2-a]pyrazine;

2-cyclopropyl-8-(4-morpholinyl)-3-[6-(tetrahydro-2H-pyran-4-yl)-3-pyridinyl]-imidazo[1,2-a]pyrazine;

2-cyclopropyl-3-[6-(2-methoxy-2-methylpropyl)-3-pyridinyl]-8-(4-morpholinyl)-imidazo[1,2-a]pyrazine;

3-[6-(2-methoxyethyl)-3-pyridinyl]-8-(4-morpholinyl)-imidazo[1,2-a]pyrazine;

2-methoxy-3-[6-(2-methoxy-2-methylpropyl)-3-pyridinyl]-8-(4-morpholinyl)-imidazo[1,2-a]pyrazine;

2-cyclopropyl-8-(4-morpholinyl)-3-[6-(1-piperazinyl)-3-pyridinyl]-imidazo[1,2-a]pyrazine;

2-cyclopropyl-3-(6-ethyl-3-pyridinyl)-8-(4-morpholinyl)-imidazo[1,2-a]pyrazine;

3-[5-fluoro-6-(2-methoxyethyl)-3-pyridinyl]-2-methyl-8-(4-morpholinyl)-imidazo[1,2-a]pyrazine;

3-[2-(2-methoxyethyl)-5-pyrimidinyl]-2-methyl-8-(4-morpholinyl)-imidazo[1,2-a]pyrazine;

2-methyl-8-(4-morpholinyl)-3-(1H-pyrazol-4-yl)-imidazo[1,2-a]pyrazine; and 3-(6-ethoxy-5-fluoro-3-pyridinyl)-2-methyl-8-(4-morpholinyl)-imidazo[1,2-a]pyrazine; and the stereoisomeric forms, acid addition salts and solvates thereof.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Conversely, said salt forms can be converted into the free base form by treatment with an appropriate base.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxyethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Conversely, said salt forms can be converted into the free acid forms by treatment with an appropriate acid.

The term solvate comprises the solvent addition forms as well as the salts thereof, which the compounds of formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{3}H$, $^{11}C$, $^{18}F$, $^{122}I$, $^{123}I$, $^{125}I$, $^{131}I$, $^{74}Br$, $^{76}Br$, $^{77}Br$ and $^{82}Br$. Preferably, the radioactive isotope is selected from the group of $^{3}H$, $^{11}C$ and $^{18}F$.

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

The preparation of some typical examples is shown below.

Preparation

A compound of Formula (I) wherein $R^1$, $R^3$, $R^4$ and $R^5$ are as defined before, $R^2$ is as defined before except cyano and Het is pyridinyl, can be prepared by reacting a compound of Formula (II)

(II)

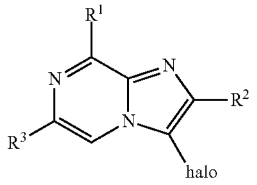

wherein $R^1$ and $R^3$ are as defined before, $R^2$ is as defined before except cyano and halo represents bromo or iodo, with a boronic acid derivative of Formula (III)

(III)

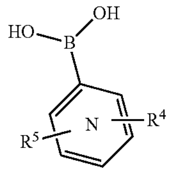

where $R^4$ and $R^5$ are as defined before, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

Alternatively, compounds of Formula (I) wherein $R^1$, $R^3$, $R^4$ and $R^5$ are as defined before, $R^2$ is as defined before except cyano and Het is pyridinyl, can also be prepared by reacting a compound of Formula (II) wherein $R^1$ and $R^3$ are as defined before, $R^2$ is as defined before except cyano and halo represents bromo or iodo, with a boronate derivative of Formula (IV)

(IV)

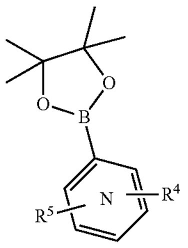

where $R^4$ and $R^5$ are as defined before, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A compound of Formula (I) wherein $R^1$, $R^3$, $R^4$ and $R^5$ are as defined before, $R^2$ is as defined before except cyano and Het is pyridinyl, can also be prepared by reacting a compound of Formula (II) wherein $R^1$ and $R^3$ are as defined before, $R^2$ is as defined before except cyano and halo represents bromo or iodo, with a stannyl derivative of Formula (V)

(V)

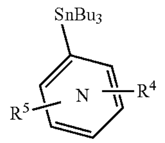

where $R^4$ and $R^5$ are as defined before, in the presence of a suitable catalyst, such as tetrakis(triphenylphosphine)palladium (0), in the presence of a suitable inorganic salt, such as copper (I) bromide, in a suitable inert solvent, such as 1,4-dioxane, under suitable reaction conditions, such as heating at a convenient temperature, either by conventional heating or under microwave irradiation for a period of time to ensure the completion of the reaction.

Alternatively, a compound of Formula (I) wherein $R^1$, $R^4$ and $R^5$ are as defined before, $R^2$ is as defined before except cyano and $R^3$ is hydrogen and Het is pyridinyl, can be prepared by reacting a compound of Formula (VI)

(VI)

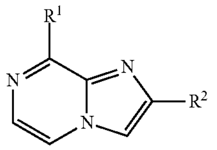

where $R^1$ is as defined before and $R^2$ is as defined before except cyano, with a halopyridine of Formula (VII)

(VII)

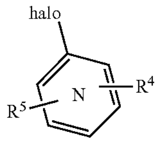

where $R^4$ and $R^5$ are as defined before and halo represents a bromo or iodo, in the presence of a suitable catalyst, such as palladium (II) acetate, in the presence of a suitable phosphine ligand, such as tricyclohexylphosphine, in the presence of a suitable base, such as potassium phosphate, in a suitable inert solvent, such as DMF, under suitable reaction conditions, such as heating at a convenient temperature, either by conventional heating or under microwave irradiation for a period of time to ensure the completion of the reaction.

A compound of Formula (II) wherein $R^1$ is a radical of formula (a-1), (a-2) or (a-3) hereby represented as

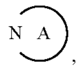, $R^2$ is as defined before except cyano, $R^3$ is $C_{1-4}$alkyl or $C_{3-8}$cycloalkyl and halo represents bromo, can be prepared by reacting a compound of Formula (VIII)

(VIII)

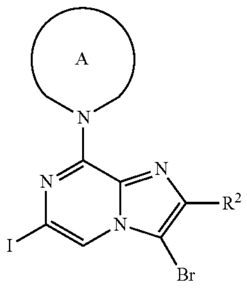

wherein $R^2$ is as defined before except cyano and

is as defined before with a organometallic derivative of Formula $R^3Li$ or $R^3MgBr$ where $R^3$ is $C_{1-4}$alkyl or $C_{3-8}$cycloalkyl, in the presence of a suitable catalyst, such as tetrakis (triphenylphosphine)palladium (0) or palladium (II) acetate, in the presence of a suitable catalyst, such as indium chloride (III), in the presence of a suitable base, such as sodium carbonate or potassium phosphate, in a suitable inert solvent, such as THF, under suitable reaction conditions, such as heating at a convenient temperature, either by conventional heating or under microwave irradiation for a period of time to ensure the completion of the reaction.

A compound of Formula (II) wherein $R^1$ is

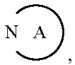
, $R^2$ is as defined before except cyano and $R^3$ is trifluoromethyl$C_{1-3}$alkyl, can be prepared by reacting a compound of Formula (VIII) where $R^2$ is as defined before except cyano and

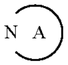

is as defined before, with an organozinc reagent of Formula $Zn(R^3)_2$ where $R^3$ is trifluoromethyl-$C_{1-3}$alkyl in the presence of a suitable catalyst, such as bis(triphenylphosphine)palladium (II) dichloride, in a suitable inert solvent, such as DMF, under suitable reaction conditions, such as heating at a convenient temperature, either by conventional heating or under microwave irradiation for a period of time to ensure the completion of the reaction.

An organozinc reagent of Formula $Zn(R^3)_2$ where $R^3$ is trifluoromethyl$C_{1-3}$alkyl can be prepared in situ by reacting a compound of Formula $R^3$-LG wherein $R^3$ is trifluoromethyl$C_{1-3}$alkyl and LG represents a leaving group, such as halo, e.g. chloro, bromo or iodo, with zinc and 1,2-dibromoethane, in the presence of a suitable chlorosilane derivative, such as chlorotrimethylsilane in a suitable inert solvent, such as DMF and under suitable reaction conditions, such as heating at a convenient temperature, either by conventional heating or under microwave irradiation for a period of time to ensure the completion of the reaction.

Compounds of Formula $R^3$-LG wherein $R^3$ is trifluoromethyl$C_{1-3}$alkyl and LG represents a leaving group, such as halo, e.g. chloro, bromo or iodo, can be obtained commercially.

A compound of Formula (II) wherein $R^1$ is

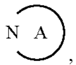
, $R^2$ is as defined before except cyano, $R^3$ is trifluoromethyl and halo represents bromo, can be prepared by reacting a compound of Formula (VIII) wherein $R^2$ is as defined before except cyano with methylfluorosulfonyldifluoroacetate, in the presence of a suitable catalyst, such as copper (I) iodide, in a suitable inert solvent, such as DMF, under suitable reaction conditions, such as heating at a convenient temperature, either by conventional heating or under microwave irradiation for a period of time to ensure the completion of the reaction.

A compound of Formula (VIII) wherein $R^2$ is as defined before except cyano and

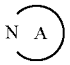

is as defined before can be prepared by reacting a compound of Formula (IX)

(IX)

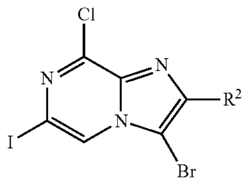

where $R^2$ is as defined before except cyano, with an amine derivative of Formula

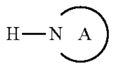

wherein

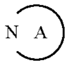

is as defined before, either neat or in a suitable inert solvent, such as ACN, under suitable reaction conditions, such as heating at a convenient temperature, either by conventional heating or under microwave irradiation for a period of time to ensure the completion of the reaction.

A compound of Formula (IX) wherein $R^2$ is as defined before except cyano, can be prepared by reacting an intermediate of Formula (X)

(X)

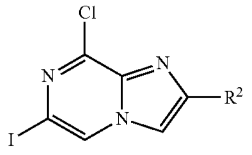

where $R^2$ is as defined before except cyano with N-bromo-succinimide in a suitable inert solvent, such as DCM, under suitable reaction conditions, such as a convenient temperature, typically ranging between −10° C. and 60° C. for a period of time to ensure the completion of the reaction.

A compound of Formula (X) where $R^2$ is as defined before except cyano can be prepared by reacting a compound of Formula (XI)

(XI)

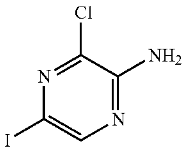

with a compound of Formula (XII)

(XII)

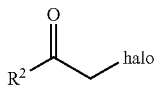

wherein $R^2$ is as defined before except cyano, and halo represents chloro or bromo, either neat or in a suitable inert solvent, such as EtOH, isopropanol or 1,2-dimethoxyethane, under suitable reaction conditions, such as heating at a convenient temperature either by conventional heating or under microwave irradiation for a period of time to ensure the completion of the reaction.

A compound of Formula (XII) where $R^2$ is as defined before except cyano and halo represents chloro or bromo, can be obtained commercially or can be obtained by procedures similar to those described in Gaudry, M.; Marquet, A. Organic Syntheses. 1976, 55.

A compound of Formula (XI) can be prepared by reacting a compound of Formula (XIII)

(XIII)

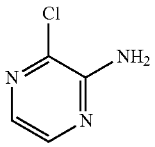

with N-iodo-succinimide in a suitable inert solvent, such as ACN in the presence of a suitable acid such as trifluoroacetic acid, under suitable reaction conditions, such as a convenient temperature, typically ranging between −10° C. and 25° C., for a period of time to ensure the completion of the reaction.

A compound of Formula (II) where $R^1$ is

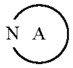, $R^2$ is as defined before except cyano, $R^3$ is hydrogen,

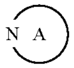

is as defined before and halo represents bromo or iodo, can be prepared by reacting a compound of Formula (XIV)

(XIV)

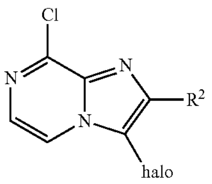

wherein $R^2$ is as defined before except cyano and halo represents bromo or iodo, with an amine derivative of Formula

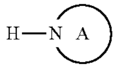

wherein

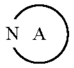

is as defined before, either neat or in a suitable inert solvent, such as ACN, under suitable reaction conditions, such as heating at a convenient temperature, either by conventional heating or under microwave irradiation for a period of time to ensure the completion of the reaction.

A compound of Formula (XIV) wherein $R^2$ is as defined before except cyano and halo represents bromo or iodo, can be prepared by reacting an intermediate of Formula (XV)

(XV)

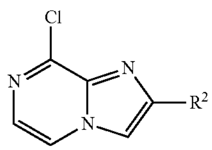

where $R^2$ is as defined before except cyano with N-bromo- or N-iodo-succinimide in a suitable inert solvent, such as DCM, under suitable reaction conditions, such as a convenient temperature, typically ranging between −10° C. and 60° C. for a period of time to ensure the completion of the reaction.

A compound of Formula (XV) where $R^2$ is as defined before except cyano can be prepared by reacting a compound of Formula (XIII) with a compound of Formula (XII) wherein $R^2$ is as defined before except cyano and halo represents chloro or bromo, either neat or in a suitable inert solvent, such as EtOH, isopropanol or 1,2-dimethoxyethane, under suitable reaction conditions, such as heating at a convenient temperature either by conventional heating or under microwave irradiation for a period of time to ensure the completion of the reaction.

A compound of Formula (XII) can be obtained as described before.

A compound of Formula (II) where $R^1$ is pyridinyl, pyridinyl optionally substituted with halogen, $C_{1-4}$alkyl, trifluoromethyl or $C_{1-4}$alkyloxy or tetrahydropyranyl, $R^2$ is as defined before except cyano, $R^3$ is hydrogen and halo represents bromo or iodo, can be prepared by reacting a compound of Formula (VI) wherein $R^1$ is pyridinyl, pyridinyl optionally substituted with halogen, $C_{1-4}$alkyl, trifluoromethyl or $C_{1-4}$alkyloxy or tetrahydropyranyl, $R^2$ is as defined before except cyano, with N-bromo or N-iodo-succinimide in a suitable inert solvent, such as DCM, under suitable reaction conditions, such as a convenient temperature, typically ranging between −10° C. and 60° C. for a period of time to ensure the completion of the reaction.

A compound of Formula (VI) where $R^1$ is pyridinyl or pyridinyl optionally substituted with halogen, $C_{1-4}$alkyl, trifluoromethyl or $C_{1-4}$alkyloxy and $R^2$ is as defined before except cyano, can be prepared by reacting a compound of Formula (XV) where $R^2$ is as defined before except cyano, with a boronic acid derivative of Formula $R^1B(OH)_2$ wherein $R^1$ is pyridinyl or pyridinyl optionally substituted with halogen, $C_{1-4}$alkyl, trifluoromethyl or $C_{1-4}$alkyloxy in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A compound of Formula (VI) wherein $R^1$ is tetrahydropyranyl and $R^2$ is as defined before except cyano, can be prepared by reacting a compound of Formula (XVI)

(XVI)

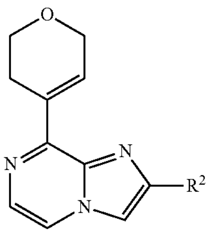

where $R^2$ is as defined before except cyano, with hydrogen in the presence of a suitable catalyst, such as 10% palladium on charcoal, in a suitable inert solvent, such as MeOH or EtOH, under suitable reaction conditions, such as a convenient temperature, typically ranging between 25° C. and 40° C. or with ammonium formate in the presence of a suitable catalyst such as 10% palladium on charcoal, in a suitable inert solvent, such as MeOH, EtOH, EtOAc or DCM or mixtures thereof, under suitable reaction conditions, such as heating at a convenient temperature, typically ranging between 40° C. and 100° C.

A compound of Formula (XVI) where $R^2$ is as defined before except cyano, can be prepared by reacting a compound of Formula (XV) where $R^2$ is as defined before except cyano, with 3,6-dihydro-2H-pyran-4-boronic acid pinacol ester, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

3,6-Dihydro-2H-pyran-4-boronic acid pinacol ester can be obtained by procedures similar to those described in, Qiu, Y. et al. WO 2004075846 A2.

A compound of Formula (VI) where $R^1$ is

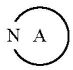, and $R^2$ is as defined before except cyano, can be prepared by reacting a compound of Formula (XV) wherein $R^2$ is as defined before except cyano, with a reagent of Formula

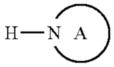, where

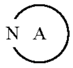

is as defined before, either neat or in a suitable inert solvent, such as ACN, under suitable reaction conditions, such as heating at a convenient temperature, either by conventional heating or under microwave irradiation for a period of time to ensure the completion of the reaction.

Alternatively, a compound of Formula (II) where $R^1$ is

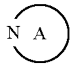, $R^2$ is $C_{1-4}$alkyloxy, and $R^3$ is hydrogen, halo represents bromo or iodo, can also be prepared by reacting a compound of Formula (VIa)

(VIa)

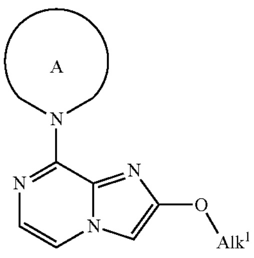

where

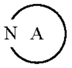

is as defined before and $Alk^1$ represents $C_{1-4}$alkyl group, with N-bromo- or N-iodo-succinimide in a suitable inert solvent, such as DCM, under suitable reaction conditions, such as a convenient temperature, typically ranging between −10° C. and 25° C., for a period of time to ensure the completion of the reaction.

A compound of Formula (VIa) where

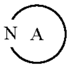

is as defined before and $Alk^1$ is $C_{1-4}$alkyl, can be prepared by reacting compound of Formula (XVII)

(XVII)

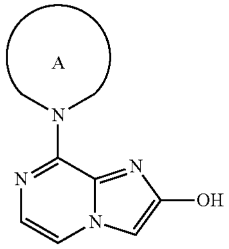

where

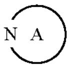

is as defined before with a reagent of Formula $Alk^1$-LG wherein $Alk^1$ is $C_{1-4}$alkyl and LG represents a leaving group such as halo, e.g. chloro, bromo or iodo, in the presence of a suitable base, such as cesium carbonate, in a suitable inert solvent, such as DMF, under suitable reaction conditions, such as heating at a convenient temperature either by conventional heating or under microwave irradiation for a period of time to ensure the completion of the reaction.

A compound of Formula $Alk^1$-LG wherein $Alk^1$ is $C_{1-4}$alkyl and LG represents a leaving group, such as halo, e.g. chloro, bromo or iodo, can be obtained commercially.

A compound of Formula (XVII) wherein

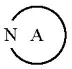

is as defined before can be prepared by reacting a compound of Formula (XVIII)

(XVIII)

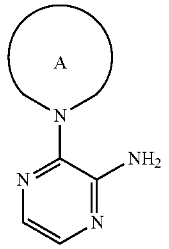

wherein

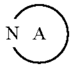

is as defined before, with bromoacetic acid in a suitable inert solvent such as isopropanol, under suitable reaction conditions, such as heating at a convenient temperature, either by conventional heating or under microwave irradiation for a period of time to ensure the completion of the reaction.

A compound of Formula (XVIII), wherein

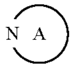

is as defined before can be obtained commercially or can be prepared by reacting a compound of Formula (XIII), with a reagent of Formula

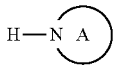, where

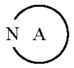

is as defined before, either neat or in a suitable inert solvent, such as ACN, under suitable reaction conditions, such as heating at a convenient temperature, either by conventional heating or under microwave irradiation for a period of time to ensure the completion of the reaction.

A compound of Formula (Ia)

(Ia)

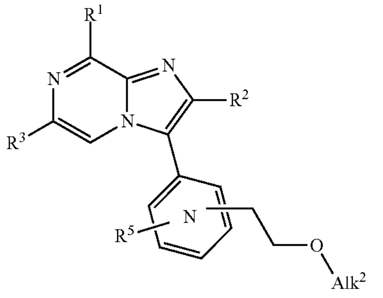

wherein $R^1$, $R^3$ and $R^5$ are as defined before, $R^2$ is as defined before except cyano, $R^4$ is $Alk^2$-oxyethyl and $Alk^2$ is $C_{1-4}$alkyl, can be prepared by reacting a compound of (XIX)

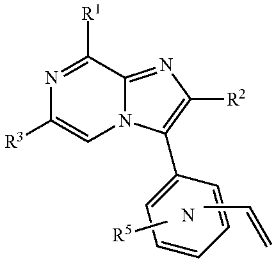

where $R^1$, $R^3$ and $R^5$ are as defined before and $R^2$ is as defined before except cyano, with an alcohol derivative of Formula $Alk^2$-OH wherein $Alk^2$ is $C_{1-4}$alkyl, in the presence of a suitable base, such as the sodium or potassium salt of the corresponding alcohol, in a suitable inert solvent, such as the corresponding alcohol, under suitable reaction conditions, such as heating at a convenient temperature, either by conventional heating or under microwave irradiation for a period of time to ensure the completion of the reaction.

Alternatively, a compound of Formula (Ia) wherein $R^1$, $R^3$ and $R^5$ are as defined before, $R^2$ is as defined before except cyano, $R^4$ is $Alk^2$-oxyethyl and $Alk^2$ is $C_{1-4}$alkyl, can be prepared by reacting a compound of Formula (XIX), where $R^1$, $R^3$ and $R^5$ are as defined before, $R^2$ is as defined before except cyano, with an alcohol derivative of Formula $Alk^2$-OH wherein $Alk^2$ is $C_{1-4}$alkyl, in the presence of a suitable acid, such as potassium hydrogensulfate, in a suitable inert solvent, such as the corresponding alcohol, under suitable reaction conditions, such as heating at a convenient temperature, either by conventional heating or under microwave irradiation for a period of time to ensure the completion of the reaction.

An alcohol of Formula $Alk^2$-OH can be obtained commercially or alternatively can also be prepared by procedures similar to those described in Morel, P. US 2008102028A1.

A compound of Formula (Ib)

(Ib)

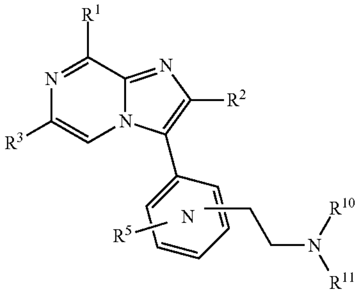

wherein $R^1$, $R^3$ and $R^5$ are as defined before, $R^2$ is as defined before except cyano, $R^4$ is $NR^{10}R^{11}$ ethyl and $R^{10}$ and $R^{11}$ are as defined before, can be prepared by reacting a compound of Formula (XIX) where $R^1$, $R^3$ and $R^5$ are as defined before and $R^2$ is as defined before except cyano, with a reagent of Formula $R^{10}R^{11}NH$, where $R^{10}$ and $R^{11}$ are as defined before, in the presence of a suitable base, such as sodium tert-butoxide, in a suitable inert solvent, such as THF, under suitable reaction conditions, such as heating at a convenient temperature, either by conventional heating or under microwave irradiation for a period of time to ensure the completion of the reaction.

A compound of Formula (I) wherein $R^1$, $R^3$ and $R^5$ are as defined before, $R^2$ is as defined before except cyano and $R^4$ is ethyl can be prepared by reacting a compound of Formula (XIX) where $R^1$, $R^3$ and $R^5$ are as defined before and $R^2$ is as defined before except cyano, with hydrogen in the presence of a suitable catalyst such as 10% palladium on charcoal, in a suitable inert solvent such as MeOH, under suitable reaction conditions, such as heating at a convenient temperature, typically ranging between 25° C. and 40° C.

A compound of Formula (XIX) where $R^1$, $R^3$ and $R^5$ are as defined before and $R^2$ is as defined before except cyano, can be prepared by reacting a compound of Formula (XX)

(XX)

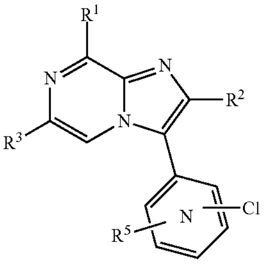

where $R^1$, $R^3$ and $R^5$ are as defined before, $R^2$ is as defined before except cyano, with a compound of Formula (XXI)

(XXI)

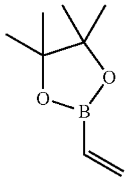

in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A compound of Formula (Ic) wherein $R^1$, $R^3$ and $R^5$ are as defined before, $R^2$ is as defined before except cyano, $R^4$ is tetrahydropyranyl and Het is pyridinyl, can also be prepared by reacting a compound of Formula (XXII)

(XXII)

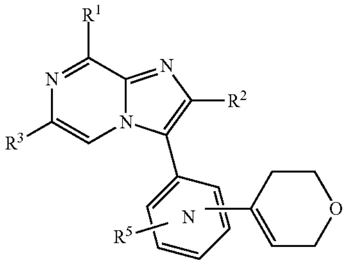

where $R^1$, $R^3$ and $R^5$ are as defined before and $R^2$ is as defined before except cyano, with hydrogen in the presence of a suitable catalyst such as 10% palladium on charcoal, in a suitable inert solvent such as MeOH, under suitable reaction conditions, such as heating at a convenient temperature, typically ranging between 25° C. and 40° C. or with ammonium formate in the presence of a suitable catalyst such as 10% palladium on charcoal, in a suitable inert solvent, such as MeOH, EtOH, EtOAc or DCM or mixtures thereof, under suitable reaction conditions, such as heating at a convenient temperature, typically ranging between 40° C. and 100° C.

A compound of Formula (XXII) wherein $R^1$, $R^3$ and $R^5$ are as defined before and $R^2$ is as defined before except cyano, can be prepared by reacting a compound of Formula (XX) wherein $R^1$, $R^2$, $R^3$ and $R^5$ are as defined before, with 3,6-dihydro-2H-pyran-4-boronic acid pinacol ester, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

3,6-Dihydro-2H-pyran-4-boronic acid pinacol ester can be obtained as described before.

A compound of Formula (Id)

(Id)

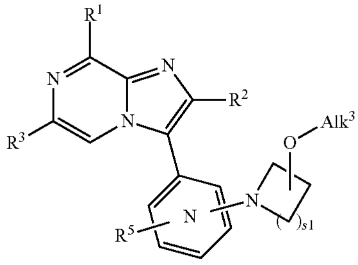

wherein $R^1$, $R^3$, $R^5$ are as defined before, $R^2$ is as defined before except cyano, $R^4$ is a radical of Formula (b-1), s1 is as defined before and $Alk^3$ is $C_{1-4}$alkyl, can be prepared by reacting a compound of Formula (XXIII)

(XXIII)

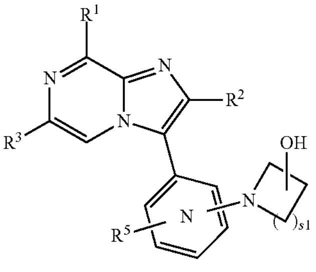

where $R^1$, $R^3$ and $R^5$ are as defined before, $R^2$ is as defined before except cyano and s1 is as defined before with a reagent of Formula $Alk^3$-LG where $Alk^3$ is $C_{1-4}$alkyl and LG represents a leaving group, such as halo, e.g. chloro, bromo or iodo, or a sulfonyloxy group, e.g. methylsulfonyloxy, trifluoromethylsulfonyloxy, or methylphenylsulfonyloxy, in the presence of a suitable base, such as sodium tert-butoxide, in the presence of a suitable crown ether, such as 18-crown-6, in a suitable inert solvent, such as THF, under suitable reaction conditions, such as heating at a convenient temperature, typically ranging from 25° C. to 80° C.

A reagent of Formula $Alk^3$-LG where $Alk^3$ is $C_{1-4}$alkyl and LG represents a leaving group, such as halo, e.g. chloro, bromo or iodo can be obtained commercially.

A compound of Formula (I) wherein $R^1$, $R^3$ and $R^5$ are as defined before, $R^2$ is as defined before except cyano, $R^4$ is $NR^{10}NR^{10}R^{11}$ and $R^{10}$ and $R^{11}$ are as defined before, can be prepared by reacting a compound of Formula (XX) where $R^1$, $R^3$ and $R^5$ are as defined before, $R^2$ is as defined before except cyano and the chlorine atom is ortho to the pyridinyl nitrogen, with a reagent of Formula $R^{10}R^{11}NH$ where $R^{10}$ and $R^{11}$ are as defined before, either neat or in a suitable inert solvent, such as ACN, under suitable reaction conditions, such as heating at a convenient temperature, either by conventional heating or under microwave irradiation for a period of time to ensure the completion of the reaction.

Alternatively, a compound of Formula (I) wherein $R^1$, $R^3$ and $R^5$ are as defined before, $R^2$ is as defined before except cyano, $R^4$ is $NR^{10}R^{11}$ and $R^{10}$ and $R^{11}$ are as defined before, can also be prepared by reacting a compound of Formula (XX) where $R^1$, $R^3$ and $R^5$ are as defined before, $R^2$ is as defined before except cyano and the chlorine atom is ortho to the pyridinyl nitrogen with a reagent of Formula R where $R^{10}$ and $R^{11}$ are as defined before, in the presence of a suitable catalyst, such as palladium (II) acetate, in the presence of a suitable phosphine ligand, such as racemic-2,2'-bis(diphenylphosphino)-1,1'-binaphthyl and in the presence of a suitable base, such as cesium carbonate, in a suitable inert solvent, such as toluene, under suitable reaction conditions, such as heating at a convenient temperature, either by conventional heating or under microwave irradiation for a period of time to ensure the completion of the reaction.

A compound of Formula (I) wherein $R^1$, $R^3$ and $R^5$ are as defined before, $R^2$ is as defined before except cyano, $R^4$ is $C_{1-4}$alkyl or $C_{3-8}$cycloalkyl and Het is pyridinyl, can also be prepared by reacting a compound of Formula (XX) where $R^1$, $R^3$ and $R^5$ are as defined before, $R^2$ is as defined before except cyano, and the chlorine atom is ortho to the pyridinyl nitrogen, with a Grignard reagent of Formula $R^4$Mghalo, where $R^4$ is $C_{1-4}$alkyl or $C_{3-8}$cycloalkyl and halo represents a chloro, bromo or iodo, in the presence of a suitable catalyst, such as [1,3-bis(diphenylphosphino)propane]dichloronickel (II), in a suitable inert solvent, such as a THF, under suitable reaction conditions, such as a convenient temperature, typically ranging between −10° C. and 15° C.

A Grignard reagent of Formula $R^4$Mghalo where is $C_{1-4}$alkyl or $C_{3-8}$cycloalkyl and halo represents chloro, bromo or iodo, can be obtained commercially.

A compound of Formula (I) wherein $R^1$, $R^3$ and $R^5$ are as defined before, $R^2$ is as defined before except cyano, and $R^4$ is $C_{1-4}$alkyloxy$C_{1-6}$alkyl, $C_{1-4}$alkyl or $C_{3-8}$cycloalkyl and Het is pyridinyl, can also be prepared by reacting a compound of Formula (XX) where $R^1$, $R^3$ and $R^5$ are as defined before, $R^2$ is as defined before except cyano and the chlorine atom is ortho to the pyridinyl nitrogen, with an organozinc reagent of Formula $Zn(R^4)_2$ where $R^4$ is $C_{1-4}$alkyloxy$C_{1-6}$alkyl, $C_{1-4}$alkyl or $C_{3-8}$cycloalkyl, in the presence of a suitable catalyst, such as tetrakis(triphenylphosphine)palladium (0), in a suitable inert solvent, such as THF, under suitable reaction conditions, such as heating at a convenient temperature, either by conventional heating or under microwave irradiation for a period of time to ensure the completion of the reaction.

A reagent of Formula $Zn(R^4)_2$ wherein $R^4$ is $C_{1-4}$alkyloxy$C_{1-6}$alkyl, $C_{1-4}$alkyl or $C_{3-8}$cycloalkyl, can be obtained commercially or alternatively can also be prepared by reacting a compound of Formula $R^4$-halo wherein $R^4$ is $C_{1-4}$alkyloxy$C_{1-6}$alkyl, $C_{1-4}$alkyl or $C_{3-8}$cycloalkyl and halo represents iodo, with zinc and 1,2-dibromoethane, in the presence of a suitable chlorosilane derivative, such as chlorotrimethylsilane in a suitable inert solvent, such as DMF and under suitable reaction conditions, such as heating at a convenient temperature, typically ranging between 25° C. and 100° C.

A reagent of Formula $R^4$-halo wherein $R^4$ is $C_{1-4}$alkyloxy$C_{1-6}$alkyl, $C_{1-4}$alkyl or $C_{3-8}$cycloalkyl and halo represents iodo can be obtained commercially or alternatively can also be prepared by reacting a compound of Formula $R^4$-halo wherein $R^4$ is $C_{1-4}$alkyloxy$C_{1-6}$alkyl, $C_{1-4}$alkyl or $C_{3-8}$cycloalkyl and halo represents chloro or bromo with sodium iodide in a suitable inert solvent, such as acetone, under suitable reaction conditions such as a convenient temperature, typically ranging between 25° C. and 40° C.

A compound of Formula $R^4$-halo wherein $R^4$ is $C_{1-4}$alkyloxy$C_{1-6}$alkyl, $C_{1-4}$alkyl or $C_{3-8}$cycloalkyl and halo represents chloro or bromo, can be obtained commercially.

Alternatively, a compound of Formula (I) wherein $R^1$, $R^3$ and $R^5$ are as defined before, $R^2$ is as defined before except cyano, $R^4$ is $C_{1-4}$alkyl or $C_{3-8}$cycloalkyl, phenyl or phenyl optionally substituted with halogen, $C_{1-4}$alkyl, trifluoromethyl, trifluoromethoxy, cyano or $C_{1-4}$alkyloxy and Het is pyridinyl can also be prepared by reacting a compound of Formula (XX) where $R^1$, $R^3$ and $R^5$ are as defined before, $R^2$ is as defined before except cyano and the chlorine atom is ortho to the pyridinyl nitrogen with a boronic acid derivative of Formula $R^4B(OH)_2$, where $R^4$ is $C_{1-4}$alkyl, $C_{3-8}$cycloalkyl, phenyl or phenyl optionally substituted with halogen, $C_{1-4}$alkyl, trifluoromethyl, trifluoromethoxy, cyano or $C_{1-4}$alkyloxy, in the presence of a suitable catalyst, such as palladium (II) acetate, in the presence of a suitable phosphine ligand, such as triphenylphosphine or 2-dicyclohexylphosphino-2',6'-dimethoxybiphenyl, in the presence of a suitable base, such as potassium phosphate, in a suitable inert solvent, such as a toluene, under suitable reaction conditions, such as heating at a convenient temperature, either by conventional heating or under microwave irradiation for a period of time to ensure the completion of the reaction.

A boronic acid derivative of Formula $R^4B(OH)_2$ where $R^4$ is $C_{1-4}$alkyl, $C_{3-8}$cycloalkyl, phenyl or phenyl optionally substituted with halogen, $C_{1-4}$alkyl, trifluoromethyl, trifluoromethoxy, cyano or $C_{1-4}$alkyloxy can be obtained commercially or prepared by procedures known by those skilled in the art.

A compound of Formula (XX) where $R^1$, $R^3$ and $R^5$ are as defined before and $R^2$ is as defined before except cyano, can be prepared by reacting a compound of Formula (II) wherein $R^1$ and $R^3$ are as defined before, $R^2$ is as defined before except cyano and halo represents bromo or iodo, with a boronic acid derivative of Formula (XXIV)

(XXIV)

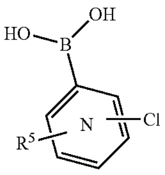

where $R^5$ is as defined before, in the presence of a suitable catalyst, such as tetrakis(triphenylphosphine)palladium (0), in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction.

A boronic acid derivative of Formula (XXIV) where $R^5$ is as defined before, can be obtained commercially or alternatively can also be prepared by reacting a halopyridine of Formula (XXV)

(XXV)

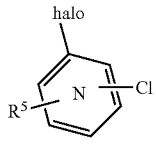

where $R^5$ is as defined before and halo represents bromo or iodo, with triisopropyl borate, in the presence of a suitable base, such as n-buthyllithium in the presence of a suitable diamine such as N,N,N',N'-tetramethylenediamine, in a suitable inert solvent such as $Et_2O$, under suitable reaction conditions, such as a convenient temperature, typically ranging between −78° C. and 25° C.

A halopyridine of Formula (XXV) where $R^5$ is as defined before and halo represents bromo or iodo, can be obtained commercially.

A compound of Formula (II) can be obtained as described before.

Alternatively, a compound of Formula (XX) where $R^1$ and $R^3$ are as defined before, $R^2$ is as defined before except cyano and $R^5$ is fluoro, can be prepared by reacting a compound of Formula (Ie)

(Ie)

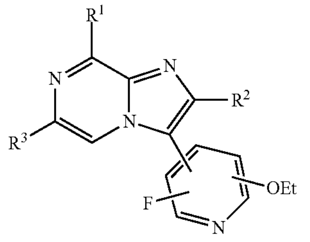

wherein $R^1$ and $R^3$ are as defined before, $R^2$ is as defined before except cyano, $R^4$ is ethyloxy and ortho to the pyridinyl nitrogen and $R^5$ is fluoro, with phosphorus oxychloride in the presence of a suitable base such as N,N-diisopropylethylamine, in a suitable inert solvent such as ACN, under suitable reaction conditions, such as heating at a convenient temperature, either by conventional heating or under microwave irradiation for a period of time to ensure the completion of the reaction.

A boronic acid of Formula (III) wherein $R^4$ and $R^5$ are as defined before, can be obtained commercially. Alternatively, a boronic acid of Formula (III) wherein $R^4$ and $R^5$ are as defined before, can also be prepared by reacting a halopyridine of Formula (VII) wherein $R^4$ and $R^5$ are as defined before and halo represents bromo or iodo, with triisopropyl borate, in the presence of a suitable base, such as n-buthyllithium, in a suitable inert solvent, such as THF, under suitable reaction conditions, such as a convenient temperature, typically ranging between −78° C. and 25° C.

A boronate derivative of Formula (IV) wherein $R^4$ and $R^5$ are as defined before, can be obtained commercially. Alternatively, a compound of Formula (IV) wherein $R^4$ and $R^5$ are as defined before, can also be prepared by reacting a halopyridine of Formula (VII) wherein $R^4$ and $R^5$ are as defined before and halo represents bromo or iodo, with bis(pinacolato)diboron in the presence of a suitable catalyst, such as [1,1'-bis(diphenylphosphino)ferrocene]dichloropalladium (II), in the presence of a suitable base, such as potassium acetate, in a suitable inert solvent, such as DMF or dimethyl sulfoxide, under suitable reaction conditions, such as heating at a convenient temperature, either by conventional heating or under microwave irradiation for a period of time to ensure the completion of the reaction.

A stannyl derivative of Formula (V) wherein $R^4$ and $R^5$ are as defined before, can be prepared by reacting a halopyridine of Formula (VII), wherein $R^4$ and $R^5$ are as defined before and halo represents bromo or iodo, with tributyltin chloride, in the presence of a suitable base, such as n-buthyllithium, in a suitable inert solvent, such as THF, under suitable reaction conditions, such as a convenient temperature, typically ranging between −78° C. and 25° C.

A halopyridine of Formula (VII) wherein $R^4$ and $R^5$ are as defined before and halo represents bromo or iodo, can be obtained commercially. Alternatively, a compound of Formula (VII) wherein $R^4$ is $C_{1-4}$alkyloxy, $C_{1-4}$alkyloxy$C_{1-4}$ alkyloxy or $C_{3-8}$cycloalkyl$C_{1-4}$alkyloxy, $R^5$ is as defined before and halo represents bromo or iodo, can be prepared by reacting a halopyridine of Formula (XXV) where $R^5$ is as defined before, halo represents bromo or iodo and the chlorine atom is ortho to the pyridinyl nitrogen, with a reagent of Formula $Alk^4$-OH, where $Alk^4$ is $C_{1-4}$alkyl, $C_{1-4}$alkyloxy-$C_{1-4}$ alkyl or $C_{3-8}$cycloalkyl$C_{1-4}$alkyl in the presence of a suitable base, such as sodium hydride, in a suitable inert solvent, such as DMF or DMSO, under suitable reaction conditions, such as heating at a convenient temperature, either by conventional heating or under microwave irradiation for a period of time to ensure the completion of the reaction.

A reagent of Formula $Alk^4$-OH wherein $Alk^4$ is $C_{1-4}$alkyl, $C_{1-4}$alkyloxy$C_{1-4}$alkyl or $C_{3-8}$cycloalkyl$C_{1-4}$alkyl, can be obtained commercially or alternatively can also be prepared by procedures similar to those described in Morel, P. US 2008102028 A1.

A compound of Formula (VII) wherein $R^4$ is $NR^{10}R^{11}$ and $R^5$ is as defined before can also be prepared by reacting a halo pyridine of Formula (XXV) where $R^5$ is as defined before, halo represents bromo or iodo and the chlorine atom is ortho to the pyridinyl nitrogen, with a compound of Formula $R^{10}R^{11}NH$, wherein $R^{10}$ and $R^{11}$ are as defined before, either neat or in a suitable inert solvent, such as ACN, under suitable reaction conditions, such as heating at a convenient temperature, either by conventional heating or under microwave irradiation for a period of time to ensure the completion of the reaction.

A halopyridine of Formula (VII) wherein $R^4$ is $C_{1-4}$alkyloxy$C_{1-6}$alkyl, $C_{1-4}$alkyl or $C_{3-8}$cycloalkyl, $R^5$ is as defined before and halo represents bromo can be prepared by reacting a halopyridine of Formula (XXVI)

(XXVI)

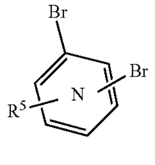

where $R^5$ is as defined before and one of the bromine atoms is ortho to the pyridinyl nitrogen, with an organozinc reagent of Formula $Zn(R^4)_2$ where $R^4$ is $C_{1-4}$alkyloxy-$C_{1-6}$alkyl, $C_{1-4}$alkyl or $C_{3-8}$cycloalkyl, in the presence of a suitable catalyst, such as tetrakis(triphenylphosphine)palladium (0), in a suitable inert solvent, such as THF, under suitable reaction conditions, such as heating at a convenient temperature, either by conventional heating or under microwave irradiation for a period of time to ensure the completion of the reaction.

A reagent of Formula $Zn(R^4)_2$ wherein $R^4$ is $C_{1-4}$alkyloxy$C_{1-6}$alkyl, $C_{1-4}$alkyl or $C_{3-8}$cycloalkyl can be obtained as described before.

A compound of Formula (VII) wherein $R^4$ is $C_{1-4}$alkyloxy$C_{1-6}$alkyl, $R^5$ is as defined before and halo represents bromo can be prepared by reacting a compound of Formula (VIIa)

(VIIa)

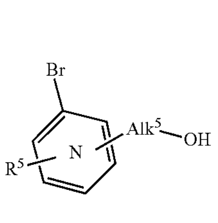

wherein $R^5$ is as defined before and $Alk^5$ is $C_{1-4}$alkyl, with a reagent of Formula $Alk^6$-LG wherein $Alk^6$ is $C_{1-6}$alkyl and LG represents a leaving group, such as halo, e.g. chloro, bromo or iodo, or a sulfonyloxy group, e.g. methylsulfonyloxy, trifluoromethylsulfonyloxy, or methylphenylsulfonyloxy, in the presence of a base, such as sodium hydride or sodium tert-butoxyde, in the presence of a suitable crown ether, such as 18-crown-6, in a suitable inert solvent, such as THF and under suitable reaction conditions, such as heating at a convenient temperature, typically ranging from 0° C. to 40° C.

Reagents of Formula $Alk^6$-LG wherein $Alk^6$ is $C_{1-6}$alkyl and LG represents a leaving group, such as halo, e.g. chloro, bromo or iodo, or a sulfonyloxy group, e.g. methylsulfonyloxy, trifluoromethylsulfonyloxy, or methylphenylsulfonyloxy, can be obtained commercially.

A compound of Formula (VIIb)

(VIIb)

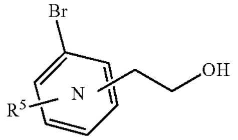

wherein $R^5$ is as defined before, can be prepared by reacting a methylpyridine of Formula (VIIc)

(VIIc)

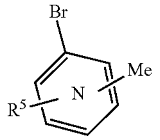

wherein $R^5$ is as defined before and the methyl group is ortho to the pyridinyl nitrogen, with DMF in the presence of a suitable base, such as lithium diisopropylamide, in a suitable inert solvent, such as THF, under suitable reaction conditions, such as a convenient temperature, typically ranging between −78° C. and −10° C., followed by in situ reaction with sodium borohydride in a suitable inert solvent, such as MeOH, under suitable reaction conditions, such as a convenient temperature, typically ranging between −10° C. and 40° C.

A compound of Formula (VIId)

(VIId)

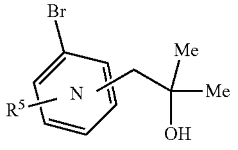

wherein $R^5$ is as defined before, can be prepared by reacting a methylpyridine of Formula (VIIc), wherein $R^5$ is as defined before, halo represents bromo or iodo and the methyl group is ortho to the pyridinyl nitrogen, with acetone in the presence of a suitable base, such as lithium diisopropylamide, in a suitable inert solvent, such as THF, under suitable reaction conditions, such as a convenient temperature, typically ranging between −78° C. and −10° C.

A methylpyridine of Formula (VIIc) wherein $R^5$ is as defined before, can be obtained commercially.

A compound of Formula (VIId)

(VIId)

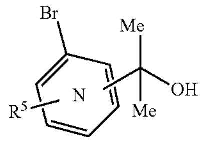

wherein $R^5$ is as defined before, can be prepared by reacting a compound of Formula (XXVI) where $R^5$ is as defined before, with acetone, in the presence of a suitable base, such as n-buthyllithium, in a suitable inert solvent, such as toluene, under suitable reaction conditions, such as a convenient temperature, typically ranging between −78° C. and 25° C.

A compound of Formula (Vile)

(VIIe)

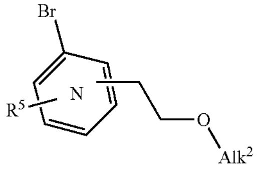

wherein $R^5$ is as defined before and $Alk^2$ is $C_{1-4}$alkyl, can be prepared by reacting a compound of Formula (XXVII)

(XXVII)

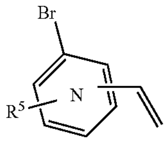

where $R^5$ is as defined before, with an alcohol of Formula $Alk^2$-OH wherein $Alk^2$ represents $C_{1-4}$alkyl, in the presence of a suitable base, such as the sodium or potassium salt of the corresponding alcohol, in a suitable inert solvent, such as the corresponding alcohol, under suitable reaction conditions, such as heating at a convenient temperature, either by conventional heating or under microwave irradiation for a period of time to ensure the completion of the reaction.

Alternatively, a compound of Formula (VIIe) wherein $R^5$ is as defined before and $Alk^2$ is $C_{1-4}$alkyl, can also be prepared by reacting a compound of Formula (XXVII) where $R^5$ is as defined before, with an alcohol of Formula $Alk^2$-OH wherein $Alk^2$ represents $C_{1-4}$alkyl, in the presence of a suitable acid, such as potassium hydrogensulfate, in a suitable inert solvent, such as the corresponding alcohol, under suitable reaction conditions, such as heating at a convenient temperature, either by conventional heating or under microwave irradiation for a period of time to ensure the completion of the reaction.

An alcohol of Formula $Alk^2$-OH can be obtained as described before.

A compound of Formula (XXVII) where $R^5$ is as defined before, can be prepared by reacting a compound of Formula (XXVI) wherein $R^5$ is as defined before and one of the bromine atoms is ortho to the pyridinyl nitrogen, with a vinylboronic acid pinacol ester of Formula (XXI) in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A vinylboronic acid pinacol ester of Formula (XXI) can be obtained as described before.

A compound of Formula (XXVI) wherein $R^5$ is as defined before, can be obtained commercially.

Alternatively, a compound of Formula (VIIe) wherein $R^5$ is as defined before, $Alk^2$ is methyl, can also be obtained by reacting a compound of Formula (XXVIII)

(XXVIII)

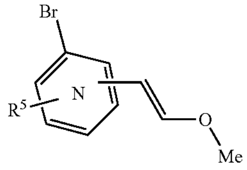

where $R^5$ is as defined before, with hydrogen in the presence of a suitable catalyst, such as 5% rhodium on charcoal, in a suitable inert solvent, such as EtOH, under suitable reaction conditions, such as a convenient temperature, typically ranging between 25° C. and 40° C.

A compound of Formula (XXVIII) where $R^5$ is as defined before, can be obtained by reacting a compound of Formula (XXIX)

(XXIX)

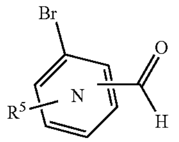

where $R^5$ is as defined before, with (methoxymethyl)triphenylphosphonium chloride, in the presence of a suitable base, such as n-buthyllithium, in a suitable inert solvent, such as THF, under suitable reaction conditions, such as a convenient temperature, typically ranging between −78° C. and 25° C.

A compound of Formula (XXIX) where $R^5$ is as defined before, can be obtained commercially.

A compound of Formula (If)

(If)

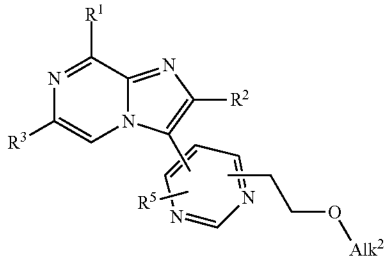

wherein $R^1$, $R^3$ and $R^5$ are as defined before, $R^2$ is as defined before except cyano, $R^4$ is $Alk^2$-oxyethyl, Het is pyrimidinyl and $Alk^2$ is $C_{1-4}$alkyl, can be prepared by reacting a compound of Formula (XXX)

(XXX)

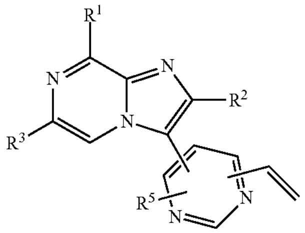

where $R^1$, $R^3$ and $R^5$ are as defined before and $R^2$ is as defined before except cyano, with an alcohol of Formula $Alk^2$-OH wherein $Alk^2$ is $C_{1-4}$alkyl, in the presence of a suitable acid, such as sodium hydrogensulfate, in a suitable inert solvent, such as the corresponding alcohol, under suitable reaction conditions, such as heating at a convenient temperature, either by conventional heating or under microwave irradiation for a period of time to ensure the completion of the reaction.

An alcohol of Formula $Alk^2$-OH where $Alk^2$ is $C_{1-4}$alkyl, can be obtained as described before.

A compound of Formula (XXX) where $R^1$, $R^3$ and $R^5$ are as defined before and $R^2$ is as defined before except cyano, can be prepared by reacting a compound of Formula (XXXI)

(XXXI)

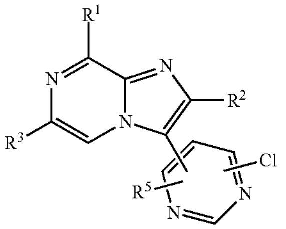

where $R^1$, $R^3$ and $R^5$ are as defined before and $R^2$ is as defined before except cyano, with a vinylboronic acid pinacol ester of Formula (XXI) in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A compound of Formula (XXXI) where $R^1$, $R^3$ and $R^5$ are as defined before and $R^2$ is as defined before except cyano, can be prepared by reacting a compound of Formula (Ig)

(Ig)

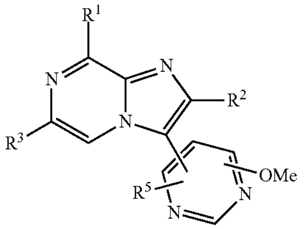

where $R^1$, $R^3$ and $R^5$ are as defined before, $R^4$ is methoxy and ortho to the pyrimidinyl nitrogen and $R^2$ is as defined before except cyano, with phosphorus oxychloride in the presence of a suitable base such as N,N-diisopropylethylamine in a suitable inert solvent such as ACN, under suitable reaction conditions, such as heating at a convenient temperature, either by conventional heating or under microwave irradiation for a period of time to ensure the completion of the reaction.

A compound of Formula (Ig) wherein $R^1$ and $R^3$ are as defined before, $R^2$ is as defined before except cyano and Het is pyrimidinyl can be prepared by reacting a compound of Formula (II) wherein $R^1$ and $R^3$ are as defined before and $R^2$ is as defined before except cyano and halo represents a bromo or iodo, with a boronic acid derivative of Formula (XXXII)

(XXXII)

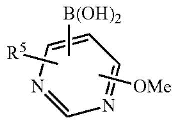

where $R^5$ is as defined before and $R^4$ is methoxy, in the presence of a suitable catalyst, such as tetrakis(triphenylphosphine)palladium (0), in the presence of a suitable base, such as sodium carbonate, in a suitable inert solvent such as a mixture of 1,4-dioxane and water, under suitable reaction conditions, such as convenient temperature, either by conventional heating or under microwave irradiation for a period of time to ensure the completion of the reaction.

A compound of Formula (Ih)

(Ih)

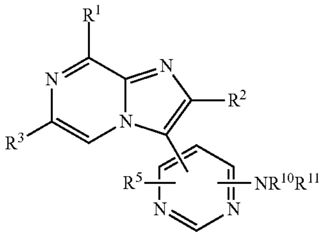

where $R^1$, $R^3$, $R^5$ are as defined before, $R^2$ is as defined before except cyano, $R^4$ is $NR^{10}R^{11}$ and $R^{10}$ and $R^{11}$ are as defined before, can be prepared by reacting a compound of Formula (II) wherein $R^1$ and $R^3$ are as defined before, $R^2$ is as defined before except cyano and halo represents a bromo or iodo, with a boronic acid derivative of Formula (XXXIII)

(XXXIII)

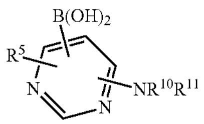

where $R^5$, $R^{10}$ and $R^{11}$ are as defined before, in the presence of a suitable catalyst, such as tetrakis(triphenylphosphine) palladium (0), in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction.

Compounds of Formula (II) can be obtained as described before.

A boronic acid derivative of Formula (XXXIII) where $R^5$, $R^{10}$ and $R^{11}$ are as defined before, can be obtained commercially or, alternatively, can also be prepared by reacting a boronic acid of Formula (XXXIV)

(XXXIV)

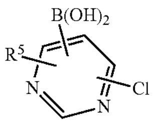

where $R^5$ is as defined before and the chlorine atom is ortho to any of the pyrimidinyl nitrogens, with an amine derivative of Formula $R^{10}R^{11}NH$ wherein $R^{10}$ and $R^{11}$ are as defined before, either neat or in a suitable inert solvent, such as ACN, under suitable reaction conditions, such as heating at a convenient temperature, either by conventional heating or under microwave irradiation for a period of time to ensure the completion of the reaction.

A boronic acid of Formula (XXXIV) where $R^5$ is as defined before, can be prepared by reacting a chloropyrimidine of Formula (XXXV)

(XXXV)

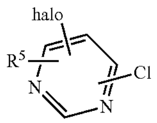

wherein $R^5$ is as defined before and halo is chloro or bromo, with triisopropyl borate, in the presence of a suitable base, such as n-buthyllithium in the presence of a suitable diamine such as N,N,N',N'-tetramethylenediamine, in a suitable inert solvent such as $Et_2O$, under suitable reaction conditions, such as a convenient temperature, typically ranging between −78° C. and 25° C.

A halopyrimidine of Formula (XXXV) where $R^5$ is as defined before and halo represents chloro or bromo, can be obtained commercially.

A compound of Formula (I) wherein $R^1$, $R^3$, $R^4$ and $R^5$ are as defined before, $R^2$ is as defined before except cyano and Het is pyrazolyl, can be prepared by reacting a compound of Formula (XXXVI)

(XXXVI)

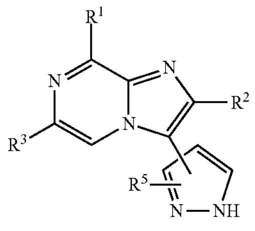

where $R^1$, $R^3$ and $R^5$ are as defined before and $R^2$ is as defined before except cyano, with a reagent of Formula $R^4$-LG wherein $R^4$ is attached to the nitrogen atom of the pyrazole is as defined before and LG represents a leaving group, such as halo, e.g. chloro, bromo or iodo, or a sulfonyloxy group, e.g. methylsulfonyloxy, trifluoromethylsulfonyloxy, or methylphenylsulfonyloxy in the presence of a suitable base such as cesium carbonate or N,N-diisopropylethylamine, in a suitable inert solvent, such as DMF or ACN and under suitable reaction conditions, such as heating at a convenient temperature, either by conventional heating or under microwave irradiation for a period of time to ensure the completion of the reaction.

A compound of Formula $R^4$-LG wherein $R^4$ is as defined before and LG represents a leaving group, such as halo, e.g. chloro, bromo or iodo, can be obtained commercially.

A compound of Formula $R^4$-LG wherein $R^4$ is as defined before and LG represents a leaving group, such as a sulfonyloxy group, e.g. methylsulfonyloxy, trifluoromethylsulfonyloxy, or methylphenylsulfonyloxy can be prepared by reacting a compound of Formula $R^4$—OH with a sulfonyl chloride, e.g. methylsulfonyl chloride, trifluoromethylsulfonyl chloride, or methylphenylsulfonyl chloride in the presence of a suitable base, such as pyridine or diisopropylethylamine, in a suitable inert solvent, such as DCM and under suitable reaction conditions, such as a convenient temperature, typically ranging from −10° C. to 25° C.

A compound of Formula (XXXVI) wherein $R^1$, $R^3$ and $R^5$ are as defined before and $R^2$ is as defined before except cyano, can be prepared by reacting a compound of Formula (II), where $R^1$ and $R^3$ are as defined before, $R^2$ is as defined before except cyano and halo represents bromo or iodo, with a boronate of Formula (XXXVII)

(XXXVII)

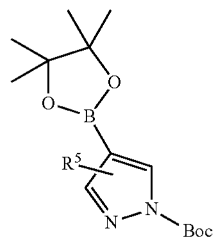

where $R^5$ is as described before, in the presence of a suitable catalyst, such as tetrakis(triphenylphosphine)palladium (0) or [1,1'-bis(diphenylphosphino)ferrocene]dichloropalladium (II) complex with DCM, in the presence of a suitable base, such as sodium carbonate or potassium phosphate, in a suitable inert solvent such as a mixture of 1,4-dioxane and water or 1,2-dimethoxyethane and water, under suitable reaction conditions, such as heating at a convenient temperature, either by conventional heating or under microwave irradiation for a period of time to ensure the completion of the reaction.

Alternatively, a compound of Formula (I) wherein $R^1$, $R^3$, $R^4$ and $R^5$ are as defined before, $R^2$ is as defined before except cyano and Het is pyrazolyl, can be prepared by reacting a compound of Formula (II), where $R^1$ and $R^3$ are as defined before, $R^2$ is as defined before except cyano and halo represents bromo or iodo, with a compound of Formula (XXXVIII)

(XXXVIII)

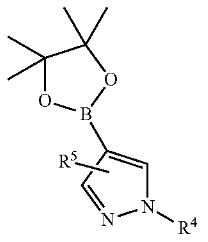

where $R^4$ and $R^5$ are as defined before, in the presence of a suitable catalyst, such as tetrakis(triphenylphosphine)palladium (0) or [1,1'-bis(diphenylphosphino)ferrocene]dichloropalladium (II) complex with DCM, in the presence of a suitable base, such as sodium carbonate or potassium phosphate, in a suitable inert solvent such as a mixture of 1,4-dioxane or 1,2-dimethoxyethane and water, under suitable reaction conditions, such as heating at a convenient temperature, either by conventional heating or under microwave irradiation for a period of time to ensure the completion of the reaction.

A compound of Formula (XXXVIII) where $R^4$ and $R^5$ are as defined before, can be obtained commercially or alternatively, can be prepared by reacting a compound of Formula (XXXIX)

(XXXIX)

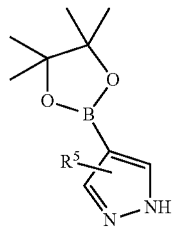

wherein $R^5$ is as defined before, with a reagent of Formula $R^4$-LG wherein $R^4$ is as defined before and LG represents a leaving group, such as halo, e.g. chloro, bromo or iodo, or a sulfonyloxy group, e.g. methylsulfonyloxy, trifluoromethylsulfonyloxy, or methylphenylsulfonyloxy in the presence of a base such as cesium carbonate or N,N-diisopropylethylamine, in a suitable inert solvent, such as DMF or ACN and under suitable reaction conditions, such as heating at a convenient temperature, either by conventional heating or under microwave irradiation for a period of time to ensure the completion of the reaction.

A compound of Formula $R^4$-LG wherein $R^4$ is as defined before, can be obtained as described before.

A compound of Formula (XXXVIII) where $R^4$ and $R^5$ are as defined before, can also be prepared by reacting a compound of Formula (XXXIX) wherein $R^5$ is as defined before, with a reagent of Formula $R^4$—OH wherein $R^4$ is as defined before, in the presence of diisopropyl azodicarboxylate, in the presence of a suitable phosphine ligand such as triphenylphosphine, in a suitable inert solvent, such as THF and under suitable reaction conditions, such as heating at a convenient temperature, either by conventional heating or under microwave irradiation for a period of time to ensure the completion of the reaction.

An alcohol of Formula $R^4$—OH can be obtained as described before.

A compound of Formula (XXXVIIIa)

(XXXVIIIa)

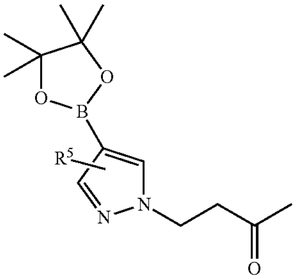

where $R^5$ is as defined before and $R^4$ is methylcarbonylethyl, can be prepared by reacting a compound of Formula (XXXIX) wherein $R^5$ is as defined before, with methyl vinyl ketone, in the presence of a suitable base such as 1,8-diazabicyclo[5.4.0]undec-7-ene, in a suitable inert solvent, such as ACN, under suitable reaction conditions, such as a convenient temperature, typically ranging from −10° C. to 25° C.

A compound of Formula (XXXVIII) wherein $R^4$ and $R^5$ are as defined before, can also be prepared by reacting a compound of Formula (XL)

(XL)

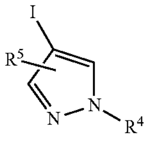

wherein $R^4$ and $R^5$ are as defined before, with bis(pinacolato) diboron in the presence of a suitable catalyst, such as [1,1'-bis(diphenylphosphino)ferrocene]dichloropalladium (II), in the presence of a suitable base, such as potassium acetate, in a suitable inert solvent, such as DMF or dimethyl sulfoxide, under suitable reaction conditions, such as heating at a convenient temperature, either by conventional heating or under microwave irradiation for a period of time to ensure the completion of the reaction.

A compound of Formula (XL) wherein $R^4$ and $R^5$ are as defined before, can be prepared by reacting a 4-iodo-1H-pyrazole of Formula (XLI)

(XLI)

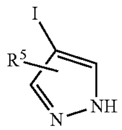

wherein $R^5$ is as defined before, with a reagent of Formula $R^4$-LG wherein $R^4$ is as defined before and LG represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a suitable base, such as cesium carbonate or N,N-diisopropylethylamine, in a suitable inert solvent, such as DMF or ACN, under suitable reaction conditions, such as heating at a convenient temperature, either by conventional heating or under microwave irradiation for a period of time to ensure the completion of the reaction.

A 4-iodo-1H-pyrazole of Formula (XLI) where $R^5$ is as defined before, can be obtained commercially.

A compound of Formula $R^4$-LG can be obtained as described before.

A compound of Formula (XLa)

(XLa)

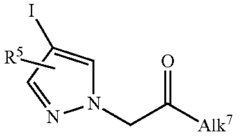

wherein $R^5$ is as defined before and $Alk^7$ is $C_{1-4}$alkyl or $C_{3-8}$cycloalkyl, can be prepared by reacting a 4-iodo-1H-pyrazole of Formula (XLI) with an alpha bromoketone of (XLII)

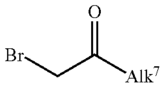

wherein $Alk^7$ is $C_{1-4}$alkyl or $C_{3-8}$cycloalkyl, in the presence of a suitable base, such as cesium carbonate, in a suitable inert solvent, such as ACN, under suitable reaction conditions, such as a convenient temperature, either by conventional heating or under microwave irradiation for a period of time to ensure the completion of the reaction.

An alpha bromoketone of Formula (XLII) wherein $Alk^7$ is $C_{1-4}$alkyl or $C_{3-8}$cycloalkyl groups, either can be obtained commercially or alternatively can be obtained by procedures similar to those described in Carverley, M. J. Tetrahedron, 1987, 43(20), 4609-19.

A compound of Formula (XLb)

(XLb)

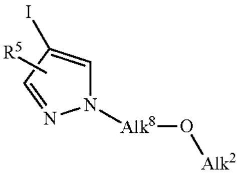

wherein $R^5$ is as defined before and $Alk^8$ and $Alk^2$ are $C_{1-4}$alkyl, can be prepared by reacting a compound of Formula (XLc)

(XLc)

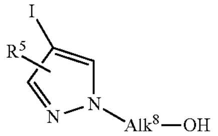

where $R^5$ is as defined before and $Alk^8$ is $C_{1-4}$alkyl, with a compound of Formula $Alk^2$-LG where $Alk^2$ is $C_{1-4}$alkyl and LG represents a leaving group such as halo, e.g. chloro, bromo or iodo, or a sulfonyloxy group, e.g. methylsulfonyloxy, trifluoromethylsulfonyloxy, or methylphenylsulfonyloxy, in the presence of a suitable base, such as sodium hydride, in a suitable inert solvent such as THF and under suitable reaction conditions, such as a convenient temperature, typically ranging from 0° C. to 40° C.

A reagent of Formula $Alk^2$-LG wherein $Alk^2$ is $C_{1-4}$alkyl, can be prepared as described before.

A compound of Formula (XLc) where $R^5$ is as defined before, can be prepared by reacting a 4-iodo-1H-pyrazole of Formula (XLI) where $R^5$ is as defined before, with a reagent of Formula LG-$Alk^8$-OH, wherein LG represents a leaving group such as halo, e.g. chloro, bromo or iodo, or a sulfonyloxy group, e.g. methylsulfonyloxy, trifluoromethylsulfonyloxy, or methylphenylsulfonyloxy and $Alk^8$ is a $C_{1-4}$alkyl group, in the presence of a suitable base, such as cesium carbonate, in a suitable inert solvent, such as DMF, under suitable reaction conditions, such as heating at a convenient temperature, either by conventional heating or under microwave irradiation for a period of time to ensure the completion of the reaction.

A reagent of Formula LG-$Alk^8$-OH wherein LG represents a leaving group such as halo, e.g. chloro, bromo or iodo, or a sulfonyloxy group, e.g. methylsulfonyloxy, trifluoromethylsulfonyloxy, or methylphenylsulfonyloxy and $Alk^8$ is $C_{1-4}$alkyl, can be obtained commercially.

A compound of Formula (I) wherein $R^1$, $R^4$ and $R^5$ are as defined before, $R^2$ is cyano, $R^3$ is hydrogen and Het is pyrazolyl can be prepared by reacting a compound of Formula (XLIII)

(XLIII)

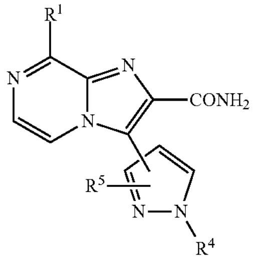

where $R^1$, $R^4$ and $R^5$ are as defined before, $R^3$ is hydrogen and Het is pyrazolyl, with phosphorus oxychloride as solvent, under suitable reaction conditions, such as heating at a convenient temperature, either by conventional heating or under microwave irradiation for a period of time to ensure the completion of the reaction.

A compounds of Formula (XLIII) wherein $R^1$, $R^4$ and $R^5$ are as defined before, $R^3$ is hydrogen and Het is pyrazolyl can be obtained by reacting a compound of Formula (XLIV)

(XLIV)

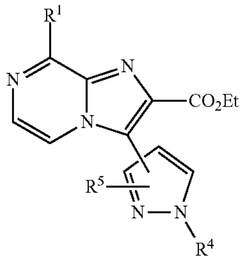

where $R^1$, $R^4$ and $R^5$ are as defined before, $R^3$ is hydrogen and Het is pyrazolyl with ammonium hydroxide, under suitable reaction conditions, such as heating at a convenient temperature, either by conventional heating or under microwave irradiation for a period of time to ensure the completion of the reaction.

A compound of Formula (XLIV) where $R^1$, $R^4$ and $R^5$ are as defined before, $R^3$ is hydrogen and Het is pyrazolyl, can be prepare by reacting a compound of Formula (XLV)

(XLV)

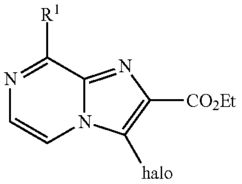

where $R^1$ is as defined before, $R^3$ is hydrogen and halo represents bromo or iodo, in the presence of a suitable catalyst, such as tetrakis(triphenylphosphine)palladium (0) DCM adduct, in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction A compound of Formula (XLV) where $R^1$ is a radical of formula

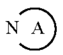

as defined before and halo represents a bromo or iodo, can be prepared by reacting a (XLVI)

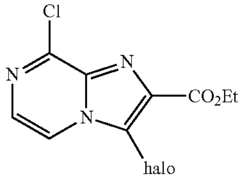

where halo represents a bromo or iodo and $R^3$ is hydrogen with an amine derivative of Formula

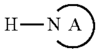

wherein

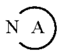

is as defined before, either neat or in a suitable inert solvent, such as ACN, under suitable reaction conditions, such as heating at a convenient temperature, either by conventional heating or under microwave irradiation for a period of time to ensure the completion of the reaction.

A compound of Formula (XLVI) where halo represents bromo or iodo can be prepared by reacting a compound of Formula (XLVII)

(XLVII)

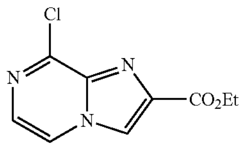

with N-bromo or N-iodo-succinimide in a suitable inert solvent, such as DCM, under suitable reaction conditions, such as a convenient temperature, typically ranging between −10° C. and 60° C. for a period of time to ensure the completion of the reaction.

A compound of Formula (XLVII) can be prepared by reacting a compound of Formula (XIII), with ethyl bromopyruvate either neat or in a suitable inert solvent, such as EtOH, isopropanol or 1,2-dimethoxyethane, under suitable reaction conditions, such as heating at a convenient temperature either by conventional heating or under microwave irradiation for a period of time to ensure the completion of the reaction.

A compound of Formula (XIII), can be obtained as described before.

A compound of Formula (I) wherein $R^1$ is

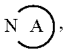, $R^3$ and $R^5$ are hydrogen, $R^2$ is as defined before except cyano, $R^4$ is as defined before and Het is oxazolyl can be prepared by reacting a compound of Formula (XLVIII)

(XLVIII)

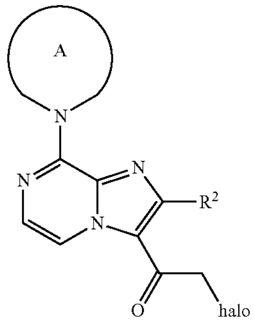

wherein $R^2$ is as defined before except cyano,

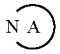

is as defined before and halo represents chloro, bromo or iodo, with an amide of Formula $R^4CONH_2$, in a suitable inert solvent such as a mixture of 1,4-dioxane and DMF, under suitable reaction conditions, such as heating at a convenient temperature, either by conventional heating or under microwave irradiation for a period of time to ensure the completion of the reaction.

Compounds of Formula (I) wherein $R^1$ is

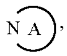, $R^3$ and $R^5$ are hydrogen, $R^2$ is as defined before except cyano, $R^4$

is as defined before and Het is imidazolyl, can be prepared by reacting a compound of Formula (XLVIII) wherein $R^2$ is as defined before except cyano,

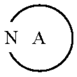

is as defined before and halo represents chloro, bromo or iodo, with an amidine of Formula (XLIX)

(XLIX)

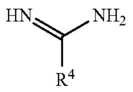

where $R^4$ is as defined before, in a suitable inert solvent such as DMF, in the presence of a suitable base such as potassium carbonate under suitable reaction conditions, such as heating at a convenient temperature, either by conventional heating or under microwave irradiation for a period of time to ensure the completion of the reaction.

A compound of Formula (XLVIII) where $R^2$ is as defined before except cyano,

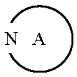

is as defined before and halo represents a chloro, bromo or iodo, can be prepared by reacting a compound of Formula (L)

(L)

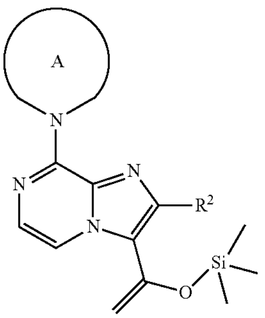

wherein $R^2$ is as defined before except cyano and

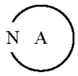

is as defined before, with N-bromo-succinimide in a suitable inert solvent, such as THF, in the presence of a suitable base such as sodium hydrogen carbonate, under suitable reaction conditions, such as low temperature, typically ranging between −78° C. and 25° C., for a period of time to ensure the completion of the reaction.

A compound of Formula (L) where $R^2$ is as defined before except cyano and

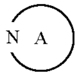

is as defined before, can be prepared by reacting a compound of Formula (LI)

(LI)

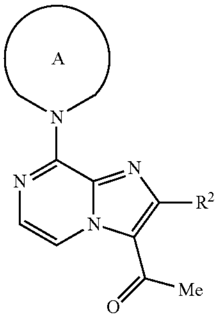

wherein $R^2$ is as defined before except cyano and

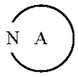

is as defined before with trimethylsilyl trifluoromethane-sulfonate in a suitable inert solvent, such as DCM, in the presence of a suitable base such as N,N-diisopropylethylamine, under suitable reaction conditions, such as at low temperature, typically ranging between −20° C. and 25° C., for a period of time to ensure the completion of the reaction. A compound of Formula (LI) where $R^2$ is as defined before except cyano and

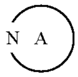

is as defined before can be prepared by reacting a compound of Formula (LII)

(LII)

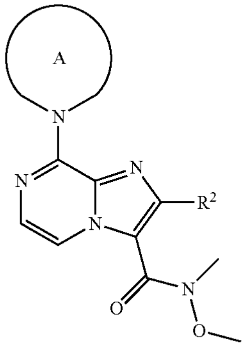

where $R^2$ is as defined before except cyano and

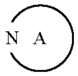

is as defined before with a suitable Grignard reagent such as methylmagnesium bromide, in a suitable inert solvent, such as THF, under suitable reaction conditions, such as at low temperature, typically ranging between −20° C. and 25° C. for a period of time to ensure the completion of the reaction.

A compound of Formula (LII) where $R^2$ is as defined before except cyano,

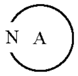

is as defined before can be prepared by reacting a compound of Formula (LIII)

(LIII)

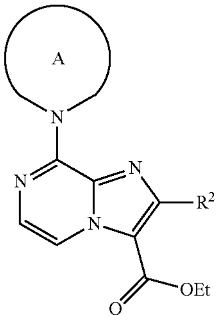

where $R^2$ is as defined before except cyano and

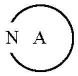

is as defined before with N,O-dimethylhydroxylamine, in the presence of a suitable Grignard reagent such as isopropylmagnesium bromide, in a suitable inert solvent, such as a mixture of THF and DCM, under suitable reaction conditions, such as low temperature, typically ranging between −20° C. to 25° C., for a period of time to ensure the completion of the reaction.

A compound of Formula (LII), where $R^2$ is as defined before except cyano and

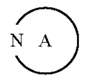

is as defined before, can be prepared by reacting a compound of Formula (XVIII) where

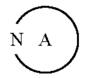

is as defined before, with ethyl chloroacetoacetate, in a suitable inert solvent, such as EtOH, under suitable reaction conditions, such as heating at a convenient temperature, either by conventional heating or under microwave irradiation for a period of time to ensure the completion of the reaction.

A compound of Formula (XVIII) can be obtained as described before.

A compound of Formula (I) wherein $R^1$, $R^3$, $R^4$ and $R^5$ are as defined before, $R^2$ is as defined before except cyano and Het is pyrrolyl, can be prepared by reacting compound of Formula (II)

(Ii)

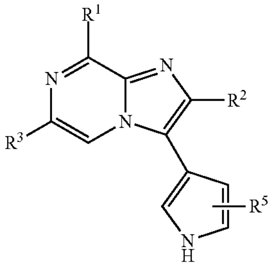

wherein $R^1$, $R^3$ and $R^5$ are as defined before and $R^2$ is as defined before except cyano, with a reagent of Formula $R^4$-LG wherein $R^4$ is as defined before and is attached to the pyrrole nitrogen and LG represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a suitable base, such as cesium carbonate, in a suitable inert solvent, such as DMF, under suitable reaction conditions, such as heating at a convenient temperature, either by conventional heating or under microwave irradiation for a period of time to ensure the completion of the reaction.

A compound of Formula $R^4$-LG can be obtained as described before.

A compound of Formula (II) wherein $R^1$, $R^3$ and $R^5$ are as defined before and $R^2$ is as defined before except cyano, can be prepared by reacting a compound of Formula (II) where $R^1$ and $R^3$ are as defined before, $R^2$ is as defined before except cyano and halo represents a bromo or iodo, with a compound of Formula (LIV)

(LIV)

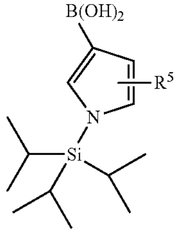

wherein $R^5$ is as defined before, in the presence of a suitable catalyst, such as tetrakis(triphenylphosphine)palladium (0), in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction.

A compound of Formula (LIV) where $R^5$ is as defined before, can be obtained commercially.

A compound of Formula (II) can be obtained as described before.

A compound of Formula (I) wherein $R^1$, $R^4$ and $R^5$ are as defined before, $R^3$ is hydrogen, $R^2$ is as defined before except cyano and Het is thiazolyl, can be prepared by reacting a compound of Formula (VI) where $R^1$ is as defined before, $R^2$ is as defined before except cyano and $R^3$ is hydrogen with a compound of Formula (LV)

(LV)

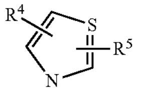

wherein $R^4$ and $R^5$ are as defined before in the presence of a suitable catalyst, such as palladium (II) acetate, in the presence of a suitable base, such as potassium phosphate, and a suitable phosphine ligand such as tert-butyldicyclohexylphosphine in a suitable inert solvent such as N-methylpyrrolidine, under a suitable reaction conditions, such as heating at a convenient temperature, either by conventional heating or under microwave irradiation for a period of time to ensure the completion of the reaction.

A compound of Formula (LV) wherein $R^4$ and $R^5$ are as defined before, can be obtained commercially.

Compounds of Formula (VI) where $R^1$ is as defined before, $R^2$ is as defined before except cyano and $R^3$ is hydrogencan be obtained as described before.

Compounds of Formula

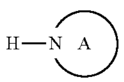

wherein

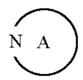

is as defined before, reagents of Formula $R^{10}R^{11}NH$, where $R^{10}$ and $R^{11}$ are as defined before, vinylboronic acid pinacol esters of Formula (XXI), boronic acids of formula (XXXII), compounds of formula (XIII), and compounds of formula (XLIX) can be obtained commercially.

Pharmacology

The compounds according to the invention inhibit PDE10 enzyme activity, in particular PDE10A enzyme activity and hence raise the levels of cAMP or cGMP within cells that express PDE10. Accordingly, inhibition of PDE10 enzyme activity may be useful in the treatment of diseases caused by deficient amounts of cAMP or cGMP in cells. PDE10 inhibitors may also be of benefit in cases in which raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological or metabolic diseases and urological diseases.

Hence, the present invention relates to a compound according to the present invention for use as a medicine, as well as to the use of a compound according to the invention or a pharmaceutical composition according to the invention for the manufacture of a medicament. The present invention also relates to a compound according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 10 enzyme. The present invention also relates to the use of a compound according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 10 enzyme.

The present invention also relates to a compound according to the invention, or a pharmaceutical composition according to the invention for use in the treatment, prevention, amelioration, control or reduction of the risk of various neurological, psychiatric and metabolic disorders associated with phosphodiesterase 10 dysfunction in a mammal, including a human, the treatment or prevention of which is affected or facilitated by the inhibition of phosphodiesterase 10.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with phosphodiesterase 10 dysfunction in a mammal, including a human, the treatment or prevention of which is affected or facilitated by the inhibition of phosphodiesterase 10.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the indications that may be treated with PDE10 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain and metabolic disorders.

In particular, the psychotic disorders and conditions associated with PDE10 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder and substance-induced mood disorder.

In particular, neurodegenerative disorders include Parkinson's disease; Huntington's disease; dementia such as for example Alzheimer's disease; multi-infarct dementia; AIDS-related dementia or fronto temperal dementia. The neurodegenerative disorder or condition comprises neurodegeneration of striatal medium spiny neurons.

In particular, disorders or conditions comprising as a symptom a deficiency in attention and/or cognition include dementia, such as Alzheimer's disease; multi-infarct dementia; alcoholic dementia or drug-related dementia; dementia associated with intracranial tumours or cerebral trauma; dementia associated with Huntington's disease;

dementia associated with Parkinson's disease; AIDS-related dementia; other diseases include delirium; amnestic disorder; post-traumatic stress disorder; mental retardation; a learning disorder; attention-deficit/hyperactivity disorder (ADHD); and age-related cognitive impairment.

In particular, pain includes acute and chronic states, severe pain, intractable pain, neuropathic pain and post-traumatic pain.

In particular, metabolic disorders include diabetes, in particular type 1 or type 2 diabetes, and related disorders such as obesity. Additional related disorders include syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

Additionally, the growth of some cancer cells is inhibited by cAMP and cGMP, the compounds of the invention may be useful in the treatment of cancer, such as renal carcinoma and breast cancer.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by the compounds of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; pain; diabetes and obesity.

Of the disorders mentioned above, the treatment of anxiety, obsessive-compulsive disorder, schizophrenia, depression, attention-deficit/hyperactivity disorder, Alzheimer's disease and diabetes are of particular importance.

Preferably, the disorders treated by the compounds of the present invention are schizophrenia, including positive and negative symptoms thereof, and cognitive deficits, such as impaired attention or memory.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the invention, for use in the treatment of any one of the diseases mentioned hereinbefore.

The invention also relates to a compound according to the invention for use in treating any one of the diseases mentioned hereinbefore.

The invention also relates to a compound according to the invention, for the treatment or prevention, in particular treatment, of any one of the diseases mentioned hereinbefore.

The invention also relates to the use of a compound according to the invention, for the manufacture of a medicament for the treatment or prevention of any one of the disease conditions mentioned hereinbefore.

The invention also relates to the use of a compound according to the invention for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds according to the invention, there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound according to the invention to warm-blooded animals, including humans.

Therefore, the invention also relates to a method for the prevention and/or treatment of any one of the diseases mentioned hereinbefore comprising administering a therapeutically effective amount of compound according to the invention to a patient in need thereof.

The PDE10 inhibitors described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic $\alpha$-7 agonists and positive allosteric modulators, PDE4 inhibitors, other PDE10 inhibitors, calcium channel blockers, muscarinic M1 and M2 modulators, adenosine receptor modulators, ampakines, NMDA-R modulators, mGluR modulators, dopamine modulators, serotonin modulators, cannabinoid modulators, and cholinesterase inhibitors (e.g. donepezil, rivastigmine, and galantamine). In such combinations, the compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

One skilled in the art will recognize that a therapeutically effective amount of the PDE10 inhibitors of the present invention is the amount sufficient to inhibit the PDE10 enzyme and that this amount varies inter alia, depending on the type of disease, the concentration of the compound in the therapeutic formulation, and the condition of the patient. Generally, an amount of PDE10 inhibitor to be administered as a therapeutic agent for treating diseases in which inhibition of the PDE10 enzyme is beneficial, such as the disorders described herein, will be determined on a case by case by an attending physician.

Generally, a suitable dose is one that results in a concentration of the PDE10 inhibitor at the treatment site in the range of 0.5 nM to 200 μM, and more usually 5 nM to 50 μM.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, more preferably from about 0.01 mg/kg to about 2.50 mg/kg, even more preferably from about 0.01 mg/kg to about 1 mg/kg, more preferably from about 0.05 mg/kg to about 1 mg/kg body weight and most preferably from about 0.1 mg/kg to about 0.5 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of the PDE10 enzyme is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical (for example via a nose spray, eye drops or via a cream, gel, shampoo or the like), rectal or percutaneous administration, by parenteral injection or by inhalation, such as a nose spray. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are employed. For parenteral compositions, the carrier will usually comprise sterile water, at least in large part, though other ingredients, for example, surfactants to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, said additives do not introduce a significant deleterious effect on the skin. Said additives may facilitate the administration to the skin and/or may be helpful for preparing the desired compositions. These compositions may be administered in various ways, e.g., as a transdermal patch, as a spot-on treatment, as an ointment.

It is especially advantageous to formulate the aforementioned pharmaceutical compositions in unit dosage form for ease of administration and uniformity of dosage.

Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility as well. The use of such a composition for the manufacture of a medicament, as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional pharmaceutical agent. The present invention also relates to such a combination for use as a medicine. The present invention also relates to a product comprising (a) a compound according to the present invention, a pharmaceutically acceptable salt thereof or a solvate thereof, and (b) an additional pharmaceutical agent, as a combined preparation for simultaneous, separate or sequential use in the treatment or prevention of a condition in a mammal, including a human, the treatment or prevention of which is affected or facilitated by the effect of PDE10 inhibitors, in particular PDE10A inhibitors. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

EXAMPLES

Chemistry

Several methods for preparing the compounds of this invention are illustrated in the following Examples. Unless otherwise noted, all starting materials were obtained from commercial suppliers and used without further purification.

Herein, the term "ACN" means acetonitrile, "DCM" means dichloromethane, "DMF" means N,N-dimethylformamide, "DMSO" means dimethylsulfoxide, "DIPEA" means N,N-diisopropylethylamine, "$Et_2O$" means diethyl ether, "EtOAc" means ethyl acetate, "EtOH" means ethanol, "iPrOH" means isopropanol, "THF" means tetrahydrofuran, "min." means minutes, "h." means hours, "LCMS" means liquid chromatography/mass spectrometry, "MeOH" means methanol, "GCMS" means gas chromatography/mass spectrometry, "HPLC" means high-performance liquid chromatography, "SFC" means supercritical fluid chromatography, "SFC-MS" means supercritical fluid chromatography/mass spectrometry, "HPLC" means ultra-performance liquid chromatography, "RT" means room temperature, "RP" means reverse phase, "$R_t$" means retention time (in minutes), "$[M+H]^+$" means the protonated mass of the free base of the compound, "$[M-H]^-$" means the deprotonated mass of the free base of the compound, 'm.p." means melting point, "i.v." means intravenous; "s.c." means subcutaneous; "PCP" means phencyclidine; "PVC" means polyvinyl chloride; "Scop." means scopolamine; "MP-10" means 2-[4-[1-methyl-4-(4-pyridyl)-1H-pyrazol-3-yl]phenoxymethyl]quinoline; "PQ-10" means 6,7-dimethoxy-4-[3(R)-(quinoxalin-2-yloxy)pyrrolidin-1-yl]quinazoline. Isolute® SCX-2 is a strong cation exchange cartridge containing benzenesulfonic acid groups.

Microwave assisted reactions were performed in a single-mode reactor: Emrys™ Optimizer microwave reactor (Personal Chemistry A.B., currently Biotage).

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from Merck, on irregular silica gel, particle size 15-40 μm (normal phase disposable flash columns) on an SPOT or LAFLASH system from Armen Instrument.

Optical rotations were measured on a Perkin-Elmer 341 polarimeter with a sodium lamp and reported as follows: [α]° (λ, T° C., c g/100 ml, solvent).

$[\alpha]_\lambda^T=(100\alpha)/(l\times c)$: where/is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

A. Preparation of the Intermediates

Example A1

3-Morpholin-4-yl-pyrazin-2-ylamine

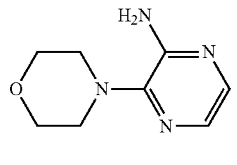 [SMILES: Nc1nccnc1N1CCOCC1]

A mixture of morpholine (37 ml, 433 mmol) and 3-chloro-pyrazin-2-ylamine (10.2 g, 79 mmol) was stirred at 120° C. for 16 h. The excess morpholine was evaporated in vacuo and the crude product was washed with a 5% solution of ammonium hydroxide. The organic layer was separated, dried ($MgSO_4$), filtered and the solvent evaporated in vacuo to yield intermediate 1 (12 g, 84%) as a white solid. m. p. 158.1-160.4° C.

Example A2

3-Chloro-5-iodo-pyrazin-2-ylamine

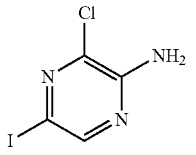

N-Iodosuccinimide (2.6 g, 11.6 mmol) was added to a stirred suspension of 3-chloro-pyrazin-2-ylamine (1 g, 7.7 mmol) and trifluoroacetic acid (0.178 ml, 2.32 mmol) in ACN (20 ml). The mixture was stirred at RT for 18 h. and then filtered off. The filtrate was diluted with EtOAc and washed with a saturated solution of sodium thiosulfate. The organic layer was separated, dried ($Na_2SO_4$), filtered and the solvents concentrated in vacuo. The crude product was purified by open column chromatography (silica; DCM in EtOAc 100/0 to 50/50). The desired fractions were collected and evaporated in vacuo to yield intermediate 2 (1.8 g, 91%) as a white solid. m.p. 158.1-160.4° C. (WRS-2A).

Example A3

8-Chloro-imidazo[1,2-a]pyrazine

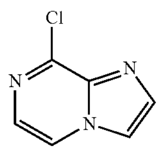

Bromoacetaldehyde diethyl acetal (17.4 ml, 115.8 mmol) was added dropwise to a 48% aqueous solution of hydrobromic acid (4.45 ml, 38.6 mmol) at RT. The mixture was stirred at reflux temperature for 2 h. and then poured onto a suspension of sodium hydrogen carbonate (74.5 g, 0.88 mol) in isopropanol (220 ml). The mixture was stirred for a further 30 min. and then filtered off. 3-Chloro-pyrazin-2-ylamine (5 g, 38.6 mmol) was added to the filtrate and the mixture was stirred at 85° C. for 4 h. The solvent was evaporated in vacuo and the crude product suspended in a saturated solution of sodium hydrogen carbonate and extracted with DCM. The organic layer was dried ($Na_2SO_4$), filtered and the solvents evaporated in vacuo. The crude product was precipitated from $Et_2O$ to yield intermediate 3 (4.1 g, 70%) as a brown solid which was used in the next step without further purification.

Example A4

8-Chloro-2-methyl-imidazol[1,2-a]pyrazine

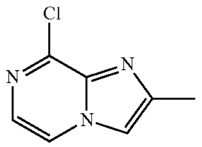

A mixture of 3-chloro-pyrazin-2-ylamine (48.7 g, 375.8 mmol) and chloroacetone (120 ml, 1504.5 mmol) was stirred at 90° C. for 16 h. in a sealed tube protected from light. After cooling to RT, $Et_2O$ was added and the solid formed was filtered off, washed with further $Et_2O$, suspended in a saturated solution of sodium carbonate and extracted with DCM. The organic layer was separated, dried ($Na_2SO_4$), filtered and the solvents evaporated in vacuo. The crude product was precipitated from $Et_2O$ to yield intermediate 4 (43.2 g, 68%) as a white solid which was used in the next step without further purification. m.p. 133.5-138.6° C. (WRS-2A).

The following intermediates were prepared from the corresponding precursors according to an analogous protocol to A4.

Example A5

8-Chloro-2-cyclopropyl-imidazo[1,2-a]pyrazine

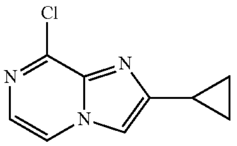 [SMILES: Clc1nccn2cc(C3CC3)nc12]

From 3-chloro-pyrazin-2-ylamine and 2-bromo-1-cyclopropyl-ethanone (obtained by procedures similar to those described in Gaudry, M. et al. Organic Syntheses. 1976, 55). Precipitation from $Et_2O$ yielded intermediate 5 as a white solid (85%). m.p. 63.5-66.3° C. (WRS-2A).

Example A6

8-Chloro-2-isopropyl-imidazol[1,2-a]pyrazine

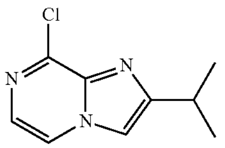

From 3-chloro-pyrazin-2-ylamine and 2-bromo-1-isopropyl-ethanone (obtained by procedures similar to those described in Gaudry, M.; Marquet, A. Organic Syntheses. 1976, 55). Precipitation from $Et_2O$ yielded intermediate 6 as a pale brown solid (80%).

Example A7

8-Hydroxy-2-trifluoromethyl-imidazo[1,2-a]pyrazine

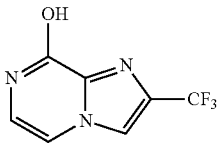 [SMILES: Oc1nccn2cc(C(F)(F)F)nc12]

A mixture of 3-chloro-pyrazin-2-ylamine (0.50 g, 3.86 mmol) and 1-chloro-3,3,3-trifluoroacetone (4 ml, 0.027 mmol) was stirred at 100° C. for 16 h. The mixture was partitioned between DCM and a saturated solution of sodium hydrogen carbonate. The organic layer was separated, dried ($Na_2SO_4$), filtered and the solvents evaporated in vacuo to yield intermediate 7 (0.31 g, 39%) as a pale brown solid which was used in the next step without further purification.

Example A8

8-Chloro-2-trifluoromethyl-imidazo[1,2-a]pyrazine

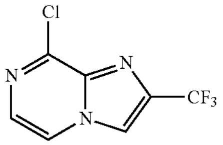 [SMILES: FC(F)(F)c1cn2ccnc(Cl)c2n1]

A mixture of intermediate 7 (0.30 g, 1.48 mmol) and N,N-dimethylaniline (0.06 ml, 0.0005 mmol) in phosphorus oxychloride (0.60 ml, 0.004 mmol) was stirred at 90° C. for 5 h. The mixture was allowed to cool down to RT and then the red solid obtained was poured onto crushed ice and extracted with DCM. The organic layer was separated, dried ($Na_2SO_4$), filtered and the solvents evaporated in vacuo to yield intermediate 8 (0.31 g, 96%) as a red solid which was used in the next step without further purification.

Example A9

8-Chloro-imidazo[1,2-a]pyrazine-2-carboxylic acid ethyl ester

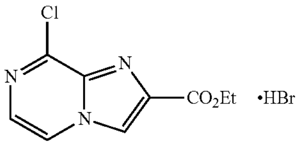 [SMILES: CCOC(=O)c1cn2ccnc(Cl)c2n1 ; Br]

A mixture of 3-chloro-pyrazin-2-ylamine (2.50 g, 19.3 mmol) and ethyl bromopyruvate (2.9 ml, 23.16 mmol) in 1,2-dimethoxyethane was stirred at RT for 2.5 h. Then the reaction mixture was cooled to 0° C. and stirred for a further 30 min. The white solid formed was filtered off, washed with $Et_2O$, suspended in EtOH and stirred at RT for a further 20 h. The solvent was evaporated in vacuo and the crude product precipitated from DCM to yield intermediate 9 (4.0 g, 92%) as a white solid (.HBr) which was used in the next step without further purification.

Example A10

8-Chloro-6-iodo-2-methyl-imidazo[1,2-a]pyrazine

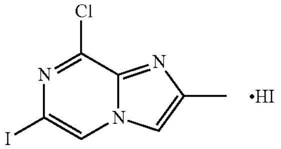

A mixture of intermediate 2 (2.5 g, 9.78 mmol), sodium iodide (2.93 g, 19.57 mmol) and chloroacetone (4.67 ml, 58.72 mmol) was stirred at 90° C. for 24 h. in a sealed tube protected from light. After cooling to RT, $Et_2O$ was added and the solid formed was suspended in a saturated solution of sodium hydrogen carbonate and extracted with DCM. The organic layer was dried ($Na_2SO_4$), filtered and the solvents evaporated in vacuo. The crude product was purified by open column chromatography (silica; DCM). The desired fractions were collected and evaporated in vacuo to yield intermediate 10 (0.85 g, 28%) as a white solid (.HI).

Example A11

2-Methyl-8-pyridin-4-yl-imidazol[1,2-a]pyrazine

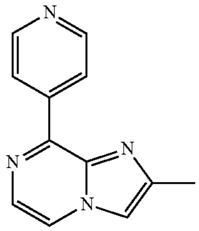 [SMILES: Cc1cn2ccnc(-c3ccncc3)c2n1]

Palladium (II) acetate (0.47 g, 2.09 mmol) was added to a stirred solution of intermediate 4 (5.0 g, 29.83 mmol), 4-pyridineboronic acid (8.15 g, 59.67 mmol) and triphenylphosphine (0.78 g, 2.98 mmol) in a mixture of 1,4-dioxane (125 ml) and a 1.5 M solution of potassium carbonate (74.5 ml, 111.87 mmol). The mixture was stirred at 80° C. for 16 h. and then the solvents were evaporated in vacuo. The mixture was partitioned between water and DCM and the organic layer was separated, dried ($Na_2SO_4$), filtered and the solvents evaporated in vacuo. The crude product was purified by flash column chromatography (silica; MeOH in DCM 5/95). The desired fractions were collected and evaporated in vacuo to yield intermediate 11 (4.2 g, 53%) as a pale brown solid.

The following intermediate was prepared according to a protocol analogous to example A11.

Example A12

2-Methyl-8-pyridin-3-yl-imidazo[1,2-a]pyrazine

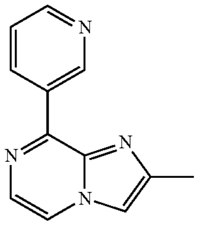 [SMILES: Cc1cn2ccnc(-c3cccnc3)c2n1]

From intermediate 4 and 3-pyridineboronic acid. Flash column chromatography (silica; MeOH in DCM 1/99) yielded intermediate 12 as a pale brown solid (63%).

Example A13

8-Morpholin-4-yl-imidazo[1,2-a]pyrazin-2-ol

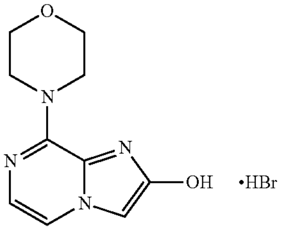 [SMILES: Oc1cn2ccnc(N3CCOCC3)c2n1 ; Br]

Bromoacetic acid (5.55 g, 39.9 mmol) was added to a stirred solution of intermediate 1 (6.0 g, 33.3 mmol) in isopropanol (48 ml). The mixture was stirred at 90° C. for 16 h. and the solid formed was filtered off to yield intermediate 13 (7.7 g, 77%) as a pale brown solid (.HBr).

Example A14

2-M
ethoxy-8-morpholin-4-yl-imidazo[1,2-a]pyrazine

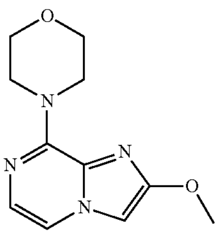 [SMILES: COc1cn2ccnc(N3CCOCC3)c2n1]

Cesium carbonate was added to a stirred solution of iodomethane (1.24 ml, 19.92 mmol) and intermediate 13 (4.0 g, 13.28 mmol) in DMF (150 ml). The mixture was stirred at RT for 1 h. and then the solvent was evaporated in vacuo. The crude product was purified by flash column chromatography (silica; EtOAc in heptane 30/70). The desired fractions were collected and evaporated in vacuo to yield intermediate 14 (1.38 g, 39%) as a white solid.

Example A15

Mixture of
3-bromo-8-chloro-imidazo[1,2-a]pyrazine and
3,8-dibromo-imidazo[1,2-a]pyrazine

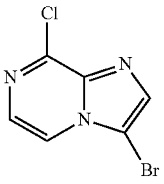
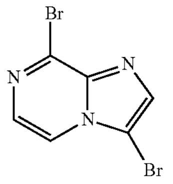

N-Bromosuccinimide (2.0 g, 11.6 mmol) was added to a stirred solution of intermediate 3 (1.78 g, 11.58 mmol) in DCM (50 ml). The mixture was stirred at RT for 2 h. and then diluted with further DCM and washed with a saturated solution of sodium carbonate. The organic layer was separated, dried ($Na_2SO_4$), filtered and the solvent evaporated in vacuo to yield a 72/28 mixture of 3-bromo-8-chloro-imidazo[1,2-c]-pyrazine and 3,8-dibromo-imidazo[1,2-a]pyrazine (intermediate 15) (5.89 g, 99%) as white solid.

The following intermediates were prepared according to a protocol analogous to example A15.

Example A16

3-Bromo-8-chloro-2-methyl-imidazo[1,2-a]pyrazine

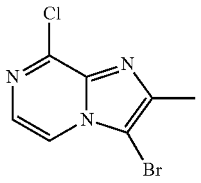

From intermediate 4. Precipitation from $Et_2O$ yielded intermediate 16 as a white solid (99%).

Example A17

3-Bromo-8-chloro-2-cyclopropyl-imidazo[1,2-a]
pyrazine

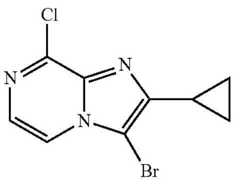 [SMILES: Clc1nccn2c(Br)c(C3CC3)nc12]

From intermediate 5. Precipitation from $Et_2O$ yielded intermediate 17 as a white solid (73%).

Example A18

3-Bromo-8-chloro-2-isopropyl-imidazo[1,2-a]pyrazine

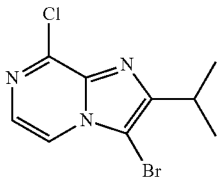

From intermediate 6. Precipitation from $Et_2O$ yielded A18 as a white solid (99%).

Example A19

3-Bromo-8-chloro-2-trifluoromethyl-imidazo[1,2-a]pyrazine

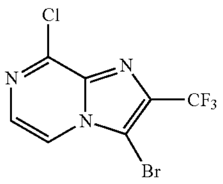 [SMILES: FC(F)(F)c1nc2c(Cl)nccn2c1Br]

From intermediate 8. Flash column chromatography (silica; EtOAc in heptane 20/80) yielded intermediate 19 as a white solid (73%).

Example A20

3-Bromo-8-chloro-imidazo[1,2-a]pyrazine-2-carboxylic acid ethyl ester

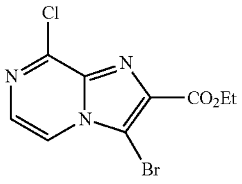 [SMILES: CCOC(=O)c1nc2c(Cl)nccn2c1Br]

From intermediate 9. Precipitation from $Et_2O$ yielded intermediate 20 as a white solid (83%).

Example A21

3-Bromo-8-chloro-6-iodo-2-methyl-imidazo[1,2-a]pyrazine

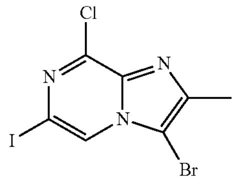

From intermediate 10. Flash column chromatography (silica; EtOAc in heptane (0/100 to 40/60) yielded intermediate 21 as a white solid (83%).

Example A22

3-Bromo-2-methyl-8-pyridin-4-yl-imidazo[1,2-a]pyrazine

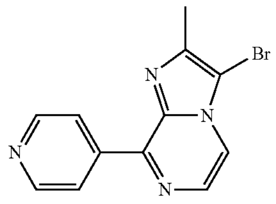 [SMILES: Cc1nc2c(-c3ccncc3)nccn2c1Br]

From intermediate 11. Precipitation from $Et_2O$ yielded intermediate 22 as a pale brown solid (86%).

Example A23

3-Bromo-2-methyl-8-pyridin-3-yl-imidazo[1,2-a]pyrazine

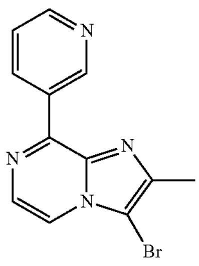 [SMILES: Cc1nc2c(-c3cccnc3)nccn2c1Br]

From intermediate 12. Precipitation from $Et_2O$ yielded intermediate 23 as a pale brown solid (89%).

Example A24

3-Bromo-2-methoxy-8-morpholin-4-yl-imidazo[1,2-a]pyrazine

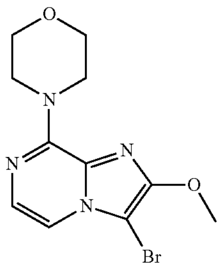 [SMILES: COc1nc2c(N3CCOCC3)nccn2c1Br]

From intermediate 14. Flash column chromatography (silica; EtOAc in DCM 10/90) yielded intermediate 24 as a white solid (86%).

Example A25

3-Iodo-8-chloro-2-methyl-imidazo[1,2-a]pyrazine

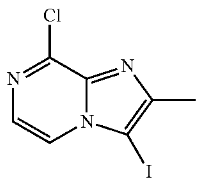

N-Iodosuccinimide (14.1 g, 62 mmol) was added to a stirred solution of intermediate 4 (9.58 g, 57 mmol) in a mixture of DCM and acetic acid at 0° C. The mixture was allowed to warm to RT and then stirred for 16 h. The mixture was diluted with further DCM and washed with a saturated solution of sodium carbonate and sodium thiosulfite. The organic layer was separated, dried ($Na_2SO_4$), filtered and the solvents evaporated in vacuo. The crude product was precipitated from diisopropyl ether to yield intermediate 25 (16 g, 97%) as a pale brown solid which was used in the next step without further purification.

Example A26

3-Bromo-8-morpholin-4-yl-imidazo[1,2-a]pyrazine

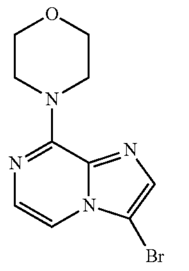 [SMILES: Brc1cnc2c(N3CCOCC3)nccn12]

Morpholine (2.0 ml, 23.2 mmol) was added to a stirred solution of a mixture 72/28 of 3-bromo-8-chloro-imidazo[1,2-a]pyrazine and 3,8-dibromo-imidazo[1,2-a]pyrazine (intermediate 15) (5.9 g, 11.6 mmol) and DIPEA (1.93 ml, 13.9 mmol) in ACN (54 ml). The mixture was stirred at 80° C. for 7 h. and then the solvent was evaporated in vacuo. The crude product was dissolved in DCM and washed with a saturated solution of sodium carbonate. The organic layer was separated, dried ($Na_2SO_4$), filtered and the solvents evaporated in vacuo. The crude product was purified by flash column chromatography (silica; EtOAc in DCM 10/90). The desired fractions were collected and evaporated in vacuo and the crude product precipitated from $Et_2O$ to yield intermediate 26 (2.79 g, 85%) as a white solid.

The following intermediates were prepared according to a protocol analogous to example A26.

Example A27

3-Bromo-2-methyl-8-morpholin-4-yl-imidazo[1,2-a]pyrazine

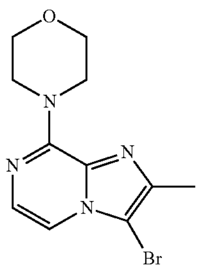 [SMILES: Cc1nc2c(N3CCOCC3)nccn2c1Br]

From intermediate 16. Flash column chromatography (silica; DCM in EtOAc 50/50) yielded intermediate 27 as a white solid (71%). m.p. 159.3-159.8° C. (WRS-2A).

Example A28

3-Bromo-2-cyclopropyl-8-morpholin-4-yl-imidazo[1,2-a]pyrazine

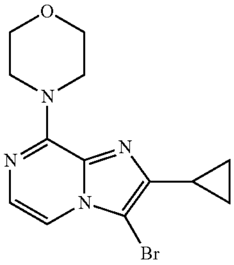 [SMILES: Brc1c(C2CC2)nc2c(N3CCOCC3)nccn12]

From intermediate 17. Flash column chromatography (silica; 7 M solution of ammonia in MeOH in DCM 1/99 to 2/98) yielded intermediate 28 as a pale brown solid (48%).

Example A29

3-Bromo-2-isopropyl-8-morpholin-4-yl-imidazo[1,2-a]pyrazine

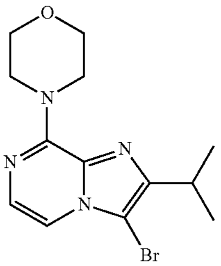 [SMILES: CC(C)c1nc2c(N3CCOCC3)nccn2c1Br]

From intermediate 18. Flash column chromatography (silica; 7 M solution of ammonia in MeOH in DCM 1/99 to 2/98) yielded intermediate 29 as a pale brown solid (51%).

Example A30

3-Bromo-8-morpholin-4-yl-2-trifluoromethyl-imidazo[1,2-a]pyrazine

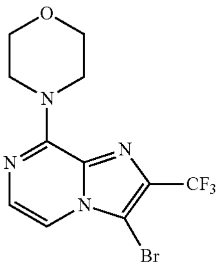 [SMILES: FC(F)(F)c1nc2c(N3CCOCC3)nccn2c1Br]

From intermediate 19. Flash column chromatography (silica; EtOAc in heptane 10/90) yielded intermediate 30 as a white solid (99%).

Example A31

3-Bromo-8-morpholin-4-yl-imidazo[1,2-a]pyrazine-2-carboxylic acid ethyl ester

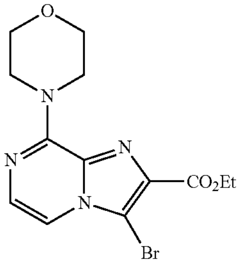 [SMILES: CCOC(=O)c1nc2c(N3CCOCC3)nccn2c1Br]

From intermediate 20. Flash column chromatography (silica; EtOAc in heptane 50/50) yielded intermediate 31 as a white solid (99%).

Example A32

3-Iodo-2-methyl-8-morpholin-4-yl-imidazo[1,2-a]pyrazine

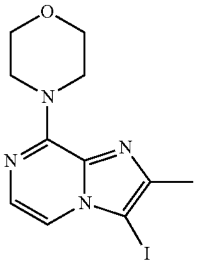 [SMILES: Cc1nc2c(N3CCOCC3)nccn2c1I]

From intermediate 25. Flash column chromatography (silica; EtOAc in DCM 10/90) yielded intermediate 32 as a white solid (87%). m.p. 135.3-136.7° C. (WRS-2A).

Example A33

2-Methyl-8-morpholin-4-yl-imidazo[1,2-a]pyrazine

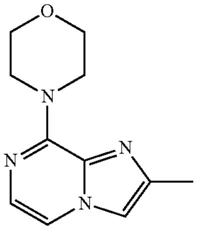 [SMILES: Cc1cn2ccnc(N3CCOCC3)c2n1]

From intermediate 4. 160° C., 30 min., microwave irradiation. Flash column chromatography (silica; 7 M solution of ammonia in MeOH in DCM 0/100 to 1/99) yielded intermediate 33 as a white solid (51%).

Example A34

3-Bromo-6-iodo-2-methyl-8-morpholin-4-yl-imidazo[1,2-a]pyrazine

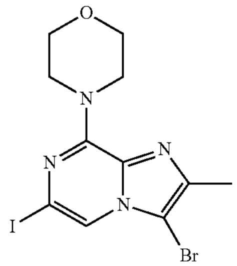 [SMILES: Cc1nc2c(N3CCOCC3)nc(I)cn2c1Br]

From intermediate 21. 160° C., 30 min., microwave irradiation. Flash column chromatography (silica; 7 M solution of ammonia in MeOH in DCM 0/100 to 1/99) yielded intermediate 34 as a white solid (83%). m.p. 181.2-182.1° C. (WRS-2A).

Example A35

3-Bromo-2,6-dimethyl-8-morpholin-4-yl-imidazo[1,2-a]pyrazine

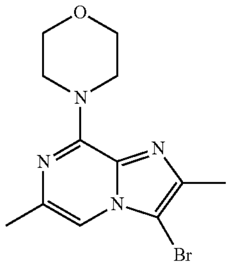

A 1.6 M solution of methyllithium in THF (2.66 ml, 4.25 mmol) was added dropwise to a solution of indium (III) chloride (0.35 g, 1.59 mmol) in THF (35 ml) at −78° C. The mixture was stirred at −78° C. for 30 min. and then allowed to warm to RT. The trimethylindium pale white solution obtained was transferred via cannula to a stirred solution of intermediate 34 (1.5 g, 3.55 mmol) and tetrakistriphenylphosphine palladium (0) (0.21 g, 0.18 mmol) in THF (20 ml). The mixture was stirred at 80° C. for 16 h. and then the solvent was evaporated in vacuo. The crude product was dissolved in DCM and washed with a saturated solution of ammonium chloride. The organic layer was separated, dried ($Na_2SO_4$), filtered and the solvents evaporated in vacuo. The crude product was purified by flash column chromatography (silica; MeOH in DCM 0/100 to 2/98). The desired fractions were collected and evaporated in vacuo to yield intermediate 35 (0.86 g, 78%) as a white solid.

The following intermediate was prepared according to a protocol analogous to example A35.

Example A36

3-Bromo-6-cyclopropyl-2-methyl-8-morpholin-4-yl-imidazo[1,2-a]pyrazine

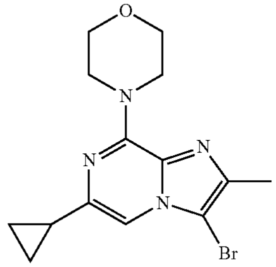 [SMILES: Cc1nc2c(N3CCOCC3)nc(C3CC3)cn2c1Br]

From intermediate 34 and cyclopropylmagnesium bromide. Flash column chromatography (silica; EtOAc in heptane 0/100 to 30/70) yielded intermediate 36 as a white solid (68%).

Example A37

3-Bromo-2-methyl-6-trifluoromethyl-8-morpholin-4-yl-imidazo[1,2-a]pyrazine

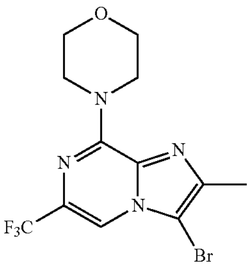 [SMILES: Cc1nc2c(N3CCOCC3)nc(C(F)(F)F)cn2c1Br]

Copper (I) iodide (0.18 g, 0.95 mmol) and fluorosulfonyl (difluoro)acetic acid methyl ester (0.12 ml, 0.95 mmol) were added to a stirred solution of intermediate 34 (0.20 g, 0.47 mmol) in DMF (2 ml). The mixture was stirred at 90° C. for 16 h. in a sealed tube under nitrogen and then diluted with $Et_2O$ and washed with a saturated solution of ammonium hydroxide. The organic layer was separated, dried ($Na_2SO_4$), filtered and the solvents evaporated in vacuo. The crude product was purified by flash column chromatography (silica; EtOAc in heptane 0/100 to 50/50). The desired fractions were collected and evaporated in vacuo to yield intermediate 37 (0.15 g, 60%) as a pale brown solid.

Example A38

3-Bromo-2-methyl-8-morpholin-4-yl-6-(3,3,3-trifluoro-propyl)-imidazo[1,2-a]pyrazine

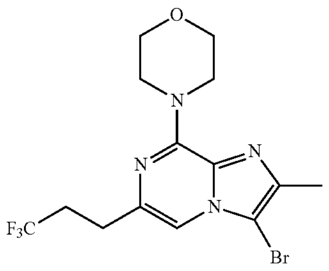 [SMILES: Cc1nc2c(N3CCOCC3)nc(CCC(F)(F)F)cn2c1Br]

1,2-Dibromoethane (0.04 ml, 0.51 mmol) was added to a stirred suspension of zinc (0.45 g, 6.82 mmol) in DMF (3.5 ml). The mixture was stirred at 90° C. for 30 min. under nitrogen and then chlorotrimethylsilane (0.013 ml, 0.102 mmol) was added. The mixture was stirred at RT for a further 30 min. and then a solution of 3-iodo-1,1,1-trifluoropropane in DMF (2 ml) was added dropwise. The mixture was stirred at 45° C. for 2.5 h. and the resulting solution was transferred via syringe to a second flask charged with intermediate 34 (0.144 g, 0.34 mmol) and bis(triphenylphosphine)palladium (II) dichloride (0.024 g, 0.034 mmol) under nitrogen. The mixture was stirred at 40° C. for 1 h. and then allowed to cool down to RT. A saturated solution of ammonium chloride was added and the mixture was extracted with EtOAc. The organic layer was separated, washed with a saturated solution of ammonium chloride and brine, dried ($Na_2SO_4$), filtered and the solvents evaporated in vacuo. The crude product was purified by flash column chromatography (silica; EtOAc in heptane 0/100 to 100/0). The desired fractions were collected and evaporated in vacuo to yield intermediate 38 (0.07 g, 52%) as a pale brown solid.

Example A39

2-Methyl-8-morpholin-4-yl-imidazo[1,2-a]pyrazine-3-carboxylic acid ethyl ester

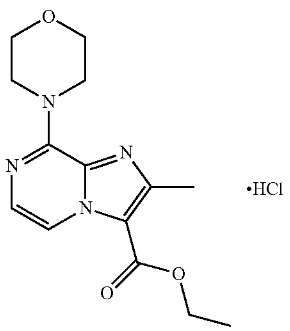 [SMILES: CCOC(=O)c1c(C)nc2c(N3CCOCC3)nccn12 ; Cl]

A mixture of intermediate 1 (2 g, 11.1 mmol) and ethyl 2-chloroacetoacetate (7.7 ml, 55.5 mmol) in EtOH (8 ml) was stirred at 90° C. for 18 h. The mixture was cooled down to RT and diluted with $Et_2O$. The solid formed was filtered off and dried in vacuo to yield intermediate 39 (2.98 g, 82%) as a white solid (.HCl).

Example A40

2-Methyl-8-morpholin-4-yl-imidazo[1,2-a]pyrazine-3-carboxylic acid methoxy-methyl-amide

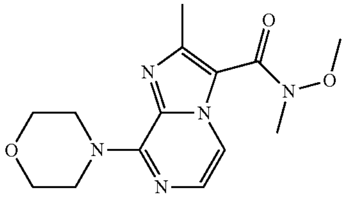 [SMILES: CON(C)C(=O)c1c(C)nc2c(N3CCOCC3)nccn12]

A 2 M solution of isopropylmagnesium chloride in THF (10.33 ml, 20.67 mmol) was added over 15 min. to a stirred suspension of intermediate 39 (2 g, 6.89 mmol) and N,O-dimethylhydroxylamine hydrochloride (1. g, 10.33 mmol) in a mixture of THF (15 ml) and DCM (8 ml) at −20° C. under nitrogen. The mixture was stirred at −5° C. for 1 h. and then allowed to warm to RT and stirred for a further 16 h. The mixture was cooled to −20° C. and further N,O-dimethylhydroxylamine hydrochloride (1 g, 10.33 mmol) and a 2 M solution of isopropylmagnesium chloride in THF (10 ml) were added. The mixture was stirred at −20° C. for 5 min. allowed to warm to RT and then stirred for a further 5 h. The mixture was cooled to −10° C. and a saturated solution of ammonium chloride was added. The organic layer was separated, dried ($Na_2SO_4$), filtered and the solvents evaporated in vacuo. The crude product was purified by flash column chromatography (silica; EtOAc in DCM 0/100 to 50/50). The desired fractions were collected and evaporated in vacuo to yield intermediate 40 (1.43 g, 68%) as a pink solid.

Example A41

1-(2-Methyl-8-morpholin-4-yl-imidazo[1,2-c]pyrazin-3-yl)-ethanone

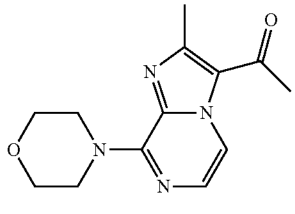 [SMILES: CC(=O)c1c(C)nc2c(N3CCOCC3)nccn12]

A 1.4 M solution of methylmagnesium bromide in THF (4.3 ml, 5.96 mmol) was added to a stirred solution of intermediate 40 (1.4 g, 4.59 mmol) in THF (30 ml) at −78° C., under nitrogen. The mixture was allowed to warm to RT and then stirred for 16 h. A saturated solution of ammonium chloride was added and the mixture was extracted with EtOAc. The organic layer was separated, dried ($Na_2SO_4$), filtered and the solvents evaporated in vacuo. The crude product was purified by flash column chromatography (silica;

EtOAc in DCM 0/100 to 40/60). The desired fractions were collected and evaporated in vacuo to yield intermediate 41 (1.1 g, 92%) as a white solid.

Example A42

2-Methyl-8-morpholin-4-yl-3-(1-trimethylsilanyloxy-vinyl)-imidazo[1,2-a]pyrazine

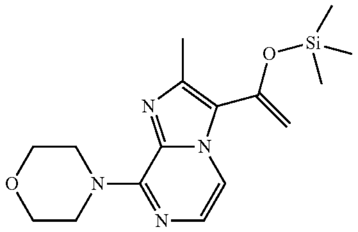 [SMILES: C=C(O[Si](C)(C)C)c1c(C)nc2c(N3CCOCC3)nccn12]

Trimethylsilyl trifluoromethanesulfonate (2.23 ml, 12.3 mmol) and N,N-diisopropylethylamine (2.84 ml, 16.3 mmol) were added to a stirred solution of intermediate 41 (0.8 g, 3.1 mmol) in DCM (12 ml). The mixture was stirred at 0° C. for 1.5 h, allowed to warm to RT and then stirred for a further 16 h. The mixture was partitioned between a cold saturated solution of sodium hydrogen carbonate and DCM. The organic layer was separated, dried ($Na_2SO_4$), filtered and the solvents evaporated in vacuo to yield intermediate 42 (0.99 g, 97%) as a colourless oil which was used in next step without further purification.

Example A43

2-Bromo-1-(2-methyl-8-morpholin-4-yl-imidazo[1,2-a]pyrazin-3-yl)-ethanone

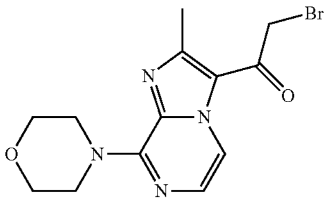 [SMILES: Cc1nc2c(N3CCOCC3)nccn2c1C(=O)CBr]

N-Bromosuccinimide (0.224 g, 1.26 mmol) and sodium hydrogen carbonate (0.192 g, 2.29 mmol) were added to a stirred solution of intermediate 42 (0.38 g, 1.14 mmol) in THF (8 ml). The mixture was stirred at −78° C. for 1 h. and then diluted with $Et_2O$ and extracted with a cold saturated solution of sodium hydrogen carbonate. The organic layer was separated, dried ($Na_2SO_4$), filtered and the solvents evaporated in vacuo. The crude product was purified by flash column chromatography (silica; EtOAc in DCM 0/100 to 10/90). The desired fractions were collected and evaporated in vacuo to yield intermediate 43 (0.26 g, 67%) as a pale yellow solid.

Example A44

1-Bromo-3-methoxy-3-methyl-butane

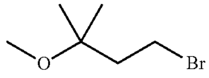

Triphenylphosphine (12.3 g, 47.0 mmol) was added to a stirred solution of 3-methoxy-3-methyl-butan-1-ol (4 ml, 31.3 mmol) and carbon tetrabromide (15.6 g, 47.0 mmol) in DCM (300 ml) at 0° C. The mixture was stirred at RT for 18 h. and then a solution of sodium thiosulphate was added. The organic layer was separated, dried ($Na_2SO_4$), filtered and the solvents evaporated in vacuo. The crude product was triturated with $Et_2O$, filtered off and purified by flash column chromatography (silica; petroleum ether in DCM 0/100 to 50/50). The desired fractions were collected and evaporated in vacuo to yield intermediate 44 (2.1 g, 37%).

Example A45

3-M ethoxy-3-methyl-1-iodobutane

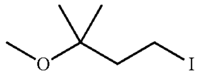

Sodium iodide (2.9 g, 19.3 mmol) was added to a stirred solution of intermediate 44 (1.4 g, 7.7 mmol) in dry acetone (10 ml). The mixture was stirred at reflux temperature for 3 h. and then filtered off. The filtrate was carefully evaporated in vacuo. The crude product was purified by flash column chromatography (silica; DCM). The desired fractions were collected and evaporated in vacuo to yield intermediate 45 (1.7 g, 81%).

The following intermediate was prepared according to a protocol analogous to example A45.

Example A46

1-Iodo-3-methoxy-propane

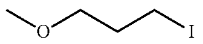

From 1-bromo-3-methoxy-propane. Flash column chromatography (silica; DCM) yielded intermediate 46 as a colourless oil (84%).

Example A47

5-Chloro-2-ethoxy-3-fluoro-pyridine

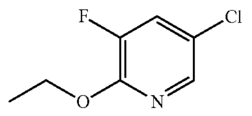

A solution of 5-chloro-2,3-difluoro-pyridine in EtOH was stirred at 80° C. for 16 h. The mixture was poured onto a saturated solution of sodium hydrogen carbonate and extracted with DCM. The organic layer was separated, dried ($MgSO_4$), filtered and the solvents evaporated in vacuo to yield intermediate 47 (1.64 g, 99%) as a white solid.

Example A48

5-Bromo-2-(2-methoxy-ethoxy)-pyridine

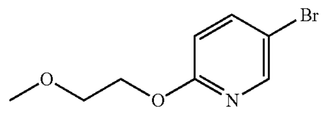

2-Methoxy-ethanol (3.08 ml, 39 mmol) was added dropwise to a stirred suspension of a 60% dispersion of sodium hydride in mineral oils (1.46 g, 36.4 mmol) in DMSO (50 ml). The mixture was stirred at RT for 30 min. and then 5-bromo-2-chloro-pyridine (5 g, 26 mmol) was added. The mixture was stirred at 60° C. for 1 h. and then diluted with heptane and washed with water. The organic layer was separated, dried ($Na_2SO_4$), filtered and the solvents evaporated in vacuo. The crude product was purified by flash column chromatography (silica; DCM in heptane 30/70 to 70/30). The desired fractions were collected and evaporated in vacuo to yield intermediate 48 (4.55 g, 75%) as a colourless oil.

The following intermediate was prepared according to a protocol analogous to example A48.

Example A49

5-Bromo-2-(2-methoxy-2-methyl-prop oxy)-pyridine

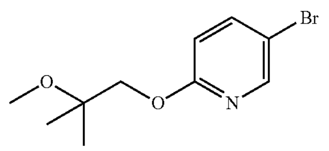

From 2-methoxy-2-methyl-propanol (obtained by procedures similar to those described in, Morel, P. US 2008102028 A1) and 5-bromo-2-chloro-pyridine. Flash column chromatography (silica; DCM in heptane 50/50 to 70/30) yielded intermediate 49 as a colourless oil (75%).

Example A50

5-Bromo-2-(1-methoxy-1-methyl-ethyl)-pyridine

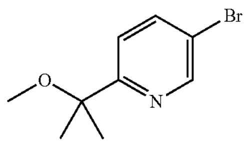

A solution of 2-(5-bromo-pyridin-2-yl)-propan-2-ol (0.50 g, 2.3 mmol) (obtained by procedures similar to those described in, Wang, X.; et al. Tetrahedron Lett, 2000, 4335) in THF (12 ml) was added dropwise to a stirred suspension of a 60% dispersion of sodium hydride in mineral oils (0.440 mg, 11.1 mmol) in THF (6 ml). The mixture was stirred at 0° C. for 20 min. and then dimethylsulfate (0.55 ml, 9.95 mmol) was added dropwise. The mixture was stirred at RT for 4 days and then diluted with DCM and washed with water. The organic layer was separated, dried ($Na_2SO_4$), filtered and the solvents evaporated in vacuo. The crude product was purified by flash column chromatography (silica; DCM in heptane 0/100 to 50/50). The desired fractions were collected and evaporated in vacuo to yield intermediate 50 (0.4 g, 69%) as a colourless oil.

Example A51

2-(5-Bromo-pyridin-2-yl)-ethanol

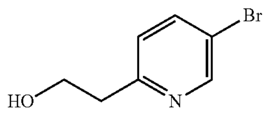

A 2.5 M solution of n-butyllithium in pentane (6.97 ml, 17.44 mmol) was added dropwise to a solution of DIPEA (3.29 ml, 23.25 mmol) in THF (50 ml). The mixture was stirred at 0° C. for 30 min., cooled down to −78° C. and then a solution of 5-bromo-2-methylpyridine (2.0 g, 11.63 mmol) in THF (50 ml) was added. The mixture was stirred at −78° C. for a further 2 h. and then DMF (8.5 g, 116.26 mmol) was added dropwise. The mixture was stirred at −78° C. for 2 h, at 0° C. for 30 min. and finally allowed to warm to RT. MeOH (25 ml) and sodium borohydride (0.439 g, 11.6 mmol) were added and the mixture was stirred at RT for a further 30 min. A saturated solution of ammonium chloride was added and the organic layer was separated. The aqueous layer was extracted with EtOAc and the combined organic extracts were dried ($Na_2SO_4$), filtered and the solvents evaporated in vacuo to yield intermediate 51 (2.8 g, 87%) as a colourless oil.

Example A52

5-Bromo-2-(2-methoxy-ethyl)-pyridine

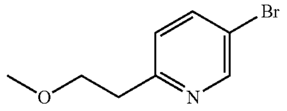

A 60% dispersion of sodium hydride in mineral oils, (0.43 g, 11.1 mmol) was added portionwise to a stirred solution of intermediate 51 (2.8 g, 10.1 mmol) in THF (50 ml). The mixture was stirred at 0° C. for 30 min. and at RT for 16 h. A saturated solution of ammonium chloride was added and the organic layer was separated. The aqueous layer was extracted with DCM and the combined organic extracts were dried ($Na_2SO_4$), filtered and the solvents evaporated in vacuo to yield 52 (0.9 g, 41%) as a colourless oil.

Example A53

1-(5-Bromo-pyridin-2-yl)-2-methyl-propan-2-ol

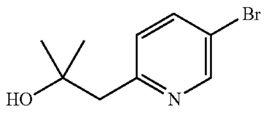

A 2.5 M solution of n-butyllithium in pentane (8.37 ml, 20.9 mmol) was added dropwise to a stirred solution of DIPEA (3.45 ml, 24.4 mmol) in THF (20 ml) at −78° C. The mixture was stirred at 0° C. for 30 min., cooled down to −78° C. and then added dropwise to a solution of 5-bromo-2-picoline (3.0 g, 17.4 mmol) in THF (20 ml). The mixture was stirred at −78° C. for 15 min. and then acetone (3.85 ml, 52.3 mmol) was added dropwise. The mixture was stirred at −78° C. for 20 min. and then a saturated solution of ammonium chloride was added. The organic layer was separated and the aqueous layer was extracted with DCM. The combined organic extracts were dried ($Na_2SO_4$), filtered and the solvents evaporated in vacuo. The crude product was purified by flash column chromatography (silica; EtOAc in DCM 0/100 to 20/80). The desired fractions were collected and evaporated in vacuo to yield intermediate 53 (1.75 g, 43%) as a colourless oil.

Example A54

5-Bromo-2-(-methoxy-2-methyl-propyl)-pyridine

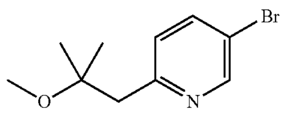

A 60% suspension of sodium hydride in mineral oils (2.36 g, 58.9 mmol) was added portionwise to a stirred solution of intermediate 53 (2.36 g, 58.9 mmol) in THF (10 ml). The mixture was stirred at 0° C. for 30 min. and then iodomethane (3.67 ml, 58.9 mmol) was added. The mixture was stirred at RT for 18 h. and then further 60% suspension of sodium hydride in mineral oils (2.36 g, 58.9 mmol) and iodomethane (3.67 ml, 58.9 mmol) were added. The mixture was stirred at RT for 3 h. and then the solvents were evaporated in vacuo. The crude product was diluted with DCM and washed with a saturated solution of ammonium chloride and a saturated solution of sodium hydrogen carbonate. The organic layer was separated, dried ($Na_2SO_4$), filtered and the solvents evaporated in vacuo. The crude product was purified by flash column chromatography (silica; EtOAc in DCM 0/100 to 10/90). The desired fractions were collected and evaporated in vacuo to yield intermediate 54 (6.90 g, 53%).

Example A55

5-Bromo-2-(1-methoxy-propyl)-pyridine

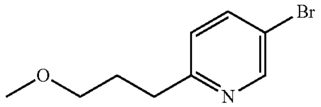

1,2-Dibromoethane (0.237 ml, 2.75 mmol) was added to a stirred suspension of zinc (3.6 g, 54.99 mmol) in dry DMF (40 ml). The mixture was stirred at 90° C. for 30 min. under nitrogen and then allowed to warm to RT. Chlorotrimethylsilane (0.09 ml, 0.69 mmol) was added and the mixture was stirred at RT for 15 min. A solution of intermediate 46 (5.5 g, 27.5 mmol) in THF (20 ml) was added dropwise and the mixture was stirred at 45° C. for 2.5 h. The excess of zinc was allowed to settle for 1 h. and the supernatant liquid was transferred via cannula to a mixture of 2,5-dibromopyridine (2.17 g, 9.17 mmol) and tetrakis(triphenylphosphine)palladium (0) (0.212 g, 0.18 mmol). The mixture was stirred at 55° C. for 4 h. under nitrogen, and then the solvents were evaporated in vacuo. The crude product was partitioned between DCM and a saturated solution of sodium hydrogen carbonate. The organic layer was separated, dried ($Na_2SO_4$), filtered and the solvents evaporated in vacuo. The crude product was purified by flash column chromatography (silica; EtOAc in DCM 0/100 to 20/80). The desired fractions were collected and evaporated in vacuo to yield intermediate 55 (1.4 g, 66%).

Example A56

5-Bromo-2-ethoxymethyl-pyridine

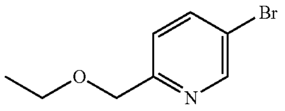

A 60% suspension of sodium hydride in mineral oils (0.073 g, 3.19 mmol) was added to a stirred solution of 5-bromo-2-(hydroxymethyl)pyridine (0.5 g, 2.66 mmol) in THF (10 ml). The mixture was stirred at 0° C. for 30 min. and then iodoethane (0.498 g, 3.19 mmol) was added. The mixture was stirred at 60° C. for 18 h. and then diluted with $Et_2O$ and washed with a saturated solution of ammonium chloride in water. The organic layer was separated, dried ($Na_2SO_4$), filtered and the solvents evaporated in vacuo to yield intermediate 56 (0.520 g, 90%) as a colourless oil.

Example A57

2-Bromo-5-(2-methoxy-vinyl)-pyridine

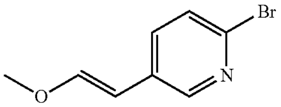

A 2.5M solution of n-butyllithium in hexanes (9.94 ml, 24.8 mmol) was added dropwise to a stirred solution of (methoxymethyl)triphenylphosphonium chloride (8.51 g, 24.8 mmol) in THF (150 ml) at 0° C. and then 6-bromonicotinaldehyde (3.3 g, 17.7 mmol) was slowly added to the red mixture. The mixture was stirred at RT for 16 h. and then diluted with $Et_2O$ and washed with water. The aqueous layer was extracted with DCM and the organic layer was dried ($Na_2SO_4$), filtered and the solvents evaporated in vacuo. The crude product was purified by flash column chromatography (silica; DCM in heptane 0/100 to 50/50). The desired fractions were collected and evaporated in vacuo to yield intermediate 57 (2.8 g, 73%) as a mixture 57/43 of E and Z isomers.

Example A58

2-Bromo-5-(2-methoxy-ethyl)-pyridine

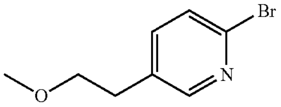

A solution of intermediate 57 (2.3 g, 10.7 mmol) in EtOH (100 ml) was hydrogenated in a H-cube reactor (1.5 ml/min., long $Rh/C_5$% cartridge, full $H_2$ mode, 70° C., 3 cycles). The solvent was evaporated in vacuo and the crude product purified by flash column chromatography (silica; EtOAc in heptane and DCM 0/50/50 to 0/0/100 to 20/0/80). The desired fractions were collected and evaporated in vacuo to yield intermediate 58 (0.48 g, 21%) as a colourless oil.

Example A59

2-Ethoxy-3-fluoro-5-(4,4,5,5-tetramethyl-[1,3,2]dioxaborolan-2-yl)-pyridine

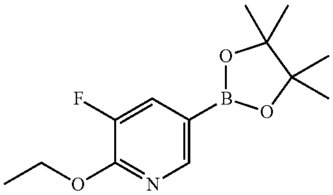 [SMILES: CCOc1ncc(B2OC(C)(C)C(C)(C)O2)cc1F]

Palladium (II) acetate (0.021 g, 0.094 mmol) and 2-dicyclohexylphosphino-2',6'-dimethoxy-1,1'-biphenyl (0.115 g, 0.28 mmol) were added to stirred solution of intermediate 47 (1.64 g, 9.36 mmol), 4,4,4',4',5,5,5',5'-octamethyl-2,2'-bi-1,3,2-dioxaborolane (7.13 g, 28.08 mmol) and potassium phosphate (1.99 g, 9.36 mmol) in 1,4-dioxane (20 ml). The mixture was stirred at RT for 16 h. under nitrogen and then at 85° C. for a further 4 h. The mixture was filtered through a pad of diatomaceous earth, and the filtrate diluted with EtOAc and washed with water. The organic layer was separated, dried ($Na_2SO_4$), filtered and the solvents evaporated in vacuo. The crude product was purified by flash column chromatography (silica; EtOAc in DCM 0/100 to 30/70). The desired fractions were collected and evaporated in vacuo to yield intermediate 59 (1.8 g, 72%).

Example A60

2-(2-Methoxyethyl)-5-(4,4,5,5-tetramethyl-[1,3,2]dioxaborolan-2-yl)-pyridine

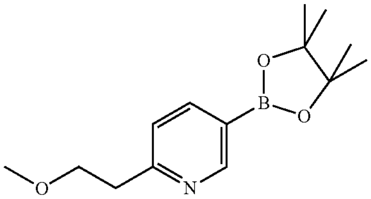

[1,1'-Bis(diphenylphosphino)ferrocene]dichloropalladium (II) (0.061 g, 0.083 mmol) was added to a stirred suspension of intermediate 52 (0.6 g, 2.77 mmol), 4,4,4',4',5,5,5',5'-octamethyl-2,2'-bi-1,3,2-dioxaborolane (0.846 g, 3.33 mmol) and potassium acetate (0.817 g, 8.33 mmol) in a mixture of 1,4-dioxane (9 ml) and DMF (1.2 ml). The mixture was stirred at 150° C. for 40 min. in a sealed tube under nitrogen and under microwave irradiation. The mixture was filtered through a pad of diatomaceous earth and the filtrate diluted with DCM and washed with water. The organic layer was separated, dried ($Na_2SO_4$), filtered and the solvents evaporated in vacuo to yield intermediate 60 (1.1 g, 64%, 43% purity) used in the next step without further purification.

The following intermediates were prepared according to a protocol analogous to example A60.

Example A61

2-(2-Methoxy-2-methyl-propyl)-5-(4,4,5,5-tetramethyl-[1,3,2]dioxaborolan-2-yl)-pyridine

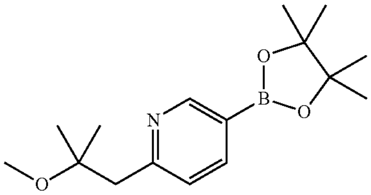

From intermediate 54 and DMSO as solvent at 80° C. for 4 h. Extraction with heptane yielded intermediate 61 as a colourless oil (17%).

Example A62

2-(2-Methoxy-ethoxy)-5-(4,4,5,5-tetramethyl-[1,3,2]dioxaborolan-2-yl)-pyridine

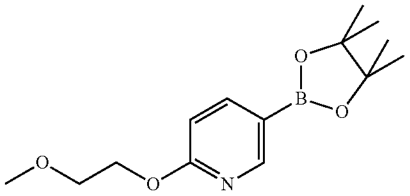

From intermediate 48 and DMSO as solvent at 80° C. for 4 h. Extraction with heptane yielded intermediate 62 as a colourless oil (93%).

Example A63

2-(2-Methoxy-2-methyl-propoxy)-5-(4,4,5,5-tetramethyl-[1,3,2]dioxaborolan-2-yl)-pyridine

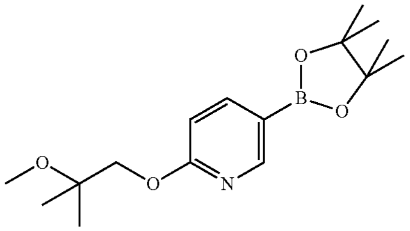

From intermediate 49 and DMSO as solvent at 80° C. for 4 h. Extraction with heptane yielded intermediate 63 as a colourless oil (97%).

Example A64

2-Ethoxymethyl-5-(4,4,5,5-tetramethyl-[1,3,2]dioxaborolan-2-yl)-pyridine

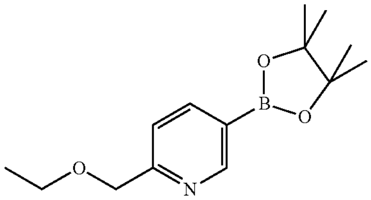 [SMILES: CCOCc1ccc(B2OC(C)(C)C(C)(C)O2)cn1]

From intermediate 55 and DMSO as solvent, 80° C. 4 h. Extraction with heptane yielded intermediate 64 as a colourless oil (84%).

Example A65

2-(1-Methoxy-propyl)-5-(4,4,5,5-tetramethyl-[1,3,2]dioxaborolan-2-yl)-pyridine

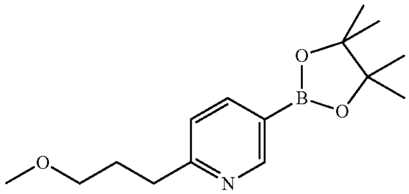

From intermediate 55. Extraction with heptane yielded intermediate 65 as a colourless oil (10%).

Example A66

5-(2-Methoxy-ethyl)-2-tributylstannanyl-pyridine

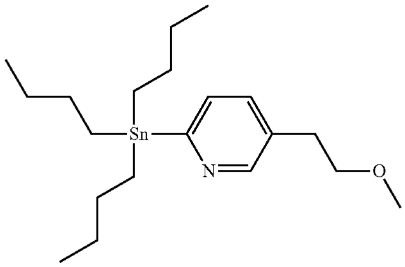 [SMILES: CCC[CH2][Sn]([CH2]CCC)([CH2]CCC)[c]1ccc(CCOC)cn1]

A 2.5 M solution of n-butyllithium in hexanes (1.1 ml, 2.72 mmol) was added dropwise to a solution of intermediate 58 (0.245 g, 1.13 mmol) in THF (10 ml). The mixture was stirred at −78° C. for 1 h. and then tributyltin chloride (0.74 ml, 2.72 mmol) was slowly added. The mixture was allowed to warm to RT over 1 h. and then a saturated solution of ammonium chloride was added. The mixture was extracted with $Et_2O$ and EtOAc. The combined organic layers were dried ($Na_2SO_4$), filtered and the solvents evaporated in vacuo to yield intermediate 66 (0.72 g, >100%) which was used in the next step without any further purification.

Example A67

1-(2-Methoxy-ethyl)-4-(4,4,5,5-tetramethyl-[1,3,2]dioxaborolan-2-yl)-1H-pyrazole

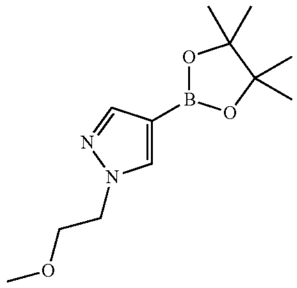

2-Chloroethyl methyl ether (0.050 ml, 0.63 mmol) was added to a stirred solution of 4-(4,4,5,5-tetramethyl-[1,3,2]dioxaborolan-2-yl)-1H-pyrazole (5.0 g, 25.77 mmol) and cesium carbonate (12.59 g, 38.65 mmol) in DMF (27 ml). The mixture was stirred at 160° C. for 30 min. under microwave irradiation and then the solvent was evaporated in vacuo. The crude product was purified by flash column chromatography (silica; MeOH in DCM 2/98). The desired fractions were collected and evaporated in vacuo to yield intermediate 67 (4.6 g, 72%) as a pale yellow oil.

Example A68

4-[4-(4,4,5,5-Tetramethyl-[1,3,2]dioxaborolan-2-yl)-pyrazol-1-yl]-butan-2-one

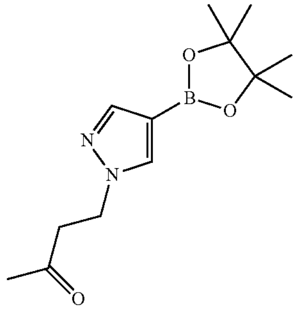 [SMILES: CC(=O)CCn1cc(B2OC(C)(C)C(C)(C)O2)cn1]

1,8-diazabicyclo[5.4.0]undec-7-ene (0.77 ml, 5.15 mmol) was added to a stirred solution of 4-(4,4,5,5-tetramethyl-[1,3,2]dioxaborolan-2-yl)-1H-pyrazole (2 g, 10.31 mmol) and methyl vinyl ketone (1.08 g, 15.46 mmol) in ACN (50 ml). The mixture was stirred at RT for 2 days and then the solvent was evaporated in vacuo. The crude product was purified by flash column chromatography (silica; EtOAc in DCM 0/100 to 20/80) to yield intermediate 68 (1.8 g, 41%, 79% purity) as a pale yellow oil which was used in the next step without any further purification.

Example A70

3-(6-Chloro-pyridin-3-yl)-2-methyl-8-morpholin-4-yl-imidazo[1,2-a]pyrazine

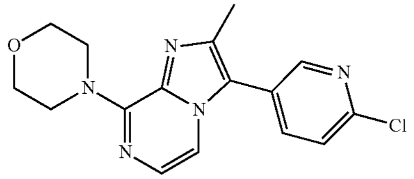 [SMILES: Cc1nc2c(N3CCOCC3)nccn2c1-c1ccc(Cl)nc1]

Tetrakis(triphenylphosphine)palladium (0) (1.5 g, 1.3 mmol) was added to a stirred solution of intermediate 32 (11.5 g, 33.42 mmol) and 2-chloropyridine-5-boronic acid (6.1 g, 38.76 mmol) in a mixture of 1,4-dioxane (200 ml) and a saturated solution of sodium hydrogen carbonate (50 ml). The mixture was stirred at 100° C. for 18 h. under nitrogen, and then further tetrakis(triphenylphosphine)palladium (0) (0.35 g, 0.3 mmol) and 2-chloropyridine-5-boronic acid (0.6 g, 2.8 mmol) were added. The mixture was stirred at 100° C. for a further 5 h. and then concentrated in vacuo and partitioned between DCM, water and a saturated solution of sodium carbonate. The organic layer was separated, dried ($Na_2SO_4$), filtered and the solvents evaporated in vacuo. The crude product was precipitated from MeOH to yield intermediate 70 (10.3 g, 93%) as a white solid.

The following intermediates were prepared according to a protocol analogous to example A70.

Example A71

3-(2-Chloro-pyridin-4-yl)-2-methyl-8-morpholin-4-yl-imidazo[1,2-a]pyrazine

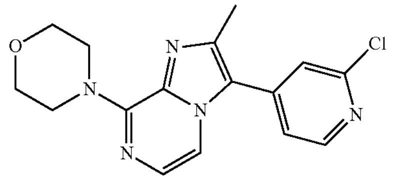 [SMILES: Cc1nc2c(N3CCOCC3)nccn2c1-c1ccnc(Cl)c1]

From intermediate 32 and 2-chloropyridine-4-boronic acid. Flash column chromatography (silica; EtOAc in DCM 0/100 to 80/20) yielded intermediate 71 as a white solid (83%).

Example A72

3-(6-Chloro-pyridin-3-yl)-2-cyclopropyl-8-morpholin-4-yl-imidazo[1,2-a]pyrazine

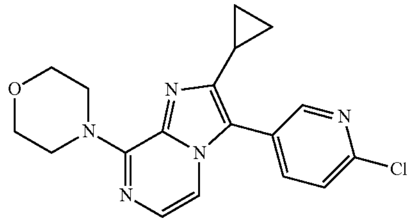 [SMILES: Clc1ccc(-c2c(C3CC3)nc3c(N4CCOCC4)nccn23)cn1]

From intermediate 28 and 2-chloropyridine-5-boronic acid. Flash column chromatography (silica; EtOAc) yielded intermediate 72 as a white solid (63%).

Example A73

3-(6-Chloro-5-fluoro-pyridin-3-yl)-2-methyl-8-morpholin-4-yl-imidazo[1,2-a]pyrazine

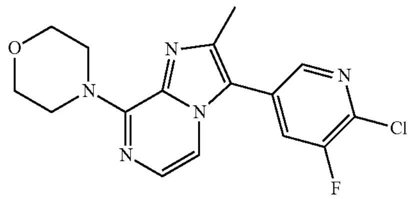 [SMILES: Cc1nc2c(N3CCOCC3)nccn2c1-c1cnc(Cl)c(F)c1]

A mixture of compound 143 (0.1 g, 0.28 mmol) and phosphorus oxychloride (0.26 ml, 2.8 mmol) was stirred at 100° C. for 16 h. The mixture was evaporated in vacuo and the crude product purified by flash column chromatography (silica; EtOAc in DCM 0/100 to 50/50). The desired fractions were collected and evaporated in vacuo to yield intermediate 73 (75 mg, 77%) as a pale brown solid.

Example A74

2-Methyl-8-morpholin-4-yl-3-(6-vinyl-pyridin-3-yl)-imidazo[1,2-a]pyrazine

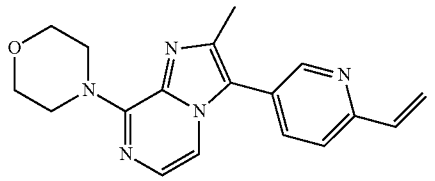 [SMILES: C=Cc1ccc(-c2c(C)nc3c(N4CCOCC4)nccn23)cn1]

Tetrakis(triphenylphosphine)palladium (0) (0.623 g, 0.54 mmol) was added to a stirred solution of intermediate 70 (8.9 g, 26.99 mmol) and 4,4,5,5-tetramethyl-2-vinyl-1,3,2-dioxaborolane (5.91 ml, 35.08 mmol) in a mixture of 1,4-dioxane (60 ml) and a saturated solution of sodium carbonate (30 ml). The mixture was stirred at 100° C. for 1 h. under nitrogen and then diluted with DCM and extracted with water. The organic layer was separated, dried ($Na_2SO_4$), filtered and the solvents evaporated in vacuo. The crude product was purified by flash column chromatography (silica; 7 M ammonia solution in MeOH in DCM 0/100 to 2/98). The desired fractions were collected and evaporated in vacuo to yield intermediate 74 (7.8 g, 90%) as a white solid.

The following intermediates were prepared according to a protocol analogous to example A74.

Example A75

2-Methyl-8-morpholin-4-yl-3-(2-vinyl-pyridin-4-yl)-imidazo[1,2-a]pyrazine

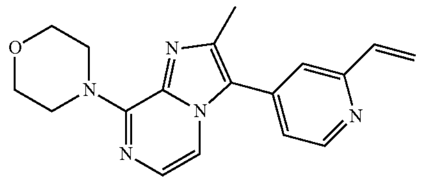 [SMILES: C=Cc1cc(-c2c(C)nc3c(N4CCOCC4)nccn23)ccn1]

From intermediate 71. Flash column chromatography (silica; EtOAc in DCM 20/80 to 70/30) yielded intermediate 75 as a white solid.

Example A76

2-Cyclopropyl-8-morpholin-4-yl-3-(6-vinyl-pyridin-3-yl)-imidazo[1,2-a]pyrazine

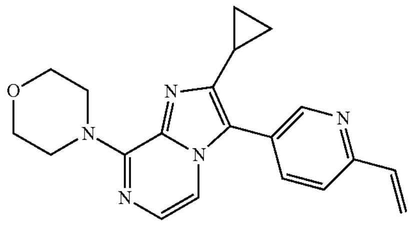 [SMILES: C=Cc1ccc(-c2c(C3CC3)nc3c(N4CCOCC4)nccn23)cn1]

From intermediate 72. Flash column chromatography (silica; EtOAc) yielded intermediate 76 as a white solid (60%).

Example A77

3-(5-Fluoro-6-vinyl-pyridin-3-yl)-2-methyl-8-morpholin-4-yl-imidazo[1,2-a]pyrazine

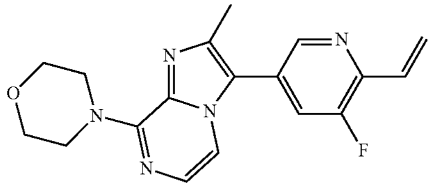 [SMILES: C=Cc1ncc(-c2c(C)nc3c(N4CCOCC4)nccn23)cc1F]

From intermediate 73. Flash column chromatography (silica; EtOAc) yielded intermediate 77 as a white solid (96%).

Example A78

3-[6-(3,6-Dihydro-2H-pyran-4-yl)-pyridin-3-yl]-2-methyl-8-morpholin-4-yl-imidazo[1,2-a]pyrazine

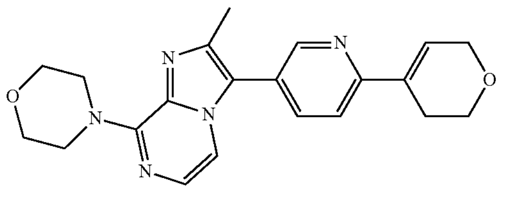 [SMILES: Cc1nc2c(N3CCOCC3)nccn2c1-c1ccc(C2=CCOCC2)nc1]

Tetrakis(triphenylphosphine)palladium (0) (0.32 g, 0.28 mmol) was added to a stirred solution of intermediate 70 (3 g, 9.1 mmol) and 4-(4,4,5,5-tetramethyl-[1,3,2]dioxaborolan-2-yl)-3,6-dihydro-2H-pyran (2.87 g, 13.65 mmol) (obtained by procedures similar to those described in Qiu, Y. et al. WO 2004075846 A2) in a mixture of 1,4-dioxane (30 ml) and a saturated solution of sodium carbonate (15 ml). The mixture was stirred at 90° C. for 16 h. under nitrogen and then diluted with DCM and washed with water and brine. The organic layer was separated, dried ($Na_2SO_4$), filtered and the solvents evaporated in vacuo. The crude product was purified by flash column chromatography (silica; 7 M solution of ammonia in MeOH in DCM 2/98). The desired fractions were collected and evaporated in vacuo to yield intermediate 78 (4.5 g, 99%) as a white solid.

Example A79

3-[1-(2-Methoxy-ethyl)-1H-pyrazol-4-yl]-8-morpholin-4-yl-imidazo[1,2-a]pyrazine-2-carboxylic acid ethyl ester

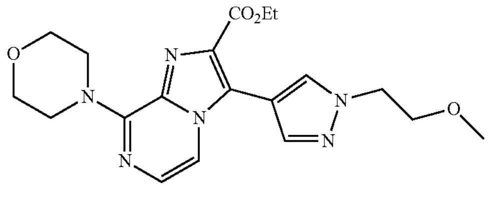 [SMILES: CCOC(=O)c1nc2c(N3CCOCC3)nccn2c1-c1cnn(CCOC)c1]

Palladium acetate (0) (0.043 g, 0.189 mmol) was added to a stirred solution of intermediate 31 (0.96 g, 2.7 mmol) and intermediate 67 (1.36 g, 5.40 mmol) in 1,4-dioxane (48 ml). The mixture was stirred at 80° C. for 18 h. under nitrogen and then the solvent was evaporated in vacuo. The crude product was partitioned between water and DCM and the organic layer was separated, dried ($Na_2SO_4$), filtered and the solvents evaporated in vacuo. The crude product was purified by flash column chromatography (silica; MeOH in DCM 0/100 to 10/90). The desired fractions were collected and evaporated in vacuo and the crude product purified by RP HPLC (0.1% solution of ammonium formate/ammonium hydroxide buffer pH 9 in ACN 80/20 to 0/100) to yield intermediate 79 (0.31 g, 28%) as a white solid.

Example A80

3-[1-(2-Methoxy-ethyl)-1H-pyrazol-4-yl]-8-morpholin-4-yl-imidazo[1,2-a]pyrazine-2-carboxylic acid amide

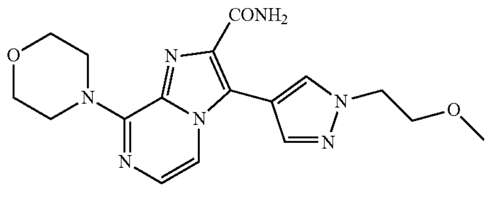 [SMILES: COCCn1cc(-c2c(C(N)=O)nc3c(N4CCOCC4)nccn23)cn1]

Intermediate 79 (0.3 g, 0.75 mmol) was dissolved in an ammonium hydroxide solution (5 ml). The mixture was stirred at 80° C. for 16 h. and then the solvent was evaporated in vacuo. The crude product was purified by flash column chromatography (silica; 7 M solution of ammonia in MeOH in DCM 0/100 to 5/95). The desired fractions were collected and evaporated in vacuo to yield intermediate 80 (0.31 g, 28%) as a white solid.

B. Preparation of the Final Compounds

Example B1

3-[6-(2-Methoxy-ethoxy)-pyridin-3-yl]-2-methyl-8-morpholin-4-yl-imidazo[1,2-a]pyrazine

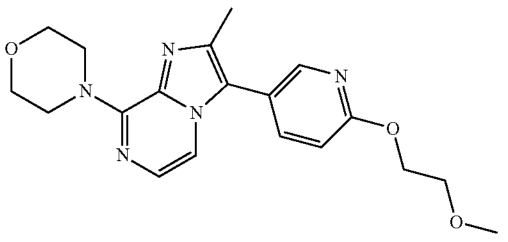 [SMILES: COCCOc1ccc(-c2c(C)nc3c(N4CCOCC4)nccn23)cn1]

Tetrakis(triphenylphosphine)palladium (0) (0.058 g, 0.050 mmol) was added to a stirred solution of intermediate 27 (0.30 g, 1.0 mmol) and intermediate 62 (0.42 g, 1.51 mmol) in a mixture of 1,4-dioxane (10 ml) and a saturated solution of sodium carbonate (5 ml). The mixture was stirred at 140° C. for 20 min. in a sealed tube under nitrogen and under microwave irradiation. The solvent was evaporated in vacuo and the crude product was partitioned between water and DCM. The organic layer was separated, dried ($Na_2SO_4$), filtered and the solvents evaporated in vacuo. The crude product was purified by flash column chromatography (silica; MeOH in DCM 5/95). The desired fractions were collected, evaporated in vacuo and triturated with $Et_2O$ to yield compound 1 (0.16 g, 43%) as a white solid.

The following compounds were prepared according to a protocol analogous to example B1.

Example B2

3-[6-(2-Methoxy-2-methyl-propoxy)-pyridin-3-yl]-2-methyl-8-pyridin-4-yl-imidazo[1,2-a]pyrazine

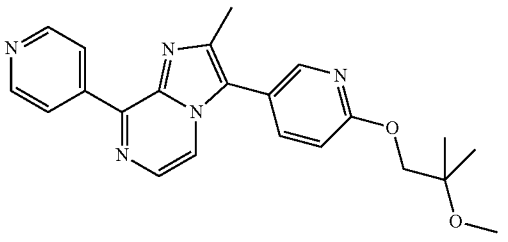 [SMILES: COC(C)(C)COc1ccc(-c2c(C)nc3c(-c4ccncc4)nccn23)cn1]

From intermediate 22 and intermediate 63. Flash column chromatography (silica; 7 M solution of ammonia in MeOH in DCM 3/97) and flash column chromatography (silica; EtOAc in heptane 40/60 to 100/0) yielded compound 2 as a white solid (44%).

Example B3

3-[6-(2-Methoxy-2-methyl-propoxy)-pyridin-3-yl]-2-methyl-8-morpholin-4-yl-imidazo[1,2-a]pyrazine

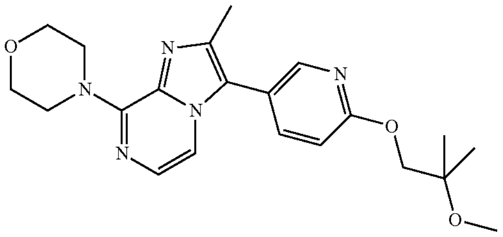 [SMILES: COC(C)(C)COc1ccc(-c2c(C)nc3c(N4CCOCC4)nccn23)cn1]

From intermediate 27 and intermediate 63 at 140° C. for 20 min. and under microwave irradiation. Flash column chromatography (silica; MeOH in DCM 5/95) and freeze-drying yielded compound 3 as a white solid (42%).

Example B4

2-Methyl-8-morpholin-4-yl-3-(6-morpholin-4-yl-pyridin-3-yl)-imidazo[1,2-a]pyrazine

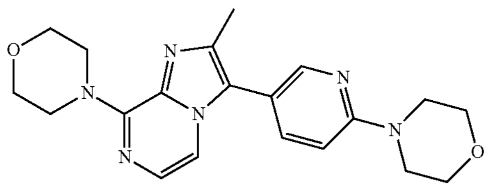 [SMILES: Cc1nc2c(N3CCOCC3)nccn2c1-c1ccc(N2CCOCC2)nc1]

From intermediate 27 and commercially available 4-[5-(4,4,5,5-tetramethyl-1,3,2-dioxaborolan-2-yl)-2-pyridinyl]morpholine at 150° C. for 15 min. and under microwave irradiation. Flash column chromatography (silica; 7 M solution of ammonia in MeOH in DCM 2/98) yielded compound 4 as a pale brown solid (89%).

Example B5

3-(6-Ethoxymethyl-pyridin-3-yl)-2-methyl-8-morpholin-4-yl-imidazo[1,2-a]pyrazine

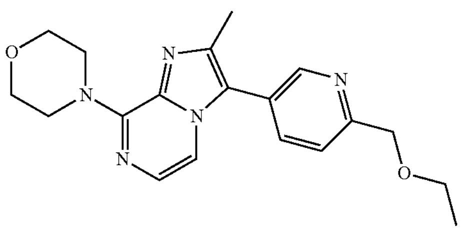 [SMILES: CCOCc1ccc(-c2c(C)nc3c(N4CCOCC4)nccn23)cn1]

From intermediate 27 and intermediate 64 at 150° C. for 15 min. and under microwave irradiation. Flash column chromatography (silica; 7 M solution of ammonia in MeOH in DCM 0/100 first) and RP HPLC (0.1% solution of ammonium formate/ammonium hydroxide buffer pH 9 in EtOAc 80/20 to 0/100) yielded compound 5 as a white solid (48%).

Example B6

3-[6-(3-Methoxy-propyl)-pyridin-3-yl]-2-methyl-8-morpholin-4-yl-imidazo[1,2-a]pyrazine

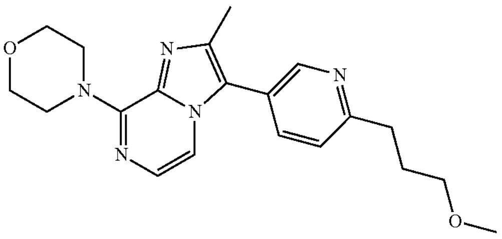 [SMILES: COCCCc1ccc(-c2c(C)nc3c(N4CCOCC4)nccn23)cn1]

From intermediate 27 and intermediate 65 at 150° C. for 20 min. and under microwave irradiation. Flash column chromatography (silica; EtOAc in heptane 50/50 to 20/80) yielded compound 6 as a white solid (11%).

Example B7

3-[6-(2-Methoxy-2-methyl-propyl)-pyridin-3-yl]-2-methyl-8-morpholin-4-yl-imidazo[1,2-a]pyrazine

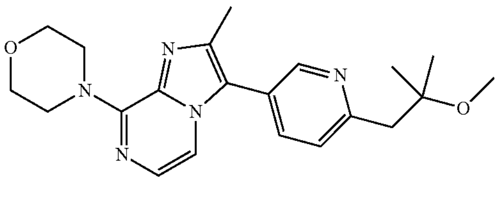 [SMILES: COC(C)(C)Cc1ccc(-c2c(C)nc3c(N4CCOCC4)nccn23)cn1]

From intermediate 27 and intermediate 61 at 140° C. for 15 min. and under microwave irradiation. Flash column chromatography (silica; EtOAc in DCM 50/50 to 80/20), flash column chromatography (silica; 7 M solution of ammonia in MeOH in DCM 0/100 to 2/98) and precipitation from heptane yielded compound 7 as a white solid (71%).

Example B8

3-[6-(2-Methoxy-ethyl)-pyridin-3-yl]-2-methyl-8-pyridin-4-yl-imidazo[1,2-a]pyrazine

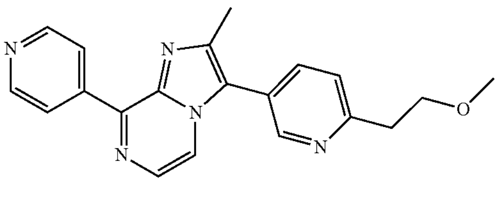 [SMILES: COCCc1ccc(-c2c(C)nc3c(-c4ccncc4)nccn23)cn1]

From intermediate 22 and intermediate 60 at 150° C. for 15 min. and under microwave irradiation. Flash column chromatography (silica; 7 M solution of ammonia in MeOH in DCM 0/100 to 2/98) and precipitation from $Et_2O$ yielded compound 8 as a white solid (90%).

Example B9

3-[6-(2-Methoxy-ethyl)-pyridin-3-yl]-2-methyl-8-morpholin-4-yl-6-trifluoromethyl-imidazo[1,2-a]pyrazine

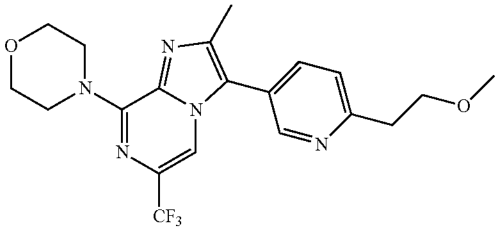 [SMILES: COCCc1ccc(-c2c(C)nc3c(N4CCOCC4)nc(C(F)(F)F)cn23)cn1]

From intermediate 37 and intermediate 60 at 150° C. for 15 min. and under microwave irradiation. Flash column chromatography (silica; EtOAc in DCM 0/100 to 100/0) and trituration with diisopropyl ether yielded compound 9 as a white solid (41%).

Example B10

2-Cyclopropyl-3-[6-(2-methoxy-ethyl)-pyridin-3-yl]-8-morpholin-4-yl-imidazo[1,2-a]pyrazine

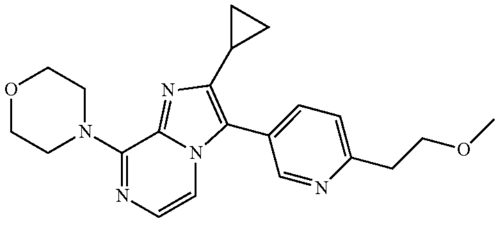 [SMILES: COCCc1ccc(-c2c(C3CC3)nc3c(N4CCOCC4)nccn23)cn1]

From intermediate 28 and intermediate 60 at 150° C. for 15 min. and under microwave irradiation. Flash column chromatography (silica; 7 M solution of ammonia in MeOH in DCM 4/96) and precipitation with $Et_2O$ yielded compound 10 as a brown solid (43%).

Example B11

3-[6-(2-Methoxy-ethyl)-pyridin-3-yl]-2,6-dimethyl-8-morpholin-4-yl-imidazo[1,2-a]pyrazine

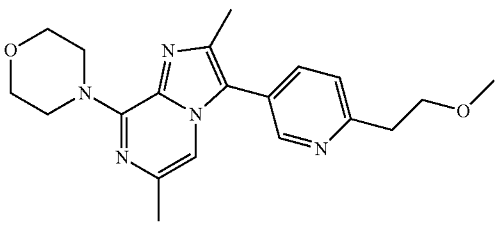 [SMILES: COCCc1ccc(-c2c(C)nc3c(N4CCOCC4)nc(C)cn23)cn1]

From intermediate 35 and intermediate 60 at 150° C. for 30 min. and under microwave irradiation. Flash column chromatography (silica; MeOH in DCM 4/96) yielded compound 11 as a white solid (82%).

Example B12

3-[6-(2-Methoxy-ethyl)-pyridin-3-yl]-8-morpholin-4-yl-2-trifluoromethyl-imidazo[1,2-a]pyrazine

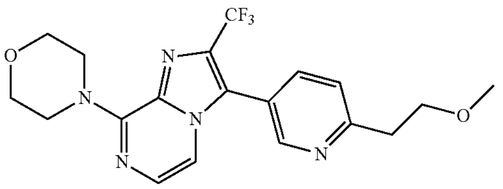 [SMILES: COCCc1ccc(-c2c(C(F)(F)F)nc3c(N4CCOCC4)nccn23)cn1]

From intermediate 30 and intermediate 60 at 150° C. for 15 min. and under microwave irradiation. Flash column chromatography (silica; EtOAc and 7 M solution of ammonia in MeOH in DCM 3/0.3/96.7), flash column chromatography (silica; 7 M solution of ammonia in MeOH in DCM 0/100 to 0.5/99.5) and freeze-drying yielded compound 12 as a white solid (50%).

Example B13

2-Isopropyl-3-[6-(2-methoxy-ethyl)-pyridin-3-yl]-8-morpholin-4-yl-imidazo[1,2-a]pyrazine

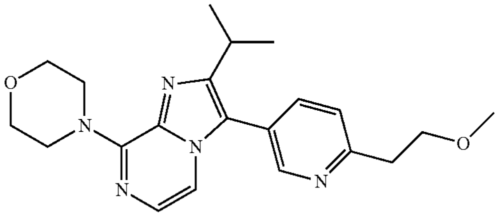 [SMILES: COCCc1ccc(-c2c(C(C)C)nc3c(N4CCOCC4)nccn23)cn1]

From intermediate 29 and intermediate 60 at 150° C. for 15 min. and under microwave irradiation. Flash column chromatography (silica; 7 M solution of ammonia in MeOH in DCM 2/98) and filtration through an Isolute® SCX-2 cartridge and elution by a 7 M solution of ammonia in MeOH addition yielded compound 13 as a clear syrup (52%).

Example B14

3-[6-(2-Methoxy-ethyl)-pyridin-3-yl]-2-methyl-8-pyridin-3-yl-imidazo[1,2-a]pyrazine

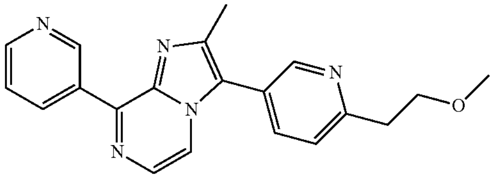 [SMILES: COCCc1ccc(-c2c(C)nc3c(-c4cccnc4)nccn23)cn1]

From intermediate 23 and intermediate 60 at 150° C. for 15 min. and under microwave irradiation. Flash column chromatography (silica; 7 M solution of ammonia in MeOH in DCM 1/99 first, then EtOAc in DCM 0/100 to 100/0) and precipitation from $Et_2O$ yielded compound 14 as a white solid (48%).

Example B15

2-Methoxy-3-[6-(2-methoxy-ethyl)-pyridin-3-yl]-8-morpholin-4-yl-imidazo[1,2-a]pyrazine

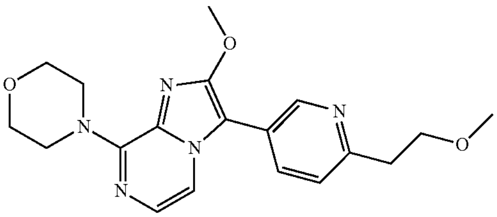 [SMILES: COCCc1ccc(-c2c(OC)nc3c(N4CCOCC4)nccn23)cn1]

From intermediate 24 and intermediate 60 at 150° C. for 15 min. and under microwave irradiation. Flash column chromatography (silica; 7 M solution of ammonia in MeOH in DCM 2/98), flash column chromatography (silica; EtOAc in heptane 30/70 to 100/0) and freeze-drying, yielded compound 15 as a brown solid (50%).

Example B16

3-[6-(2-Methoxy-ethyl)-pyridin-3-yl]-2-methyl-8-morpholin-4-yl-imidazo[1,2-a]pyrazine

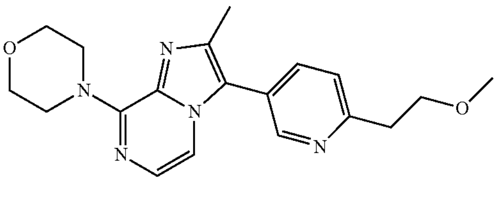 [SMILES: COCCc1ccc(-c2c(C)nc3c(N4CCOCC4)nccn23)cn1]

Potassium hydrogensulphate (12 g, 88.13 mmol) was added to a stirred solution of intermediate 74 (6 g, 18.67 mmol) in MeOH (120 ml). The mixture was stirred at 80° C. for 3 days and then poured onto a saturated solution of sodium carbonate and extracted with DCM. The organic layer was separated, dried ($Na_2SO_4$), filtered and the solvents evaporated in vacuo. The crude product was purified by open column chromatography (silica; 7 M solution of ammonia in MeOH in DCM 0/100 to 1.5/98.5). The impure fractions were collected and evaporated in vacuo and the crude product purified by flash column chromatography (silica; 7 M solution of ammonia in MeOH in DCM 0/100 to 2/98). The combined desired fractions were collected, evaporated in vacuo and triturated with heptane to yield compound 16 (4.13 g, 63%) as a white solid.

The following products were prepared according to a protocol analogous to example B16.

Example B17

3-[5-Fluoro-6-(2-methoxy-ethyl)-pyridin-3-yl]-2-methyl-8-morpholin-4-yl-imidazo[1,2-a]pyrazine

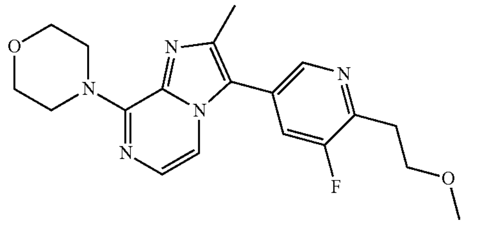 [SMILES: COCCc1ncc(-c2c(C)nc3c(N4CCOCC4)nccn23)cc1F]

From intermediate 77. Flash column chromatography (silica; EtOAc in DCM 0/100 to 70/30) yielded compound 17 as a white solid (87%).

Example B18

2-[5-(2-Methyl-8-morpholin-4-yl-imidazo[1,2-a]pyrazin-3-yl)-pyridin-2-yl]-ethanol

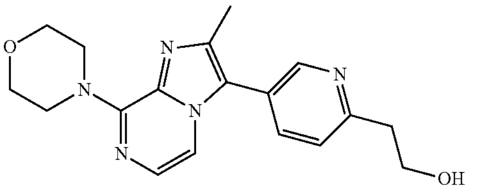 [SMILES: Cc1nc2c(N3CCOCC3)nccn2c1-c1ccc(CCO)nc1]

From intermediate 74 and water. Flash column chromatography (silica; 7 M solution of ammonia in MeOH in DCM 3/97) and flash column chromatography (silica; MeOH in EtOAc 0/100 to 2/98) yielded compound 18 as a white solid (18%).

Example B19

3-[2-(2-Methoxy-ethyl)-pyridin-4-yl]-2-methyl-8-morpholin-4-yl-imidazo[1,2-a]pyrazine

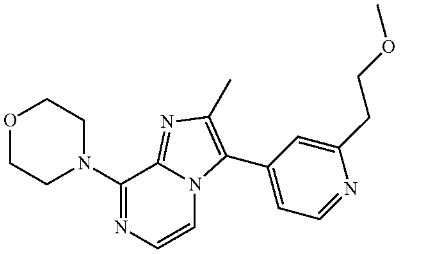 [SMILES: COCCc1cc(-c2c(C)nc3c(N4CCOCC4)nccn23)ccn1]

Sodium methoxide (0.22 g, 4.04 mmol) was added to a stirred solution of intermediate 75 (0.23 g, 0.67 mmol) in MeOH (8 ml). The mixture was stirred at 100° C. for 18 h. in a sealed tube and then poured into a saturated solution of sodium hydrogen carbonate and extracted with DCM. The organic layer was separated, dried ($Na_2SO_4$), filtered and the solvents evaporated in vacuo. The crude product was purified by flash column chromatography (silica; 7 M solution of ammonia in MeOH and EtOAc in DCM 0/50/50 to 10/90/0). The desired fractions were collected and evaporated in vacuo to yield compound 19 (2.65 g, 80%) as a white solid.

The following compounds were prepared according to a protocol analogous to example B19.

Example B20

3-[6-(2-Ethoxy-ethyl)-pyridin-3-yl]-2-methyl-8-morpholin-4-yl-imidazo[1,2-a]pyrazine

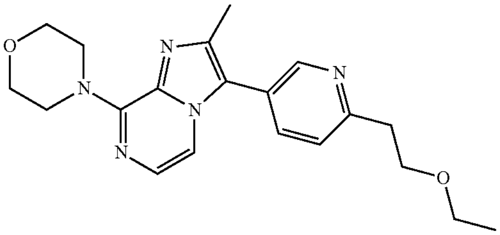 [SMILES: CCOCCc1ccc(-c2c(C)nc3c(N4CCOCC4)nccn23)cn1]

From intermediate 74 and sodium ethoxide. Flash column chromatography (silica; EtOAc in DCM 50/50 to 0/100), flash column chromatography (silica; 7 M solution of ammonia in MeOH in DCM 2/98) and precipitation from heptane, yielded compound 20 as a white solid (47%).

Example B21

3-[6-(2-Isopropoxy-ethyl)-pyridin-3-yl]-2-methyl-8-morpholin-4-yl-imidazo[1,2-a]pyrazine

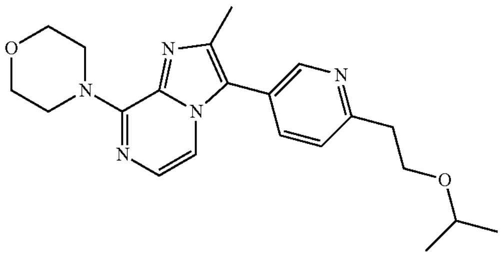 [SMILES: Cc1nc2c(N3CCOCC3)nccn2c1-c1ccc(CCOC(C)C)nc1]

From intermediate 74 and sodium isopropoxide. Flash column chromatography (silica; EtOAc in DCM 0/100 to 100/0) and precipitation from heptane yielded compound 21 as a white solid (25%).

Example B22

Isopropyl-[4-(2-methyl-8-morpholin-4-yl-imidazo[1,2-a]pyrazin-3-yl)-pyridin-2-yl]-amine

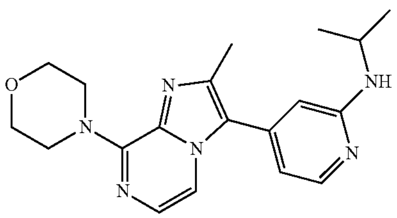 [SMILES: Cc1nc2c(N3CCOCC3)nccn2c1-c1ccnc(NC(C)C)c1]

Palladium (II) acetate (0.009 g, 0.038 mmol) and racemic-2,2'-bis(diphenylphosphino)-1,1'-binaphthyl (0.036 g, 0.057 mmol) were added to a stirred solution of intermediate 71 (0.25 g, 0.76 mmol), N,N-isopropylamine (0.5 ml, 5.84 mmol) and cesium carbonate (0.62 g, 1.91 mmol) in toluene (4 ml). The mixture was stirred at 50° C. for 16 h. and then diluted with EtOAc and filtered through a pad of diatomaceous earth. The filtrate was extracted with water and brine and the organic layer was separated, dried ($Na_2SO_4$), filtered and the solvents evaporated in vacuo. The crude product was purified by flash column chromatography (silica; EtOAc in DCM 0/100 to 100/0). The desired fractions were collected, evaporated in vacuo and crystallized from $Et_2O$/diisopropyl ether to yield compound 22 (0.115 g, 42%) as a white solid.

Example B23

2-Methyl-8-morpholin-4-yl-3-(6-piperazin-1-yl-pyridin-3-yl)-imidazo[1,2-a]pyrazine

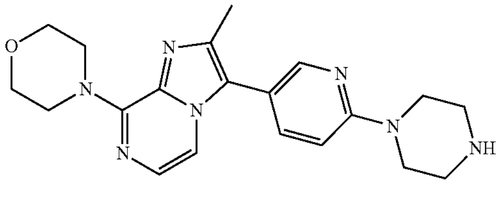 [SMILES: Cc1nc2c(N3CCOCC3)nccn2c1-c1ccc(N2CCNCC2)nc1]

A mixture of intermediate 70 (0.3 g, 0.91 mmol) and piperazine (0.314 g, 3.64 mmol) was stirred at 120° C. for 24 h. The mixture was diluted with EtOAc and extracted with water and a 1 N solution of sodium hydroxide. The organic layer was separated, dried ($Na_2SO_4$), filtered and the solvents evaporated in vacuo. The crude product was purified by flash column chromatography (silica; 7 M solution of ammonia in MeOH in DCM 0/100 to 10/90). The desired fractions were collected and evaporated in vacuo and the crude product purified again by flash column chromatography (silica; 7 M solution of ammonia in MeOH in DCM 0/100 to 3/97) and by RP HPLC (0.1% solution of ammonium formate/ammonium hydroxide buffer pH 9 in ACN 80/20 to 0/100). The desired fractions were collected and evaporated and the crude product triturated with diisopropyl ether to yield compound 23 (0.074 g, 22%) as a white solid.

Example B24

(S)-3-[6-(3-Methoxy-pyrrolidin-1-yl)-pyridin-3-yl]-2-methyl-8-morpholin-4-yl-imidazo[1,2-a]pyrazine

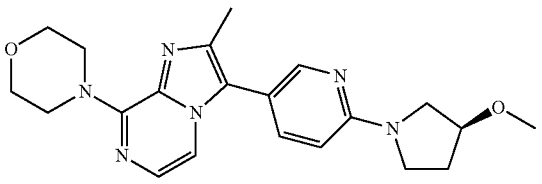 [SMILES: CO[C@H]1CCN(c2ccc(-c3c(C)nc4c(N5CCOCC5)nccn34)cn2)C1]

A mixture of intermediate 70 (0.15 g, 0.45 mmol) and (S)-3-hydroxypyrrolidine (0.159 g, 1.82 mmol) was stirred at 120° C. for 3 h. and then the mixture was diluted with EtOAc and extracted with water. The organic layer was separated, dried ($Na_2SO_4$), filtered and the solvents evaporated in vacuo. The crude product was dissolved in THF (3 ml) and a 60% dispersion of sodium hydride in mineral oils (0.020 g, 0.5 mmol) was added. The mixture was stirred at RT for 5 min. and then iodomethane (0.07 g, 0.49 mmol) was added. The mixture was stirred at RT for a further 3 days and then extracted with a saturated solution of ammonium chloride. The organic layer was separated, dried ($Na_2SO_4$), filtered and the solvents evaporated in vacuo. The crude product was purified by flash column chromatography (silica; 7 M solution of ammonia in MeOH in DCM 2/98 to 10/90). The desired fractions were collected and evaporated in vacuo to yield compound 24 (0.033 g, 19%) as a white solid.

Example B25

2-Methyl-8-morpholin-4-yl-3-[6-(tetrahydro-pyran-4-yl)-pyridin-3-yl]-imidazo[1,2-a]pyrazine

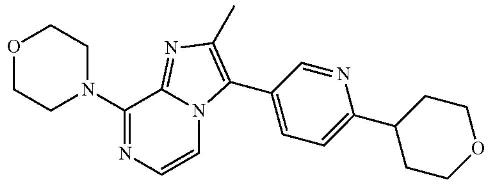 [SMILES: Cc1nc2c(N3CCOCC3)nccn2c1-c1ccc(C2CCOCC2)nc1]

10% Palladium on charcoal (1.69 g) was added to a suspension of intermediate 78 (6 g, 15.9 mmol) and ammonium formate (5.01 g, 79.48 mmol) in MeOH (60 ml). The mixture was stirred at 80° C. for 2 h. and then filtered through a pad of diatomaceous earth and the filtrate evaporated in vacuo. The crude product was suspended in DCM and extracted with brine. The organic layer was separated, dried ($Na_2SO_4$), filtered and the solvents evaporated in vacuo. The crude product was triturated with diisopropyl ether to yield compound 25 (2.9 g, 48%) as a white solid.

Example B26

3-(6-Ethyl-pyridin-3-yl)-2-methyl-8-morpholin-4-yl-imidazo[1,2-a]pyrazine

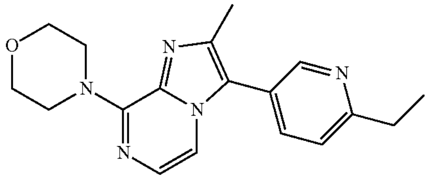 [SMILES: CCc1ccc(-c2c(C)nc3c(N4CCOCC4)nccn23)cn1]

10% Palladium on charcoal (0.042 g) was added to a suspension of intermediate 74 (0.25 g, 0.78 mmol) in a mixture of EtOH (3 ml), EtOAc (2 ml) and DCM (1 ml). The mixture was hydrogenated (atmospheric pressure) at RT for 16 h. and then filtered through a pad of diatomaceous earth. The filtrate was evaporated in vacuo and the crude product purified by flash column chromatography (silica; 7 M solution of ammonia in MeOH in DCM 2/98). The desired fractions were collected and evaporated in vacuo and triturated with $Et_2O$ to yield compound 26 (0.23 g, 91%) as a white solid.

Example B27

3-(2-Isobutyl-pyridin-4-yl)-2-methyl-8-morpholin-4-yl-imidazo[1,2-a]pyrazine

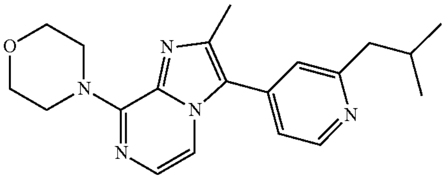 [SMILES: Cc1nc2c(N3CCOCC3)nccn2c1-c1ccnc(CC(C)C)c1]

A 2 M solution of isobutylmagnesium bromide in $Et_2O$ (0.45 ml, 0.91 mmol) was slowly added to a stirred mixture of intermediate 71 (0.15 g, 0.45 mmol) and [1,3-bis(diphenylphosphino)propane]dichloronickel (II) (0.013 g, 0.02 mmol) in THF (5 ml). The mixture was stirred at 0° C. for 1 h. and at RT for a further 2 h. and then diluted with DCM and extracted with a saturated solution of ammonium chloride. The organic layer was separated, dried ($Na_2SO_4$), filtered and the solvents evaporated in vacuo. The crude product was purified by flash column chromatography (silica; EtOAc in heptane 60/40). The desired fractions were collected, evaporated in vacuo and trituared with $Et_2O$ to yield compound 27 (98 mg, 61%) as a grey solid.

Example B28

3-(6-Cyclopropyl-pyridin-3-yl)-2-methyl-8-morpholin-4-yl-imidazo[1,2-a]pyrazine

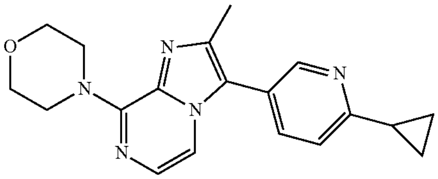 [SMILES: Cc1nc2c(N3CCOCC3)nccn2c1-c1ccc(C2CC2)nc1]

Palladium (II) acetate (0.036 g, 0.16 mmol) and 2-dicyclohexylphosphino-2',6'-dimethoxy-1,1'-biphenyl (0.131 g, 0.32 mmol) were added to a stirred mixture of intermediate 70 (0.35 g, 1.06 mmol), cyclopropylboronic acid (0.137 g, 1.59 mmol) and potassium phosphate (0.451 g, 2.12 mmol) in toluene (5 ml). The mixture was stirred at 80° C. for 22 h. under nitrogen and then diluted with DCM and extracted with water. The organic layer was separated, dried ($MgSO_4$), filtered and the solvents evaporated in vacuo. The crude product was purified by flash column chromatography (silica; 7 M solution of ammonia in MeOH in DCM 30/70). The desired fractions were collected and evaporated in vacuo and the crude product purified again by flash column chromatography (silica; EtOAc in heptane 50/50 to 100/0). The desired fractions were collected, evaporated in vacuo and triturated with diisopropyl ether to yield compound 28 (0.103 g, 29%) as a pale brown solid.

Example B29

3-[6-(3-Methoxy-3-methyl-butyl)-pyridin-3-yl]-2-methyl-8-morpholin-4-yl-imidazo[1,2-a]pyrazine

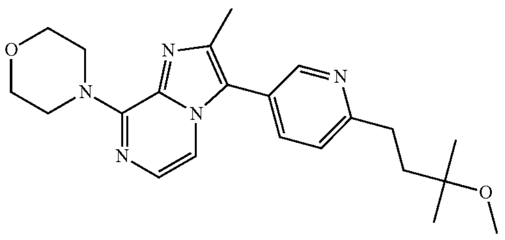 [SMILES: COC(C)(C)CCc1ccc(-c2c(C)nc3c(N4CCOCC4)nccn23)cn1]

1,2-Dibromoethane (0.016 ml, 0.18 mmol) was added to a stirred suspension of zinc (0.24 g, 3.64 mmol) in dry DMF (5 ml). The mixture was stirred at 90° C. for 30 min. under nitrogen and then allowed to cool down to RT. Chlorotrimethylsilane (0.006 ml, 0.045 mmol) was added, the mixture was stirred for 15 min. and then a solution of intermediate 45 (0.41 g, 1.82 mmol) in DMF (3 ml) was added dropwise. The mixture was stirred at 50° C. for 1.5 h. The excess of zinc was allowed to settle for 1 h. and the supernatant liquid was transferred via cannula to a mixture of intermediate 70 (0.2 g, 0.61 mmol) and tetrakis(triphenylphosphine)palladium (0) (0.014 g, 0.012 mmol) under nitrogen. The mixture was stirred at 55° C. for 5 h. and then water and DCM were added. The organic layer was separated, dried ($Na_2SO_4$), filtered and the solvents evaporated in vacuo. The crude product was purified by flash column chromatography (silica; EtOAc in DCM 0/100 to 20/80). The desired fractions were collected and evaporated in vacuo and the crude product dissolved in DCM and extracted with a saturated solution of sodium carbonate. The organic layer was separated, dried ($Na_2SO_4$), filtered and the solvents evaporated in vacuo and the crude product purified again by flash column chromatography (silica; EtOAc in DCM 0/100 to 20/80). The desired fractions were collected and evaporated in vacuo to yield compound 29 (0.088 g, 37%) as a white solid.

Example B30

3-[6-(1-Methoxy-1-methyl-ethyl)-pyridin-3-yl]-2-methyl-8-morpholin-4-yl-imidazo[1,2-a]pyrazine

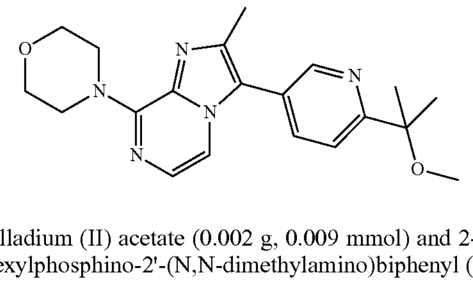

Palladium (II) acetate (0.002 g, 0.009 mmol) and 2-dicyclohexylphosphino-2'-(N,N-dimethylamino)biphenyl (0.004 g, 0.010 mmol) were added to a stirred solution of intermediate 33 (0.0050 g, 0.23 mmol), intermediate 50 (0.053 mg, 0.23 mmol), potassium carbonate (0.048 g, 0.34 mmol) and pivalic acid (7 mg, 0.69 mmol) in N,N-dimethylacetamide (1.5 ml). The mixture was stirred at 100° C. for 20 h. under nitrogen and then diluted with EtOAc and extracted with water. The organic layer was separated, dried ($Na_2SO_4$), filtered and the solvents evaporated in vacuo. The crude product was purified by flash column chromatography (silica; DCM in heptane 20/80 to 50/50). The desired fractions were evaporated in vacuo and the crude product purified by RP HPLC (0.1% solution of ammonium formate/ammonium hydroxide buffer pH 9 in ACN 80/20 to 0/100). The desired fractions were collected and evaporated in vacuo to yield compound 30 (0.034 g, 40%) as a white solid.

Example B31

3-[5-(2-Methoxy-ethyl)-pyridin-2-yl]-2-methyl-8-morpholin-4-yl-imidazo[1,2-a]pyrazine

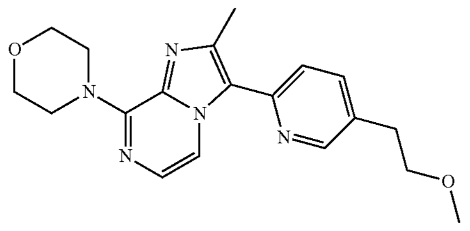 [SMILES: COCCc1ccc(-c2c(C)nc3c(N4CCOCC4)nccn23)nc1]

Intermediate 27 (0.392 g, 1.32 mmol), tetrakis(triphenylphosphine)palladium (0) (0.038 g, 0.032 mmol) and copper (I) bromide (0.010 g, 0.066 mmol) were added to a stirred solution of intermediate 66 (0.468 g, 1.1 mmol) in 1,4-dioxane (20 ml). The mixture was stirred at 160° C. for 20 min. in a sealed tube under nitrogen and under microwave irradiation and then the solvent was evaporated in vacuo. The crude product was purified by flash column chromatography (silica; EtOAc in DCM 40/60 to 90/10). The desired fractions were collected and evaporated in vacuo and the crude product purified again by flash column chromatography (silica; 7 M solution of ammonia in MeOH in DCM 0/100 to 1/99). The desired fractions were collected and evaporated in vacuo to yield compound 31 (0.044 g, 11%) as a white solid.

Example B32

3-(2-Methoxy-pyrimidin-5-yl)-2-methyl-8-morpholin-4-yl-imidazo[1,2-a]pyrazine

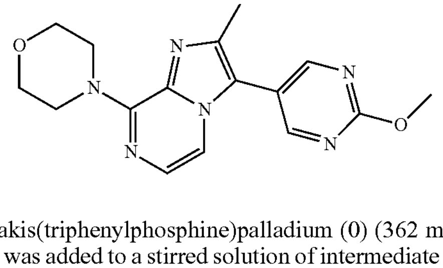

Tetrakis(triphenylphosphine)palladium (0) (362 mg, 0.31 mmol) was added to a stirred solution of intermediate 27 (3.1 g, 10.4 mmol) and commercially available 2-methoxypyrimidine-5-boronic acid (1.93 g, 12.5 mmol) in a mixture of 1,4-dioxane (30 ml) and a saturated solution of sodium carbonate (10 ml). The mixture was stirred at 150° C. for 15 min.

in a sealed tube under nitrogen and under microwave irradiation and then diluted with water and extracted with DCM. The organic layer was separated, extracted with brine, dried ($Na_2SO_4$), filtered and the solvents evaporated in vacuo. The crude product was purified by flash column chromatography (silica; 7 M solution of ammonia in MeOH in DCM 0/100 to 2/98). The desired fractions were collected and evaporated in vacuo to yield compound 32 (2.06 g, 60%) as a white solid.

Example B33

3-[2-(2-Methoxy-ethyl)-pyrimidin-5-yl]-2-methyl-8-morpholin-4-yl-imidazo[1,2-a]pyrazine

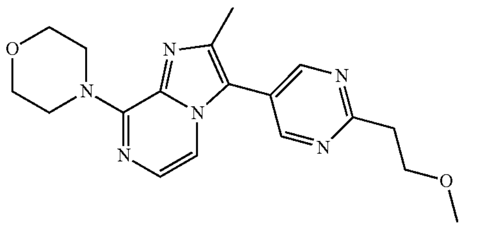 [SMILES: COCCc1ncc(-c2c(C)nc3c(N4CCOCC4)nccn23)cn1]

A mixture of compound 32 (0.65 g, 1.99 mmol), phosphorus oxychloride (0.93 ml, 9.96 mmol) and DIPEA (2.57 ml, 14.9 mmol) in ACN (6.5 ml) was stirred at 175° C. for 15 min. in a sealed tube under microwave irradiation. The solvent was evaporated in vacuo and the crude product diluted with DCM and extracted with a saturated solution of sodium hydrogen carbonate. The organic layer was separated, dried ($Na_2SO_4$), filtered and the solvents evaporated in vacuo. The crude product was purified by flash column chromatography (silica; EtOAc in DCM 0/100 to 100/0). The desired fractions were collected and evaporated in vacuo and a portion of the crude product (0.4 g) was dissolved in a mixture of 1,4-dioxane (0.9 ml) and a saturated solution of sodium carbonate (0.3 ml), vinylboronic acid pinacolester (0.31 ml, 1.81 mmol) and tetrakis(triphenylphosphine)palladium (0) (0.14 g, 0.12 mmol) were added. The mixture was stirred at 150° C. for 15 min. in a sealed tube under nitrogen and under microwave irradiation and then diluted with water and extracted with DCM. The organic layer was separated, extracted with brine, dried ($Na_2SO_4$), filtered and the solvents evaporated in vacuo. The crude product was purified by flash column chromatography (silica; 7 M solution of ammonia in MeOH in DCM 0/100 to 3/97). The desired fractions were collected and evaporated in vacuo and the crude product dissolved in MeOH (5 ml) and potassium hydrogensulfate (0.78 g, 5.71 mmol) was added. The mixture was stirred at 110° C. for 2.5 days in a sealed tube and then the solvent was evaporated in vacuo and the crude product dissolved with DCM and extracted with a saturated solution of sodium carbonate. The organic layer was separated, dried ($Na_2SO_4$), filtered and the solvents evaporated in vacuo. The crude product was purified by flash column chromatography (silica; EtOAc in DCM 90/10). The desired fractions were collected and evaporated in vacuo to yield compound 33 (0.035 mg, 7%) as a white solid.

Example B34

3-[1-(2-Methoxy-ethyl)-1H-pyrazol-4-yl]-2-methyl-8-pyridin-4-yl-imidazo[1,2-a]pyrazine

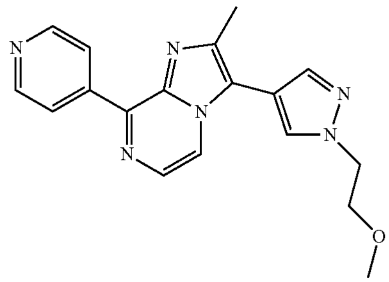 [SMILES: COCCn1cc(-c2c(C)nc3c(-c4ccncc4)nccn23)cn1]

Palladium (II) acetate (0.016 g, 0.073 mmol) was added to a stirred solution of intermediate 22 (0.3 g, 1.04 mmol), intermediate 67 (0.52 g, 2.08 mmol) and triphenylphosphine (0.027 g, 0.1 mmol) in a mixture of 1,4-dioxane (10 ml) and a 1.5 M solution of potassium carbonate (2.6 ml, 3.9 mmol). The mixture was stirred at 80° C. for 16 h. and then the solvents were evaporated in vacuo. The crude product was partitioned between water and DCM and the organic layer was separated, dried ($Na_2SO_4$), filtered and the solvents evaporated in vacuo. The crude product was purified by flash column chromatography (silica; 7 M solution of ammonia in MeOH in DCM 10/90). The desired fractions were collected and evaporated in vacuo to yield compound 34 (0.168 g, 48%) as a white solid.

The following compounds were prepared according to a protocol analogous to example B34.

Example B35

2-Methyl-3-[1-(2-methoxy-ethyl)-1H-pyrazol-4-yl]-8-morpholin-4-yl-imidazo[1,2-a]pyrazine

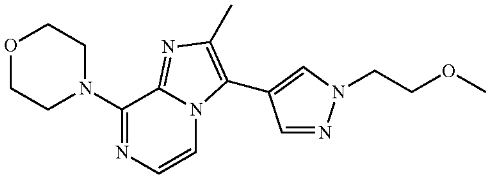 [SMILES: COCCn1cc(-c2c(C)nc3c(N4CCOCC4)nccn23)cn1]

From intermediate 27 and intermediate 67. Flash column chromatography (7 M solution of ammonia in MeOH in DCM 2/98) and RP HPLC (0.1% solution of ammonium formate/ammonium hydroxide buffer pH 9 and ACN 80/20 to 0/100) yielded compound 35 as a white solid (85%).

Example B36

4-[4-(2-Methyl-8-morpholin-4-yl-imidazo[1,2-a]pyrazin-3-yl)-pyrazol-1-yl]-butan-2-one

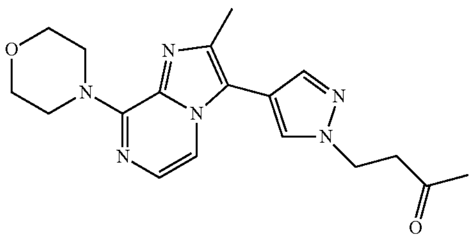 [SMILES: CC(=O)CCn1cc(-c2c(C)nc3c(N4CCOCC4)nccn23)cn1]

From intermediate 27 and intermediate 68. Flash column chromatography (7 M solution of ammonia in MeOH in DCM 1/99) and RP HPLC (0.1% solution of ammonium formate/ammonium hydroxide buffer pH 9 and ACN 80/20 to 0/100) yielded compound 36 as a white solid (58%).

Example B37

6-Cyclopropyl-3-[1-(2-methoxy-ethyl)-1H-pyrazol-4-yl]-2-methyl-8-morpholin-4-yl-imidazo[1,2-a]pyrazine

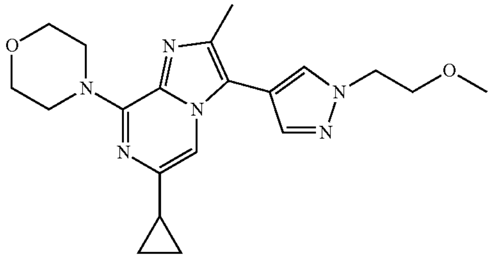 [SMILES: COCCn1cc(-c2c(C)nc3c(N4CCOCC4)nc(C4CC4)cn23)cn1]

From intermediate 36 and intermediate 67. Flash column chromatography (7 M solution of ammonia in MeOH in DCM 5/95) yielded compound 37 as a white solid (78%).

Example B38

3-(1-Ethyl-1H-pyrazol-4-yl)-2-methyl-8-morpholin-4-yl-imidazo[1,2-a]pyrazine

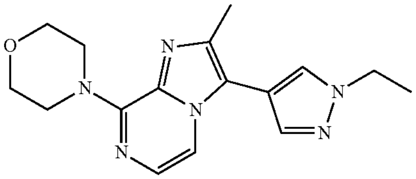 [SMILES: CCn1cc(-c2c(C)nc3c(N4CCOCC4)nccn23)cn1]

A mixture of compound 142 (0.15 g, 0.53 mmol), iodoethane (0.050 ml, 0.63 mmol) and cesium carbonate (257 mg, 0.79 mmol) in DMF (2 ml) was stirred at 160° C. for 40 min. in a sealed tube under microwave irradiation. The solvent was evaporated in vacuo and the crude product was purified by flash column chromatography (silica; EtOAc in heptane 50/50 to 100/0). The desired fractions were collected and evaporated in vacuo to yield compound 38 (0.103 g, 62%) as a white solid.

Example B39

3-[1-(2-Methoxy-ethyl)-1H-pyrazol-4-yl]-2-methyl-8-morpholin-4-yl-6-(3,3,3-trifluoro-propyl)-imidazo[1,2-a]pyrazine

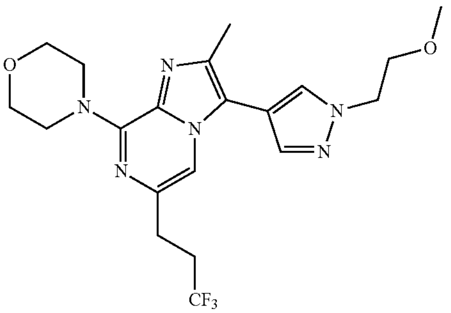 [SMILES: COCCn1cc(-c2c(C)nc3c(N4CCOCC4)nc(CCC(F)(F)F)cn23)cn1]

Tetrakis(triphenylphosphine)palladium (0) (0.005 g, 0.0045 mmol) was added to a stirred solution of intermediate 38 (0.070 g, 0.18 mmol) and intermediate 67 (0.054 mg, 0.21 mmol) in a mixture of 1,4-dioxane (1.5 ml) and a saturated solution of sodium carbonate (0.5 ml). The mixture was stirred at 150° C. for 15 min. in a sealed tube under nitrogen and under microwave irradiation. The mixture was partitioned between water and DCM and the organic layer was separated, extracted with brine, dried ($Na_2SO_4$), filtered and the solvent evaporated in vacuo. The crude product was purified by flash column chromatography (silica; EtOAc in heptane 0/100 to 100/0). The desired fractions were collected and evaporated in vacuo and the crude product purified again by flash column chromatography (silica; EtOAc in DCM 0/100 to 50/50). The desired fractions were collected and evaporated in vacuo and the residue triturated with diisopropyl ether to yield compound 39 (0.029 g, 37%) as a white solid.

Example B40

3-[1-(2-Methoxy-ethyl)-1H-pyrazol-4-yl]-8-morpholin-4-yl-imidazo[1,2-a]pyrazine-2-carbonitrile

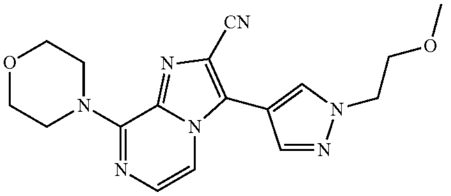 [SMILES: COCCn1cc(-c2c(C#N)nc3c(N4CCOCC4)nccn23)cn1]

A solution of intermediate 80 (0.13 g, 0.35 mmol) in phosphorus oxychloride (0.019 ml, 0.35 mmol) was stirred at 80° C. for 1 h. The mixture was allowed to cool down to RT and then poured onto ice, basified by a saturated solution of sodium carbonate addition and extracted with DCM. The organic layer was separated, dried ($Na_2SO_4$), filtered and the solvents evaporated in vacuo. The crude product was purified by flash column chromatography (silica; MeOH in DCM 0/100 to 2/98). The desired fractions were collected and evaporated in vacuo to yield compound 40 (0.048 g, 39%) as a white solid.

Example B41

3-(2-Isobutyl-oxazol-4-yl)-2-methyl-8-morpholin-4-yl-imidazo[1,2-a]pyrazine

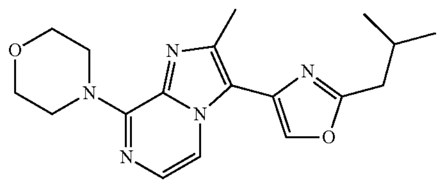 [SMILES: Cc1nc2c(N3CCOCC3)nccn2c1-c1coc(CC(C)C)n1]

Isovaleramide (0.082 g, 0.81 mmol) was added to a stirred solution of intermediate 43 (0.25 g, 0.74 mmol) in 1,4-dioxane (5 ml). The mixture was stirred at 90° C. for 18 h. under nitrogen and then the solvent was evaporated in vacuo and DMF (5 ml) and further isovaleramide (0.082 g, 0.81 mmol) were added. The mixture was stirred at 90° C. for a further 24 h, further isovaleramide (0.082 g, 0.81 mmol) was added and the mixture was stirred at 90° C. for a further 24 h. The mixture was diluted with $Et_2O$ and extracted with water. The organic layer was separated, dried ($Na_2SO_4$), filtered and the solvents evaporated in vacuo. The crude product was purified by flash column chromatography (silica; EtOAc in DCM 0/100 to 50/50). The desired fractions were collected and evaporated in vacuo to yield compound 41 (0.26 g, 67%) as a white solid.

Example B42

3-(2-Isobutyl-thiazol-5-yl)-2-methyl-8-morpholin-4-yl-imidazo[1,2-a]pyrazine

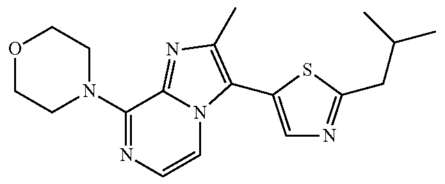 [SMILES: Cc1nc2c(N3CCOCC3)nccn2c1-c1cnc(CC(C)C)s1]

Palladium (II) acetate (0.011 g, 0.05 mmol) and tert-butyl-dicyclohexylphosphine (0.027 ml, 0.1 mmol) were added to a stirred solution of intermediate 33 (0.3 g, 1.01 mmol), 2-isobutylthiazole (0.142 g, 1.01 mmol) and potassium phosphate (0.428 g, 2.01 mmol) in N-methylpyrrolidine (4 ml). The mixture was stirred at RT for 15 min. under nitrogen and then at 125° C. for 18 h. The mixture was diluted with $Et_2O$ and extracted with a 1% solution of potassium hydroxide. The organic layer was separated, dried ($Na_2SO_4$), filtered and the solvents evaporated in vacuo. The crude product was purified by flash column chromatography (silica; EtOAc in DCM 0/100 to 40/60). The desired fractions were collected and evaporated in vacuo and the crude product purified by RP HPLC (0.1% solution of ammonium formate/ammonium hydroxide buffer pH 9 in ACN 80/20 to 0/100). The desired fractions were collected and evaporated in vacuo to yield compound 42 (0.104 g, 29%) as a yellow solid.

Example B43

2-Methyl-8-morpholin-4-yl-3-(1H-pyrrol-3-yl)-imidazo[1,2-a]pyrazine

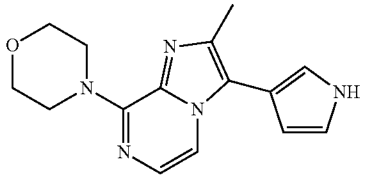 [SMILES: Cc1nc2c(N3CCOCC3)nccn2c1-c1cc[nH]c1]

Dichlorobis(triphenylphosphine)palladium (II) (0.008 g, 0.012 mmol) was added to a stirred solution of intermediate 27 (0.071 g, 0.24 mmol) and (triisopropylsilyl)pyrrole-3-boronic acid (0.096 g, 0.36 mmol) in a mixture of 1,4-dioxane (2 ml) and a 1 M solution of sodium carbonate (0.72 ml, 0.72 mmol). The mixture was stirred at 100° C. for 16 h. and then the solid formed was filtered off and the filtrate was evaporated. The crude product was purified by flash column chromatography (silica; EtOAc in heptane 40/60). The desired fractions were collected and evaporated in vacuo to yield compound 43 (0.056 g, 82%) as a white solid.

Example B44

3-[1-(2-Methoxy-ethyl)-1H-pyrrol-3-yl]-2-methyl-8-morpholin-4-yl-imidazo[1,2-a]pyrazine

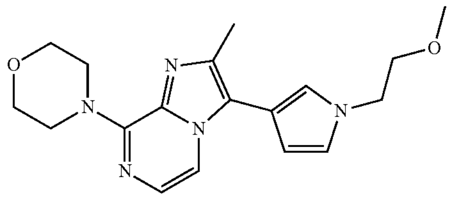 [SMILES: COCCn1ccc(-c2c(C)nc3c(N4CCOCC4)nccn23)c1]

2-Bromoethyl methyl ether (0.024 ml, 0.254 mmol) and cesium carbonate (0.088 g, 0.271 mmol) were added to a stirred solution of compound 43 (0.048 g, 0.169 mmol) in DMF (3 ml). The mixture was stirred at 160° C. for 30 min. under nitrogen and under microwave irradiation and then further 2-bromoethyl methyl ether (0.072 ml, 0.762 mmol) was added. The mixture was stirred at 160° C. for a further 30 min. under microwave irradiation and then the solid formed was filtered off and the filtrate evaporated in vacuo. The crude product was purified by flash column chromatography (silica;

EtOAc in heptane 40/60). The desired fractions were collected and evaporated in vacuo to yield compound 44 (0.042 g, 73%) as an oil.

Example B142

2-Methyl-8-morpholin-4-yl-3-(1H-pyrazol-4-yl)-imidazo[1,2-a]pyrazine

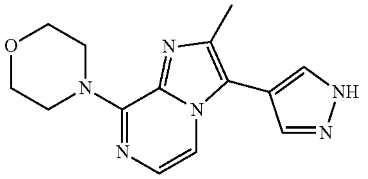 [SMILES: Cc1nc2c(N3CCOCC3)nccn2c1-c1cn[nH]c1]

Palladium (II) acetate (0.026 g, 0.011 mmol) and a 1.5 M solution of potassium carbonate (4.2 ml, 6.31 mmol) were added to a stirred solution of intermediate 27 (0.5 g, 1.68 mmol), commercially available 4-(4,4,5,5-tetramethyl-1,3,2-dioxaborolan-2-yl)-pyrazole-1-carboxylic acid tert-butyl ester (0.99 g, 3.37 mmol) and triphenylphosphine (44 mg, 0.17 mmol) in 1,4-dioxane (9 ml). The mixture was stirred at 80° C. for 18 h. under nitrogen and the solid formed was filtered off and the filtrate evaporated. The crude product was purified by flash column chromatography (silica; EtOAc). The desired fractions were collected, evaporated in vacuo and combined with the solid previously obtained to yield compound 142 (0.39 g, 81%) as a solid.

Example B143

3-(6-Ethoxy-5-fluoro-pyridin-3-yl)-2-methyl-8-morpholin-4-yl-imidazo[1,2-a]pyrazine

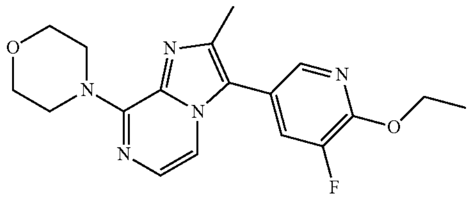 [SMILES: CCOc1ncc(-c2c(C)nc3c(N4CCOCC4)nccn23)cc1F]

Tetrakis(triphenylphosphine)palladium (0) (0.02 g, 0.017 mmol) was added to a stirred solution of intermediate 27 (0.1 g, 0.34 mmol) and intermediate 59 (0.18 g, 0.67 mmol) in a mixture of 1,4-dioxane (2 ml) and a saturated solution of sodium carbonate (0.5 ml). The mixture was stirred at 150° C. for 20 min. under nitrogen and under microwave irradiation and then filtered through a pad of diatomaceous earth. The filtrate was diluted with DCM and washed with water. The organic layer was separated, dried ($MgSO_4$), filtered and the solvents evaporated in vacuo. The crude product was purified by flash column chromatography (silica; EtOAc in DCM 0/100 to 50/50). The desired fractions were collected and evaporated in vacuo to yield compound 143 (0.102 g, 85%).

The following compounds were prepared from the corresponding intermediates according to protocols similar to those used for the synthesis of the corresponding reference compounds, as denoted in the column labeled Ex. No. The corresponding intermediates were prepared by similar protocols to those previously described either in the Experimental Part or in the Preparation section.

TABLE 1

Compounds according to formula (I) prepared according to the above methods. The assignment of configuration in compounds 24, 57, 75, 79, 101, 104 and 110 derives from the reagent used in the synthesis of the compound.

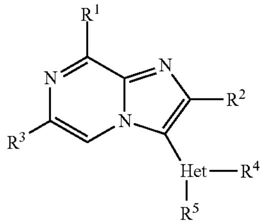

| Co. No. | Ex. No. | $R^1$ | $R^2$ | $R^3$ | 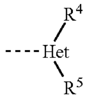 |
|---|---|---|---|---|---|
| 1 | B1 | 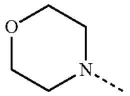 | ----$CH_3$ | ----H | 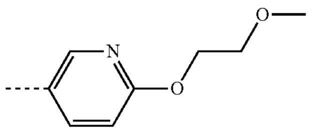 |
| 2 | B2 | 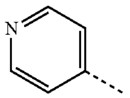 | ----$CH_3$ | ----H | 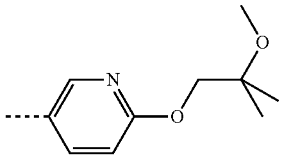 |

TABLE 1-continued
Compounds according to formula (I) prepared according to the above methods. The assignment of configuration in compounds 24, 57, 75, 79, 101, 104 and 110 derives from the reagent used in the synthesis of the compound.
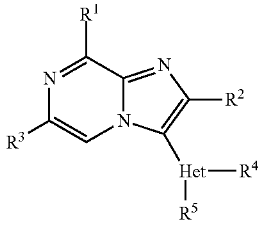
| Co. No. | Ex. No. | $R^1$ | $R^2$ | $R^3$ | 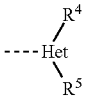 |
|---|---|---|---|---|---|
| 3 | B3 | 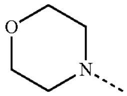 | ----$CH_3$ | ----H | 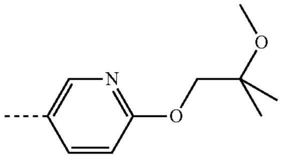 |
| 4 | B4 | 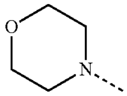 | ----$CH_3$ | ----H | 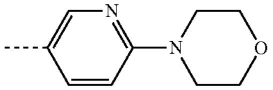 |
| 5 | B5 | 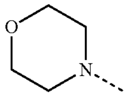 | ----$CH_3$ | ----H | 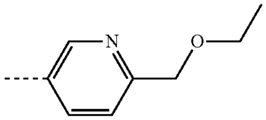 |
| 6 | B6 | 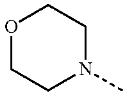 | ----$CH_3$ | ----H | 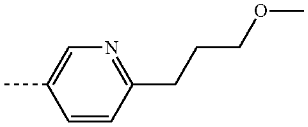 |
| 7 | B7 | 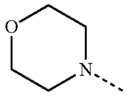 | ----$CH_3$ | ----H | 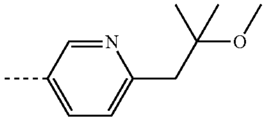 |
| 8 | B8 | 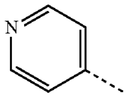 | ----$CH_3$ | ----H | 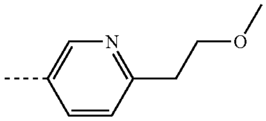 |
| 9 | B9 | 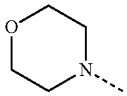 | ----$CH_3$ | ----$CF_3$ | 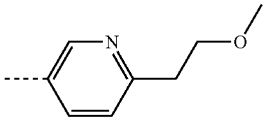 |
| 10 | B10 | 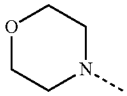 | 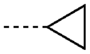 | ----H | 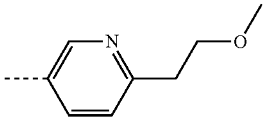 |

TABLE 1-continued
Compounds according to formula (I) prepared according to the above methods. The assignment of configuration in compounds 24, 57, 75, 79, 101, 104 and 110 derives from the reagent used in the synthesis of the compound.
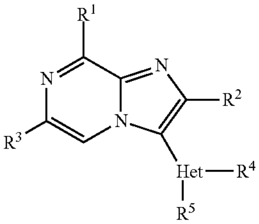
| Co. No. | Ex. No. | $R^1$ | $R^2$ | $R^3$ | 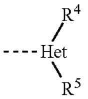 |
|---|---|---|---|---|---|
| 11 | B11 | 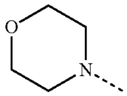 | ----$CH_3$ | ----$CH_3$ | 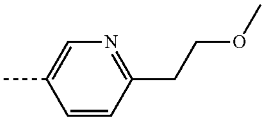 |
| 12 | B12 | 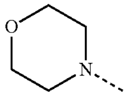 | ----$CF_3$ | ----H | 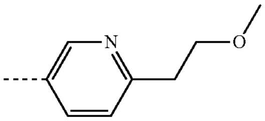 |
| 13 | B13 | 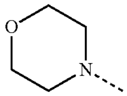 | 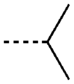 | ----H | 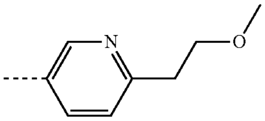 |
| 14 | B14 | 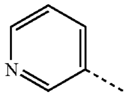 | ----$CH_3$ | ----H | 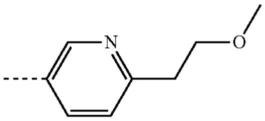 |
| 15 | B15 | 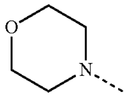 | ----$OCH_3$ | ----H | 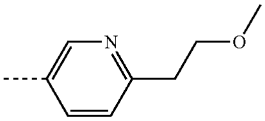 |
| 16 | B16 | 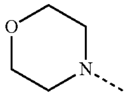 | ----$CH_3$ | ----H | 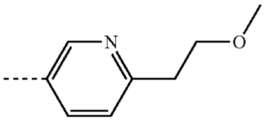 |
| 17 | B17 | 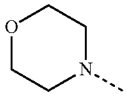 | ----$CH_3$ | ----H | 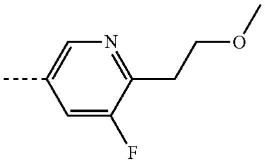 |
| 18 | B18 | 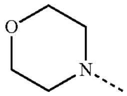 | ----$CH_3$ | ----H | 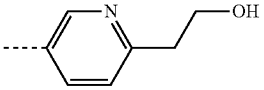 |

TABLE 1-continued
Compounds according to formula (I) prepared according to the above methods. The assignment of configuration in compounds 24, 57, 75, 79, 101, 104 and 110 derives from the reagent used in the synthesis of the compound.
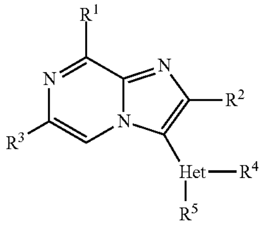
| Co. No. | Ex. No. | $R^1$ | $R^2$ | $R^3$ | 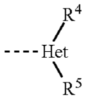 |
|---|---|---|---|---|---|
| 19 | B19 | 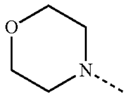 | ----$CH_3$ | ----H | 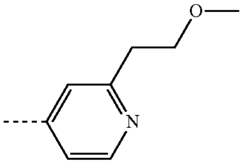 |
| 20 | B20 | 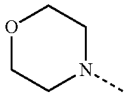 | ----$CH_3$ | ----H | 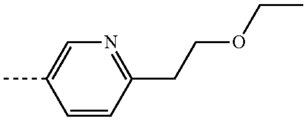 |
| 21 | B21 | 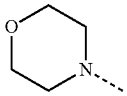 | ----$CH_3$ | ----H | 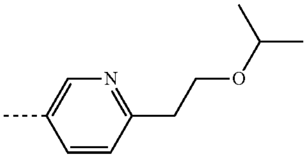 |
| 22 | B22 | 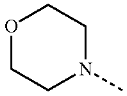 | ----$CH_3$ | ----H | 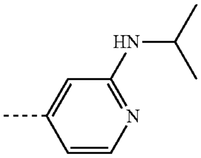 |
| 23 | B23 | 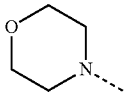 | ----$CH_3$ | ----H | 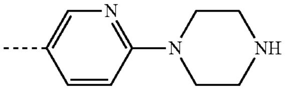 |
| 24 | B24 | 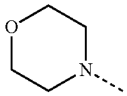 | ----$CH_3$ | ----H | 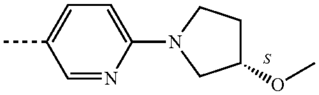 |
Optical Rotation: +8.9° (589 nm, 20° C., 0.51 w/v %, DMF)
| Co. No. | Ex. No. | $R^1$ | $R^2$ | $R^3$ | |
|---|---|---|---|---|---|
| 25 | B25 | 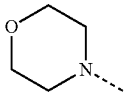 | ----$CH_3$ | ----H | 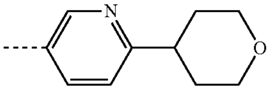 |
| 26 | B26 | 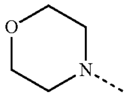 | ----$CH_3$ | ----H | 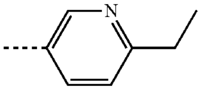 |

TABLE 1-continued
Compounds according to formula (I) prepared according to the above methods. The assignment of configuration in compounds 24, 57, 75, 79, 101, 104 and 110 derives from the reagent used in the synthesis of the compound.
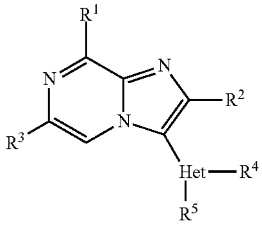
| Co. No. | Ex. No. | $R^1$ | $R^2$ | $R^3$ | 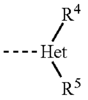 |
|---|---|---|---|---|---|
| 27 | B27 | 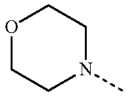 | ----$CH_3$ | ----H | 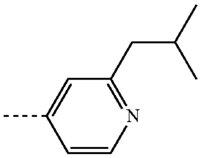 |
| 28 | B28 | 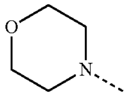 | ----$CH_3$ | ----H | 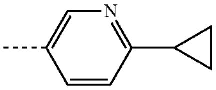 |
| 29 | B29 | 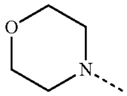 | ----$CH_3$ | ----H | 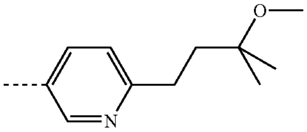 |
| 30 | B30 | 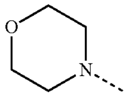 | ----$CH_3$ | ----H | 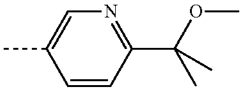 |
| 31 | B31 | 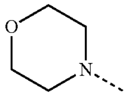 | ----$CH_3$ | ----H | 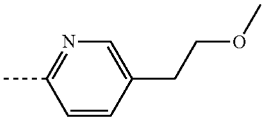 |
| 32 | B32 | 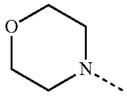 | ----$CH_3$ | ----H | 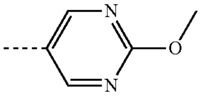 |
| 33 | B33 | 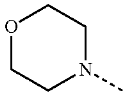 | ----$CH_3$ | ----H | 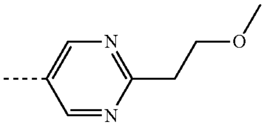 |
| 34 | B34 | 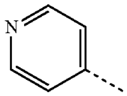 | ----$CH_3$ | ----H | 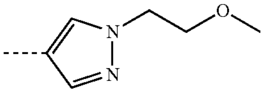 |
| 35 | B35 | 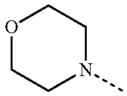 | ----$CH_3$ | ----H | 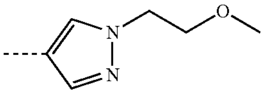 |

TABLE 1-continued
Compounds according to formula (I) prepared according to the above methods. The assignment of configuration in compounds 24, 57, 75, 79, 101, 104 and 110 derives from the reagent used in the synthesis of the compound.
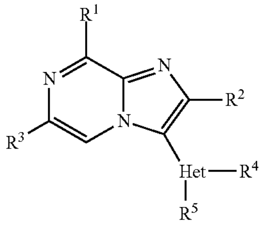
| Co. No. | Ex. No. | $R^1$ | $R^2$ | $R^3$ | 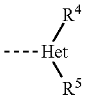 |
|---|---|---|---|---|---|
| 36 | B36 | 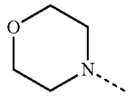 | ----$CH_3$ | ----H | 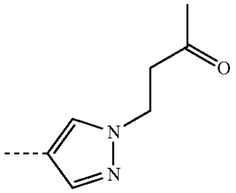 |
| 37 | B37 | 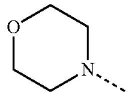 | ----$CH_3$ | 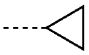 | 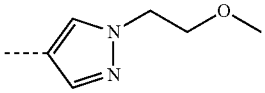 |
| 38 | B38 | 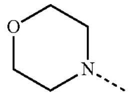 | ----$CH_3$ | ----H | 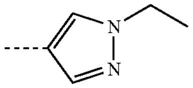 |
| 39 | B39 | 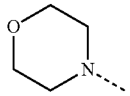 | ----$CH_3$ | 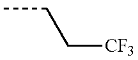 | 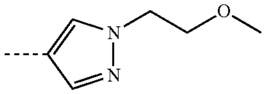 |
| 40 | B40 | 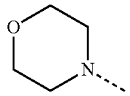 | ----CN | ----H | 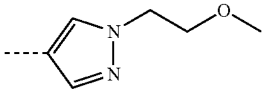 |
| 41 | B41 | 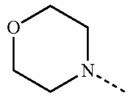 | ----$CH_3$ | ----H | 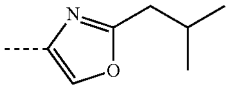 |
| 42 | B42 | 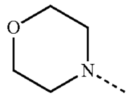 | ----$CH_3$ | ----H | 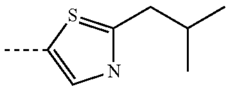 |
| 43 | B43 | 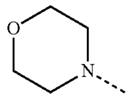 | ----$CH_3$ | ----H | 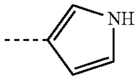 |
| 44 | B44 | 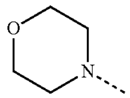 | ----$CH_3$ | ----H | 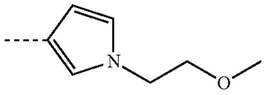 |

TABLE 1-continued
Compounds according to formula (I) prepared according to the above methods. The assignment of configuration in compounds 24, 57, 75, 79, 101, 104 and 110 derives from the reagent used in the synthesis of the compound.
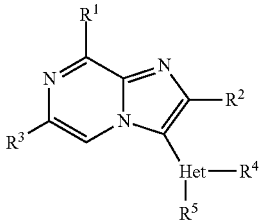
| Co. No. | Ex. No. | $R^1$ | $R^2$ | $R^3$ | 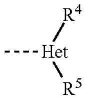 |
|---|---|---|---|---|---|
| 45 | B34 | 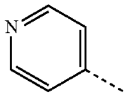 | 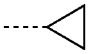 | ----H | 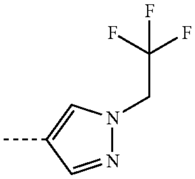 |
| 46 | B34 | 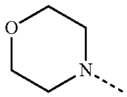 | 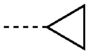 | ----H | 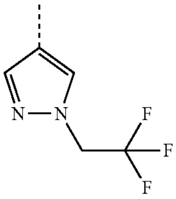 |
| 47 | B34 | 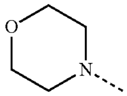 | ----$CH_3$ | ----H | 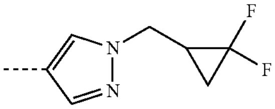 |
Optical Rotation: −10.6° (589 nm, 20° C., 0.64 w/v %, $CH_3OH$)
| Co. No. | Ex. No. | $R^1$ | $R^2$ | $R^3$ | Het |
|---|---|---|---|---|---|
| 48 | B34 | 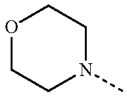 | 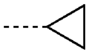 | ----H | 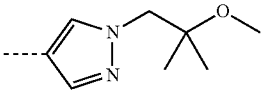 |
| 49 | B34 | 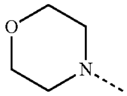 | ----$CH_3$ | ----H | 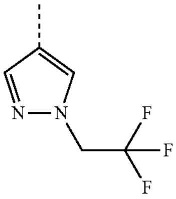 |
| 50 | B34 | 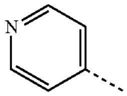 | 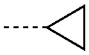 | ----H | 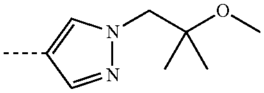 |
| 51 | B34 | 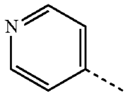 | 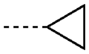 | ----H | 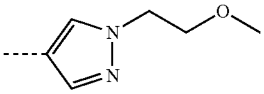 |

TABLE 1-continued
Compounds according to formula (I) prepared according to the above methods. The assignment of configuration in compounds 24, 57, 75, 79, 101, 104 and 110 derives from the reagent used in the synthesis of the compound.
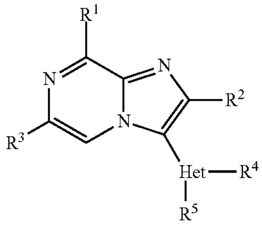
| Co. No. | Ex. No. | $R^1$ | $R^2$ | $R^3$ | 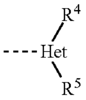 |
|---|---|---|---|---|---|
| 52 | B34 | 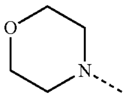 | ----$CH_3$ | ----H | 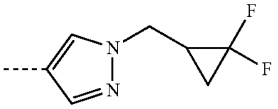 |
| 53 | B34 | 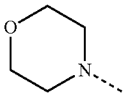 | 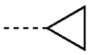 | ----H | 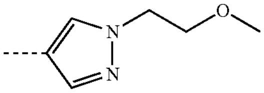 |
| 54 | B34 | 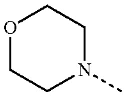 | ----$CH_3$ | ----H | 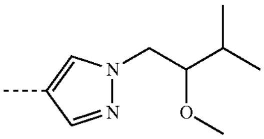 |
| Optical Rotation: +3.0° (589 nm, 20° C., 0.591 w/v %, DMF) | | | | | |
| 55 | B30 | 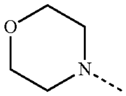 | ----$CH_3$ | ----H | 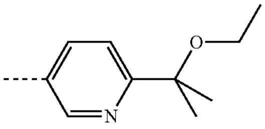 |
| 56 | B34 | 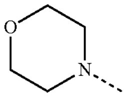 | ----$CH_3$ | ----H | 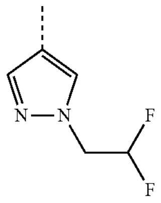 |
| 57 | B34 | 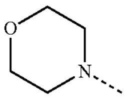 | ----$CH_3$ | ----H | 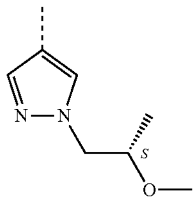 |
| Optical Rotation: n.d. | | | | | |
| 58 | B34 | 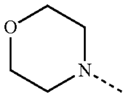 | ----$CH_3$ | ----H | 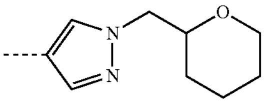 |

TABLE 1-continued

Compounds according to formula (I) prepared according to the above methods. The assignment of configuration in compounds 24, 57, 75, 79, 101, 104 and 110 derives from the reagent used in the synthesis of the compound.

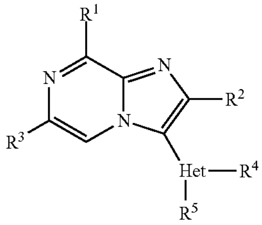

| Co. No. | Ex. No. | $R^1$ | $R^2$ | $R^3$ | 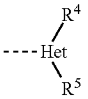 |
|---|---|---|---|---|---|
| Optical Rotation: +3.0° (589 nm, 20° C., 0.68 w/v %, $CH_3OH$) | | | | | |
| 59 | B34 | 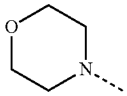 | ----$CH_3$ | ----H | 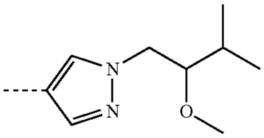 |
| Optical Rotation: −2.9° (589 nm, 20° C., 0.534 w/v %, DMF) | | | | | |
| 60 | B7 | 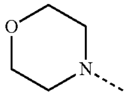 | 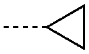 | ----H | 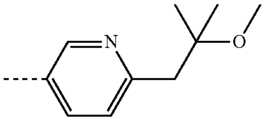 |
| 61 | B38 | 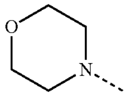 | ----$CH_3$ | ----H | 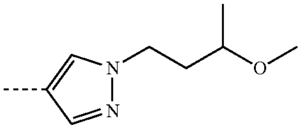 |
| Optical Rotation: n.d. | | | | | |
| 62 | B34 | 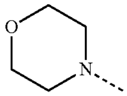 | ----$CH_3$ | ----H | 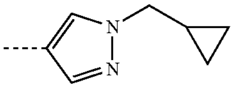 |
| 63 | B4 | 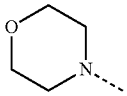 | 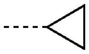 | ----H | 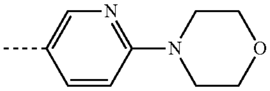 |
| 64 | B34 | 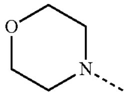 | ----$CH_3$ | ----H | 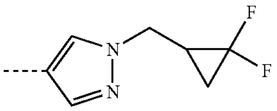 |
| Optical Rotation: +11.1° (589 nm, 20° C., 0.59 w/v %, $CH_3OH$) | | | | | |
| 65 | B34 | 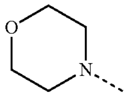 | ----$CH_3$ | ----H | 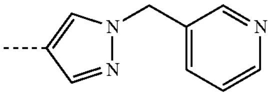 |
| 66 | B26 | 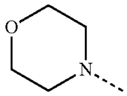 | 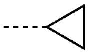 | ----H | 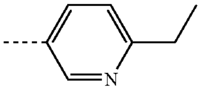 |

TABLE 1-continued

Compounds according to formula (I) prepared according to the above methods. The assignment of configuration in compounds 24, 57, 75, 79, 101, 104 and 110 derives from the reagent used in the synthesis of the compound.

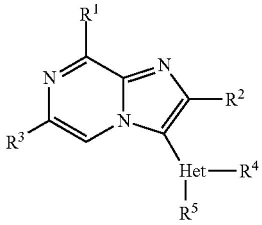

| Co. No. | Ex. No. | $R^1$ | $R^2$ | $R^3$ | 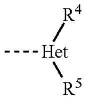 |
|---|---|---|---|---|---|
| 67 | B34 | 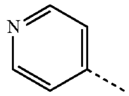 | ----$CH_3$ | ----H | 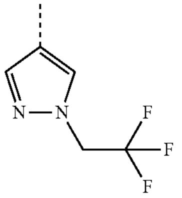 |
| 68 | B34 | 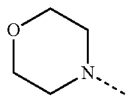 | ----$CH_3$ | ----H | 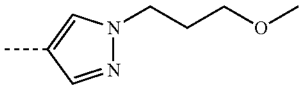 |
| 69 | B34 | 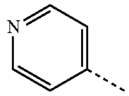 | ----$CH_3$ | ----H | 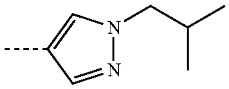 |
| 70 | B34 | 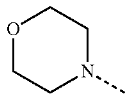 | ----$CH_3$ | ----H | 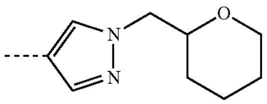 |
| | Optical Rotation: −2.4° (589 nm, 20° C., 0.68 w/v %, $CH_3OH$) | | | | |
| 71 | B38 | 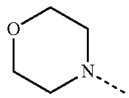 | ----$CH_3$ | ----H | 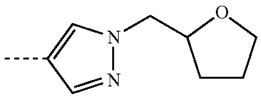 |
| | Optical Rotation: −31.6° (589 nm, 20° C., 0.52 w/v %, $CH_3OH$) | | | | |
| 72 | B38 | 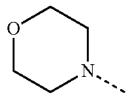 | ----$CH_3$ | ----H | 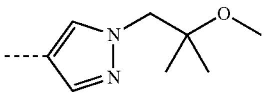 |
| 73 | B34 | 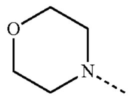 | ----$CH_3$ | ----H | 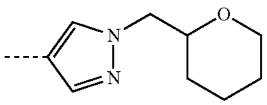 |
| 74 | B34 | 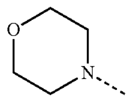 | ----$CH_3$ | ----H | 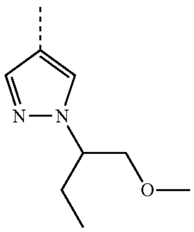 |

TABLE 1-continued

Compounds according to formula (I) prepared according to the above methods. The assignment of configuration in compounds 24, 57, 75, 79, 101, 104 and 110 derives from the reagent used in the synthesis of the compound.

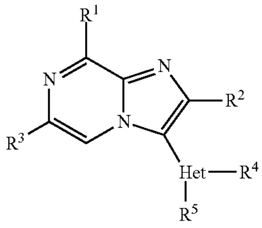

| Co. No. | Ex. No. | $R^1$ | $R^2$ | $R^3$ | 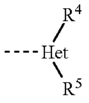 |
|---|---|---|---|---|---|
| Optical Rotation: +6.6° (578 nm, 20° C., 0.51 w/v %, $CH_3OH$) | | | | | |
| 75 | B34 | 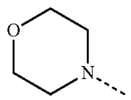 | ----$CH_3$ | ----H | 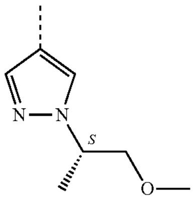 |
| Optical Rotation: n.d. | | | | | |
| 76 | B34 | 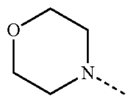 | ----$CH_3$ | ----H | 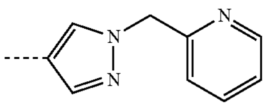 |
| 77 | B34 | 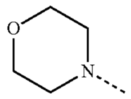 | ----$CH_3$ | ----H | 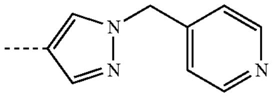 |
| 78 | B38 | 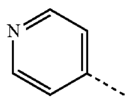 | ----$CH_3$ | ----H | 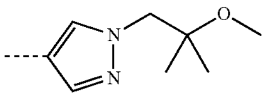 |
| 79 | B34 | 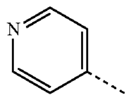 | ----$CH_3$ | ----H | 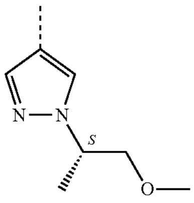 |
| Optical Rotation: +6.6° (589 nm, 20° C., 0.545 w/v %, DMF) | | | | | |
| 80 | B34 | 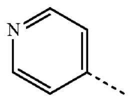 | ----$CH_3$ | ----H | 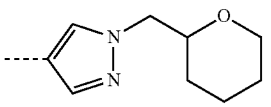 |

TABLE 1-continued
Compounds according to formula (I) prepared according to the above methods. The assignment of configuration in compounds 24, 57, 75, 79, 101, 104 and 110 derives from the reagent used in the synthesis of the compound.
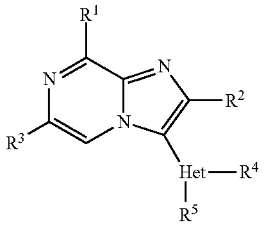
| Co. No. | Ex. No. | $R^1$ | $R^2$ | $R^3$ | 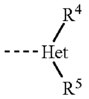 |
|---|---|---|---|---|---|
| Optical Rotation: −4.3° (589 nm, 20° C., 0.58 w/v %, $CH_3OH$) | | | | | |
| 81 | B34 | 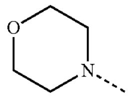 | ----$CH_3$ | ----H | 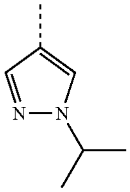 |
| 82 | B38 | 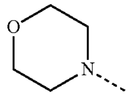 | ----$CH_3$ | ----H | 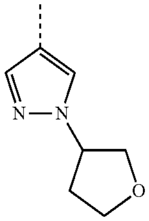 |
| 83 | B25 | 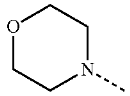 | 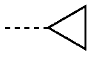 | ----H | 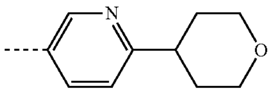 |
| 84 | B38 | 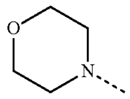 | ----$CH_3$ | ----H | 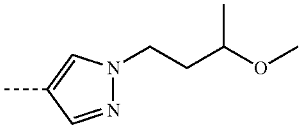 |
| Optical Rotation: n.d. | | | | | |
| 85 | B32 | 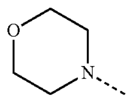 | ----$CH_3$ | ----H | 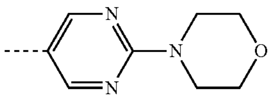 |
| 86 | B34 | 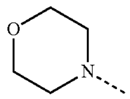 | ----$CH_3$ | ----H | 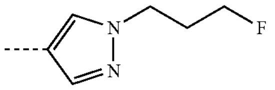 |
| 87 | B23 | 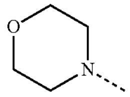 | 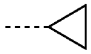 | ----H | 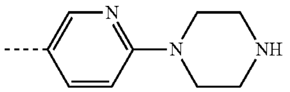 |

TABLE 1-continued

Compounds according to formula (I) prepared according to the above methods. The assignment of configuration in compounds 24, 57, 75, 79, 101, 104 and 110 derives from the reagent used in the synthesis of the compound.

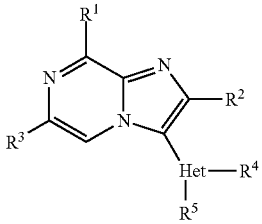

| Co. No. | Ex. No. | $R^1$ | $R^2$ | $R^3$ | 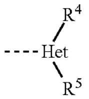 |
|---|---|---|---|---|---|
| 88 | B38 | 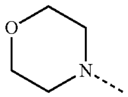 | ----$CH_3$ | ----H | 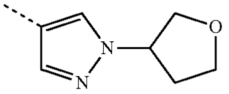 |

Optical Rotation: −16.8° (589 nm, 20° C., 0.59 w/v %, $CH_3OH$)

| Co. No. | Ex. No. | $R^1$ | $R^2$ | $R^3$ | Het |
|---|---|---|---|---|---|
| 89 | B34 | 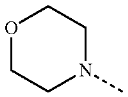 | ----$CH_3$ | ----H | 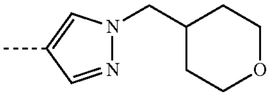 |
| 90 | B38 | 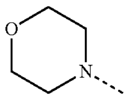 | ----$CH_3$ | ----H | 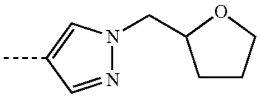 |

Optical Rotation: +33.7° (589 nm, 20° C., 0.54 w/v %, $CH_3OH$)

| Co. No. | Ex. No. | $R^1$ | $R^2$ | $R^3$ | Het |
|---|---|---|---|---|---|
| 91 | B23 | 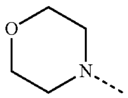 | ----$CH_3$ | ----H | 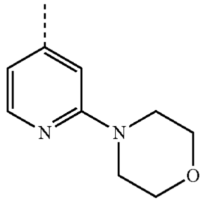 |
| 92 | B34 | 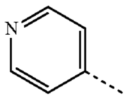 | ----$CH_3$ | ----H | 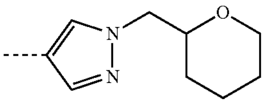 |

Optical Rotation: +7.2° (589 nm, 20° C., 0.54 w/v %, $CH_3OH$)

| Co. No. | Ex. No. | $R^1$ | $R^2$ | $R^3$ | Het |
|---|---|---|---|---|---|
| 93 | B34 | 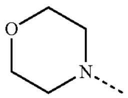 | ----$CH_3$ | ----H | 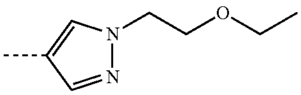 |
| 94 | B34 | 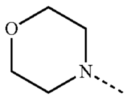 | ----$CH_3$ | ----H | 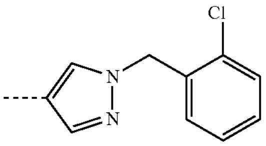 |
| 95 | B1 | 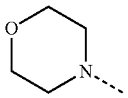 | ----$OCH_3$ | ----H | 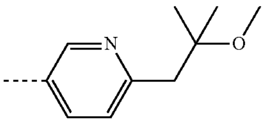 |

TABLE 1-continued
Compounds according to formula (I) prepared according to the above methods. The assignment of configuration in compounds 24, 57, 75, 79, 101, 104 and 110 derives from the reagent used in the synthesis of the compound.
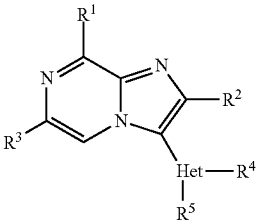
| Co. No. | Ex. No. | $R^1$ | $R^2$ | $R^3$ | 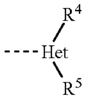 |
|---|---|---|---|---|---|
| 96 | B34 | 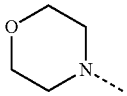 | ----$CH_3$ | ----H | 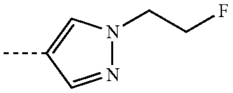 |
| 97 | B34 | 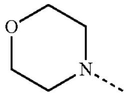 | ----$CH_3$ | ----H | 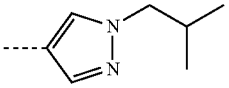 |
| 98 | B34 | 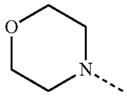 | ----$CH_3$ | ----H | 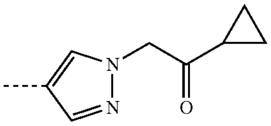 |
| 99 | B23 | 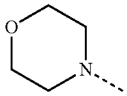 | ----$CH_3$ | ----H | 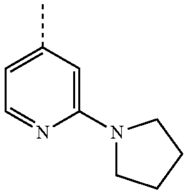 |
| 100 | B34 | 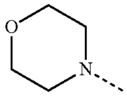 | ----$CH_2CH_3$ | ----H | 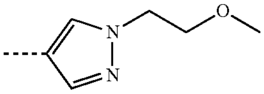 |
| 101 | B34 | 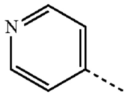 | ----$CH_3$ | ----H | 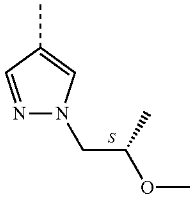 |
| Optical Rotation: n.d. | | | | | |
| 102 | B34 | 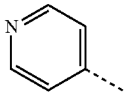 | ----$CH_3$ | ----H | 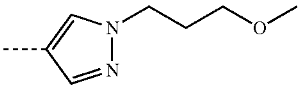 |
| 103 | B22 | 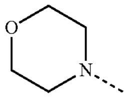 | ----$CH_3$ | ----H | 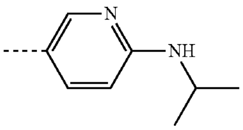 |

TABLE 1-continued

Compounds according to formula (I) prepared according to the above methods. The assignment of configuration in compounds 24, 57, 75, 79, 101, 104 and 110 derives from the reagent used in the synthesis of the compound.

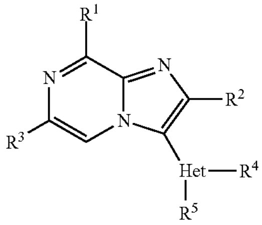

| Co. No. | Ex. No. | $R^1$ | $R^2$ | $R^3$ | 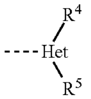 |
|---|---|---|---|---|---|
| 104 | B34 | 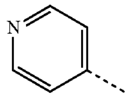 | ----$CH_3$ | ----H | 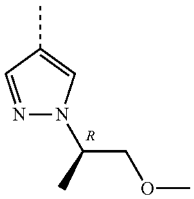 |

Optical Rotation: n.d.

| Co. No. | Ex. No. | $R^1$ | $R^2$ | $R^3$ | Het |
|---|---|---|---|---|---|
| 105 | B1 | 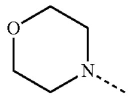 | 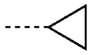 | ----H | 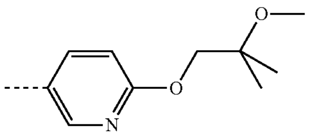 |
| 106 | B27 | 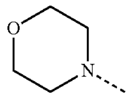 | ----$CH_3$ | ----H | 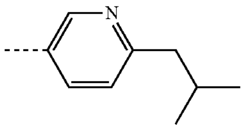 |
| 107 | B27 | 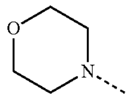 | ----$CH_3$ | ----H | 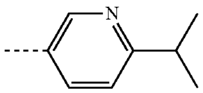 |
| 108 | B1 | 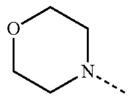 | 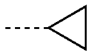 | ----H | 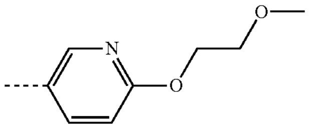 |
| 109 | B38 | 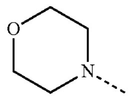 | ----$CH_3$ | ----H | 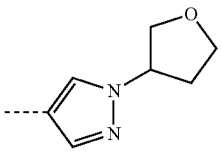 |

Optical Rotation: +15.8° (589 nm, 20° C., 0.57 w/v % $CH_3OH$)

| Co. No. | Ex. No. | $R^1$ | $R^2$ | $R^3$ | Het |
|---|---|---|---|---|---|
| 110 | B34 | 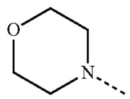 | ----$CH_3$ | ----H | 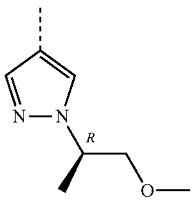 |

TABLE 1-continued
Compounds according to formula (I) prepared according to the above methods. The assignment of configuration in compounds 24, 57, 75, 79, 101, 104 and 110 derives from the reagent used in the synthesis of the compound.
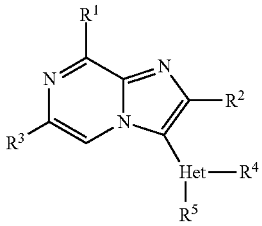
| Co. No. | Ex. No. | $R^1$ | $R^2$ | $R^3$ | 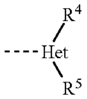 |
|---|---|---|---|---|---|
| Optical Rotation: n.d. | | | | | |
| 111 | B34 | 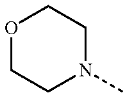 | ----$CH_3$ | ----H | 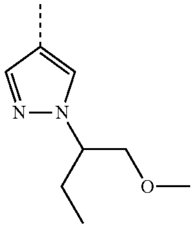 |
| Optical Rotation: n.d. | | | | | |
| 112 | B34 | 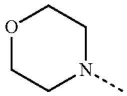 | ----$CH_3$ | ----H | 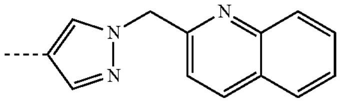 |
| 113 | B1 | 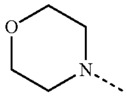 | ----$CH_3$ | ----H | 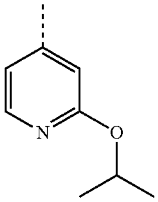 |
| 114 | B41 | 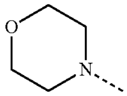 | ----$CH_3$ | ----H | 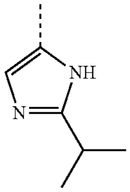 |
| 115 | B1 | 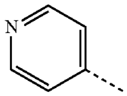 | ----$CH_3$ | ----H | 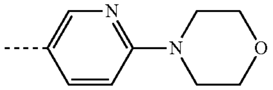 |
| 116 | B34 | 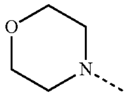 | ----$CH_3$ | ----H | 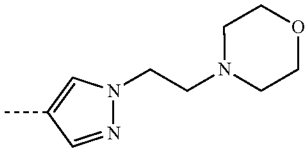 |

TABLE 1-continued
Compounds according to formula (I) prepared according to the above methods. The assignment of configuration in compounds 24, 57, 75, 79, 101, 104 and 110 derives from the reagent used in the synthesis of the compound.
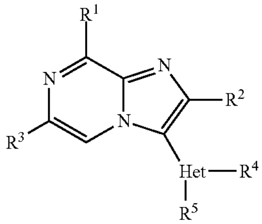
| Co. No. | Ex. No. | $R^1$ | $R^2$ | $R^3$ | 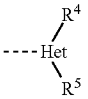 |
|---|---|---|---|---|---|
| 117 | B34 | 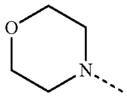 | ----$CH_3$ | ----H | 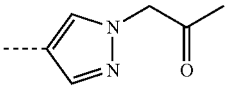 |
| 118 | B34 | 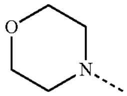 | ----$CF_3$ | ----H | 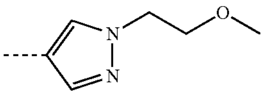 |
| 119 | B34 | 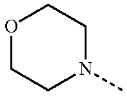 | ----H | ----H | 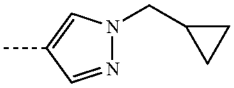 |
| 120 | B1 | 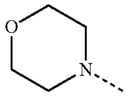 | ----$CH_3$ | ----H | 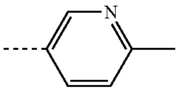 |
| 121 | B34 | 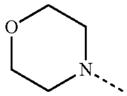 | ----$CH_3$ | ----H | 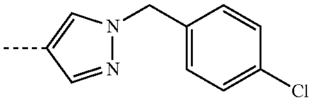 |
| 122 | B1 | 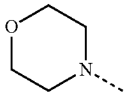 | ----$CH_3$ | ----H | 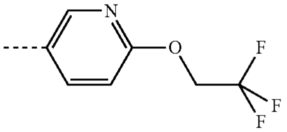 |
| 123 | B23 | 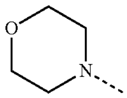 | ----$CH_3$ | ----H | 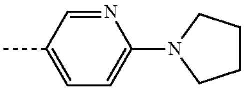 |
| 124 | B1 | 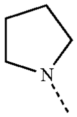 | ----$CH_3$ | ----H | 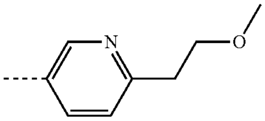 |
| 125 | B1 | 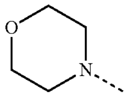 | ----$CH_3$ | ----H | 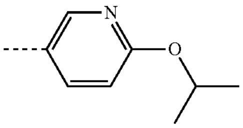 |

TABLE 1-continued
Compounds according to formula (I) prepared according to the above methods. The assignment of configuration in compounds 24, 57, 75, 79, 101, 104 and 110 derives from the reagent used in the synthesis of the compound.
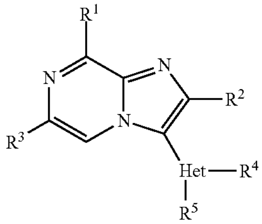
| Co. No. | Ex. No. | $R^1$ | $R^2$ | $R^3$ | 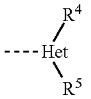 |
|---|---|---|---|---|---|
| 126 | B34 | 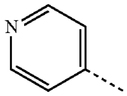 | ----$CH_3$ | ----H | 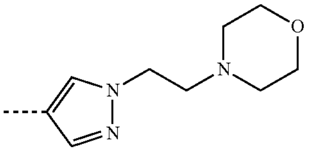 |
| 127 | B34 | 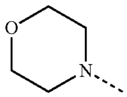 | ----$CH_3$ | ----H | 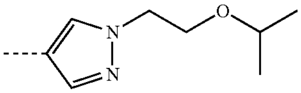 |
| 128 | B34 | 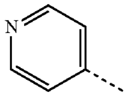 | ----$CH_3$ | ----H | 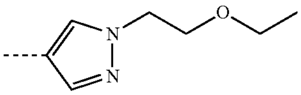 |
| 129 | B1 | 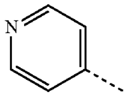 | ----$CH_3$ | ----H | 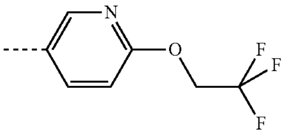 |
| 130 | B34 | 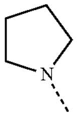 | ----$CH_3$ | ----H | 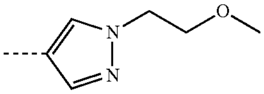 |
| 131 | B34 | 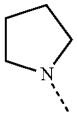 | ----$OCH_3$ | ----H | 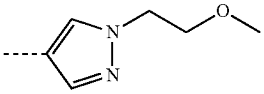 |
| 132 | B1 | 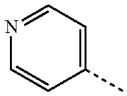 | ----$CH_3$ | ----H | 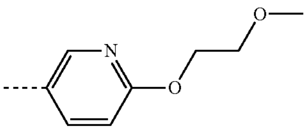 |
| 133 | B30 | 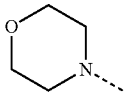 | ----$CH_3$ | ----H | 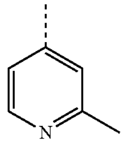 |
| 134 | B1 | 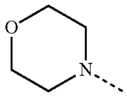 | ----$CH_3$ | ----H | 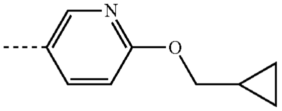 |

TABLE 1-continued
Compounds according to formula (I) prepared according to the above methods. The assignment of configuration in compounds 24, 57, 75, 79, 101, 104 and 110 derives from the reagent used in the synthesis of the compound.
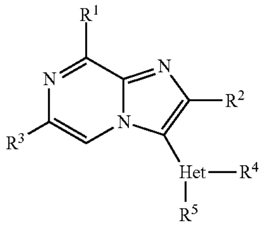
| Co. No. | Ex. No. | $R^1$ | $R^2$ | $R^3$ | 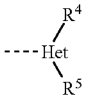 |
|---|---|---|---|---|---|
| 135 | B34 | 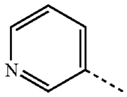 | ----$CH_3$ | ----H | 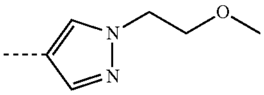 |
| 136 | B1 | 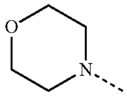 | ----H | ----H | 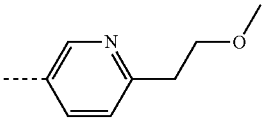 |
| 137 | B34 | 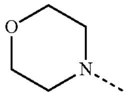 | ----$OCH_3$ | ----H | 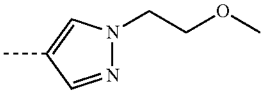 |
| 138 | B34 | 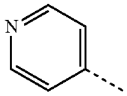 | ----$CH_3$ | ----H | 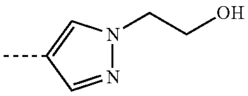 |
| 139 | B28 | 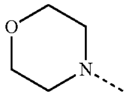 | ----$CH_3$ | ----H | 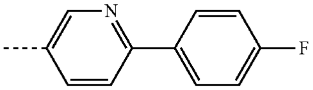 |
| 140 | B19 | 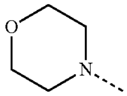 | ----$CH_3$ | ----H | 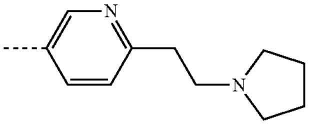 |
| 141 | B34 | 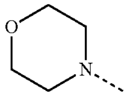 | ----H | ----H | 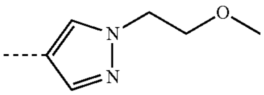 |
| 142 | B142 | 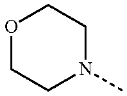 | ----$CH_3$ | ----H | 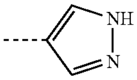 |
| 143 | B143 | 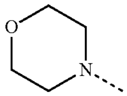 | ----$CH_3$ | ----H | 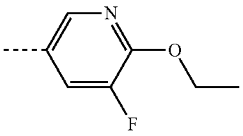 |

C. Analytical Part

LCMS

For LCMS-characterization of the compounds of the present invention, the following methods were used.

General Procedure for HP 1100-MS Instruments (TOF, SQD or MSD)

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

General Procedure for Acquity-SQD Instrument

The HPLC (Ultra Performance Liquid Chromatography) measurement was performed using an Acquity HPLC (Waters) system comprising a sampler organizer, a binary pump with degasser, a four column's oven, a diode-array detector (DAD) and a column as specified in the respective methods. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

MS Procedure for LC Methods 1, 2 and 10:

High-resolution mass spectra (Time of Flight, TOF detector) were acquired only in positive ionization mode or in positive/negative modes by scanning from 100 to 750 umas. The capillary needle voltage was 2.5 kV for positive mode 2.9 Kv for negative ionization mode. The cone voltage was 20 V for both positive and negative ionization modes. Leucine-Enkephaline was the standard substance used for the lock mass calibration.

MS Procedure for LC Methods 3-9 and 11:

Low-resolution mass spectra (single quadrupole, SQD detector) were acquired only in positive ionization mode or in positive/negative modes by scanning from 100 to 1000 umas. The capillary needle voltage was 3 kV. For positive ionization mode the cone voltage was 20V, 25V or 20V/50V. For negative ionization mode the cone voltage was 30V.

Method 1

In addition to the general procedure: Reversed phase HPLC was carried out on an XDB-C18 cartridge (1.8 μm, 2.1×30 mm) from Agilent, at 60° C. with a flow rate of 1 ml/min., at 60° C. The gradient conditions used are: 90% A (0.5 g/l ammonium acetate solution), 5% B (ACN), 5% C (MeOH) to 50% B and 50% C, then to 100% B and equilibrated to initial conditions up to 9.0 min. run. Injection volume 2 μl.

Method 2

In addition to the general procedure: Reversed phase HPLC was carried out on a Sunfire-C18 column (2.5 μm, 2.1×30 mm) from Waters, with a flow rate of 1.0 ml/min., at 60° C. The gradient conditions used are: 95% A (0.5 g/l ammonium acetate solution+5% of ACN), 5% B (ACN or or ACN/MeOH 1/1), to 100% B and equilibrated to initial conditions up to 7 or 9 min. run. Injection volume 2 μl.

Method 3

In addition to the general procedure: Reversed phase HPLC was carried out on a XDB-C18 cartridge (1.8 μm, 2.1×30 mm) from Agilent, with a flow rate of 0.8 ml/min., at 60° C. The gradient conditions used are: 90% A (0.5 g/l ammonium acetate solution), 10% B (mixture of ACN/MeOH, 1/1), to 100% B and equilibrated to initial conditions up to 9.0 min. run. Injection volume 2 μl.

Method 4

In addition to the general procedure: Reversed phase HPLC was carried out on a Sunfire-C18 column (2.5 μm, 2.1×30 mm) from Waters, with a flow rate of 1.0 ml/min., at 60° C. The gradient conditions used are: 95% A (0.5 g/l ammonium acetate solution+5% ACN), 5% B (mixture of ACN/MeOH, 1/1), to 100% B and equilibrated to initial conditions up to 7 or 9 min. run. Injection volume 2 μl.

Method 5

In addition to the general procedure: Reversed phase HPLC was carried out on a XBridge-C18 column (2.5 μm, 2.1×30 mm) from Waters, with a flow rate of 1.0 ml/min., at 60° C. The gradient conditions used are: 95% A (0.5 g/l ammonium acetate solution+5% ACN), 5% B (mixture of ACN/MeOH, 1/1), to 100% B and equilibrated to initial conditions up to 9.0 min. run. Injection volume 2 μl.

Method 6

In addition to the general procedure: Reversed phase HPLC was carried out on an Eclipse Plus-C18 column (3.5 μm, 2.1×30 mm) from Agilent, with a flow rate of 1.0 ml/min., at 60° C. The gradient conditions used are: 95% A (0.5 g/l ammonium acetate solution+5% ACN), 5% B (ACN or mixture of ACN/MeOH, 1/1), to 100% B and equilibrated to initial conditions up to 5, 7 or 9 min. run. Injection volume 2 μl.

Method 7

In addition to the general procedure: Reversed phase HPLC was carried out on a BEH-C18 column (1.7 μm, 2.1×50 mm) from Waters, with a flow rate of 0.8 ml/min., at 60° C. The gradient conditions used are: 95% A (0.5 g/l ammonium acetate solution+5% ACN), 5% B (mixture of ACN/MeOH, 1/1), to 20% A, 80% B, then to 100% B and equilibrated to initial conditions up to 5, 7 or 9 min. run. Injection volume 0.5 μl.

Method 8

In addition to the general procedure: Reversed phase HPLC was carried out on a BEH-C18 column (1.7 μm, 2.1×50 mm) from Waters, with a flow rate of 1.0 ml/min., at 50° C. The gradient conditions used are: 95% A (0.5 g/l ammonium acetate solution+5% ACN), 5% B (ACN), to 40% A, 60% B, then to 5% A, 95% B and equilibrated to initial conditions up to 5, 7, or 9 min. run. Injection volume 0.5 μl.

Method 9

In addition to the general procedure: Reversed phase HPLC was carried out on a XDB-C18 cartridge (1.8 μm, 2.1×30 mm) from Agilent, with a flow rate of 0.8 ml/min., at 60° C. The gradient conditions used are: 90% A (0.5 g/l ammonium acetate solution), 10% B (mixture of ACN/MeOH, 1/1), to 100% B in 6.0 min., kept till 6.5 min. and equilibrated to initial conditions at 7.0 min. until 9.0 min. Injection volume 2 μl.

Method 10

In addition to the general procedure: Reversed phase HPLC was carried out on an XDB-C18 cartridge (1.8 μm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol), to 50% B, 50% C in 5.20 minutes, kept till 5.6 minutes and equilibrated to initial conditions at 5.8 minutes until 7.0 minutes. Injection volume 2 μl.

Method 11

In addition to the general procedure: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μl.

General Procedure A

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50V. Drying gas temperature was maintained at 350° C. at a flow of 10 l/min.

Method 1

In addition to general procedure A: Reversed phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: ACN with 0.05% TFA) were used. First, 100% A was hold for 1 min. Then a gradient was applied to 40% A and 60% B in 4 min. and hold for 2.5 min. Typical injection volumes of 2 μl were used. Oven temperature was 50° C. (MS polarity: positive)

Method 2

In addition to general procedure A: Reversed phase HPLC was carried out on an Ultimate XB-C18, 50×2.1 mm 5 μm column with a flow rate of 0.8 ml/min. Two mobile phases (mobile phase C: 10 mmol/L $NH_4HCO_3$; mobile phase D: ACN) were used. First, 100% C was hold for 1 min. Then a gradient was applied to 40% C and 60% D in 4 min. and hold for 2.5 min. Typical injection volumes of 2 μl were used. Oven temperature was 50° C. (MS polarity: positive)

Melting Points

Values are peak values or melt ranges, and are obtained with experimental uncertainties that are commonly associated with this analytical method. For a number of compounds, melting points were determined in open capillary tubes either on a Mettler FP62 or on a Mettler FP81HT-FP90 apparatus. Melting points were measured with a temperature gradient of 10° C./min. Maximum temperature was 300° C. The melting point was read from a digital display.

For a number of compounds, melting points (m.p.) were determined with a Diamond DSC (PerkinElmer). Melting points were measured with a temperature gradient of 10° C./minute. Maximum temperature was 300° C. (indicated by DSC). Values are peak values.

For a number of compounds, melting points (m.p.) were determined with a WRS-2A melting point apparatus (Shanghai Precision and Scientific Instrument Co. Ltd.). Melting points were measured with a linear heating up rate of 0.2-5.0° C./minute. The reported values are melt ranges. The maximum temperature was 300° C. (indicated by WRS-2A).

The results of the analytical measurements are shown in table 2.

TABLE 2

Retention time ($R_t$) in min., $[M+H]^+$ peak (protonated molecule), LCMS method and m.p. (melting point in ° C.). (n.d. means not determined)

| Co. No. | mp | $[M+H]^+$ | $R_t$ | LCMS Method |
|---|---|---|---|---|
| 1 | n.d. | 370 | 2.34 | 8 |
| 2 | 125.1 | 390 | 3.23 | 6 |
| 3 | n.d. | 398 | 2.92 | 8 |
| 4 | 172.1 | 381 | 2.95 | 2 |
| 5 | >300 dec | 354 | 2.23 | 8 |
| 6 | n.d. | 368 | 2.20 | 8 |
| 7 | 133.2 | 382 | 2.40 | 8 |
| 8 | 279.0 | 346 | 2.44 | 2 |
| 9 | 118.4 | 422 | 3.24 | 8 |
| 10 | 103.9 | 380 | 2.67 | 8 |
| 11 | 112.2 | 368 | 2.39 | 8 |
| 12 | n.d. | 408 | 2.80 | 8 |
| 13 | n.d. | 382 | 2.90 | 8 |
| 14 | >300 dec | 346 | 1.68 | 8 |
| 15 | >300 dec | 370 | 2.34 | 8 |
| 16 | >300 dec | 354 | 1.94 | 8 |
| 17 | >300 dec | 372 | 2.29 | 8 |
| 18 | n.d. | 340 | 1.36 | 8 |
| 19 | n.d. | 354 | 1.92 | 8 |
| 20 | 87.6 | 368 | 2.27 | 8 |
| 21 | n.d. | 382 | 2.62 | 8 |
| 22 | 174.2 | 353 | 2.56 | 8 |
| 23 | n.d. | 380 | 1.19 | 8 |
| 24 | n.d. | 395 | 2.44 | 8 |
| 25 | 174.8 | 380 | 2.14 | 8 |
| 26 | 80.3 | 324 | 2.32 | 8 |
| 27 | >300 dec | 352 | 3.01 | 8 |
| 28 | >300 dec | 336 | 2.65 | 8 |
| 29 | n.d. | 396 | 2.69 | 8 |
| 30 | 102.2 | 368 | 2.53 | 8 |
| 31 | n.d. | 354 | 2.29 | 8 |
| 32 | 175.6 | 327 | 1.32 | 8 |
| 33 | 113.3 | 355 | 1.56 | 8 |
| 34 | n.d. | 335 | 2.69 | 4 |
| 35 | n.d. | 343 | 2.84 | 1 |
| 36 | n.d. | 355 | 3.09 | 9 |
| 37 | 141.7 | 383 | 3.41 | 8 |
| 38 | n.d. | 313 | 3.29 | 9 |
| 39 | n.d. | 439 | 3.19 | 8 |
| 40 | n.d. | 354 | 3.01 | 1 |
| 41 | 121.0 | 342 | 3.85 | 6 |
| 42 | 84.1 | 358 | 4.68 | 2 |
| 43 | n.d. | 384 | 2.74 | 1 |
| 44 | n.d. | 342 | 3.48 | 1 |
| 45 | 80.5 | 385 | 3.3 | 6 |
| 46 | n.d. | 393 | 3.49 | 6 |
| 47 | n.d. | 375 | 3.18 | 7 |
| 48 | n.d. | 397 | 3.53 | 6 |
| 49 | 137.9-138.9[a] | 367 | 4.84 | 2a |
| 50 | n.d. | 389 | 2.71 | 8 |
| 51 | >300 Dec. | 361 | 2.15 | 8 |
| 52 | n.d. | 375 | 3.52 | 2 |
| 53 | n.d. | 369 | 2.78 | 7 |
| 54 | n.d. | 385 | 3.24 | 7 |
| 55 | 128.0 | 382 | 2.99 | 8 |
| 56 | n.d. | 349 | 2.91 | 1 |
| 57 | n.d. | 357 | 3.17 | 1 |
| 58 | n.d. | 383 | 3.41 | 7 |
| 59 | n.d. | 385 | 3.24 | 7 |
| 60 | n.d. | 408 | 4.03 | 8 |
| 61 | n.d. | 371 | 2.62 | 7 |
| 62 | 128[b] | 339 | 3.47 | 1 |
| 63 | 185.8 | 407 | 3.08 | 8 |
| 64 | n.d. | 375 | 3.18 | 7 |
| 65 | n.d. | 376 | 2.83 | 1 |
| 66 | n.d. | 350 | 3.84 | 2 |
| 67 | n.d. | 359 | 2.75 | 6 |
| 68 | 122.8-128.3[a] | 357 | 4.55 | 2a |
| 69 | n.d. | 333 | 2.78 | 7 |
| 70 | n.d. | 383 | 3.41 | 7 |
| 71 | n.d. | 369 | 2.38 | 7 |
| 72 | n.d. | 371 | 2.65 | 7 |
| 73 | n.d. | 383 | 3.68 | 1 |
| 74 | n.d. | 371 | 3.43 | 5 |

TABLE 2-continued

Retention time ($R_t$) in min., $[M + H]^+$ peak (protonated molecule), LCMS method and m.p. (melting point in ° C.). (n.d. means not determined)

| Co. No. | mp | $[M + H]^+$ | $R_t$ | LCMS Method |
|---|---|---|---|---|
| 75 | n.d. | 357 | 3.15 | 1 |
| 76 | n.d. | 376 | 2.99 | 1 |
| 77 | n.d. | 376 | 2.80 | 1 |
| 78 | 132.4 | 363 | 1.95 | 8 |
| 79 | n.d. | 349 | 3.28 | 9 |
| 80 | n.d. | 375 | 3.13 | 7 |
| 81 | 103.0-108.6[b] | 327 | 3.92 | 1a |
| 82 | n.d. | 355 | 2.80 | 1 |
| 83 | 137.1 | 406 | 2.92 | 8 |
| 84 | n.d. | 371 | 2.62 | 7 |
| 85 | n.d. | 382 | 2.20 | 8 |
| 86 | n.d. | 345 | 3.23 | 4 |
| 87 | >300 Dec. | 406 | 1.79 | 8 |
| 88 | n.d. | 355 | 2.75 | 5 |
| 89 | 149.3-151.2[a] | 383 | 4.55 | 2a |
| 90 | n.d. | 369 | 2.37 | 7 |
| 91 | >300 Dec. | 381 | 2.31 | 8 |
| 92 | n.d. | 375 | 3.13 | 7 |
| 93 | n.d. | 357 | 3.20 | 1 |
| 94 | 122.3-128.3[a] | 409 | 4.65 | 1a |
| 95 | 109.9 | 398 | 2.86 | 8 |
| 96 | 151.5 | 331 | 1.99 | 7 |
| 97 | 83.65-87.69[a] | 341 | 2.97 | 7 |
| 98 | 148.5-152.9[a] | 367 | 4.49 | 2a |
| 99 | >300 Dec. | 365 | 2.83 | 8 |
| 100 | n.d. | 357 | 3.24 | 1 |
| 101 | n.d. | 349 | 2.93 | 1 |
| 102 | n.d. | 349 | 2.89 | 1 |
| 103 | 105.2 | 353 | 2.57 | 8 |
| 104 | n.d. | 349 | 2.9 | 1 |
| 105 | 101.3 | n.d. | n.d. | — |
| 106 | >300 Dec. | 352 | 3.11 | 8 |
| 107 | n.d. | 338 | 3.37 | 6 |
| 108 | 121.8 | 365 | 2.72 | 8 |
| 109 | n.d. | 355 | 2.74 | 5 |
| 110 | n.d. | 357 | 3.10 | 1 |
| 111 | n.d. | 371 | 3.42 | 5 |
| 112 | n.d. | 426 | 3.94 | 1 |
| 113 | 111.3 | 354 | 3.83 | 6 |
| 114 | >300 Dec. | 327 | 2.35 | 6 |
| 115 | >300 Dec. | 373 | 2.43 | 7 |
| 116 | 140.4-144.4[a] | 398 | 4.5 | 2a |
| 117 | n.d. | 341 | 2.83 | 9 |
| 118 | n.d. | 397 | 3.65 | 1 |
| 119 | n.d. | 325 | 3.25 | 1 |
| 120 | 87.3 | 310 | 1.88 | 8 |
| 121 | 119.6-123.4[a] | 409 | 4.90 | 1a |
| 122 | n.d. | 394 | 3.38 | 8 |
| 123 | 132.2 | 365 | 2.88 | 8 |
| 124 | 111.0 | 338 | 2.35 | 8 |
| 125 | 57.8 | 354 | 3.85 | 2 |
| 126 | n.d. | 390 | 2.94 | 3 |
| 127 | 107.5-110.7[a] | 371 | 4.33 | 1a |
| 128 | n.d. | 349 | 2.98 | 1 |
| 129 | n.d. | 386 | 3.54 | 6 |
| 130 | n.d. | 327 | 2.53 | 8 |
| 131 | n.d. | 343 | 3.06 | 7 |
| 132 | n.d. | 362 | 2.73 | 6 |
| 133 | n.d. | 310 | 3.11 | 1 |
| 134 | n.d. | 366 | 3.34 | 8 |
| 135 | n.d. | 335 | 2.42 | 4 |
| 136 | n.d. | 340 | 1.71 | 8 |
| 137 | n.d. | 359 | 2.73 | 2 |
| 138 | n.d. | 321 | 1.28 | 8 |
| 139 | 293.6 | 390 | 3.43 | 8 |
| 140 | >300 Dec. | 393 | 1.17 | 8 |
| 141 | n.d. | 329 | 2.62 | 1 |
| 142 | n.d | 285 | 2.15 | 10 |
| 143 | n.d. | 358 | 2.96 | 11 |

[a]DSC instrument
[b]WRS-2A instrument
Dec means decomposition

SFC-MS Methods:

General Procedure for SFC-MS Methods

The SFC measurement was performed using an Analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Method SFC: 1

In addition to the general procedure: The chiral separation in SFC was carried out on a CHIRALCEL OJ-H column (4.6×500 mm) at 50° C. with a flow rate of 3.0 ml/min. The mobile phase is 10% MeOH/$CO_2$ hold 16.66 min, then from 20-50% MeOH/$CO_2$ at 5% rate and hold 3.34 min. at 50%.

Method SFC: 2

In addition to the general procedure: The chiral separation in SFC was carried out on a CHIRALPAK AD-H column (4.6×500 mm) at 50° C. with a flow rate of 3.0 ml/min. The mobile phase is 25% MeOH/$CO_2$ hold 18.20 min, then from 25-50% MeOH/$CO_2$ at 10% rate and hold 4.0 min. at 50%.

Method SFC: 3

In addition to the general procedure: The chiral separation in SFC was carried out on a CHIRALPAK AD-H column (4.6×500 mm) at 50° C. with a flow rate of 3.0 ml/min. The mobile phase is 5% iPrOH/$CO_2$ hold 3.0 min, then from 5-25% iPrOH/$CO_2$ at 1% rate and hold 5.0 min. at 25%.

Method SFC: 4

In addition to the general procedure: The chiral separation in SFC was carried out on a CHIRALPAK AD-H column (4.6×500 mm) at 50° C. with a flow rate of 3.0 ml/min. The mobile phase is 20% EtOH/$CO_2$ hold 17.50 min, then from 20-50% EtOH/$CO_2$ at 10% rate and hold 4.10 min. at 50%.

Method SFC: 5

In addition to the general procedure: The chiral separation in SFC was carried out on a CHIRALPAK AD-H column (4.6×500 mm) at 50° C. with a flow rate of 3.0 ml/min. The mobile phase is 15% EtOH/$CO_2$ hold 15.16 min, then from 15-50% EtOH/$CO_2$ at 10% rate and hold 3.34 min. at 50%.

Method SFC: 6

In addition to the general procedure: The chiral separation in SFC was carried out on a CHIRALPAK AD-H column (4.6×500 mm) at 50° C. with a flow rate of 3.0 ml/min. The mobile phase is 15% EtOH/$CO_2$ hold 17.16 min, then from 15-50% EtOH/$CO_2$ at 10% rate and hold 1.34 min. at 50%.

TABLE 3

Analytical SFC data - $R_t$ means retention time (in minutes), $[M + H]^+$ means the protonated mass of the compound, method refers to the method used for (SFC)MS analysis of enantiomerically pure compounds.

| Co. Nr. | $R_t$ | $[M + H]^+$ | UV Area % | Method | Isomer Elution Order |
|---|---|---|---|---|---|
| 70 | 11.97 | 383 | 94.6 | 1 | A |
| 58 | 13.13 | 383 | 99.0 | 1 | B |
| 92 | 13.26 | 375 | 100 | 2 | A |

TABLE 3-continued

Analytical SFC data - $R_t$ means retention time (in minutes), $[M + H]^+$ means the protonated mass of the compound, method refers to the method used for (SFC)MS analysis of enantiomerically pure compounds.

| Co. Nr. | $R_t$ | $[M + H]^+$ | UV Area % | Method | Isomer Elution Order |
|---|---|---|---|---|---|
| 80 | 16.72 | 375 | 100 | 2 | B |
| 47 | 17.10 | 375 | 100 | 3 | A |
| 64 | 17.36 | 375 | 96.24 | 3 | B |
| 111 | 5.88 | 371 | 100 | 2 | A |
| 74 | 7.35 | 371 | 100 | 2 | B |
| 88 | 9.58 | 355 | 98.90 | 2 | A |
| 109 | 13.41 | 355 | 100 | 2 | B |
| 71 | 11.14 | 369 | 100 | 4 | A |
| 90 | 12.30 | 369 | 98.81 | 4 | B |
| 61 | 11.04 | 371 | 98.53 | 5 | A |
| 84 | 12.75 | 371 | 97.35 | 5 | B |
| 59 | 7.68 | 385 | 97.17 | 6 | A |
| 54 | 9.76 | 385 | 99.23 | 6 | B |

Isomer Elution Order: A means first eluting isomer; B means second eluting isomer.

Nuclear Magnetic Resonance (NMR)

For a number of compounds, $^1H$ NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Co. No. 1: $^1H$ NMR (400 MHz, DMSO-$d_6$) δ ppm 2.34 (s, 3H), 3.32 (s, 3H), 3.67-3.73 (m, 2H), 3.75 (br. t, J=4.9 Hz, 4H), 4.17 (br. t, J=4.9 Hz, 4H), 4.40-4.53 (m, 2H), 7.04 (d, J=8.6 Hz, 1H), 7.34 (d, J=4.6 Hz, 1H), 7.55 (d, J=4.6 Hz, 1H), 7.88 (dd, J=8.7, 2.4 Hz, 1H), 8.30 (d, J=2.3 Hz, 1H).

Co. No. 2: $^1H$ NMR (500 MHz, DMSO-$d_6$) δ ppm 1.25 (s, 6H), 2.50 (s, 3H), 3.20 (s, 3H), 4.27 (s, 2H), 7.10 (d, J=8.7 Hz, 1H), 8.00 (dd, J=8.5, 2.5 Hz, 1H), 8.05 (d, J=4.3 Hz, 1H), 8.37 (d, J=4.3 Hz, 1H), 8.42 (d, J=2.3 Hz, 1H), 8.68-8.73 (m, 2H), 8.78-8.84 (m, 2H).

Co. No. 3: $^1H$ NMR (400 MHz, DMSO-$d_6$) δ ppm 1.24 (s, 6H), 2.34 (s, 3H), 3.18 (s, 3H), 3.69-3.81 (m, 4H), 4.12-4.21 (m, 4H), 4.24 (s, 2H), 7.05 (d, J=8.6 Hz, 1H), 7.34 (d, J=4.6 Hz, 1H), 7.55 (d, J=4.6 Hz, 1H), 7.87 (dd, J=8.4, 2.2 Hz, 1H), 8.30 (d, J=2.3 Hz, 1H).

Co. No. 4: $^1H$ NMR (400 MHz, DMSO-$d_6$) δ ppm 2.33 (s, 3H), 3.50-3.61 (m, 4H), 3.68-3.81 (m, 8H), 4.10-4.23 (m, 4H), 7.02 (d, J=8.8 Hz, 1H), 7.33 (d, J=4.6 Hz, 1H), 7.53 (d, J=4.6 Hz, 1H), 7.70 (dd, J=8.8, 2.5 Hz, 1H), 8.25 (d, J=2.1 Hz, 1H).

Co. No. 5: $^1H$ NMR (500 MHz, DMSO-$d_6$) δ ppm 1.23 (t, J=6.9 Hz, 3H), 2.38 (s, 3H), 3.63 (q, J=7.1 Hz, 2H), 3.76 (br. t, J=4.9 Hz, 4H), 4.18 (br. t, J=4.9 Hz, 4H), 4.64 (s, 2H), 7.37 (d, J=4.6 Hz, 1H), 7.63 (d, J=8.1 Hz, 1H), 7.64 (d, J=4.6 Hz, 1H), 8.00 (dd, J=8.1, 2.3 Hz, 1H), 8.68 (d, J=1.7 Hz, 1H).

Co. No. 6: $^1H$ NMR (400 MHz, $CDCl_3$) δ ppm 2.03-2.14 (m, 2H), 2.44 (s, 3H), 2.91-3.01 (m, 2H), 3.38 (s, 3H), 3.49 (t, J=6.4 Hz, 2H), 3.84-3.94 (m, 4H), 4.22-4.33 (m, 4H), 7.34 (d, J=4.6 Hz, 1H), 7.34 (d, J=7.9 Hz, 1H), 7.38 (d, J=4.4 Hz, 1H), 7.67 (dd, J=7.9, 2.3 Hz, 1H), 8.61 (d, J=2.1 Hz, 1H).

Co. No. 7: $^1H$ NMR (400 MHz, $CDCl_3$) δ ppm 1.26 (s, 6H), 2.44 (s, 3H), 3.07 (s, 2H), 3.34 (s, 3H), 3.84-3.94 (m, 4H), 4.22-4.33 (m, 4H), 7.34 (d, J=4.4 Hz, 1H), 7.40 (d, J=4.6 Hz, 1H), 7.42 (d, J=8.1 Hz, 1H), 7.67 (dd, J=7.9, 2.3 Hz, 1H), 8.61 (d, J=2.3 Hz, 1H).

Co. No. 8: $^1H$ NMR (400 MHz, DMSO-$d_6$) δ ppm 2.53 (s, 3H), 3.10 (t, J=6.6 Hz, 2H), 3.29 (s, 3H), 3.79 (t, J=6.6 Hz, 2H), 7.56 (d, J=7.9 Hz, 1H), 8.03 (dd, J=8.1, 2.3 Hz, 1H), 8.06 (d, J=4.6 Hz, 1H), 8.44 (d, J=4.6 Hz, 1H), 8.70 (dd, J=4.6, 1.6 Hz, 2H), 8.76 (d, J=2.1 Hz, 1H), 8.82 (dd, J=4.4, 1.6 Hz, 2H).

Co. No. 9: $^1H$ NMR (400 MHz, $CDCl_3$) δ ppm 2.43 (s, 3H), 3.17 (t, J=6.5 Hz, 2H), 3.41 (s, 3H), 3.82-3.93 (m, 6H), 4.30-4.46 (m, 4H), 7.43 (d, J=7.9 Hz, 1H), 7.67 (dd, J=8.1, 2.3 Hz, 1H), 7.71 (s, 1H), 8.61 (d, J=2.3 Hz, 1H).

Co. No. 10: $^1H$ NMR (400 MHz, DMSO-$d_6$) δ ppm 0.86-0.97 (m, 4H), 1.90-2.01 (m, 1H), 3.07 (t, J=6.6 Hz, 2H), 3.27 (s, 3H), 3.70-3.75 (m, 4H), 3.77 (t, J=6.7 Hz, 2H), 4.07-4.18 (m, 4H), 7.34 (d, J=4.6 Hz, 1H), 7.52 (d, J=7.9 Hz, 1H), 7.59 (d, J=4.6 Hz, 1H), 7.94 (dd, J=8.1, 2.3 Hz, 1H), 8.69 (d, J=1.6 Hz, 1H).

Co. No. 11: $^1H$ NMR (400 MHz, $CDCl_3$) δ ppm 2.21-2.26 (m, 3H), 2.41 (s, 3H), 3.15 (t, J=6.5 Hz, 2H), 3.41 (s, 3H), 3.80-3.95 (m, 6H), 4.20-4.35 (m, 4H), 7.18-7.23 (m, 1H), 7.39 (d, J=7.9 Hz, 1H), 7.67 (dd, J=8.0, 2.2 Hz, 1H), 8.59-8.64 (m, 1H).

Co. No. 12: $^1H$ NMR (400 MHz, $CDCl_3$) δ ppm 3.17 (t, J=6.5 Hz, 2H), 3.40 (s, 3H), 3.81-3.93 (m, 6H), 4.27-4.39 (m, 4H), 7.24 (d, J=4.6 Hz, 1H), 7.38-7.42 (m, 1H), 7.43 (d, J=4.6 Hz, 1H), 7.70 (dd, J=8.0, 2.2 Hz, 1H), 8.63 (d, J=2.1 Hz, 1H).

Co. No. 13: $^1H$ NMR (400 MHz, DMSO-$d_6$) δ ppm 1.24 (d, J=6.7 Hz, 6H), 2.95-3.05 (m, 1H), 3.07 (t, J=6.6 Hz, 2H), 3.28 (s, 3H), 3.74-3.80 (m, 6H), 4.16-4.23 (m, 4H), 7.33 (d, J=4.6 Hz, 1H), 7.49 (d, J=4.6 Hz, 1H), 7.51 (d, J=8.1 Hz, 1H), 7.86 (dd, J=7.9, 2.3 Hz, 1H), 8.58 (d, J=2.3 Hz, 1H).

Co. No. 14: $^1H$ NMR (400 MHz, DMSO-$d_6$) δ ppm 2.52 (s, 3H), 3.09 (t, J=6.6 Hz, 2H), 3.29 (s, 3H), 3.79 (t, J=6.6 Hz, 2H), 7.56 (d, J=8.1 Hz, 1H), 7.63 (dd, J=8.1, 4.9 Hz, 1H), 8.02 (dd, J=5.8, 2.3 Hz, 1H), 8.03 (d, J=4.4 Hz, 1H), 8.38 (d, J=4.6 Hz, 1H), 8.74 (dd, J=4.6, 1.6 Hz, 1H), 8.76 (d, J=2.3 Hz, 1H), 9.04 (dt, J=8.0, 1.9 Hz, 1H), 9.85 (d, J=2.1 Hz, 1H).

Co. No. 15: $^1H$ NMR (400 MHz, DMSO-$d_6$) δ ppm 3.02 (t, J=6.6 Hz, 2H), 3.26 (s, 3H), 3.73 (t, J=6.5 Hz, 2H), 3.74-3.78 (m, 4H), 4.00 (s, 3H), 4.07-4.12 (m, 4H), 7.45 (d, J=8.3 Hz, 1H), 7.46 (d, J=4.6 Hz, 1H), 7.85 (d, J=4.6 Hz, 1H), 7.92 (dd, J=8.1, 2.3 Hz, 1H), 8.70 (d, J=2.1 Hz, 1H).

Co. No. 16: $^1H$ NMR (500 MHz, $CDCl_3$) δ ppm 2.44 (s, 3H), 3.16 (t, 2H), 3.40 (s, 3H), 3.86 (t, 2H), 3.89 (br. t, J=4.9 Hz, 4H), 4.27 (br. t, J=4.9 Hz, 4H), 7.34 (d, 1H), 7.39 (d, J=4.6 Hz, 1H), 7.40 (d, J=8.1 Hz, 1H), 7.68 (dd, J=8.1, 2.3 Hz, 1H), 8.63 (d, J=1.7 Hz, 1H).

Co. No. 17: $^1H$ NMR (500 MHz, $CDCl_3$) δ ppm 2.45 (s, 3H), 3.22 (td, J=6.6, 2.2 Hz, 2H), 3.41 (s, 3H), 3.88 (t, J=6.6 Hz, 2H), 3.89 (t, J=4.9 Hz, 4H), 4.25-4.29 (m, 4H), 7.37 (d, J=4.6 Hz, 1H), 7.41 (d, J=4.6 Hz, 1H), 7.43 (dd, J=9.8, 1.7 Hz, 1H), 8.46 (br. t, J=1.3, 1.3 Hz, 1H).

Co. No. 18: $^1H$ NMR (400 MHz, $CDCl_3$) δ ppm 2.44 (s, 3H), 3.13 (t, J=5.4 Hz, 2H), 3.83-3.98 (m, 5H), 4.11 (t, J=5.4 Hz, 2H), 4.25-4.30 (m, 4H), 7.33-7.38 (m, 3H), 7.70 (dd, J=7.9, 2.3 Hz, 1H), 8.59 (d, J=2.1 Hz, 1H).

Co. No. 19: $^1H$ NMR (400 MHz, $CDCl_3$) δ ppm 2.49 (s, 3H), 3.14 (t, J=6.4 Hz, 2H), 3.38 (s, 3H), 3.83 (t, J=6.4 Hz, 2H), 3.87-3.91 (m, 4H), 4.24-4.29 (m, 4H), 7.22 (dd, J=5.2, 1.5 Hz, 1H), 7.31 (br. s, 1H), 7.37 (d, J=4.6 Hz, 1H), 7.54 (d, J=4.6 Hz, 1H), 8.69 (d, J=5.1 Hz, 1H).

Co. No. 20: $^1H$ NMR (400 MHz, $CDCl_3$) δ ppm 1.22 (t, J=7.1 Hz, 3H), 2.44 (s, 3H), 3.16 (t, J=6.7 Hz, 2H), 3.56 (q, J=6.9 Hz, 2H), 3.85-3.92 (m, 6H), 4.24-4.30 (m, 4H), 7.34 (d, J=4.4 Hz, 1H), 7.38 (d, J=4.6 Hz, 1H), 7.41 (d, J=8.1 Hz, 1H), 7.68 (dd, J=7.9, 2.3 Hz, 1H), 8.61 (d, J=2.1 Hz, 1H).

Co. No. 21: $^1H$ NMR (400 MHz, $CDCl_3$) δ ppm 1.17 (d, J=6.2 Hz, 6H), 2.43 (s, 3H), 3.14 (t, J=6.7 Hz, 2H), 3.63 (spt, J=6.1 Hz, 1H), 3.87 (t, J=6.9 Hz, 2H), 3.87-3.92 (m, 4H), 4.23-4.31 (m, 4H), 7.34 (d, J=4.6 Hz, 1H), 7.37 (d, J=4.6 Hz, 1H), 7.42 (d, J=7.9 Hz, 1H), 7.67 (dd, J=8.0, 2.2 Hz, 1H), 8.61 (d, J=2.3 Hz, 1H).

Co. No. 22: $^1$H NMR (400 MHz, $CDCl_3$) δ ppm 1.28 (d, J=6.5 Hz, 6H), 2.47 (s, 3H), 3.89 (m, J=9.7 Hz, 4H), 3.88-3.98 (m, 1H), 4.22-4.30 (m, 4H), 4.53 (d, J=7.9 Hz, 1H), 6.36 (br. s, 1H), 6.61 (dd, J=5.3, 1.4 Hz, 1H), 7.35 (d, J=4.6 Hz, 1H), 7.54 (d, J=4.6 Hz, 1H), 8.21 (d, J=5.1 Hz, 1H).

Co. No. 23: $^1$H NMR (400 MHz, DMSO-$d_6$) δ ppm 2.32 (s, 3H), 2.81 (br. t, J=5.1 Hz, 4H), 3.32 (br. s., 1H), 3.51 (dd, J=5.3, 4.9 Hz, 4H), 3.74 (br. t, J=4.9 Hz, 4H), 4.16 (dd, J=4.9, 4.4 Hz, 4H), 6.96 (d, J=8.8 Hz, 1H), 7.32 (d, J=4.6 Hz, 1H), 7.52 (d, J=4.6 Hz, 1H), 7.64 (dd, J=8.8, 2.3 Hz, 1H), 8.20 (d, J=2.3 Hz, 1H).

Co. No. 24: $^1$H NMR (500 MHz, $CDCl_3$) δ ppm 2.10-2.19 (m, 1H), 2.20-2.28 (m, 1H), 2.40 (s, 3H), 3.40 (s, 3H), 3.61 (dd, J=8.8, 5.3 Hz, 2H), 3.65 (dd, J=11.6, 4.8 Hz, 1H), 3.70 (br. d, J=11.6 Hz, 1H), 3.86-3.92 (m, 4H), 4.12-4.16 (m, 1H), 4.22-4.29 (m, 4H), 6.51 (d, J=8.7 Hz, 1H), 7.30 (d, J=4.6 Hz, 1H), 7.34 (d, J=4.3 Hz, 1H), 7.47 (dd, J=8.7, 2.3 Hz, 1H), 8.20 (d, J=2.3 Hz, 1H).

Co. No. 25: $^1$H NMR (500 MHz, DMSO-$d_6$) δ ppm 1.76-1.91 (m, 4H), 2.37 (s, 3H), 2.98-3.11 (m, 1H), 3.43-3.55 (m, 2H), 3.76 (br. t, J=4.6 Hz, 4H), 3.93-4.05 (m, 2H), 4.17 (dd, J=4.9, 4.3 Hz, 4H), 7.35 (d, J=4.6 Hz, 1H), 7.52 (d, J=8.1 Hz, 1H), 7.62 (d, J=4.6 Hz, 1H), 7.93 (dd, J=8.1, 2.3 Hz, 1H), 8.67 (d, J=1.7 Hz, 1H).

Co. No. 26: $^1$H NMR (500 MHz, DMSO-$d_6$) δ ppm 1.30 (t, J=7.7 Hz, 3H), 2.36 (s, 3H), 2.85 (q, J=7.5 Hz, 2H), 3.73-3.78 (m, 4H), 4.14-4.20 (m, 4H), 7.35 (d, J=4.6 Hz, 1H), 7.48 (d, J=8.1 Hz, 1H), 7.60 (d, J=4.6 Hz, 1H), 7.89 (dd, J=7.9, 2.5 Hz, 1H), 8.63 (d, J=1.7 Hz, 1H).

Co. No. 27: $^1$H NMR (500 MHz, DMSO-$d_6$) δ ppm 0.93 (d, J=6.6 Hz, 6H), 2.05-2.18 (m, 1H), 2.42 (s, 3H), 2.70 (d, J=7.2 Hz, 2H), 3.74-3.78 (m, 4H), 4.15-4.20 (m, 4H), 7.37-7.40 (m, 2H), 7.41 (d, J=4.6 Hz, 1H), 7.74 (d, J=4.6 Hz, 1H), 8.66 (d, J=5.8 Hz, 1H).

Co. No. 28: $^1$H NMR (400 MHz, $CDCl_3$) δ ppm 1.00-1.19 (m, 4H), 2.05-2.19 (m, 1H), 2.42 (s, 3H), 3.89 (br. t, J=4.9 Hz, 4H), 4.27 (br. t, J=4.6 Hz, 4H), 7.31 (d, J=8.3 Hz, 1H), 7.32 (d, J=4.6 Hz, 1H), 7.35 (d, J=4.4 Hz, 1H), 7.59 (dd, J=8.1, 2.1 Hz, 1H), 8.51 (d, J=2.3 Hz, 1H).

Co. No. 29: $^1$H NMR (400 MHz, $CDCl_3$) δ ppm 1.26 (s, 6H), 1.95-2.01 (m, 2H), 2.43 (s, 3H), 2.89-2.96 (m, 2H), 3.26 (s, 3H), 3.86-3.91 (m, 4H), 4.25-4.30 (m, 4H), 7.31-7.39 (m, 3H), 7.66 (dd, J=8.1, 1.8 Hz, 1H), 8.60 (d, J=2.3 Hz, 1H).

Co. No. 30: $^1$H NMR (500 MHz, DMSO-$d_6$) δ ppm 1.54 (s, 6H), 2.39 (s, 3H), 3.15 (s, 3H), 3.76 (br. t, J=4.9 Hz, 4H), 4.18 (dd, J=4.9, 4.3 Hz, 4H), 7.37 (d, J=4.6 Hz, 1H), 7.65 (d, J=4.6 Hz, 1H), 7.72 (d, J=8.1 Hz, 1H), 8.00 (dd, J=8.1, 2.3 Hz, 1H), 8.70 (d, J=1.7 Hz, 1H).

Co. No. 31: $^1$H NMR (500 MHz, $CDCl_3$) δ ppm 2.60 (s, 3H), 2.95 (t, J=6.5 Hz, 2H), 3.39 (s, 3H), 3.68 (t, J=6.5 Hz, 2H), 3.87-3.93 (m, 4H), 4.20-4.25 (m, 4H), 7.40 (d, J=4.6 Hz, 1H), 7.47 (d, J=8.1 Hz, 1H), 7.71 (dd, J=8.1, 2.0 Hz, 1H), 8.45 (d, J=4.6 Hz, 1H), 8.63 (d, J=1.7 Hz, 1H).

Co. No. 32: $^1$H NMR (500 MHz, DMSO-$d_6$) δ ppm 2.34 (s, 3H), 3.73-3.77 (m, 4H), 4.01 (s, 3H), 4.15-4.19 (m, 4H), 7.35 (d, J=4.6 Hz, 1H), 7.64 (d, J=4.6 Hz, 1H), 8.79 (s, 2H).

Co. No. 33: $^1$H NMR (500 MHz, DMSO-$d_6$) δ ppm 2.38 (s, 3H), 3.22 (t, J=6.5 Hz, 2H), 3.28 (s, 3H), 3.76 (br. t, J=4.9 Hz, 4H), 3.89 (t, J=6.5 Hz, 2H), 4.17 (br. t, J=4.9 Hz, 4H), 7.38 (d, J=4.3 Hz, 1H), 7.71 (d, J=4.6 Hz, 1H), 8.95 (s, 2H).

Co. No. 34: $^1$H NMR (500 MHz, DMSO-$d_6$) δ ppm 2.56 (s, 3H), 3.29 (s, 3H), 3.80 (t, J=5.3 Hz, 2H), 4.41 (t, J=5.3 Hz, 2H), 7.96 (s, 1H), 8.09 (d, J=4.6 Hz, 1H), 8.32 (s, 1H), 8.46 (d, J=4.6 Hz, 1H), 8.68-8.72 (m, 2H), 8.79-8.83 (m, 2H).

Co. No. 35: $^1$H NMR (500 MHz, DMSO-$d_6$) δ ppm 2.39 (s, 3H), 3.27 (s, 3H), 3.75 (dd, J=5.2, 4.6 Hz, 4H), 3.77 (d, J=5.2 Hz, 2H), 4.15 (br. t, J=4.9 Hz, 4H), 4.37 (t, J=5.5 Hz, 2H), 7.38 (d, J=4.6 Hz, 1H), 7.68 (d, J=4.6 Hz, 1H), 7.82 (s, 1H), 8.17 (s, 1H).

Co. No. 36: $^1$H NMR (400 MHz, DMSO-$d_6$) δ ppm 2.15 (s, 3H), 2.37 (s, 3H), 3.11 (t, J=6.8 Hz, 2H), 3.72-3.76 (m, 4H), 4.12-4.17 (m, 4H), 4.39 (t, J=6.8 Hz, 2H), 7.37 (d, J=4.6 Hz, 1H), 7.67 (d, J=4.6 Hz, 1H), 7.79 (s, 1H), 8.17 (s, 1H).

Co. No. 37: $^1$H NMR (400 MHz, DMSO-$d_6$) δ ppm 0.72-0.79 (m, 2H), 0.82-0.88 (m, 2H), 1.90-1.99 (m, 1H), 2.35 (s, 3H), 3.27 (s, 3H), 3.69-3.74 (m, 4H), 3.77 (t, J=5.4 Hz, 2H), 4.07-4.13 (m, 4H), 4.37 (t, J=5.4 Hz, 2H), 7.60 (s, 1H), 7.82 (s, 1H), 8.17 (s, 1H).

Co. No. 38: $^1$H NMR (500 MHz, DMSO-$d_6$) δ ppm 1.45 (t, J=7.2 Hz, 3H), 2.38 (s, 3H), 3.72-3.76 (m, 4H), 4.12-4.18 (m, 4H), 4.24 (q, J=7.2 Hz, 2H), 7.36 (d, J=4.6 Hz, 1H), 7.69 (d, J=4.3 Hz, 1H), 7.79 (s, 1H), 8.19 (s, 1H).

Co. No. 39: $^1$H NMR (400 MHz, DMSO-$d_6$) δ ppm 2.37 (s, 3H), 2.57-2.71 (m, 2H), 2.73-2.80 (m, 2H), 3.27 (s, 3H), 3.72-3.79 (m, 6H), 4.14-4.21 (m, 4H), 4.37 (t, J=5.3 Hz, 2H), 7.66 (s, 1H), 7.83 (s, 1H), 8.16 (s, 1H).

Co. No. 40: $^1$H NMR (400 MHz, DMSO-$d_6$) δ ppm 3.26 (s, 3H), 3.72-3.80 (m, 6H), 4.13-4.19 (m, 4H), 4.41 (t, J=5.3 Hz, 2H), 7.54 (d, J=4.6 Hz, 1H), 7.83 (d, J=4.6 Hz, 1H), 8.02 (s, 1H), 8.44 (s, 1H).

Co. No. 41: $^1$H NMR (400 MHz, $CDCl_3$) δ ppm 1.04 (d, J=6.7 Hz, 6H), 2.24 (dquin, J=13.6, 6.8, 6.8, 6.8, 6.8 Hz, 1H), 2.51 (s, 3H), 2.75 (d, J=7.2 Hz, 2H), 3.86-3.91 (m, 4H), 4.19-4.24 (m, 4H), 7.40 (d, J=4.6 Hz, 1H), 7.76 (s, 1H), 8.30 (d, J=4.4 Hz, 1H).

Co. No. 42: $^1$H NMR (400 MHz, $CDCl_3$) δ ppm 1.06 (d, J=6.5 Hz, 6H), 2.19 (spt, J=6.7 Hz, 1H), 2.46 (s, 3H), 2.95 (d, J=7.2 Hz, 2H), 3.88 (br. t, J=4.9 Hz, 4H), 4.26 (br. t, J=4.9 Hz, 4H), 7.39 (d, 1H), 7.48 (d, J=4.4 Hz, 1H), 7.71 (s, 1H).

Co. No. 43: $^1$H NMR (500 MHz, DMSO-$d_6$) δ ppm 2.38 (s, 3H), 3.71-3.77 (m, 4H), 4.12-4.17 (m, 4H), 6.33 (br. q, J=2.3, 2.3, 2.3 Hz, 1H), 6.98 (q, J=2.6 Hz, 1H), 7.10-7.14 (m, 1H), 7.32 (d, J=4.6 Hz, 1H), 7.71 (d, J=4.6 Hz, 1H), 11.30 (br. s., 1H).

Co. No. 44: $^1$H NMR (500 MHz, DMSO-$d_6$) δ ppm 2.38 (s, 3H), 3.27 (s, 3H), 3.66 (t, J=5.3 Hz, 2H), 3.74 (br. t, J=4.6 Hz, 4H), 4.04-4.25 (m, 6H), 6.30 (dd, J=2.6, 1.7 Hz, 1H), 6.99 (t, J=2.3 Hz, 1H), 7.16 (t, J=1.7 Hz, 1H), 7.34 (d, J=4.6 Hz, 1H), 7.74 (d, J=4.6 Hz, 1H).

D. Pharmacological Examples

The compounds provided in the present invention are inhibitors of PDE10, particularly, of PDE10A. The behaviour of the PDE10 inhibitors according to Formula (I) in vitro and using an apomorphine induced stereotypy model in vivo is shown in Table 4. The in vitro selectivity towards PDE10A, occupancy, and results using PCP-induced hyperlocomotion, conditioned avoidance response models and object recognition tests in rats of selected compounds are shown in tables 4a, 4b, 5 and 6, respectively. Additional data is provided for the reversal of SCH-23390-induced hypolocomotion in mice.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM $MgCl_2$, 1.7 mM EGTA). 10 μl of rPDE10A enzyme in incubation buffer was added and the reaction was started by addition of 10 μl substrate to a final concentration of 60 nM cAMP and 0.008 μCi $^3$H-cAMP. The reaction was incubated for 60 min. at RT. After incubation, the reaction was stopped with 20 μl of stop solution consisting of 17.8 mg/ml PDE SPA (scintillation proximity assay) beads. After sedimentation of the beads during 30 min. the radioactivity was measured in a Perkin Elmer Topcount scintillation counter and results were expressed as cpm. For blank values the enzyme was omitted from the reaction and replaced by incubation buffer. Control values were obtained by addition of a final concentration of 1% DMSO instead of compound. The same assay principle is applied for the measurement of the affinity of the compound for other members of the PDE family with appropriate modifications in incubation buffer, substrate concentration, incubation time and stop solution. A best fit curve was fitted by a minimum sum of squares method to the plot of % of control value subtracted with blank value versus compound concentration and the half maximal inhibitory concentration ($IC_{50}$) value was derived from this curve. An overview of the results is shown in tables 4, 4a and 4b below.

PDE10 Occupancy

Dose-response or single dose experiments were performed to measure PDE10 occupancy 1 hour after subcutaneous (s.c.) or oral (p.o.) administration. Male Wistar rats (200 g) were treated by s.c. or p.o. administration of various PDE10 inhibitors. The PDE10 radioligand [$^3$H]-MP-10 (10 μCi/animal) was injected intravenously (i.v.) 30 minutes before sacrifice. Brains were immediately removed from the skull and rapidly frozen. Twenty μm-thick brain sections were cut using a cryostat-microtome, thaw-mounted on microscope slides and loaded in a β-imager to quantify PDE10 occupancy in the striatum. The results of this test are shown in table 5 below.

Apomorphine-Induced Stereotypy in Rats (APO)

Apomorphine (1.0 mg/kg, i.v.)-induced stereotypy (compulsive sniffing, licking, chewing) was scored every 5 min. over the first hour after injection of apomorphine, following a 1 hour interval pre-treatment with the test compound. The score system was: (3) pronounced, (2) moderate, (1) slight, and (O) absent. Criteria for drug-induced inhibition of stereotypy: fewer than 6 scores of 3 (0.16% false positives), fewer than 6 scores of ≥2 (0.0% false positives), or fewer than 7 scores of 1 (0.81% false positives). The results of this test are shown in table 5 below.

PCP-Induced Hyperlocomotion in Rats (PCP)

Apparatus

Motor activity [horizontal activity (locomotion) and vertical activity (rearing)] was recorded in male Wiga rats (body weight: 175-275 g; housed overnight in groups of 7 rats) using microprocessor-based activity monitors (MED Associates; length×width×height: 43.2×43.2×41.5 cm) over a period of 30 min. The resolution of the system was set at 100 msec. Total distance was defined as the distance traveled, measured by changes in the number or location of interrupted xy-beams (located in two arrays of 32 infrared light beams (1.25 cm apart) perpendicular to each other in a horizontal plane 2.0 cm above the floor). The intensity of the light within the activity meters (measured in the centre at floor level) ranged between 110 and 130 LUX.

PCP-Induced Hyperlocomotion in Rats

Male Wiga rats (200 to 260 g) were pretreated with test compound or solvent (10 ml/kg, s.c.) and placed in individual cages. At a predefined interval thereafter (60 min.), the rats were challenged with PCP (1.25 mg/kg, i.v.) and motor activity was measured over a period of 30 min starting immediately after the PCP challenge. The following all-or-none criterion was adopted for drug-induced inhibition: <11000 counts (2.9% false positives in 102 control rats). The results of this test are shown in table 5 below.

Conditioned Avoidance Response (CAR) Test

Apparatus

The apparatus consisted of an inner box surrounded by an outer box. The inner box was composed of four walls of transparent, synthetic material (length×width×height: 30×30×30 cm), an open top, and a grid floor made of 15 pairs of iron bars (2 mm diameter; 6 mm inter-bar distance). Odd and even bars were connected with a source of alternative current (1.0 mA; Coulbourn Instruments Solid State Shocker/Distributor), which could be interrupted by a switch. The outer box was composed of the same material (length×width×height: 40×40×36 cm), also with an open top, with a distance of 5 cm between the inner and outer box on all sides. To decrease the amount of environmental stimuli, three walls of the outer box were made non-transparent. The front wall was left transparent to allow the necessary inspection of the animal during the test. The upper edge of the outer and inner box served as a target for the rats on which to jump with fore- and hind-paws, respectively.

Avoidance Conditioning and Selection of Animals

From their arrival in the laboratory on the experimental day, male Wiga Wistar rats (230±30 g) were housed in individual cages provided with bedding material. The rats received 5 training sessions at 15-min time intervals over a 1-h period during which, the rats were conditioned to avoid an electric shock: the rat was placed on the non-electrified grid floor and the grid was electrified 10 s later for not more than 30 s, if the rat did not jump out of the box. Only rats that showed correct avoidance responses in all the last 3 training sessions were included for further experiments, and received the test compound or solvent immediately after the last training session.

Experimental Sessions

The rats were tested 3 times, i.e. at 60, 90 and 120 min after the injection of test compound or solvent. Latency to avoidance was recorded. The median avoidance response obtained over the three experimental sessions for each rat were used for further calculations. A median avoidance latency >8 s was selected as an all-or-none criterion for drug-induced inhibition of avoidance (occurring in only 1.5% of solvent-pretreated control rats; n=66). The results of this test are shown in table 5 below.

Object Recognition Test

Methods

Animals

Twenty-four 5-month-old male Wistar rats (Charles River, The Netherlands) were used (average body weights: 260 g). The animals were housed in individual standard cages on sawdust bedding in an air-conditioned room (about 20° C.). They were kept under a 12/12-hour light/dark cycle (lights on from 19.00 to 7.00 h) and had free access to food and water. Rats were housed in the same room as where they were tested. A radio, which was playing softly, provided background noise in the room. All testing was done between 9.00 and 17.00 h.

Treatment

Test compound was tested at three different dosages (0.3, 1 and 3 mg/kg, p.o.) against a scopolamine induced memory deficit. PQ10 (1 mg/kg, p.o.), a specific described PDE10 inhibitor, was used as a reference compound and dissolved in 98% hydroxyethylcellulose (0.5%) in water and 2% polysorbate 80. Scopolamine solution in saline (0.1 mg/kg, 1 ml/kg i.p.) was prepared daily.

Test compound was dissolved in acidified water (pH ~4). The compound solution was prepared daily and tested at doses of 0.3 mg/kg, 1 mg/kg, 3 mg/kg p.o. (injection volume 2 ml/kg) and all rats were treated once with each dose condition. The experimenter was unaware of which experimental conditions were tested. Administration was always 30 minutes before trial 1. Scopolamine was injected just after the experimental drug was given.

Object Recognition Memory

The apparatus consisted of a circular arena, 83 cm in diameter. Half of the 40 cm high wall was made of gray PVC, the other half of transparent PVC. The light intensity was equal in the different parts of the apparatus, as fluorescent red tubes provided a constant illumination of about 20 lux on the floor of the apparatus. Two objects were placed in a symmetrical position at about 10 cm from the gray wall. Each object was available in triplicate. Four different sets of objects were used.

A testing session consisted of two trials. The duration of each trial was 3 minutes. During the first trial (T1) the apparatus contained two identical objects (samples). Rats were placed in the apparatus facing the wall at the middle of the front (transparent) segment. After the first exploration period the rat was put back in its home cage. Subsequently, after a 1 h delay interval, the rat was put in the apparatus for the second trial (T2). The times spent in exploring each object during T1 and T2 were recorded manually with a personal computer.

Exploration was defined as follows: directing the nose to the object at a distance of no more than 2 cm and/or touching the object with the nose. Sitting on the object was not considered as exploratory behavior. In order to avoid the presence of olfactory cues the objects were always thoroughly cleaned after each trial. All combinations and locations of objects were used in a balanced manner to reduce potential biases due to preferences for particular locations or objects.

Historically, Wistar rats show a good object memory performance when a one-hour delay is interposed between the first trial and the second trial. After a twenty-four hour delay rats do not discriminate between the novel and the familiar object in the second trial. Using a six hour delay, the discrimination performance is between the performance of the one hour and twenty-four hour delay, suggesting a delay-dependent forgetting in this task.

Procedure

In the first two weeks, the animals were handled daily and adapted to the procedure in two days, i.e. they were allowed to explore the apparatus (without any objects) twice for 3 minutes each day. Then the rats were adapted to the testing and i.p. administration procedure by a saline injection (1.0 ml/kg) 30 minutes before the first trial until they showed a stable discrimination performance, i.e. a good discrimination at 1-h interval and no discrimination at 24-h interval. The optimal dose for scopolamine was determined as 0.1 mg/kg. The actual experiment consisted of 6 testing days. On day 1 and 6 half of the rats were treated with PQ10/scopolamine whereas the others were subjected to treatment with only the vehicle/saline. On day 2-5, the three doses of test compound (0.3, 1 and 3 mg/kg) and a group receiving its vehicle were tested against scopolamine. Every day, all three dosages and the vehicle were tested in six rats. These groups were tested in 4 consecutive testing days, resulting in 24 animals tested per condition. Each rat received each condition once. Compounds/vehicle were always tested on Monday, Wednesday and Friday in order to have a sufficient wash-out period between compound sessions.

Statistical Analysis

The basic measures were the times spent by rats in exploring an object during T1 and T2. The time spent in exploring the two identical samples is represented by 'a1' and 'a2'. The time spent in T2 in exploring the sample and new object is represented by 'a' and 'b', respectively. The following variables were calculated: e1=a1+a2, e2=a+b, and d2=(b−a)/e2; e1 and e2 are measures of the total exploration time in seconds (s) of both objects during T1 and T2 respectively; d2 is a relative measure of discrimination corrected for exploration activity (e2). Thus, there should be no differences in d2 indices between experiments with similar treatments at similar intervals. All 24 animals received each dose of test compound once during the experiment. One-sample t-statistics were performed in order to assess per treatment condition whether d2 differed from zero. However, comparison of the value of d2 with the value zero with no variance may not be the most suitable way for analyzing recognition (increased chance of making a type 1 error). Effects were therefore also assessed by a one-way ANOVA. In case of a significant difference between conditions, post hoc analyses with Bonferroni corrections were performed.

In table 6, an overview is given of the results of the test compound treatment given 30 minutes before T1 on exploratory behavior and memory performance. Differences were found between treatment conditions in exploration times in T1 (e1: $F(5,138)=3.34$, $p<0.01$), but not in T2 (e2: $F(5,138)=1.53$, n.s.). Post-hoc analysis showed that exploration in T1 was higher in the test compound 0.3 mg/kg and 3 mg/kg conditions, compared to the vehicle/saline condition.

ANOVA analysis showed differences in discrimination index d2 between conditions (d2: $F(5,138)=4.67$, $p<0.001$). Post-hoc analyses revealed a significantly better discrimination in the vehicle/saline, PQ10/scopolamine and test compound 3 mg/kg treated groups when compared to the vehicle/scopolamine condition. Furthermore, the discrimination indices of these conditions were statistically higher than zero, which was also the case for the test compound 1 mg/kg condition. The results of this test with a representative compound are shown in table 6 below.

SCH-23390-Induced Hypolocomotion in Mice

SCM-23390 (0.08 mg/kg, i.v.)-induced hypolocomotion was evaluated over a 30-min period starting immediately after the SCH-23390 challenge in male NMRI mice pretreated 0.5 h earlier with test compound or solvent. Averaged activity in solvent-treated control mice was 1540±559 counts (mean±SD; n=103). Criterion for drug-induced reversal of the SCH-23390-induced hypolocomotion: total distance: >2500 counts (2.9% false positives in controls).

For compound 25, an $ED_{50}$ of 7.1 mg/kg was obtained.

TABLE 4

Pharmacological data for compounds according to the invention. $pIC_{50}$ corresponds to the −log $IC_{50}$ expressed in mol/L. $ED_{50}$ is the dose (mg/kg body weight) at which 50% of the tested animals show the effect.

| Co. No. | PDE10A2 $pIC_{50}$ | APO $ED_{50}$ (mg/kg) | Co. No. | PDE10A2 $pIC_{50}$ | APO $ED_{50}$ (mg/kg) |
|---|---|---|---|---|---|
| 45 | 7.7 | 3.1* | 48 | 7.48 | 3.1 |
| 46 | 7.6 | 5* | 49 | 7.33 | 5 |
| 47 | 7.55 | n.t. | 50 | 7.32 | 5 |
| 51 | 7.3 | 1.2 | 30 | 6.97 | 1.2 |
| 52 | 7.28 | 3.1 | 79 | 6.97 | 5 |
| 53 | 7.27 | 5 | 80 | 6.95 | n.t. |
| 54 | 7.25 | n.t. | 81 | 6.95 | n.d. |
| 55 | 7.24 | n.d. | 82 | 6.94 | 3.1 |
| 56 | 7.24 | 3.1* | 83 | 6.94 | n.d. |
| 57 | 7.22 | 1.2 | 84 | 6.93 | n.d. |
| 58 | 7.17 | n.d. | 85 | 6.92 | n.t. |

TABLE 4-continued

Pharmacological data for compounds according to the invention. $pIC_{50}$ corresponds to the −log $IC_{50}$ expressed in mol/L. $ED_{50}$ is the dose (mg/kg body weight) at which 50% of the tested animals show the effect.

| Co. No. | PDE10A2 $pIC_{50}$ | APO $ED_{50}$ (mg/kg) | Co. No. | PDE10A2 $pIC_{50}$ | APO $ED_{50}$ (mg/kg) |
|---|---|---|---|---|---|
| 27 | 7.13 | n.d. | 86 | 6.91 | n.t. |
| 59 | 7.13 | n.t. | 87 | 6.9 | n.d. |
| 60 | 7.12 | n.t. | 88 | 6.88 | n.t. |
| 61 | 7.1 | 5 | 20 | 6.87 | 1.2 |
| 62 | 7.1 | n.d. | 89 | 6.87 | <=10 |
| 63 | 7.08 | n.d. | 90 | 6.87 | n.d. |
| 64 | 7.08 | n.t. | 91 | 6.87 | n.d. |
| 5 | 7.07 | n.d. | 92 | 6.87 | n.t. |
| 40 | 7.07 | 5 | 93 | 6.87 | n.t. |
| 65 | 7.07 | 5 | 36 | 6.86 | 3.1 |
| 66 | 7.07 | n.t. | 94 | 6.86 | n.d. |
| 67 | 7.07 | 3.1* | 4 | 6.85 | 3.1 |
| 68 | 7.06 | 3.1 | 7 | 6.85 | 1.2 |
| 69 | 7.05 | 5 | 35 | 6.85 | 5 |
| 70 | 7.04 | 5 | 95 | 6.85 | n.d. |
| 71 | 7.02 | 5 | 96 | 6.85 | 5 |
| 72 | 7.02 | 1.2 | 97 | 6.84 | 2.0 |
| 73 | 7.02 | n.t. | 98 | 6.84 | n.t. |
| 74 | 7.02 | n.d. | 33 | 6.83 | 0.8 |
| 10 | 7.01 | 1.2 | 99 | 6.82 | n.d. |
| 22 | 7.01 | n.d. | 42 | 6.81 | 5 |
| 75 | 7 | n.t. | 100 | 6.81 | 5 |
| 76 | 6.99 | 3.1 | 19 | 6.79 | n.d. |
| 77 | 6.99 | <=10 | 101 | 6.79 | 3.1 |

TABLE 4-continued

Pharmacological data for compounds according to the invention. $pIC_{50}$ corresponds to the −log $IC_{50}$ expressed in mol/L. $ED_{50}$ is the dose (mg/kg body weight) at which 50% of the tested animals show the effect.

| Co. No. | PDE10A2 $pIC_{50}$ | APO $ED_{50}$ (mg/kg) | Co. No. | PDE10A2 $pIC_{50}$ | APO $ED_{50}$ (mg/kg) |
|---|---|---|---|---|---|
| 78 | 6.98 | 1.2 | 102 | 6.78 | 5 |
| 103 | 6.78 | n.d. | 120 | 6.46 | n.t. |
| 21 | 6.77 | 1.2 | 12 | 6.43 | <=2.5 |
| 104 | 6.77 | 5 | 23 | 6.43 | n.d. |
| 105 | 6.76 | n.d. | 121 | 6.43 | n.d. |
| 106 | 6.76 | n.d. | 122 | 6.42 | n.d. |
| 107 | 6.76 | 5 | 123 | 6.4 | n.d. |
| 26 | 6.75 | n.d. | 124 | 6.39 | n.d. |
| 108 | 6.75 | n.d. | 125 | 6.35 | n.t. |
| 109 | 6.75 | n.t. | 3 | 6.34 | 5 |
| 25 | 6.72 | 1.2 | 14 | 6.34 | n.t. |
| 16 | 6.71 | 1.0 | 28 | 6.34 | 1.2* |
| 18 | 6.71 | n.d. | 126 | 6.34 | n.t. |
| 110 | 6.67 | 3.1 | 127 | 6.34 | n.t. |
| 29 | 6.66 | 1.2 | 128 | 6.33 | n.t. |
| 31 | 6.66 | n.d. | 32 | 6.32 | n.t. |
| 111 | 6.66 | n.d. | 37 | 6.31 | n.t. |
| 24 | 6.63 | n.d. | 129 | 6.3 | n.t. |

TABLE 4-continued

Pharmacological data for compounds according to the invention. $pIC_{50}$ corresponds to the −log $IC_{50}$ expressed in mol/L. $ED_{50}$ is the dose (mg/kg body weight) at which 50% of the tested animals show the effect.

| Co. No. | PDE10A2 $pIC_{50}$ | APO $ED_{50}$ (mg/kg) | Co. No. | PDE10A2 $pIC_{50}$ | APO $ED_{50}$ (mg/kg) |
|---|---|---|---|---|---|
| 38 | 6.63 | <=10 | 130 | 6.3 | n.d. |
| 41 | 6.63 | 5 | 11 | 6.29 | n.t. |
| 112 | 6.63 | n.d. | 131 | 6.27 | n.t. |
| 6 | 6.62 | <=2.5 | 132 | 6.27 | n.t. |
| 113 | 6.6 | n.d. | 133 | 6.26 | n.t. |
| 34 | 6.58 | 1.2* | 44 | 6.25 | n.t. |
| 114 | 6.58 | n.d. | 134 | 6.25 | <=10 |
| 115 | 6.58 | 5 | 135 | 6.25 | n.t. |
| 15 | 6.56 | 1.2 | 136 | 6.24 | n.d. |
| 17 | 6.56 | n.d. | 13 | 6.21 | n.d. |
| 116 | 6.56 | n.d. | 137 | 6.2 | n.t. |
| 1 | 6.51 | 0.8* | 9 | 6.17 | n.t. |
| 117 | 6.51 | n.t. | 2 | 6.15 | n.t. |
| 118 | 6.51 | n.d. | 138 | 6.14 | n.d. |
| 8 | 6.5 | 1.2 | 139 | 6.11 | n.t. |
| 119 | 6.49 | n.d. | 43 | 6.06 | n.t. |
| 140 | 6.06 | n.t. | 142 | n.t. | n.t. |
| 39 | 6.03 | n.t. | 143 | n.t. | n.t. |
| 141 | 6.02 | 5 | | | |

<= means that in 60% of the animals, the compound was found active at the indicated dose level.
n.t. means not tested.
n.d. means the compound was found not active at 2.5 or at 10 mg/kg concentration, taken as threshold value, and was not further tested.
*means the compound was not soluble and was tested orally as a suspension.

TABLE 4a

In vitro selectivity of representative compounds 16, 25 and 33.

| PDE type | 10A | 1B | 2A | 3A | 4D | 5A | 6AB | 7A | 8A | 9A | 11A |
|---|---|---|---|---|---|---|---|---|---|---|---|
| $IC_{50}$ (μM) co. no. 16 | 0.19 | 6.7 | 45.7 | 100 | 33.9 | 41.7 | 64.6 | >100 | >100 | >100 | 67.6 |
| $IC_{50}$ (μM) co. no 25 | 0.16 | >100 | 42.7 | 112 | 58.9 | 33.9 | 96.5 | >100 | >100 | >100 | 66.1 |
| $IC_{50}$ (μM) co. no 33 | 0.5 | 2.95 | >10 | >10 | >10 | >10 | n.t. | >10 | n.t. | >10 | >10 |

n.t. means not tested.

TABLE 4b

In vitro selectivity of tested compounds in tested PDE isoforms.

| PDE Isoform | Selectivity |
|---|---|
| PDE2A | ≥10 fold, except compound 119 (>3.02 fold selectivity) |
| PDE4D | ≥10 fold, except for compounds 10, 15, 45, 46, 48, 50, 51, 53, 63, 65, 66, 87, 94, 112, 124 and 130 (<10 fold selectivity) |
| PDE5A | ≥10 fold, except for compounds 10, 19, 43, 45, 46, 50, 51, 66, 87, 94, 95, 112 and 121 (<10 fold selectivity) |
| PDE6AB | >10 fold for all the compounds that were tested |
| PDE7A | >10-100 fold |
| PDE8A1 | >10 fold |
| PDE9 | >10-100 fold, except 78 (<10 fold selectivity) |
| rPDE10A | $IC_{50}$ 0.020-0.955 μM |
| PDE11A | ≥10 fold, except 22, 27, 38, 42, 45, 46, 49, 50, 51, 56, 66, 67, 69, 79, 82, 88, 96, 97, 101, 102, 104, 113, 121, 128, 133 and 138 (<10 fold selectivity) |

TABLE 5

Pharmacological data for compounds according to the invention in the occupancy, PCP and CAR tests.

| Co. No. | Occ. $ED_{50}$ (mg/kg) | % Occ. at 10 mg/kg | PCP $ED_{50}$ (mg/kg) | CAR $ED_{50}$ (mg/kg) |
|---|---|---|---|---|
| 1 | >10 39% occ.[a] | — | n.t. | n.t. |
| 4 | — | 28 | n.t. | n.t. |
| 7 | 4.1 | — | n.t. | n.t. |
| 8 | 2.6 | — | n.t. | n.t. |
| 10 | 1.8 | — | n.t. | n.t. |
| 12 | >10 22% occ. | — | n.t. | n.t. |
| 15 | 1.5 | — | n.t. | n.t. |
| 16 | 1.1 | — | 1.54 | 2.0 |
| 20 | 3.8 | — | n.t. | n.t. |
| 21 | 2.1 | — | n.t. | n.t. |
| 25 | 4.6 | — | 2.0 | 4.1 |
| 28 | >10 31% occ. | — | n.t. | n.t. |
| 30 | 3.4 | — | n.t. | n.t. |
| 34 | — | 52 | n.t. | n.t. |
| 42 | — | 59 | n.t. | n.t. |
| 45 | — | 53[a] | n.t. | n.t. |
| 46 | — | 41 | n.t. | n.t. |
| 48 | — | 53 | n.t. | n.t. |
| 50 | — | 72 | n.t. | n.t. |
| 51 | — | 61 | n.t. | n.t. |
| 52 | 5.5 | — | ≤10 | n.t. |
| 53 | n.t. | n.t. | ≤40 | n.t. |
| 57 | 8.0 | — | n.t. | 5.0 |
| 67 | — | 55 | n.t. | n.t. |
| 69 | — | 67 | 2.0 | n.t. |
| 70 | n.t. | n.t. | 3.2 | n.t. |
| 72 | 6.4 | — | 2.0 | n.t. |
| 78 | — | 76 | n.t. | n.t. |
| 97 | 5.6 | — | 5.4 | 12.3 |
| 107 | — | 62 | n.t. | n.t. |
| 113 | — | 11 | n.t. | n.t. |
| 118 | — | 0 | n.t. | n.t. |
| 130 | — | 10 | n.t. | n.t. |
| 135 | >10 29% occ.[a] | — | n.t. | n.t. |

Occ. means occupancy.

$ED_{50}$ means effective dose.

In the occupancy test all compounds were administered s.c., except compounds indicated with ([a]), which were administered p.o.

E. Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

TABLE 6

Effects of test compound on short-term memory
Mean values (±SEM) of A) exploration times (s) in the first (e1) and second (e2) trial, and B) the index of discrimination (d2).

| | | Saline Vehicle | Scop. (0.1 mg/kg) Vehicle | Scop. (0.1 mg/kg) co. no. 16 (0.3 mg/kg) | Scop. (0.1 mg/kg) co. no. 16 (1 mg/kg) | Scop. (0.1 mg/kg) co. no. 16 (3 mg/kg) | Scop. (0.1 mg/kg) PQ10 (1 mg/kg) |
|---|---|---|---|---|---|---|---|
| A) | e1 | 18.51 (±1.15) | 23.39 (±1.45) | 26.16 (±1.40) | 23.47 (±1.74) | 24.70 (±1.48) | 22.32 (±1.25) |
| | e2 | 21.55 (±1.60) | 24.94 (±1.24) | 23.35 (±1.63) | 25.63 (±1.54) | 26.20 (±1.72) | 22.63 (±1.01) |
| B) | d2 | 0.29 (±0.05)*** | 0.04 (±0.06) | 0.08 (±0.05) | 0.23 (±0.04)*** | 0.25 (±0.05)*** | 0.27 (±0.04)*** |

*indicate significant differences from zero (* $p < 0.5$;  $p < 0.1$; * $p < 0.001$)

Reasonable variations are not to be regarded as a departure from the scope of the invention. It will be obvious that the thus described invention may be varied in many ways by those skilled in the art.

The invention claimed is:

1. A compound of formula (I)

(I)

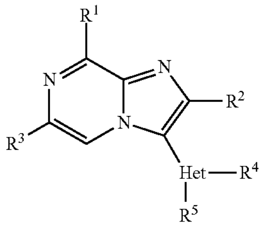

or a stereoisomeric form thereof, wherein $R^1$ is selected from the group consisting of a radical of formula (a-1), (a-2) and (a-3);

(a-1)

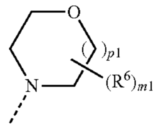

(a-2)

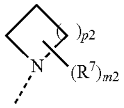

(a-3)

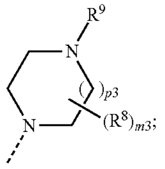

wherein each $R^6$, $R^7$, $R^8$ independently is selected from the group consisting of fluoro; $C_{1-4}$alkyl; $C_{1-4}$alkyloxy; and $C_{1-4}$alkyl substituted with 1, 2 or 3 fluoro atoms;

$R^9$ is hydrogen or $C_{1-4}$alkyl;

each $m_1$, $m_2$, and $m_3$ is independently selected from 0, 1, 2, 3 and 4;

$p_2$ is selected from 1, 2, 3, and 4;

each $p_1$ and $p_3$ is independently selected from 1 and 2;

or $R^1$ is selected from the group consisting of unsubstituted pyridinyl; pyridinyl substituted with 1 or 2 substituents selected from the group consisting of halogen, $C_{1-4}$alkyl, trifluoromethyl and $C_{1-4}$alkyloxy; and unsubstituted tetrahydropyranyl;

$R^2$ is selected from the group consisting of hydrogen; $C_{1-4}$alkyl; trifluoromethyl; $C_{3-8}$cycloalkyl; $C_{1-4}$alkyloxy; and cyano;

$R^3$ is selected from the group consisting of hydrogen; $C_{1-4}$alkyl; $C_{3-8}$cycloalkyl; and $C_{1-4}$alkyl substituted with 1, 2 or 3 fluoro atoms;

Het is a 5- or 6-membered heterocyclic ring, selected from the group consisting of pyridinyl; pyrimidinyl; pyridazinyl; pyrazinyl; pyrrolyl; oxazolyl; thiazolyl; imidazolyl; pyrazolyl; isothiazolyl; isoxazolyl; oxadiazolyl and triazolyl;

$R^4$ is selected from the group consisting of hydrogen; $C_{1-4}$alkyl; $C_{1-4}$alkyl substituted with 1, 2 or 3 fluoro atoms; (difluorocyclopropyl)methyl; (cyclopropyl)difluoromethyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; $C_{1-4}$alkyloxy substituted with 1, 2 or 3 fluoro atoms; ($C_{3-8}$cycloalkyl)$C_{1-4}$alkyloxy; ($C_{1-4}$alkyloxy$C_{1-4}$alkyl)oxy; ($C_{1-4}$alkyl)-carbonyl; ($C_{1-4}$alkyl)carbonyl$C_{1-4}$alkyl; ($C_{3-8}$cycloalkyl)carbonyl; ($C_{3-8}$cycloalkyl)-carbonyl$C_{1-4}$alkyl; unsubstituted phenyl; phenyl substituted with 1 or 2 substituents selected from the group consisting of halogen, $C_{1-4}$alkyl, trifluoromethyl, trifluoromethoxy, cyano and $C_{1-4}$alkyloxy; unsubstituted benzyl; benzyl substituted with 1 or 2 substituents selected from the group consisting of halogen, $C_{1-4}$alkyl, trifluoromethyl, trifluoromethoxy, cyano and $C_{1-4}$alkyloxy; unsubstituted tetrahydrofuranyl; tetrahydrofuranylmethyl; unsubstituted tetrahydropyranyl; tetrahydropyranylmethyl; pyridinylmethyl; quinolinylmethyl; $(NR^{10}R^{11})C_{1-4}$alkyl; and $NR^{10}R^{11}$;

$R^5$ is hydrogen or fluoro;

$R^{10}$ and $R^{11}$ are independently selected from hydrogen and $C_{1-4}$alkyl, or taken together with the ring nitrogen atom may form a radical of Formula (b-1), (b-2) or (b-3)

(b-1)

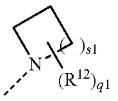

(b-2)

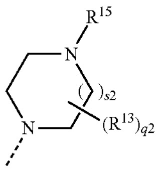

(b-3)

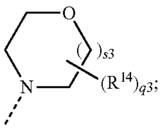

wherein each $R^{12}$, $R^{13}$ and $R^{14}$ independently is $C_{1-4}$alkyl or $C_{1-4}$alkyloxy;

$R^{15}$ is hydrogen or $C_{1-4}$alkyl;

each q1, q2 and q3 is independently selected from 0, 1, 2, 3 and 4;

$s_1$ is selected from 1, 2, 3 and 4;

each $s_2$ and $s_3$ is independently selected from 1 and 2;

or a pharmaceutically acceptable salt or a solvate thereof.

2. The compound according to claim 1, or a stereoisomeric form thereof, wherein $R^1$ is selected from the group consisting of a radical of formula (a-1), a radical of formula (a-2); a radical of formula (a-3); unsubstituted pyridinyl; pyridinyl substituted with halogen, $C_{1-4}$alkyl, trifluoromethyl or $C_{1-4}$alkyloxy; and unsubstituted tetrahydropyranyl;

wherein each $R^6$, $R^7$ and $R^8$ independently is selected from the group consisting of $C_{1-4}$alkyl; and $C_{1-4}$alkyloxy;

$R^9$ is selected from hydrogen and $C_{1-4}$alkyl;
each $m_1$, $m_2$ and $m_3$ is selected from 0, 1 and 2;
$p_2$ is selected from 2 and 3;
each $p_1$ and $p_3$ is 1;
$R^2$ is selected from the group consisting of hydrogen; methyl; ethyl; prop-2-yl; trifluoromethyl; cyano; methoxy and cyclopropyl;
$R^3$ is selected from the group consisting of hydrogen; methyl; trifluoromethyl; 3,3,3-trifluoropropyl; and cyclopropyl; and
Het is selected from the group consisting of pyridinyl; pyrimidinyl; 1H-pyrrolyl; oxazolyl; thiazolyl; 1H-imidazolyl; and 1H-pyrazolyl;
$R^4$ is selected from the group consisting of hydrogen; $C_{1-4}$alkyl; $C_{1-4}$alkyl substituted with 1, 2 or 3 fluoro atoms; (difluorocyclopropyl)methyl; (cyclopropyl)difluoromethyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; $C_{1-4}$alkyloxy substituted with 1, 2 or 3 fluoro atoms; ($C_{3-8}$cycloalkyl)$C_{1-4}$alkyloxy; ($C_{1-4}$alkyloxy$C_{1-4}$alkyl)oxy; ($C_{1-4}$alkyl)-carbonyl$C_{1-4}$alkyl; ($C_{3-8}$cycloalkyl)carbonyl$C_{1-4}$alkyl; unsubstituted phenyl; phenyl substituted with halogen, $C_{1-4}$alkyl, trifluoromethyl, trifluoromethoxy, cyano or $C_{1-4}$alkyloxy; unsubstituted benzyl; benzyl substituted with halogen, $C_{1-4}$alkyl, trifluoromethyl, trifluoromethoxy, cyano or $C_{1-4}$alkyloxy; unsubstituted tetrahydrofuranyl; tetrahydrofuranylmethyl; unsubstituted tetrahydropyranyl; tetrahydropyranylmethyl; pyridinylmethyl; quinolinylmethyl; $(NR^{10}R^{11})C_{1-4}$alkyl; and $NR^{10}R^{11}$;
wherein $R^{10}$ and $R^{11}$ are independently selected from hydrogen and $C_{1-4}$alkyl, or taken together with the ring nitrogen atom may form a radical of Formula (b-1), (b-2) or (b-3);

wherein
each $R^{12}$, $R^{13}$ and $R^{14}$ is independently selected from $C_{1-4}$alkyl and $C_{1-4}$alkyloxy;
$R^{15}$ is selected from hydrogen and $C_{1-4}$alkyl;
each $q_1$, $q_2$ and $q_3$ is selected from 0, 1 and 2;
$s_1$ is selected from 2 and 3;
each $s_2$ and $s_3$ is 1;
and $R^5$ is as defined in claim 1;
or a pharmaceutically acceptable salt or a solvate thereof.

3. The compound according to claim 1, or a stereoisomeric form thereof, wherein
$R^1$ is selected from the group consisting of a radical of formula (a-1); a radical of formula (a-2); unsubstituted pyridin-3-yl; and unsubstituted pyridin-4-yl;
wherein each $m_1$, $m_2$ and $m_3$ is 0; $p_2$ is selected from 2 and 3; and each of $p_1$ and $p_3$ is 1;
$R^4$ is selected from the group consisting of hydrogen; $C_{1-4}$alkyl; fluoroethyl; fluoropropyl; difluoroethyl; trifluoromethyl; trifluoroethyl; (difluorocyclopropyl)methyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; trifluoromethyloxy; trifluoroethyloxy; ($C_{3-8}$cycloalkyl)$C_{1-4}$alkyloxy; ($C_{1-4}$alkyloxy$C_{1-4}$alkyl)oxy; ($C_{1-4}$alkyl)carbonyl$C_{1-4}$alkyl; ($C_{3-8}$cycloalkyl)carbonyl$C_{1-4}$alkyl; unsubstituted phenyl; phenyl substituted with halogen; unsubstituted benzyl; benzyl substituted with halogen; unsubstituted tetrahydrofuranyl; unsubstituted tetrahydropyranyl; tetrahydrofuranylmethyl; tetrahydropyranylmethyl; pyridinylmethyl; quinolinylmethyl; $(NR^{10}R^{11})C_{1-4}$alkyl; and $NR^{10}R^{11}$;
wherein $R^{10}$ and $R^{11}$ are independently hydrogen or $C_{1-4}$alkyl, or taken together with the nitrogen can be a radical of formula (b-1), (b-2) or (b-3), wherein
$R^{12}$ is $C_{1-4}$alkyloxy;
$s_1$ is 2;
$q_1$ is selected from 0 and 1;
each $q_2$ and $q_3$ is 0;
each $s_2$ and $s_3$ is 1; and
$R^{15}$ is hydrogen;
and $R^2$, $R^3$, Het and $R^5$ are as defined in claim 1;
or a pharmaceutically acceptable salt or a solvate thereof.

4. The compound according to claim 1, or a stereoisomeric form thereof, wherein
$R^1$ is selected from the group consisting of unsubstituted morpholin-4-yl; unsubstituted pyridin-3-yl; unsubstituted pyridin-4-yl and unsubstituted pyrrolidin-1-yl;
$R^2$ is selected from the group consisting of hydrogen; methyl; ethyl; prop-2-yl; trifluoromethyl; cyano; methoxy and cyclopropyl;
$R^3$ is selected from the group consisting of hydrogen; methyl; trifluoromethyl; 3,3,3-trifluoropropyl; and cyclopropyl; and
Het is selected from the group consisting of pyridin-2-yl; pyridin-3-yl; pyridin-4-yl; pyrimidin-5-yl; 1H-pyrrol-3-yl; 1,3-oxazol-4-yl; 1,3-thiazol-5-yl; 1H-imidazol-5-yl; and 1H-pyrazol-5-yl;
$R^4$ is hydrogen; methyl; ethyl; prop-2-yl; 2-methylpropyl; 2-fluoroethyl; 3-fluoropropyl; 2,2-difluoroethyl; 2,2,2-trifluoroethyl; 2,2-difluorocyclopropylmethyl; 2-hydroxyethyl; cyclopropyl; cyclopropylmethyl; methyloxy; 1-methylethyloxy; ethyloxymethyl; 2-methyloxyethyl; 2-ethyloxyethyl; 3-methyloxypropyl; 1-methoxy-1-methylethyl; 1-ethoxy-1-methylethyl; 2-methoxy-2-methylpropyl; 2-(1-methylethoxy)-ethyl; 3-methoxypropyl; 2-methoxypropyl; 1-methoxyprop-2-yl; 1-methoxybut-2-yl; 2-methoxy-3-methylbutyl; 3-methoxy-3-methylbutyl; 3-methoxybutyl; 2,2,2-trifluoroethyloxy; cyclopropylmethyloxy; (2-methyloxyethyl)oxy; 2-methoxy-2-methylpropyloxy; 2-oxopropyl; 3-oxobutyl; 2-cyclopropyl-2-oxoethyl; 4-fluorophenyl; 2-chlorobenzyl; 4-chlorobenzyl; tetrahydrofuran-3-yl; tetrahydro-2H-pyran-4-yl; tetrahydrofuran-2-ylmethyl; tetrahydro-2H-pyran-2-ylmethyl; tetrahydro-2H-pyran-4-ylmethyl; pyridin-2-ylmethyl; pyridin-3-ylmethyl; pyridin-4-ylmethyl; quinolin-2-ylmethyl; (1-methylethyl)amino; pyrrolidin-1-yl; piperazin-1-yl; morpholin-4-yl; 3-methoxy-pyrrolidin-1-yl; 2-pyrrolidin-1-ylethyl; and 2-morpholin-4-ylethyl;
$R^5$ is hydrogen or fluoro;
or a pharmaceutically acceptable salt or a solvate thereof.

5. A compound of formula (I) according to claim 1, selected from the group consisting of
3-[1-(2-methoxyethyl)-1H-pyrazol-4-yl]-2-methyl-8-(4-morpholinyl)-imidazo[1,2-a]pyrazine;
3-[1-(2-methoxyethyl)-1H-pyrrol-3-yl]-2-methyl-8-(4-morpholinyl)-imidazo[1,2-a]pyrazine;
3-[6-(2-methoxyethyl)-3-pyridinyl]-2-methyl-8-(4-morpholinyl)-imidazo[1,2-a]pyrazine;
2-methyl-3-[2-(2-methylpropyl)-5-thiazolyl]-8-(4-morpholinyl)-imidazo[1,2-a]pyrazine;
3-[6-(2-methoxyethyl)-3-pyridinyl]-2-methyl-8-(4-pyridinyl)-imidazo[1,2-a]pyrazine;
3-[6-(2-methoxyethoxy)-3-pyridinyl]-2-methyl-8-(4-morpholinyl)-imidazo[1,2-a]pyrazine;
3-(6-cyclopropyl-3-pyridinyl)-2-methyl-8-(4-morpholinyl)-imidazo[1,2-a]pyrazine;
2-methyl-8-(4-morpholinyl)-3-[6-(1-piperazinyl)-3-pyridinyl]-imidazo[1,2-a]pyrazine;

2-methyl-8-(4-morpholinyl)-3-[6-(tetrahydro-2H-pyran-4-yl)-3-pyridinyl]-imidazo[1,2-a]pyrazine;

3-[6-(1-methoxy-1-methylethyl)-3-pyridinyl]-2-methyl-8-(4-morpholinyl)-imidazo[1,2-a]pyrazine;

3-[6-(ethoxymethyl)-3-pyridinyl]-2-methyl-8-(4-morpholinyl)-imidazo[1,2-a]pyrazine; and 3-[2-(2-methoxyethyl)-5-pyrimidinyl]-2-methyl-8-(4-morpholinyl)-imidazo[1,2-a]pyrazine;

or a pharmaceutically acceptable salt or a solvate thereof.

6. A pharmaceutical composition comprising a therapeutically effective amount of a compound according to claim 1 and a pharmaceutically acceptable carrier or excipient.

7. A method of treatment of a disease or disorder selected from the group consisting of schizophrenia, drug induced psychosis, obsessive-compulsive disorder, generalized anxiety disorder, Huntington's disease, dyskinesia, Parkinson's disease, depression, bipolar disorders, dementia, Alzheimer's disease dementia, attention-deficit/hyperactivity disorder, drug abuse, acute pain, chronic pain, severe pain, intractable pain, neuropathic pain, post traumatic pain, diabetes and obesity, comprising administering to a patient having said disease or disorder a therapeutically effective amount of a compound according to claim 1.

8. A pharmaceutical composition comprising a compound according to claim 1 in combination with a pharmaceutical agent.

9. A process for preparing a pharmaceutical composition comprising a therapeutically effective amount of a compound as defined in claim 1 and a pharmaceutically acceptable carrier or excipient, characterized in that a pharmaceutically acceptable carrier is intimately mixed with a therapeutically effective amount of the compound.

10. A product comprising (a) a compound as defined in claim 1; and (b) a pharmaceutical agent, as a combined preparation for simultaneous, separate or sequential administration.

* * * * *